US012495968B2

(12) United States Patent
Al-Ali et al.

(10) Patent No.: US 12,495,968 B2
(45) Date of Patent: Dec. 16, 2025

(54) SYSTEM FOR TRANSMISSION OF SENSOR DATA USING DUAL COMMUNICATION PROTOCOL

(71) Applicant: Masimo Corporation, Irvine, CA (US)

(72) Inventors: Ammar Al-Ali, San Juan Capistrano, CA (US); Stephen Scruggs, Newport Beach, CA (US); Richard Priddell, Irvine, CA (US); Chad A De Jong, Los Angeles, CA (US); Eric Karl Kinast, Santa Ana, CA (US); Jung Soo Hwang, Irvine, CA (US); Steven Hang, Santa Ana, CA (US)

(73) Assignee: Masimo Corporation, Irvine, CA (US)

( * ) Notice: Subject to any disclaimer, the term of this patent is extended or adjusted under 35 U.S.C. 154(b) by 585 days.

(21) Appl. No.: 17/316,512

(22) Filed: May 10, 2021

(65) Prior Publication Data

US 2022/0022748 A1 Jan. 27, 2022

Related U.S. Application Data

(63) Continuation-in-part of application No. 16/599,017, filed on Oct. 10, 2019, now Pat. No. 11,272,839.
(Continued)

(51) Int. Cl.
*A61B 5/00* (2006.01)
*A61B 5/0205* (2006.01)
(Continued)

(52) U.S. Cl.
CPC .......... *A61B 5/0022* (2013.01); *A61B 5/0205* (2013.01); *A61B 5/021* (2013.01);
(Continued)

(58) Field of Classification Search
CPC ..... A61B 5/0022; A61B 5/0205; A61B 5/021; A61B 5/024; A61B 5/0816;
(Continued)

(56) References Cited

U.S. PATENT DOCUMENTS

| | | | |
|---|---|---|---|
| 3,646,606 | A | 2/1972 | Buxton et al. |
| 3,690,313 | A | 9/1972 | Weber et al. |

(Continued)

FOREIGN PATENT DOCUMENTS

| | | |
|---|---|---|
| CN | 301342850 | 9/2010 |
| CN | 302423595 | 5/2013 |

(Continued)

OTHER PUBLICATIONS

US 2022/0192529 A1, 06/2022, Al-Ali et al. (withdrawn)
(Continued)

*Primary Examiner* — Franklin D Balseca
(74) *Attorney, Agent, or Firm* — Knobbe, Martens, Olson & Bear, LLP

(57) ABSTRACT

A system for collecting physiological data from a patient is disclosed. The system includes a reusable module and a disposable module. The disposable module collects and transmits physiological data to the reusable module, which in turn transmits the physiological data to a patient monitoring system. The reusable module accesses operation data from the disposable module to validate the disposable sensor assembly. Optionally, the operation data includes sensor life data that may be used to determine life expectancy of disposable module. The disposable sensor assembly may store the physiological data for a predetermined length of time when there is no wireless communication established for the reusable module.

20 Claims, 44 Drawing Sheets

Related U.S. Application Data

(60) Provisional application No. 63/062,939, filed on Aug. 7, 2020, provisional application No. 63/023,711, filed on May 12, 2020, provisional application No. 62/744,988, filed on Oct. 12, 2018.

(51) Int. Cl.
*A61B 5/021* (2006.01)
*A61B 5/024* (2006.01)
*A61B 5/08* (2006.01)
*A61B 5/1455* (2006.01)

(52) U.S. Cl.
CPC ............ *A61B 5/024* (2013.01); *A61B 5/0816* (2013.01); *A61B 5/14551* (2013.01); *A61B 5/6831* (2013.01); *A61B 2560/0214* (2013.01)

(58) Field of Classification Search
CPC . A61B 5/14551; A61B 5/6831; A61B 5/0214; A61B 5/0002; A61B 5/0004; A61B 5/0015; A61B 5/0026; A61B 2560/0214; H04Q 9/00; H04Q 2209/00; H04Q 2209/10; H04Q 2209/20; H04Q 2209/40; H04Q 2209/43; H04Q 2209/80; H04Q 2209/82; H04Q 2209/823; H04Q 2209/84
See application file for complete search history.

(56) References Cited

U.S. PATENT DOCUMENTS 3,810,102 A 5/1974 Parks, III et al.
3,815,583 A 6/1974 Scheidt
3,972,320 A 8/1976 Kalman
3,978,849 A 9/1976 Geneen
4,108,166 A 8/1978 Schmid
4,129,125 A 12/1978 Lester et al.
4,226,006 A 10/1980 Toyama
4,231,354 A 11/1980 Kurtz et al.
D265,508 S 7/1982 Rusteberg
D268,300 S 3/1983 Richards
4,589,415 A 5/1986 Haaga
4,662,378 A 5/1987 Thomis
4,815,172 A 3/1989 Ward et al.
4,838,275 A 6/1989 Lee
4,852,570 A 8/1989 Levine
4,960,128 A 10/1990 Gordon et al.
4,964,408 A 10/1990 Hink et al.
4,966,154 A 10/1990 Cooper et al.
5,041,187 A 8/1991 Hink et al.
5,069,213 A 12/1991 Hink et al.
5,092,340 A 3/1992 Yamaguchi et al.
5,140,519 A 8/1992 Friesdorf et al.
5,159,932 A 11/1992 Zanetti et al.
5,161,539 A 11/1992 Evans et al.
5,163,438 A 11/1992 Gordon et al.
5,262,944 A 11/1993 Weisner et al.
5,277,189 A 1/1994 Jacobs
5,278,627 A 1/1994 Aoyagi et al.
5,282,474 A 2/1994 Valdes Sosa et al.
5,296,688 A 3/1994 Hamilton et al.
5,318,037 A 6/1994 Evans et al.
5,319,355 A 6/1994 Russek
5,331,549 A 7/1994 Crawford, Jr.
5,333,106 A 7/1994 Lanpher et al.
5,337,744 A 8/1994 Branigan
5,341,805 A 8/1994 Stavridi et al.
5,348,008 A 9/1994 Bornn et al.
5,358,519 A 10/1994 Grandjean
D353,195 S 12/1994 Savage et al.
D353,196 S 12/1994 Savage et al.
5,375,599 A 12/1994 Schimizu
5,375,604 A 12/1994 Kelly
5,377,676 A 1/1995 Vari et al.
D356,441 S 3/1995 Scheller
5,400,794 A 3/1995 Gorman
D357,982 S 5/1995 Dahl et al.
5,416,695 A 5/1995 Stutman et al.
D359,546 S 6/1995 Savage et al.
5,431,170 A 7/1995 Mathews
5,434,611 A 7/1995 Tamura
5,436,499 A 7/1995 Namavar et al.
D361,840 S 8/1995 Savage et al.
D362,063 S 9/1995 Savage et al.
5,452,717 A 9/1995 Branigan et al.
D363,120 S 10/1995 Savage et al.
5,456,252 A 10/1995 Vari et al.
5,479,934 A 1/1996 Imran
5,482,036 A 1/1996 Diab et al.
5,483,968 A 1/1996 Adam et al.
5,490,505 A 2/1996 Diab et al.
5,494,041 A 2/1996 Wilk
5,494,043 A 2/1996 O'Sullivan et al.
5,503,149 A 4/1996 Beavin
5,505,202 A 4/1996 Mogi et al.
5,533,511 A 7/1996 Kaspari et al.
5,534,851 A 7/1996 Russek
5,537,289 A 7/1996 Dahl
5,544,649 A 8/1996 David et al.
5,553,609 A 9/1996 Chen et al.
5,558,638 A 9/1996 Evers et al.
5,561,275 A 10/1996 Savage et al.
5,562,002 A 10/1996 Lalin
5,566,676 A 10/1996 Rosenfeldt et al.
5,566,678 A 10/1996 Rosenfeldt et al.
5,576,952 A 11/1996 Stutman et al.
5,579,001 A 11/1996 Dempsey et al.
5,590,649 A 1/1997 Caro et al.
5,602,924 A 2/1997 Durand et al.
5,619,991 A 4/1997 Sloane
5,632,272 A 5/1997 Diab et al.
5,638,816 A 6/1997 Kiani-Azarbayjany et al.
5,638,818 A 6/1997 Diab et al.
5,640,967 A 6/1997 Fine et al.
5,645,440 A 7/1997 Tobler et al.
5,671,914 A 9/1997 Kalkhoran et al.
5,685,299 A 11/1997 Diab et al.
5,685,314 A 11/1997 Geheb et al.
5,687,717 A 11/1997 Halpern et al.
5,694,020 A 12/1997 Lang
5,724,580 A 3/1998 Levin et al.
5,724,983 A 3/1998 Selker et al.
5,725,308 A 3/1998 Smith et al.
5,726,440 A 3/1998 Kalkhoran et al.
5,734,739 A 3/1998 Sheehan et al.
D393,830 S 4/1998 Tobler et al.
5,743,262 A 4/1998 Lepper, Jr. et al.
5,747,806 A 5/1998 Khalil et al.
5,750,994 A 5/1998 Schlager
5,758,079 A 5/1998 Ludwig et al.
5,758,644 A 6/1998 Diab et al.
5,760,910 A 6/1998 Lepper, Jr. et al.
5,769,785 A 6/1998 Diab et al.
5,772,585 A 6/1998 Lavin et al.
5,782,757 A 7/1998 Diab et al.
5,782,805 A 7/1998 Meinzer
5,785,659 A 7/1998 Caro et al.
5,791,347 A 8/1998 Flaherty et al.
5,801,637 A 9/1998 Lomholt
5,810,734 A 9/1998 Caro et al.
5,813,403 A 9/1998 Soller et al.
5,822,544 A 10/1998 Chaco et al.
5,822,546 A 10/1998 George
5,823,950 A 10/1998 Diab et al.
5,829,723 A 11/1998 Brunner
5,830,131 A 11/1998 Caro et al.
5,833,618 A 11/1998 Caro et al.
5,855,550 A 1/1999 Lai et al.
5,860,919 A 1/1999 Kiani-Azarbayjany et al.
D406,001 S 2/1999 Nemeth
5,876,351 A 3/1999 Rohde
5,890,929 A 4/1999 Mills et al.
5,904,654 A 5/1999 Wohltmann et al.
5,910,139 A 6/1999 Cochran et al.

(56) References Cited

U.S. PATENT DOCUMENTS 5,919,134 A 7/1999 Diab
5,921,920 A 7/1999 Marshall et al.
5,924,074 A 7/1999 Evans
5,931,160 A 8/1999 Gilmore et al.
5,931,791 A 8/1999 Saltzstein et al.
5,934,925 A 8/1999 Tobler et al.
5,940,182 A 8/1999 Lepper, Jr. et al.
5,941,836 A 8/1999 Friedman
5,942,986 A 8/1999 Shabot et al.
D415,892 S 11/1999 Angus et al.
5,987,343 A 11/1999 Kinast
5,987,519 A 11/1999 Peifer et al.
5,995,855 A 11/1999 Kiani et al.
5,997,343 A 12/1999 Mills et al.
6,002,952 A 12/1999 Diab et al.
6,006,119 A 12/1999 Soller et al.
6,010,937 A 1/2000 Karam et al.
6,011,986 A 1/2000 Diab et al.
6,014,346 A 1/2000 Malone
6,018,673 A 1/2000 Chin et al.
6,024,699 A 2/2000 Surwit et al.
6,027,452 A 2/2000 Flaherty et al.
6,032,678 A 3/2000 Rottem
6,035,230 A 3/2000 Kang
6,036,642 A 3/2000 Diab et al.
6,036,718 A 3/2000 Ledford et al.
6,040,578 A 3/2000 Malin et al.
6,045,509 A 4/2000 Caro et al.
6,045,527 A 4/2000 Appelbaum et al.
6,057,758 A 5/2000 Dempsey et al.
6,066,204 A 5/2000 Haven
6,067,462 A 5/2000 Diab et al.
6,081,735 A 6/2000 Diab et al.
6,088,607 A 7/2000 Diab et al.
6,093,146 A 7/2000 Filangeri
6,101,478 A 8/2000 Brown
6,106,463 A 8/2000 Wilk
6,110,522 A 8/2000 Lepper, Jr. et al.
6,115,673 A 9/2000 Malin et al.
6,124,597 A 9/2000 Shehada et al.
6,128,521 A 10/2000 Marro et al.
6,129,675 A 10/2000 Jay
6,129,686 A 10/2000 Friedman
6,132,218 A 10/2000 Benja-Athon
6,139,494 A 10/2000 Cairnes
6,144,868 A 11/2000 Parker
6,151,516 A 11/2000 Kiani-Azarbayjany et al.
6,152,754 A 11/2000 Gerhardt et al.
6,157,850 A 12/2000 Diab et al.
6,165,005 A 12/2000 Mills et al.
6,167,258 A 12/2000 Schmidt et al.
D437,058 S 1/2001 Gozani
6,168,563 B1 1/2001 Brown
6,171,237 B1 1/2001 Avitall et al.
6,175,752 B1 1/2001 Say et al.
6,183,417 B1 2/2001 Gehab et al.
6,184,521 B1 2/2001 Coffin, IV et al.
6,185,448 B1 2/2001 Borovsky
6,195,576 B1 2/2001 John
6,206,830 B1 3/2001 Diab et al.
6,221,012 B1 4/2001 Maschke et al.
6,224,553 B1 5/2001 Nevo
6,229,856 B1 5/2001 Diab et al.
6,230,142 B1 5/2001 Benigno et al.
6,232,609 B1 5/2001 Snyder et al.
6,236,872 B1 5/2001 Diab et al.
6,241,683 B1 6/2001 Macklem et al.
6,251,113 B1 6/2001 Appelbaum
6,253,097 B1 6/2001 Aronow et al.
6,255,708 B1 7/2001 Sudharsanan et al.
6,256,523 B1 7/2001 Diab et al.
6,263,222 B1 7/2001 Diab et al.
6,267,723 B1 7/2001 Matsumura et al.
6,269,262 B1 7/2001 Kandori et al.
6,278,522 B1 8/2001 Lepper, Jr. et al.
6,280,213 B1 8/2001 Tobler et al.
6,280,381 B1 8/2001 Malin et al.
6,285,896 B1 9/2001 Tobler et al.
D449,304 S 10/2001 Herath
D449,617 S 10/2001 Herath
6,301,493 B1 10/2001 Marro et al.
6,304,767 B1 10/2001 Soller et al.
6,308,089 B1 10/2001 von der Ruhr et al.
6,312,378 B1 11/2001 Bardy
6,317,627 B1 11/2001 Ennen et al.
6,319,205 B1 11/2001 Goor et al.
6,321,100 B1 11/2001 Parker
6,322,502 B1 11/2001 Schoenberg et al.
6,322,515 B1 11/2001 Goor et al.
D452,495 S 12/2001 Murnaghan et al.
D452,496 S 12/2001 Murnaghan et al.
6,325,761 B1 12/2001 Jay
6,329,139 B1 12/2001 Nova et al.
6,334,065 B1 12/2001 Al-Ali et al.
6,338,039 B1 1/2002 Lonski et al.
6,343,224 B1 1/2002 Parker
6,349,228 B1 2/2002 Kiani et al.
6,352,504 B1 3/2002 Ise
6,354,235 B1 3/2002 Davies
6,360,114 B1 3/2002 Diab et al.
6,363,269 B1 * 3/2002 Hanna ................ A61B 5/14551
600/336
D456,074 S 4/2002 McCurry
6,364,834 B1 4/2002 Reuss et al.
6,364,839 B1 4/2002 Little et al.
6,368,283 B1 4/2002 Xu et al.
6,371,921 B1 4/2002 Caro et al.
6,377,829 B1 4/2002 Al-Ali
6,385,476 B1 5/2002 Osadchy et al.
6,385,589 B1 5/2002 Trusheim et al.
6,388,240 B2 5/2002 Schulz et al.
6,397,091 B2 5/2002 Diab et al.
6,407,335 B1 6/2002 Franklin-Lees
6,411,373 B1 6/2002 Garside et al.
6,415,167 B1 7/2002 Blank et al.
6,430,437 B1 8/2002 Marro
6,430,525 B1 8/2002 Weber et al.
6,461,305 B1 10/2002 Schnall
6,463,311 B1 10/2002 Diab
6,470,199 B1 10/2002 Kopotic et al.
6,470,893 B1 10/2002 Boesen
6,487,429 B2 11/2002 Hockersmith et al.
6,488,633 B1 12/2002 Schnall
6,501,975 B2 12/2002 Diab et al.
6,505,059 B1 1/2003 Kollias et al.
6,515,273 B2 2/2003 Al-Ali
6,517,967 B1 2/2003 Shrim et al.
6,519,487 B1 2/2003 Parker
6,524,240 B1 2/2003 Thede
6,525,386 B1 2/2003 Mills et al.
6,526,300 B1 2/2003 Kiani et al.
D471,354 S 3/2003 Daniels
6,534,012 B1 3/2003 Hazen et al.
6,541,756 B2 4/2003 Schulz et al.
6,542,764 B1 4/2003 Al-Ali et al.
6,544,173 B2 4/2003 West et al.
6,544,174 B2 4/2003 West et al.
6,551,243 B2 4/2003 Bocionek et al.
6,578,428 B1 6/2003 Dromms et al.
6,580,086 B1 6/2003 Schulz et al.
6,582,393 B2 6/2003 Sage, Jr.
6,584,336 B1 6/2003 Ali et al.
6,587,196 B1 7/2003 Stippick et al.
6,587,199 B1 7/2003 Luu
6,595,316 B2 7/2003 Cybulski et al.
6,597,932 B2 7/2003 Tian et al.
6,597,933 B2 7/2003 Kiani et al.
6,606,511 B1 8/2003 Ali et al.
6,616,606 B1 9/2003 Peterson et al.
6,632,181 B2 10/2003 Flaherty et al.
6,635,559 B2 10/2003 Greenwald et al.
6,639,668 B1 10/2003 Trepagnier
6,640,116 B2 10/2003 Diab
6,640,117 B2 10/2003 Makarewicz et al.

(56) References Cited

U.S. PATENT DOCUMENTS

D481,537 S 11/2003 Vaughn
6,641,533 B2 11/2003 Causey et al.
6,643,530 B2 11/2003 Diab et al.
6,646,556 B1 11/2003 Smith et al.
6,650,917 B2 11/2003 Diab et al.
6,650,939 B2 11/2003 Takpke, II et al.
6,654,624 B2 11/2003 Diab et al.
D483,872 S 12/2003 Cruz et al.
D483,939 S 12/2003 Kountz et al.
6,658,276 B2 12/2003 Kiani et al.
6,661,161 B1 12/2003 Lanzo et al.
6,663,570 B2 12/2003 Mott et al.
6,671,531 B2 12/2003 Al-Ali
6,678,543 B2 1/2004 Diab et al.
6,684,090 B2 1/2004 Ali et al.
6,684,091 B2 1/2004 Parker
6,694,180 B1 2/2004 Boesen
6,697,656 B1 2/2004 Ai-Ali
6,697,657 B1 2/2004 Shehada et al.
6,697,658 B2 2/2004 Al-Ali
RE38,476 E 3/2004 Diab et al.
6,699,194 B1 3/2004 Diab et al.
6,714,804 B2 3/2004 Al-Ali et al.
RE38,492 E 4/2004 Diab et al.
6,719,694 B2 4/2004 Weng et al.
6,721,582 B2 4/2004 Trepagnier et al.
6,721,585 B1 4/2004 Parker
6,725,075 B2 4/2004 Al-Ali
6,725,086 B2 4/2004 Marinello
6,728,560 B2 4/2004 Kollias et al.
6,735,459 B2 5/2004 Parker
6,738,652 B2 5/2004 Mattu et al.
6,745,060 B2 6/2004 Diab et al.
6,746,406 B2 6/2004 Lia et al.
6,750,463 B1 6/2004 Riley
6,751,492 B2 6/2004 Ben-haim
6,760,607 B2 7/2004 Al-Ali
6,766,188 B2 7/2004 Soller
6,770,028 B1 8/2004 Ali et al.
6,771,994 B2 8/2004 Kiani et al.
6,783,492 B2 8/2004 Dominguez
6,788,965 B2 9/2004 Ruchti et al.
6,790,178 B1 9/2004 Mault et al.
6,792,300 B1 9/2004 Diab et al.
6,795,724 B2 9/2004 Hogan
6,796,186 B2 9/2004 Lia et al.
6,804,656 B1 10/2004 Rosenfeld
6,807,050 B1 10/2004 Whitehorn et al.
6,813,511 B2 11/2004 Diab et al.
6,816,241 B2 11/2004 Grubisic
6,816,741 B2 11/2004 Diab
6,817,979 B2 11/2004 Nihtila et al.
6,822,564 B2 11/2004 Al-Ali
6,826,419 B2 11/2004 Diab et al.
6,830,711 B2 12/2004 Mills et al.
6,837,848 B2 1/2005 Bonner et al.
6,840,904 B2 1/2005 Goldberg
6,841,535 B2 1/2005 Divita et al.
6,850,787 B2 2/2005 Weber et al.
6,850,788 B2 2/2005 Al-Ali
6,852,083 B2 2/2005 Caro et al.
6,855,112 B2 2/2005 Kao et al.
6,860,266 B2 3/2005 Blike
6,861,639 B2 3/2005 Al-Ali
6,876,931 B2 4/2005 Lorenz et al.
6,897,788 B2 5/2005 Khair et al.
6,898,452 B2 5/2005 Al-Ali et al.
6,907,237 B1 6/2005 Dorenbosch et al.
6,915,149 B2 7/2005 Ben-haim
6,916,289 B2 7/2005 Schnall
6,920,345 B2 7/2005 Al-Ali et al.
6,931,268 B1 8/2005 Kiani-Azarbayjany et al.
6,934,570 B2 8/2005 Kiani et al.
6,939,304 B2 9/2005 Schnall et al.
6,939,305 B2 9/2005 Flaherty et al.
6,943,348 B1 9/2005 Coffin, IV
6,950,687 B2 9/2005 Al-Ali
D510,186 S 10/2005 Bell
6,952,340 B2 10/2005 Son
6,956,649 B2 10/2005 Acosta et al.
6,961,598 B2 11/2005 Diab
6,970,792 B1 11/2005 Diab
6,979,812 B2 12/2005 Ai-Ali
6,980,419 B2 12/2005 Smith et al.
6,983,179 B2 1/2006 Ben-haim
6,985,764 B2 1/2006 Mason et al.
6,988,989 B2 1/2006 Weiner et al.
6,990,364 B2 1/2006 Ruchti et al.
6,993,371 B2 1/2006 Kiani et al.
6,996,427 B2 2/2006 Ali et al.
6,997,884 B2 2/2006 Ulmsten
6,998,247 B2 2/2006 Monfre et al.
6,999,904 B2 2/2006 Weber et al.
7,003,338 B2 2/2006 Weber et al.
7,003,339 B2 2/2006 Diab et al.
7,004,907 B2 2/2006 Banet et al.
7,015,451 B2 3/2006 Dalke et al.
7,024,233 B2 4/2006 Ali et al.
7,025,729 B2 4/2006 De Chazal et al.
7,027,849 B2 4/2006 Al-Ali
7,030,749 B2 4/2006 Al-Ali
7,033,761 B2 4/2006 Shafer
7,035,686 B2 4/2006 Hogan
7,039,449 B2 5/2006 Al-Ali
7,041,060 B2 5/2006 Flaherty et al.
7,044,918 B2 5/2006 Diab
7,044,930 B2 5/2006 Stromberg
7,048,687 B1 5/2006 Reuss et al.
7,063,666 B2 6/2006 Weng et al.
7,067,893 B2 6/2006 Mills et al.
7,079,035 B2 7/2006 Bock et al.
D526,719 S 8/2006 Richie, Jr. et al.
7,096,052 B2 8/2006 Mason et al.
7,096,054 B2 8/2006 Abdul-Hafiz et al.
D529,029 S 9/2006 Sekine
D529,283 S 10/2006 Vivar et al.
D529,616 S 10/2006 Deros et al.
7,132,641 B2 11/2006 Schulz et al.
7,133,710 B2 11/2006 Acosta et al.
7,142,901 B2 11/2006 Kiani et al.
7,149,561 B2 12/2006 Diab
7,179,228 B2 2/2007 Banet
7,186,966 B2 3/2007 Al-Ali
7,188,621 B2 3/2007 DeVries et al.
7,190,261 B2 3/2007 Ai-Ai
7,208,119 B1 4/2007 Kurtock et al.
7,215,984 B2 5/2007 Diab et al.
7,215,986 B2 5/2007 Diab et al.
7,221,971 B2 5/2007 Diab et al.
7,225,006 B2 5/2007 Al-Ali et al.
7,225,007 B2 5/2007 Al-Ali et al.
RE39,672 E 6/2007 Shehada et al.
7,229,415 B2 6/2007 Schwartz
7,238,159 B2 7/2007 Banet et al.
7,239,905 B2 7/2007 Kiani-Azarbayjany et al.
7,241,287 B2 7/2007 Shehada et al.
7,244,251 B2 7/2007 Shehada et al.
7,245,373 B2 7/2007 Soller et al.
7,245,953 B1 7/2007 Parker
7,252,659 B2 8/2007 Shehada et al.
7,254,429 B2 8/2007 Schurman et al.
7,254,431 B2 8/2007 Al-Ali et al.
7,254,433 B2 8/2007 Diab et al.
7,254,434 B2 8/2007 Schulz et al.
7,256,708 B2 8/2007 Rosenfeld
7,261,697 B2 8/2007 Berstein
7,264,616 B2 9/2007 Shehada et al.
7,267,671 B2 9/2007 Shehada et al.
7,268,859 B2 9/2007 Sage, Jr. et al.
7,272,425 B2 9/2007 Al-Ali
7,274,955 B2 9/2007 Kiani et al.
D554,263 S 10/2007 Al-Ali et al.
7,280,858 B2 10/2007 Al-Ali et al.
7,285,090 B2 10/2007 Stivoric

(56) References Cited

U.S. PATENT DOCUMENTS 7,289,835 B2 10/2007 Mansfield et al.
7,292,883 B2 11/2007 De Felice et al.
7,295,866 B2 11/2007 Al-Ali
7,298,938 B2 * 11/2007 Johnston .............. G06V 30/144 385/25
7,307,543 B2 12/2007 Rosenfeld
7,313,423 B2 12/2007 Griffin et al.
7,314,446 B2 1/2008 Byrd et al.
7,315,825 B2 1/2008 Rosenfeld
7,321,862 B2 1/2008 Rosenfeld
7,322,971 B2 1/2008 Shehada et al.
7,328,053 B1 2/2008 Diab et al.
7,332,784 B2 2/2008 Mills et al.
7,336,187 B2 2/2008 Hubbard, Jr. et al.
7,340,287 B2 3/2008 Mason et al.
7,341,559 B2 3/2008 Schulz et al.
7,343,186 B2 3/2008 Lamego et al.
D566,282 S 4/2008 Al-Ali et al.
7,355,512 B1 4/2008 Al-Ali
7,356,178 B2 4/2008 Ziel et al.
7,356,365 B2 4/2008 Schurman
7,361,155 B2 4/2008 Sage, Jr. et al.
7,371,981 B2 5/2008 Abdul-Hafiz
7,373,193 B2 5/2008 Al-Ali et al.
7,373,194 B2 5/2008 Weber et al.
7,376,453 B1 5/2008 Diab et al.
7,377,794 B2 5/2008 Al-Ali et al.
7,377,899 B2 5/2008 Weber et al.
7,378,975 B1 5/2008 Smith et al.
7,382,247 B2 6/2008 Welch et al.
7,383,070 B2 6/2008 Diab et al.
7,390,299 B2 6/2008 Weiner et al.
7,395,158 B2 7/2008 Monfre et al.
7,395,216 B2 7/2008 Rosenfeld
7,396,330 B2 7/2008 Banet et al.
7,411,509 B2 8/2008 Rosenfeld
7,413,546 B2 8/2008 Agutter et al.
7,415,297 B2 8/2008 Al-Ali et al.
7,419,483 B2 9/2008 Shehada
7,428,432 B2 9/2008 Ali et al.
7,433,827 B2 10/2008 Rosenfeld
7,438,683 B2 10/2008 Al-Ali et al.
7,439,856 B2 10/2008 Weiner et al.
7,440,787 B2 10/2008 Diab
7,454,240 B2 11/2008 Diab et al.
7,454,359 B2 11/2008 Rosenfeld
7,454,360 B2 11/2008 Rosenfeld
D582,043 S 12/2008 Koike et al.
7,462,151 B2 12/2008 Childre et al.
7,467,002 B2 12/2008 Weber et al.
7,467,094 B2 12/2008 Rosenfeld
7,469,157 B2 12/2008 Diab et al.
7,471,969 B2 12/2008 Diab et al.
7,471,971 B2 12/2008 Diab et al.
7,475,019 B2 1/2009 Rosenfeld
7,481,772 B2 1/2009 Banet
7,483,729 B2 1/2009 Al-Ali et al.
7,483,730 B2 1/2009 Diab et al.
7,489,250 B2 2/2009 Bock et al.
7,489,958 B2 2/2009 Diab et al.
7,496,391 B2 2/2009 Diab et al.
7,496,393 B2 2/2009 Diab et al.
D587,657 S 3/2009 Al-Ali et al.
7,497,828 B1 3/2009 Wilk et al.
7,499,741 B2 3/2009 Diab et al.
7,499,835 B2 3/2009 Weber et al.
7,500,950 B2 3/2009 Al-Ali et al.
7,509,154 B2 3/2009 Diab et al.
7,509,494 B2 3/2009 Al-Ali
7,510,849 B2 3/2009 Schurman et al.
7,514,725 B2 4/2009 Wojtczuk et al.
7,515,043 B2 4/2009 Welch et al.
7,515,044 B2 4/2009 Welch et al.
7,519,406 B2 4/2009 Blank et al.
7,526,328 B2 4/2009 Diab et al.
D592,507 S 5/2009 Wachman et al.
7,530,942 B1 5/2009 Diab
7,530,949 B2 5/2009 Al Ali et al.
7,530,955 B2 5/2009 Diab et al.
7,532,919 B2 5/2009 Soyemi et al.
7,549,961 B1 6/2009 Hwang
7,551,717 B2 6/2009 Tome et al.
D596,635 S 7/2009 Owens et al.
D597,093 S 7/2009 Neu et al.
7,559,520 B2 7/2009 Quijano et al.
7,563,110 B2 7/2009 Al-Ali et al.
7,577,475 B2 8/2009 Consentino et al.
7,588,558 B2 9/2009 Sage, Jr. et al.
7,590,950 B2 9/2009 Collins et al.
7,593,230 B2 9/2009 Abul-Haj et al.
7,596,398 B2 9/2009 Al-Ali et al.
7,597,665 B2 10/2009 Wilk et al.
7,606,608 B2 10/2009 Blank et al.
7,612,999 B2 11/2009 Clark et al.
7,616,303 B2 11/2009 Yang et al.
7,618,375 B2 11/2009 Flaherty et al.
7,620,674 B2 11/2009 Ruchti et al.
D606,659 S 12/2009 Kiani et al.
7,629,039 B2 12/2009 Eckerbom et al.
7,639,145 B2 12/2009 Lawson et al.
7,640,140 B2 12/2009 Ruchti et al.
7,647,083 B2 1/2010 Al-Ali et al.
7,650,291 B2 1/2010 Rosenfeld
D609,193 S 2/2010 Al-Ali et al.
7,654,966 B2 2/2010 Westinskow et al.
7,658,716 B2 2/2010 Banet et al.
7,661,976 B2 2/2010 Ma
7,684,845 B2 3/2010 Juan
7,689,437 B1 3/2010 Teller et al.
RE41,236 E 4/2010 Seely
D614,305 S 4/2010 Al-Ali et al.
7,693,697 B2 4/2010 Westinskow et al.
7,697,966 B2 4/2010 Monfre et al.
7,698,105 B2 4/2010 Ruchti et al.
RE41,317 E 5/2010 Parker
RE41,333 E 5/2010 Blank et al.
7,722,542 B2 5/2010 Lia et al.
7,729,733 B2 6/2010 Al-Ali et al.
7,734,320 B2 6/2010 Al-Ali
7,736,318 B2 6/2010 Consentino et al.
7,740,590 B2 6/2010 Bernstein
7,761,127 B2 7/2010 Al-Ali et al.
7,761,128 B2 7/2010 Al-Ali et al.
7,763,420 B2 7/2010 Strizker et al.
7,764,982 B2 7/2010 Dalke et al.
D621,515 S 8/2010 Chua et al.
D621,516 S 8/2010 Kiani et al.
7,766,818 B2 8/2010 Iketani et al.
7,774,060 B2 8/2010 Westenskow et al.
7,778,851 B2 8/2010 Schoenberg et al.
7,791,155 B2 9/2010 Diab
7,794,407 B2 9/2010 Rothenberg
7,801,581 B2 9/2010 Diab
7,803,120 B2 9/2010 Banet et al.
7,806,830 B2 10/2010 Bernstein
7,820,184 B2 10/2010 Strizker et al.
7,822,452 B2 10/2010 Schurman et al.
RE41,912 E 11/2010 Parker
7,831,450 B2 11/2010 Schoenberg
7,841,986 B2 11/2010 He et al.
7,844,313 B2 11/2010 Kiani et al.
7,844,314 B2 11/2010 Al-Ali
7,844,315 B2 11/2010 Al-Ali
D628,795 S 12/2010 Sanders
D628,797 S 12/2010 Kalbach
7,848,935 B2 12/2010 Gotlib
7,858,322 B2 12/2010 Tymianski et al.
7,865,222 B2 1/2011 Weber et al.
7,865,232 B1 1/2011 Krishnaswamy et al.
7,873,497 B2 1/2011 Weber et al.
7,880,606 B2 2/2011 Al-Ali
7,880,626 B2 * 2/2011 Al-Ali .................. A61B 5/0002 600/323
7,881,892 B2 2/2011 Soyemi et al.

(56) References Cited

U.S. PATENT DOCUMENTS 7,884,314 B2 2/2011 Hamada
7,890,156 B2 2/2011 Ooi et al.
7,891,355 B2 2/2011 Al-Ali et al.
7,894,868 B2 2/2011 Al-Ali et al.
7,899,507 B2 3/2011 Al-Ali et al.
7,899,518 B2 3/2011 Trepagnier et al.
7,904,132 B2 3/2011 Weber et al.
7,909,772 B2 3/2011 Popov et al.
7,910,875 B2 3/2011 Al-Ali
7,914,514 B2 3/2011 Calderon
7,919,713 B2 4/2011 Al-Ali et al.
7,937,128 B2 5/2011 Al-Ali
7,937,129 B2 5/2011 Mason et al.
7,937,130 B2 5/2011 Diab et al.
7,941,199 B2 5/2011 Kiani
7,942,691 B1 5/2011 McSweyn
7,951,086 B2 5/2011 Flaherty et al.
7,957,780 B2 6/2011 Lamego et al.
7,962,188 B2 6/2011 Kiani et al.
7,962,190 B1 6/2011 Diab et al.
7,963,927 B2 6/2011 Kelleher et al.
7,967,749 B2 6/2011 Hutchinson et al.
7,976,472 B2 7/2011 Kiani
7,988,637 B2 8/2011 Diab
7,988,639 B2 8/2011 Starks
7,990,382 B2 8/2011 Kiani
7,991,446 B2 8/2011 Ali et al.
7,991,463 B2 8/2011 Kelleher et al.
7,991,625 B2 8/2011 Rosenfeld
7,993,275 B2 8/2011 Banet et al.
8,000,761 B2 8/2011 Al-Ali
8,008,088 B2 8/2011 Bellott et al.
RE42,753 E 9/2011 Kiani-Azarbayjany et al.
8,019,400 B2 9/2011 Diab et al.
8,027,846 B2 9/2011 Schoenberg
8,028,701 B2 10/2011 Al-Ali et al.
8,029,765 B2 10/2011 Bellott et al.
8,033,996 B2 10/2011 Behar
8,036,727 B2 10/2011 Schurman et al.
8,036,728 B2 10/2011 Diab et al.
8,036,736 B2 10/2011 Snyder et al.
8,038,625 B2 10/2011 Afonso et al.
8,046,040 B2 10/2011 Ali et al.
8,046,041 B2 10/2011 Diab et al.
8,046,042 B2 10/2011 Diab et al.
8,048,040 B2 11/2011 Kiani
8,050,728 B2 11/2011 Al-Ali et al.
8,068,104 B2 11/2011 Rampersad
8,073,707 B2 12/2011 Teller et al.
D652,379 S 1/2012 Vandiver
8,094,013 B1 1/2012 Lee et al.
RE43,169 E 2/2012 Parker
8,118,620 B2 2/2012 Al-Ali et al.
8,126,528 B2 2/2012 Diab et al.
8,128,572 B2 3/2012 Diab et al.
8,130,105 B2 3/2012 Al-Ali et al.
8,145,287 B2 3/2012 Diab et al.
8,150,487 B2 4/2012 Diab et al.
D659,836 S 5/2012 Bensch et al.
8,170,887 B2 5/2012 Rosenfeld
8,175,672 B2 5/2012 Parker
8,175,895 B2 5/2012 Rosenfeld
8,180,420 B2 5/2012 Diab et al.
8,180,440 B2 5/2012 McCombie et al.
8,182,443 B1 5/2012 Kiani
8,185,180 B2 5/2012 Diab et al.
8,190,223 B2 5/2012 Al-Ali et al.
8,190,227 B2 5/2012 Diab et al.
8,200,308 B2 6/2012 Zhang et al.
8,200,321 B2 6/2012 McCombie et al.
8,203,438 B2 6/2012 Kiani et al.
8,203,704 B2 6/2012 Merritt et al.
8,204,566 B2 6/2012 Schurman et al.
8,206,312 B2 6/2012 Farquhar
8,214,007 B2 7/2012 Baker et al.
8,219,172 B2 7/2012 Schurman et al.
8,224,411 B2 7/2012 Al-Ali et al.
8,228,181 B2 7/2012 Ai-Ai
8,229,532 B2 7/2012 Davis
8,229,533 B2 7/2012 Diab et al.
8,233,955 B2 7/2012 Al-Ali et al.
8,235,907 B2 8/2012 Wilk et al.
8,239,010 B2 8/2012 Banet et al.
8,239,780 B2 8/2012 Manetta et al.
8,241,213 B2 8/2012 Lynn et al.
8,244,325 B2 8/2012 Al-Ali et al.
8,249,815 B2 8/2012 Taylor
8,255,026 B1 8/2012 Al-Ali
8,255,027 B2 8/2012 Al-Ali et al.
8,255,028 B2 8/2012 Al-Ali et al.
8,260,577 B2 9/2012 Weber et al.
8,265,723 B1 9/2012 McHale et al.
8,274,360 B2 9/2012 Sampath et al.
D669,375 S 10/2012 Kao et al.
8,280,473 B2 10/2012 Al-Ali
8,294,588 B2 10/2012 Fisher et al.
8,294,716 B2 10/2012 Lord et al.
8,295,521 B2 10/2012 Chan et al.
8,301,217 B2 10/2012 Al-Ali et al.
8,306,596 B2 11/2012 Schurman et al.
8,310,336 B2 11/2012 Muhsin et al.
8,311,747 B2 11/2012 Taylor
8,311,748 B2 11/2012 Taylor et al.
8,315,683 B2 11/2012 Al-Ali et al.
8,315,812 B2 11/2012 Taylor
8,315,813 B2 11/2012 Taylor et al.
8,315,814 B2 11/2012 Taylor et al.
8,321,004 B2 11/2012 Moon et al.
8,321,150 B2 11/2012 Taylor
RE43,860 E 12/2012 Parker
8,326,649 B2 12/2012 Rosenfeld
8,328,793 B2 12/2012 Birkenbach
8,337,403 B2 12/2012 Al-Ali et al.
8,346,330 B2 1/2013 Lamego
8,353,842 B2 1/2013 Al-Ali et al.
8,355,766 B2 1/2013 MacNeish, III et al.
8,359,080 B2 1/2013 Diab et al.
8,360,936 B2 1/2013 Dibenedetto et al.
8,364,223 B2 1/2013 Al-Ali et al.
8,364,226 B2 1/2013 Diab et al.
8,364,250 B2 1/2013 Moon et al.
8,374,665 B2 2/2013 Lamego
8,385,995 B2 2/2013 Al-Ali et al.
8,385,996 B2 2/2013 Smith et al.
D677,792 S 3/2013 Vandiver
D679,018 S 3/2013 Fullerton et al.
8,388,353 B2 3/2013 Kiani et al.
8,399,822 B2 3/2013 Al-Ali
8,401,602 B2 3/2013 Kiani
8,401,874 B2 3/2013 Rosenfeld
8,405,608 B2 3/2013 Al-Ali et al.
8,414,499 B2 4/2013 Al-Ali et al.
8,418,524 B2 4/2013 Al-Ali
8,419,649 B2 4/2013 Banet et al.
8,423,106 B2 4/2013 Lamego et al.
8,428,967 B2 4/2013 Olsen et al.
8,430,817 B1 4/2013 Al-Ali et al.
D682,835 S 5/2013 Daniel
8,437,824 B2 5/2013 Moon et al.
8,437,825 B2 5/2013 Dalvi et al.
8,442,607 B2 5/2013 Banet et al.
8,449,469 B2 5/2013 Banet et al.
D683,960 S 6/2013 Robbins et al.
8,455,290 B2 6/2013 Siskavich
8,457,703 B2 6/2013 Al-Ali
8,457,707 B2 6/2013 Kiani
8,463,349 B2 6/2013 Diab et al.
8,466,286 B2 6/2013 Bellott et al.
8,471,713 B2 6/2013 Poeze et al.
8,473,020 B2 6/2013 Kiani et al.
D685,189 S 7/2013 Adelman et al.
8,475,370 B2 7/2013 McCombie et al.
8,483,787 B2 7/2013 Al-Ali et al.
8,485,448 B2 7/2013 Maizlin et al.

(56) References Cited

U.S. PATENT DOCUMENTS

| | | | |
|---|---|---|---|
| 8,489,167 | B2 | 7/2013 | Buxton |
| 8,489,364 | B2 | 7/2013 | Weber et al. |
| 8,498,684 | B2 | 7/2013 | Weber et al. |
| 8,504,128 | B2 | 8/2013 | Blank et al. |
| 8,506,480 | B2 | 8/2013 | Banet et al. |
| 8,509,867 | B2 | 8/2013 | Workman et al. |
| 8,515,509 | B2 | 8/2013 | Bruinsma et al. |
| 8,523,781 | B2 | 9/2013 | Al-Ali |
| 8,527,038 | B2 | 9/2013 | Moon et al. |
| 8,529,301 | B2 | 9/2013 | Al-Ali et al. |
| 8,532,727 | B2 | 9/2013 | Ali et al. |
| 8,532,728 | B2 | 9/2013 | Diab et al. |
| D692,145 | S | 10/2013 | Al-Ali et al. |
| 8,545,417 | B2 | 10/2013 | Banet et al. |
| 8,547,209 | B2 | 10/2013 | Kiani et al. |
| 8,548,548 | B2 | 10/2013 | Al-Ali |
| 8,548,549 | B2 | 10/2013 | Schurman et al. |
| 8,548,550 | B2 | 10/2013 | Al-Ali et al. |
| 8,554,297 | B2 | 10/2013 | Moon et al. |
| 8,560,032 | B2 | 10/2013 | Al-Ali et al. |
| 8,560,034 | B1 | 10/2013 | Diab et al. |
| 8,565,847 | B2 | 10/2013 | Buxton et al. |
| 8,570,167 | B2 | 10/2013 | Al-Ali |
| 8,570,503 | B2 | 10/2013 | Vo et al. |
| 8,571,617 | B2 | 10/2013 | Reichgott et al. |
| 8,571,618 | B1 | 10/2013 | Lamego et al. |
| 8,571,619 | B2 | 10/2013 | Al-Ali et al. |
| 8,574,161 | B2 | 11/2013 | Banet et al. |
| 8,577,431 | B2 | 11/2013 | Lamego et al. |
| 8,578,082 | B2 | 11/2013 | Medina et al. |
| 8,579,813 | B2 | 11/2013 | Causey |
| 8,581,732 | B2 | 11/2013 | Al-Ali et al. |
| 8,584,345 | B2 | 11/2013 | Al-Ali et al. |
| 8,588,880 | B2 | 11/2013 | Abdul-Hafiz et al. |
| 8,588,924 | B2 | 11/2013 | Dion |
| 8,591,411 | B2 | 11/2013 | Banet et al. |
| 8,594,776 | B2 | 11/2013 | McCombie et al. |
| 8,597,287 | B2 | 12/2013 | Benamou et al. |
| 8,600,467 | B2 | 12/2013 | Al-Ali et al. |
| 8,600,777 | B2 | 12/2013 | Schoenberg |
| 8,602,997 | B2 | 12/2013 | Banet et al. |
| 8,606,342 | B2 | 12/2013 | Diab |
| 8,620,678 | B2 | 12/2013 | Gotlib |
| D697,626 | S | 1/2014 | Laplante et al. |
| 8,622,922 | B2 | 1/2014 | Banet et al. |
| 8,626,255 | B2 | 1/2014 | Al-Ali et al. |
| 8,630,691 | B2 | 1/2014 | Lamego et al. |
| 8,634,889 | B2 | 1/2014 | Al-Ali et al. |
| 8,641,631 | B2 | 2/2014 | Sierra et al. |
| 8,652,060 | B2 | 2/2014 | Al-Ali |
| 8,663,107 | B2 | 3/2014 | Kiani |
| 8,666,468 | B1 | 3/2014 | Al-Ali |
| 8,667,967 | B2 | 3/2014 | Al-Ali et al. |
| 8,670,811 | B2 | 3/2014 | O'Reilly |
| 8,670,814 | B2 | 3/2014 | Diab et al. |
| 8,672,854 | B2 | 3/2014 | McCombie et al. |
| 8,676,286 | B2 | 3/2014 | Weber et al. |
| 8,682,407 | B2 | 3/2014 | Al-Ali |
| RE44,823 | E | 4/2014 | Parker |
| RE44,875 | E | 4/2014 | Kiani et al. |
| D703,671 | S | 4/2014 | Hackett et al. |
| 8,688,183 | B2 | 4/2014 | Bruinsma et al. |
| 8,690,771 | B2 | 4/2014 | Wekell et al. |
| 8,690,799 | B2 | 4/2014 | Telfort et al. |
| 8,700,112 | B2 | 4/2014 | Kiani |
| 8,702,627 | B2 | 4/2014 | Telfort et al. |
| 8,706,179 | B2 | 4/2014 | Parker |
| 8,712,494 | B1 | 4/2014 | MacNeish, III et al. |
| 8,715,206 | B2 | 5/2014 | Telfort et al. |
| 8,718,735 | B2 | 5/2014 | Lamego et al. |
| 8,718,737 | B2 | 5/2014 | Diab et al. |
| 8,718,738 | B2 | 5/2014 | Blank et al. |
| 8,720,249 | B2 | 5/2014 | Al-Ali |
| 8,721,541 | B2 | 5/2014 | Al-Ali et al. |
| 8,721,542 | B2 | 5/2014 | Al-Ali et al. |
| 8,723,677 | B1 | 5/2014 | Kiani |
| 8,727,977 | B2 | 5/2014 | Banet et al. |
| 8,738,118 | B2 | 5/2014 | Moon et al. |
| D706,752 | S | 6/2014 | Myung et al. |
| 8,740,792 | B1 | 6/2014 | Kiani et al. |
| 8,740,802 | B2 | 6/2014 | Banet et al. |
| 8,740,807 | B2 | 6/2014 | Banet et al. |
| 8,747,330 | B2 | 6/2014 | Banet et al. |
| 8,754,776 | B2 | 6/2014 | Poeze et al. |
| 8,755,535 | B2 | 6/2014 | Telfort et al. |
| 8,755,856 | B2 | 6/2014 | Diab et al. |
| 8,755,872 | B1 | 6/2014 | Marinow |
| 8,758,045 | B2 | 6/2014 | McSweyn |
| 8,761,850 | B2 | 6/2014 | Lamego |
| D709,846 | S | 7/2014 | Oswaks |
| 8,764,671 | B2 | 7/2014 | Kiani |
| 8,768,423 | B2 | 7/2014 | Shakespeare et al. |
| 8,771,204 | B2 | 7/2014 | Telfort et al. |
| 8,777,634 | B2 | 7/2014 | Kiani et al. |
| 8,781,543 | B2 | 7/2014 | Diab et al. |
| 8,781,544 | B2 | 7/2014 | Al-Ali et al. |
| 8,781,549 | B2 | 7/2014 | Al-Ali et al. |
| 8,788,003 | B2 | 7/2014 | Schurman et al. |
| 8,790,268 | B2 | 7/2014 | Al-Ali |
| 8,801,613 | B2 | 8/2014 | Al-Ali et al. |
| 8,808,188 | B2 | 8/2014 | Banet et al. |
| 8,818,477 | B2 | 8/2014 | Soller |
| 8,821,397 | B2 | 9/2014 | Al-Ali et al. |
| 8,821,415 | B2 | 9/2014 | Al-Ali et al. |
| 8,830,449 | B1 | 9/2014 | Lamego et al. |
| 8,831,700 | B2 | 9/2014 | Schurman et al. |
| 8,840,549 | B2 | 9/2014 | Al-Ali et al. |
| 8,847,740 | B2 | 9/2014 | Kiani et al. |
| 8,849,365 | B2 | 9/2014 | Smith et al. |
| D715,667 | S | 10/2014 | Shigeno et al. |
| 8,852,094 | B2 | 10/2014 | Al-Ali et al. |
| 8,852,994 | B2 | 10/2014 | Wojtczuk et al. |
| 8,866,620 | B2 | 10/2014 | Amir |
| 8,868,147 | B2 | 10/2014 | Stippick et al. |
| 8,868,150 | B2 | 10/2014 | Al-Ali et al. |
| 8,870,792 | B2 | 10/2014 | Al-Ali et al. |
| 8,873,035 | B2 | 10/2014 | Yang et al. |
| D717,309 | S | 11/2014 | Govindarajan |
| 8,878,888 | B2 | 11/2014 | Rosenfeld |
| 8,886,271 | B2 | 11/2014 | Kiani et al. |
| 8,888,539 | B2 | 11/2014 | Al-Ali et al. |
| 8,888,700 | B2 | 11/2014 | Banet et al. |
| 8,888,708 | B2 | 11/2014 | Diab et al. |
| 8,892,180 | B2 | 11/2014 | Weber et al. |
| 8,897,847 | B2 | 11/2014 | Al-Ali |
| D719,668 | S | 12/2014 | Cien et al. |
| D719,860 | S | 12/2014 | Just et al. |
| 8,907,287 | B2 | 12/2014 | Vanderpohl |
| 8,909,310 | B2 | 12/2014 | Lamego et al. |
| 8,909,330 | B2 | 12/2014 | McCombie et al. |
| 8,911,377 | B2 | 12/2014 | Al-Ali |
| 8,912,909 | B2 | 12/2014 | Al-Ali et al. |
| 8,920,317 | B2 | 12/2014 | Al-Ali et al. |
| 8,921,699 | B2 | 12/2014 | Al-Ali et al. |
| 8,922,382 | B2 | 12/2014 | Al-Ali et al. |
| 8,929,964 | B2 | 1/2015 | Al-Ali et al. |
| 8,942,777 | B2 | 1/2015 | Diab et al. |
| 8,948,834 | B2 | 2/2015 | Diab et al. |
| 8,948,835 | B2 | 2/2015 | Diab |
| 8,951,248 | B2 | 2/2015 | Messerly et al. |
| 8,956,292 | B2 | 2/2015 | Wekell et al. |
| 8,956,293 | B2 | 2/2015 | McCombie et al. |
| 8,956,294 | B2 | 2/2015 | McCombie et al. |
| 8,965,471 | B2 | 2/2015 | Lamego |
| 8,979,765 | B2 | 3/2015 | Banet et al. |
| 8,983,564 | B2 | 3/2015 | Al-Ali |
| 8,989,831 | B2 | 3/2015 | Al-Ali et al. |
| 8,996,085 | B2 | 3/2015 | Kiani et al. |
| 8,998,809 | B2 | 4/2015 | Kiani |
| D728,230 | S | 5/2015 | Oas |
| 9,028,429 | B2 | 5/2015 | Telfort et al. |
| 9,037,207 | B2 | 5/2015 | Al-Ali et al. |
| 9,055,928 | B2 | 6/2015 | McCombie et al. |
| 9,057,689 | B2 | 6/2015 | Soller |

(56) References Cited

U.S. PATENT DOCUMENTS 9,060,721 B2 6/2015 Reichgott et al.
9,066,666 B2 6/2015 Kiani
9,066,680 B1 6/2015 Al-Ali et al.
D733,598 S 7/2015 Just et al.
9,072,474 B2 7/2015 Al-Ali et al.
9,078,560 B2 7/2015 Schurman et al.
9,084,569 B2 7/2015 Weber et al.
9,095,291 B2 8/2015 Soller
9,095,316 B2 8/2015 Welch et al.
9,104,789 B2 8/2015 Gross et al.
9,106,038 B2 8/2015 Telfort et al.
9,107,625 B2 8/2015 Telfort et al.
9,107,626 B2 8/2015 Al-Ali et al.
9,113,831 B2 8/2015 Al-Ali
9,113,832 B2 8/2015 Al-Ali
9,119,595 B2 9/2015 Lamego
9,131,881 B2 9/2015 Diab et al.
9,131,882 B2 9/2015 Al-Ali et al.
9,131,883 B2 9/2015 Al-Ali
9,131,917 B2 9/2015 Telfort et al.
9,138,180 B1 9/2015 Coverston et al.
9,138,182 B2 9/2015 Al-Ali et al.
9,138,192 B2 9/2015 Weber et al.
9,142,117 B2 9/2015 Muhsin et al.
D741,865 S 10/2015 Sundermeyer et al.
9,149,192 B2 10/2015 Banet et al.
9,149,228 B2 10/2015 Kinast
9,153,112 B1 10/2015 Kiani et al.
9,153,121 B2 10/2015 Kiani et al.
9,161,696 B2 10/2015 Al-Ali et al.
9,161,700 B2 10/2015 Banet et al.
9,161,713 B2 10/2015 Al-Ali et al.
9,167,995 B2 10/2015 Lamego et al.
D744,109 S 11/2015 Yoneta et al.
9,173,593 B2 11/2015 Banet et al.
9,173,594 B2 11/2015 Banet et al.
9,176,141 B2 11/2015 Al-Ali et al.
9,186,102 B2 11/2015 Bruinsma et al.
9,192,312 B2 11/2015 Al-Ali
9,192,329 B2 11/2015 Al-Ali
9,192,351 B1 11/2015 Telfort et al.
9,195,385 B2 11/2015 Al-Ali et al.
D745,167 S 12/2015 Canas et al.
9,211,072 B2 12/2015 Kiani
9,211,095 B1 12/2015 Al-Ali
9,215,986 B2 12/2015 Banet et al.
9,218,454 B2 12/2015 Kiani et al.
9,226,696 B2 1/2016 Kiani
9,241,662 B2 1/2016 Al-Ali et al.
9,245,668 B1 1/2016 Vo et al.
9,248,299 B2 2/2016 Toy et al.
9,259,185 B2 2/2016 Abdul-Hafiz et al.
9,262,586 B2 2/2016 Steiger et al.
9,267,572 B2 2/2016 Barker et al.
9,277,880 B2 3/2016 Poeze et al.
9,289,167 B2 3/2016 Diab et al.
9,295,421 B2 3/2016 Kiani et al.
9,307,915 B2 4/2016 McCombie et al.
9,307,928 B1 4/2016 Al-Ali et al.
9,318,840 B2 4/2016 Siev et al.
9,323,894 B2 4/2016 Kiani
D755,183 S 5/2016 Patel et al.
D755,392 S 5/2016 Hwang et al.
9,326,712 B1 5/2016 Kiani
9,333,316 B2 5/2016 Kiani
9,339,209 B2 5/2016 Banet et al.
9,339,211 B2 5/2016 Banet et al.
9,339,220 B2 5/2016 Lamego et al.
9,341,565 B2 5/2016 Lamego et al.
9,351,673 B2 5/2016 Diab et al.
9,351,675 B2 5/2016 Al-Ali et al.
9,364,158 B2 6/2016 Banet et al.
9,364,181 B2 6/2016 Kiani et al.
9,368,671 B2 6/2016 Wojtczuk et al.
9,370,325 B2 6/2016 Al-Ali et al.
9,370,326 B2 6/2016 McHale et al.
9,370,335 B2 6/2016 Al-Ali et al.
9,375,185 B2 6/2016 Ali et al.
9,380,952 B2 7/2016 Banet et al.
9,386,953 B2 7/2016 Al-Ali
9,386,961 B2 7/2016 Al-Ali et al.
9,392,945 B2 7/2016 Al-Ali et al.
9,397,448 B2 7/2016 Al-Ali et al.
D765,083 S 8/2016 Breitweiser et al.
9,408,542 B1 8/2016 Kinast et al.
9,408,573 B2 8/2016 Welch et al.
9,436,645 B2 9/2016 Al-Ali et al.
9,439,574 B2 9/2016 McCombie et al.
9,443,059 B2 9/2016 Grubis
9,445,759 B1 9/2016 Lamego et al.
D769,973 S 10/2016 Benoni
9,466,919 B2 10/2016 Kiani et al.
9,474,474 B2 10/2016 Lamego et al.
D771,057 S 11/2016 Wurts et al.
9,480,422 B2 11/2016 Al-Ali
9,480,435 B2 11/2016 Olsen
9,480,846 B2 11/2016 Strother et al.
9,492,110 B2 11/2016 Al-Ali et al.
9,510,779 B2 12/2016 Poeze et al.
9,517,024 B2 12/2016 Kiani et al.
9,529,762 B2 12/2016 Gisler et al.
D776,664 S 1/2017 Hendrick
D776,916 S 1/2017 Yeruva et al.
9,532,722 B2 1/2017 Lamego et al.
9,538,949 B2 1/2017 Al-Ali et al.
9,538,980 B2 1/2017 Telfort et al.
9,549,696 B2 1/2017 Lamego et al.
9,554,737 B2 1/2017 Schurman et al.
9,560,996 B2 2/2017 Kiani
9,560,998 B2 2/2017 Al-Ali et al.
9,566,019 B2 2/2017 Al-Ali et al.
9,579,039 B2 2/2017 Jansen et al.
D782,483 S 3/2017 Patel et al.
9,591,975 B2 3/2017 Dalvi et al.
D783,170 S 4/2017 Carreon et al.
9,622,692 B2 4/2017 Lamego et al.
9,622,693 B2 4/2017 Diab
D788,312 S 5/2017 Al-Ali et al.
9,636,055 B2 5/2017 Al Ali et al.
9,636,056 B2 5/2017 Al-Ali
9,649,054 B2 5/2017 Lamego et al.
9,662,052 B2 5/2017 Al-Ali et al.
9,668,679 B2 6/2017 Schurman et al.
9,668,680 B2 6/2017 Bruinsma et al.
9,668,703 B2 6/2017 Al-Ali
9,675,286 B2 6/2017 Diab
9,687,160 B2 6/2017 Kiani
9,693,719 B2 7/2017 Al-Ali et al.
9,693,737 B2 7/2017 Ai-Ai
9,697,928 B2 7/2017 Al-Ali et al.
9,706,964 B2 7/2017 Ferber et al.
D794,807 S 8/2017 Kranz et al.
9,717,425 B2 8/2017 Kiani et al.
9,717,458 B2 8/2017 Lamego et al.
9,724,016 B1 8/2017 Al-Ali et al.
9,724,024 B2 8/2017 Al-Ali
9,724,025 B1 8/2017 Kiani et al.
9,730,640 B2 8/2017 Diab et al.
9,743,887 B2 8/2017 Al-Ali et al.
9,749,232 B2 8/2017 Sampath et al.
9,750,442 B2 9/2017 Olsen
9,750,443 B2 9/2017 Smith et al.
9,750,461 B1 9/2017 Telfort
9,775,545 B2 10/2017 Al-Ali et al.
9,775,546 B2 10/2017 Diab et al.
9,775,570 B2 10/2017 Al-Ali
9,778,079 B1 10/2017 Al-Ali et al.
9,782,077 B2 10/2017 Lamego et al.
9,782,110 B2 10/2017 Kiani
9,787,568 B2 10/2017 Lamego et al.
9,788,735 B2 10/2017 Al-Ali
9,788,768 B2 10/2017 Al-Ali et al.
9,795,300 B2 10/2017 Al-Ali
9,795,310 B2 10/2017 Al-Ali

(56) References Cited

U.S. PATENT DOCUMENTS 9,795,358 B2 10/2017 Telfort et al.
9,795,739 B2 10/2017 Al-Ali et al.
9,801,556 B2 10/2017 Kiani
9,801,588 B2 10/2017 Weber et al.
D803,841 S 11/2017 Kim et al.
D803,842 S 11/2017 Daniel
9,808,188 B1 11/2017 Perea et al.
9,814,418 B2 11/2017 Weber et al.
9,820,691 B2 11/2017 Kiani
D804,413 S 12/2017 McSweyn et al.
9,833,152 B2 12/2017 Kiani et al.
9,833,180 B2 12/2017 Shakespeare et al.
9,833,199 B2 * 12/2017 Johnson ............... A61B 5/0013
9,839,379 B2 12/2017 Al-Ali et al.
9,839,381 B1 12/2017 Weber et al.
9,847,002 B2 12/2017 Kiani et al.
9,847,749 B2 12/2017 Kiani et al.
9,848,800 B1 12/2017 Lee et al.
9,848,806 B2 12/2017 Ai-Ali
9,848,807 B2 12/2017 Lamego
D808,641 S 1/2018 Clover et al.
D809,147 S 1/2018 Coonahan et al.
9,861,298 B2 1/2018 Eckerbom et al.
9,861,304 B2 1/2018 Al-Ali et al.
9,861,305 B1 1/2018 Weber et al.
9,866,255 B1 1/2018 Ketter-Muldrow
9,867,578 B2 1/2018 Al-Ali et al.
9,872,481 B2 * 1/2018 Goldfain .............. A61B 5/6831
9,872,623 B2 1/2018 Al-Ali
9,876,320 B2 1/2018 Coverston et al.
9,877,650 B2 1/2018 Muhsin et al.
9,877,686 B2 1/2018 Al-Ali et al.
9,883,800 B2 * 2/2018 Pekander ............. A61B 5/0015
9,891,079 B2 2/2018 Dalvi
9,895,107 B2 2/2018 Al-Ali et al.
D812,229 S 3/2018 Al-Siddiq
9,913,617 B2 3/2018 Al-Ali et al.
9,924,893 B2 3/2018 Schurman et al.
9,924,897 B1 3/2018 Abdul-Hafiz
9,936,917 B2 4/2018 Poeze et al.
9,943,269 B2 4/2018 Muhsin et al.
9,949,676 B2 4/2018 Al-Ali
9,955,937 B2 5/2018 Telfort
9,965,946 B2 5/2018 Al-Ali et al.
9,973,534 B2 5/2018 Mahaffey et al.
9,980,667 B2 5/2018 Kiani et al.
D820,865 S 6/2018 Muhsin et al.
9,986,919 B2 6/2018 Lamego et al.
9,986,952 B2 6/2018 Dalvi et al.
9,989,560 B2 6/2018 Poeze et al.
9,993,207 B2 6/2018 Al-Ali et al.
10,007,758 B2 6/2018 Al-Ali et al.
D822,215 S 7/2018 Al-Ali et al.
D822,216 S 7/2018 Barker et al.
10,010,276 B2 7/2018 Al-Ali et al.
10,032,002 B2 7/2018 Kiani et al.
10,039,482 B2 8/2018 Al-Ali et al.
10,052,037 B2 8/2018 Kinast et al.
10,058,275 B2 8/2018 Al-Ali et al.
10,064,562 B2 9/2018 Al-Ali
D829,574 S 10/2018 Mane et al.
D831,462 S 10/2018 McSweyn et al.
10,086,138 B1 10/2018 Novak, Jr.
10,092,200 B2 10/2018 Al-Ali et al.
10,092,249 B2 10/2018 Kiani et al.
10,098,550 B2 10/2018 Al-Ali et al.
10,098,591 B2 10/2018 Al-Ali et al.
10,098,610 B2 10/2018 Al-Ali et al.
10,111,591 B2 10/2018 Dyell et al.
D833,624 S 11/2018 DeJong et al.
10,123,726 B2 11/2018 Al-Ali et al.
10,123,729 B2 11/2018 Dyell et al.
10,130,289 B2 11/2018 Al-Ali et al.
10,130,291 B2 11/2018 Schurman et al.
10,130,306 B2 * 11/2018 Katra ................... A61B 5/0205
D835,282 S 12/2018 Barker et al.
D835,283 S 12/2018 Barker et al.
D835,284 S 12/2018 Barker et al.
D835,285 S 12/2018 Barker et al.
10,149,616 B2 12/2018 Al-Ali et al.
10,154,815 B2 12/2018 Al-Ali et al.
10,159,412 B2 12/2018 Lamego et al.
10,188,296 B2 1/2019 Al-Ali et al.
10,188,331 B1 1/2019 Kiani et al.
10,188,348 B2 1/2019 Al-Ali et al.
RE47,218 E 2/2019 Al-Ali
RE47,244 E 2/2019 Kiani et al.
RE47,249 E 2/2019 Kiani et al.
10,194,847 B2 2/2019 Al-Ali
10,194,848 B1 2/2019 Kiani et al.
10,201,298 B2 2/2019 Al-Ali et al.
10,205,272 B2 2/2019 Kiani et al.
10,205,291 B2 2/2019 Scruggs et al.
10,213,108 B2 2/2019 Al-Ali
10,219,706 B2 3/2019 Al-Ali
10,219,746 B2 3/2019 McHale et al.
10,226,187 B2 3/2019 Al-Ali et al.
10,226,215 B2 3/2019 Cohrs et al.
10,226,576 B2 3/2019 Kiani
10,231,657 B2 3/2019 Al-Ali et al.
10,231,670 B2 3/2019 Blank et al.
10,231,676 B2 3/2019 Al-Ali et al.
RE47,353 E 4/2019 Kiani et al.
10,251,585 B2 4/2019 Al-Ali et al.
10,251,586 B2 4/2019 Lamego
10,255,994 B2 4/2019 Sampath et al.
10,258,265 B1 4/2019 Poeze et al.
10,258,266 B1 4/2019 Poeze et al.
10,271,748 B2 4/2019 Al-Ali
10,278,626 B2 5/2019 Schurman et al.
10,278,648 B2 5/2019 Al-Ali et al.
10,279,247 B2 5/2019 Kiani
10,292,628 B1 5/2019 Poeze et al.
10,292,657 B2 5/2019 Abdul-Hafiz et al.
10,292,664 B2 5/2019 Al-Ali
10,299,708 B1 5/2019 Poeze et al.
10,299,709 B2 5/2019 Perea et al.
10,299,720 B2 5/2019 Brown et al.
10,305,775 B2 5/2019 Lamego et al.
D850,628 S 6/2019 De Hoog et al.
10,307,111 B2 6/2019 Muhsin et al.
10,325,681 B2 6/2019 Sampath et al.
10,327,337 B2 6/2019 Schmidt et al.
10,327,713 B2 6/2019 Barker et al.
10,332,630 B2 6/2019 Al-Ali
10,335,033 B2 7/2019 Al-Ali
10,335,068 B2 7/2019 Poeze et al.
10,335,072 B2 7/2019 Al-Ali et al.
10,342,470 B2 7/2019 Al-Ali et al.
10,342,487 B2 7/2019 Al-Ali et al.
10,342,497 B2 7/2019 Al-Ali et al.
10,349,895 B2 7/2019 Telfort et al.
10,349,898 B2 7/2019 Al-Ali et al.
10,354,504 B2 7/2019 Kiani et al.
10,357,206 B2 7/2019 Weber et al.
10,357,209 B2 7/2019 Al-Ali
10,366,787 B2 7/2019 Sampath et al.
10,368,787 B2 8/2019 Reichgott et al.
10,374,350 B2 8/2019 Nakazono et al.
10,376,190 B1 8/2019 Poeze et al.
10,376,191 B1 8/2019 Poeze et al.
10,383,520 B2 8/2019 Wojtczuk et al.
10,383,527 B2 8/2019 Al-Ali
10,388,120 B2 8/2019 Muhsin et al.
10,398,320 B2 9/2019 Kiani et al.
10,405,804 B2 9/2019 Al-Ali
10,413,666 B2 9/2019 Al-Ali et al.
10,420,493 B2 9/2019 Al-Ali et al.
D864,120 S 10/2019 Forrest et al.
10,441,181 B1 10/2019 Telfort et al.
10,441,196 B2 10/2019 Eckerbom et al.
10,448,844 B2 10/2019 Al-Ali et al.
10,448,871 B2 10/2019 Al-Ali et al.
10,456,038 B2 10/2019 Lamego et al.

(56) References Cited

U.S. PATENT DOCUMENTS 10,463,340 B2 11/2019 Telfort et al.
10,471,159 B1 11/2019 Lapotko et al.
10,505,311 B2 12/2019 Al-Ali et al.
10,524,738 B2 1/2020 Olsen
10,532,174 B2 1/2020 Al-Ali
10,537,285 B2 1/2020 Shreim et al.
10,542,903 B2 1/2020 Al-Ali et al.
D874,657 S 2/2020 Bailey et al.
10,555,678 B2 2/2020 Dalvi et al.
10,560,532 B2 * 2/2020 Yang .................... H04W 48/02
10,568,553 B2 2/2020 O'Neil et al.
RE47,882 E 3/2020 Al-Ali
10,608,817 B2 3/2020 Haider et al.
D880,477 S 4/2020 Forrest et al.
D881,889 S 4/2020 Wang et al.
10,617,302 B2 4/2020 Al-Ali et al.
10,617,335 B2 4/2020 Al-Ali et al.
10,637,181 B2 4/2020 Al-Ali et al.
10,638,982 B2 5/2020 Ferber et al.
D886,849 S 6/2020 Muhsin et al.
D887,548 S 6/2020 Abdul-Hafiz et al.
D887,549 S 6/2020 Abdul-Hafiz et al.
10,667,764 B2 6/2020 Ahmed et al.
D890,708 S 7/2020 Forrest et al.
10,721,785 B2 7/2020 Al-Ali
10,736,518 B2 8/2020 Al-Ali et al.
10,736,552 B2 8/2020 Ferber et al.
10,750,984 B2 8/2020 Pauley et al.
D897,098 S 9/2020 Ai-Ali
10,779,098 B2 9/2020 Iswanto et al.
10,827,961 B1 11/2020 Iyengar et al.
10,828,007 B1 11/2020 Telfort et al.
10,832,818 B2 11/2020 Muhsin et al.
10,842,395 B2 11/2020 Schnall et al.
10,849,554 B2 12/2020 Shreim et al.
10,856,750 B2 12/2020 Indorf
D906,970 S 1/2021 Forrest et al.
D908,213 S 1/2021 Abdul-Hafiz et al.
D910,623 S 2/2021 Cueto et al.
10,918,281 B2 2/2021 Al-Ali et al.
10,932,705 B2 3/2021 Muhsin et al.
10,932,729 B2 3/2021 Kiani et al.
10,939,878 B2 3/2021 Kiani et al.
10,956,950 B2 3/2021 Al-Ali et al.
D916,135 S 4/2021 Indorf et al.
D916,705 S 4/2021 Liao
D917,046 S 4/2021 Abdul-Hafiz et al.
D917,550 S 4/2021 Indorf et al.
D917,564 S 4/2021 Indorf et al.
D917,704 S 4/2021 Al-Ali et al.
10,987,066 B2 4/2021 Chandran et al.
10,991,135 B2 4/2021 Al-Ali et al.
D919,094 S 5/2021 Al-Ali et al.
D919,100 S 5/2021 Al-Ali et al.
11,006,690 B2 5/2021 Gledwoyn
11,006,867 B2 5/2021 Al-Ali
D921,202 S 6/2021 Al-Ali et al.
11,024,064 B2 6/2021 Muhsin et al.
11,026,604 B2 6/2021 Chen et al.
D925,597 S 7/2021 Chandran et al.
D927,699 S 8/2021 Al-Ali et al.
11,076,777 B2 8/2021 Lee et al.
11,109,783 B2 * 9/2021 Lamego .................... G01J 3/10
11,114,188 B2 9/2021 Poeze et al.
D933,232 S 10/2021 Al-Ali et al.
D933,233 S 10/2021 Al-Ali et al.
D933,234 S 10/2021 Al-Ali et al.
D933,951 S 10/2021 Cardentey
11,145,408 B2 10/2021 Sampath et al.
11,147,518 B1 10/2021 Al-Ali et al.
11,179,107 B2 11/2021 Chae et al.
11,185,262 B2 11/2021 Al-Ali et al.
11,191,484 B2 12/2021 Kiani et al.
11,201,500 B2 * 12/2021 Partovi ............... H02J 7/00714
D944,520 S 3/2022 Akana et al.
D946,596 S 3/2022 Ahmed
D946,597 S 3/2022 Ahmed
D946,598 S 3/2022 Ahmed
D946,617 S 3/2022 Ahmed
11,259,753 B2 3/2022 Ferber et al.
11,260,238 B2 * 3/2022 Finch .................. A61N 1/3993
11,272,839 B2 3/2022 Al-Ali et al.
11,289,199 B2 3/2022 Al-Ali
RE49,034 E 4/2022 Al-Ali
11,298,021 B2 4/2022 Muhsin et al.
D950,580 S 5/2022 Ahmed
D950,599 S 5/2022 Ahmed
D950,738 S 5/2022 Al-Ali et al.
11,331,463 B2 5/2022 Damiano
D957,648 S 7/2022 Al-Ali
11,382,567 B2 7/2022 O'Brien et al.
11,389,093 B2 7/2022 Triman et al.
11,406,286 B2 8/2022 Al-Ali et al.
11,417,426 B2 8/2022 Muhsin et al.
11,439,329 B2 9/2022 Lamego
11,445,948 B2 9/2022 Scruggs et al.
D965,789 S 10/2022 Al-Ali et al.
D967,433 S 10/2022 Al-Ali et al.
D967,625 S 10/2022 Akana et al.
11,457,703 B2 10/2022 Calder
11,457,733 B2 10/2022 Gallup et al.
11,464,410 B2 10/2022 Muhsin
D968,410 S 11/2022 Zhang et al.
11,504,058 B1 11/2022 Sharma et al.
11,504,066 B1 11/2022 Dalvi et al.
11,515,664 B2 11/2022 Kiani et al.
D971,933 S 12/2022 Ahmed
D973,072 S 12/2022 Ahmed
D973,685 S 12/2022 Ahmed
D973,686 S 12/2022 Ahmed
11,534,087 B2 12/2022 Weber et al.
11,534,110 B2 12/2022 Shreim et al.
D974,193 S 1/2023 Forrest et al.
11,540,729 B2 1/2023 Lamego et al.
11,557,407 B2 1/2023 Al-Ali et al.
11,559,227 B2 1/2023 Kiani et al.
11,559,275 B2 1/2023 Telfort et al.
11,564,593 B2 1/2023 Eckerbom et al.
11,564,642 B2 1/2023 Kiani et al.
D979,516 S 2/2023 Al-Ali et al.
11,571,152 B2 2/2023 Al-Ali et al.
11,576,582 B2 2/2023 Al-Ali et al.
11,581,091 B2 2/2023 Dyell et al.
D980,091 S 3/2023 Forrest et al.
11,596,363 B2 3/2023 Lamego
11,596,365 B2 3/2023 Barker et al.
11,602,289 B2 3/2023 O'Neil et al.
11,605,188 B2 3/2023 Al-Ali et al.
11,627,919 B2 4/2023 Kiani et al.
11,637,437 B2 4/2023 Al-Ali et al.
D985,498 S 5/2023 Al-Ali et al.
11,653,862 B2 5/2023 Dalvi et al.
D989,112 S 6/2023 Muhsin et al.
D989,327 S 6/2023 Al-Ali et al.
11,678,829 B2 6/2023 Al-Ali et al.
11,679,579 B2 6/2023 Al-Ali
11,684,296 B2 6/2023 Vo et al.
11,692,934 B2 7/2023 Normand et al.
11,701,043 B2 7/2023 Al-Ali et al.
D997,365 S 8/2023 Hwang
11,721,105 B2 8/2023 Ranasinghe et al.
11,730,379 B2 8/2023 Ahmed et al.
D998,625 S 9/2023 Indorf et al.
D998,630 S 9/2023 Indorf et al.
D998,631 S 9/2023 Indorf et al.
D999,244 S 9/2023 Indorf et al.
D999,245 S 9/2023 Indorf et al.
D999,246 S 9/2023 Indorf et al.
11,755,879 B2 * 9/2023 Pascanu ................ G06N 3/044
706/31
11,766,198 B2 9/2023 Pauley et al.
D1,000,975 S 10/2023 Al-Ali et al.
11,803,623 B2 10/2023 Kiani et al.
11,832,940 B2 12/2023 Diab et al.

(56) References Cited

U.S. PATENT DOCUMENTS

| | | | |
|---|---|---|---|
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| D1,031,729 S | 6/2024 | Forrest et al. |
| 12,004,869 B2 | 6/2024 | Kiani et al. |
| 12,014,328 B2 | 6/2024 | Wachman et al. |
| D1,036,293 S | 7/2024 | Al-Ali |
| D1,037,462 S | 7/2024 | Al-Ali et al. |
| 12,029,844 B2 | 7/2024 | Pauley et al. |
| 12,048,534 B2 | 7/2024 | Vo et al. |
| 12,064,217 B2 | 8/2024 | Ahmed et al. |
| 12,066,426 B1 | 8/2024 | Lapotko et al. |
| D1,041,511 S | 9/2024 | Indorf et al. |
| D1,042,596 S | 9/2024 | DeJong et al. |
| D1,042,852 S | 9/2024 | Hwang |
| 12,076,159 B2 | 9/2024 | Belur Nagaraj et al. |
| 12,082,926 B2 | 9/2024 | Sharma et al. |
| D1,044,828 S | 10/2024 | Chandran et al. |
| D1,048,571 S | 10/2024 | Yu et al. |
| D1,048,908 S | 10/2024 | Al-Ali et al. |
| 12,106,752 B2 | 10/2024 | Campbell et al. |
| 12,114,974 B2 | 10/2024 | Al-Ali et al. |
| 12,126,683 B2 | 10/2024 | Koo et al. |
| 12,127,838 B2 | 10/2024 | Olsen et al. |
| 12,128,213 B2 | 10/2024 | Kiani et al. |
| 12,131,661 B2 | 10/2024 | Pauley et al. |
| D1,050,910 S | 11/2024 | Al-Ali et al. |
| 12,178,572 B1 | 12/2024 | Pauley et al. |
| 12,178,581 B2 | 12/2024 | Telfort et al. |
| 12,178,852 B2 | 12/2024 | Kiani et al. |
| D1,057,159 S | 1/2025 | DeJong et al. |
| D1,057,160 S | 1/2025 | DeJong et al. |
| 12,198,790 B1 | 1/2025 | Al-Ali |
| 12,200,421 B2 | 1/2025 | Campbell et al. |
| 12,207,901 B1 | 1/2025 | Lapotko et al. |
| D1,060,680 S | 2/2025 | Al-Ali et al. |
| D1,061,585 S | 2/2025 | Indorf |
| D1,063,893 S | 2/2025 | DeJong et al. |
| 12,220,207 B2 | 2/2025 | Telfort et al. |
| 12,235,941 B2 | 2/2025 | Kiani et al. |
| 12,236,767 B2 | 2/2025 | Muhsin |
| D1,066,244 S | 3/2025 | Lim et al. |
| D1,066,672 S | 3/2025 | Al-Ali et al. |
| D1,068,656 S | 4/2025 | Trevisan et al. |
| D1,071,195 S | 4/2025 | Seung |
| D1,072,836 S | 4/2025 | Indorf |
| D1,072,837 S | 4/2025 | Ahmed et al. |
| 12,272,445 B1 | 4/2025 | Kiani |
| D1,078,689 S | 6/2025 | Hwang |
| D1,079,020 S | 6/2025 | Hwang |
| 12,336,796 B2 | 6/2025 | Al-Ali |
| 2001/0011355 A1 | 8/2001 | Kawai |
| 2001/0031922 A1 | 10/2001 | Weng et al. |
| 2001/0034477 A1 | 10/2001 | Mansfield et al. |
| 2001/0039483 A1 | 11/2001 | Brand et al. |
| 2001/0046366 A1 | 11/2001 | Susskind |
| 2002/0010401 A1 | 1/2002 | Bushmakin et al. |
| 2002/0045836 A1 | 4/2002 | Alkawwas |
| 2002/0052311 A1 | 5/2002 | Solomon et al. |
| 2002/0058864 A1 | 5/2002 | Mansfield et al. |
| 2002/0063690 A1 | 5/2002 | Chung et al. |
| 2002/0072681 A1 | 6/2002 | Schnall |
| 2002/0099277 A1 | 7/2002 | Harry et al. |
| 2002/0133080 A1 | 9/2002 | Apruzzese et al. |
| 2002/0169439 A1 | 11/2002 | Flaherty |
| 2002/0177758 A1 | 11/2002 | Schoenberg |
| 2002/0198445 A1 | 12/2002 | Dominguez et al. |
| 2003/0004423 A1 | 1/2003 | Levie et al. |
| 2003/0013975 A1 | 1/2003 | Kiani |
| 2003/0018243 A1 | 1/2003 | Gerhardt et al. |
| 2003/0027326 A1 | 2/2003 | Ulmsten et al. |
| 2003/0052787 A1 | 3/2003 | Zerhusen et al. |
| 2003/0058838 A1 | 3/2003 | Wengrovitz |
| 2003/0144582 A1 | 7/2003 | Cohen et al. |
| 2003/0156288 A1 | 8/2003 | Barnum et al. |
| 2003/0158466 A1 | 8/2003 | Lynn et al. |
| 2003/0195401 A1 | 10/2003 | Tian et al. |
| 2003/0212312 A1 | 11/2003 | Coffin, IV et al. |
| 2003/0216670 A1 | 11/2003 | Beggs |
| 2004/0013647 A1 | 1/2004 | Solomon et al. |
| 2004/0073095 A1 | 4/2004 | Causey et al. |
| 2004/0090742 A1 | 5/2004 | Son et al. |
| 2004/0106163 A1 | 6/2004 | Workman, Jr. et al. |
| 2004/0116787 A1 | 6/2004 | Schnall |
| 2004/0122787 A1 | 6/2004 | Avinash et al. |
| 2004/0126007 A1 | 7/2004 | Ziel et al. |
| 2004/0139571 A1 | 7/2004 | Chang et al. |
| 2004/0147818 A1 | 7/2004 | Levy et al. |
| 2004/0152957 A1 | 8/2004 | Stivoric et al. |
| 2004/0179332 A1 | 9/2004 | Smith et al. |
| 2004/0186357 A1 | 9/2004 | Soderberg et al. |
| 2004/0215085 A1 | 10/2004 | Schnall |
| 2004/0230118 A1 | 11/2004 | Shehada et al. |
| 2004/0230132 A1 | 11/2004 | Shehada et al. |
| 2004/0230179 A1 | 11/2004 | Shehada et al. |
| 2004/0243017 A1 | 12/2004 | Causevic |
| 2004/0249670 A1 | 12/2004 | Noguchi et al. |
| 2004/0254431 A1 | 12/2004 | Shehada et al. |
| 2004/0254432 A1 | 12/2004 | Shehada et al. |
| 2004/0267103 A1 | 12/2004 | Li et al. |
| 2005/0005710 A1 | 1/2005 | Sage, Jr. |
| 2005/0009926 A1 | 1/2005 | Kreye et al. |
| 2005/0020918 A1 | 1/2005 | Wilk et al. |
| 2005/0038332 A1 | 2/2005 | Saidara et al. |
| 2005/0038680 A1 | 2/2005 | McMahon |
| 2005/0055276 A1 | 3/2005 | Kiani et al. |
| 2005/0080336 A1 | 4/2005 | Byrd et al. |
| 2005/0096542 A1 | 5/2005 | Weng et al. |
| 2005/0113653 A1 | 5/2005 | Fox et al. |
| 2005/0124864 A1 | 6/2005 | Mack et al. |
| 2005/0125256 A1 | 6/2005 | Schoenberg |
| 2005/0148882 A1 | 7/2005 | Banet et al. |
| 2005/0164933 A1 | 7/2005 | Tymianski et al. |
| 2005/0191294 A1 | 9/2005 | Arap et al. |
| 2005/0208648 A1 | 9/2005 | Sage, Jr. et al. |
| 2005/0209518 A1 | 9/2005 | Sage, Jr. et al. |
| 2005/0228244 A1 | 10/2005 | Banet |
| 2005/0228299 A1 | 10/2005 | Banet |
| 2005/0234317 A1 | 10/2005 | Kiani |
| 2005/0242946 A1 | 11/2005 | Hubbard, Jr. et al. |
| 2005/0245831 A1 | 11/2005 | Banet |
| 2005/0245839 A1 | 11/2005 | Stivoric et al. |
| 2005/0261594 A1 | 11/2005 | Banet |
| 2005/0261598 A1 | 11/2005 | Banet et al. |
| 2005/0268401 A1 | 12/2005 | Dixon et al. |
| 2005/0277872 A1 | 12/2005 | Colby et al. |
| 2006/0009697 A1 | 1/2006 | Banet et al. |
| 2006/0009698 A1 | 1/2006 | Banet et al. |
| 2006/0049936 A1 | 3/2006 | Collins, Jr. et al. |
| 2006/0058647 A1 | 3/2006 | Strommer et al. |
| 2006/0073719 A1 | 4/2006 | Kiani |
| 2006/0084878 A1 | 4/2006 | Banet et al. |
| 2006/0085952 A1 | 4/2006 | Kaneko et al. |
| 2006/0089543 A1 | 4/2006 | Kim et al. |
| 2006/0094936 A1 | 5/2006 | Russ |
| 2006/0104824 A1 | 5/2006 | Schnall |
| 2006/0149393 A1 | 7/2006 | Calderon |
| 2006/0155175 A1 | 7/2006 | Ogino et al. |
| 2006/0161054 A1 | 7/2006 | Reuss et al. |
| 2006/0189871 A1 | 8/2006 | Al-Ali et al. |
| 2006/0200009 A1 | 9/2006 | Wekell et al. |
| 2006/0217684 A1 | 9/2006 | Shehada et al. |
| 2006/0217685 A1 | 9/2006 | Shehada et al. |
| 2006/0224413 A1 | 10/2006 | Kim et al. |
| 2006/0235300 A1 | 10/2006 | Weng et al. |
| 2006/0253042 A1 | 11/2006 | Stahmann et al. |
| 2007/0000490 A1 | 1/2007 | DeVries et al. |

(56) References Cited

U.S. PATENT DOCUMENTS

2007/0002533 A1 1/2007 Kogan et al.
2007/0021675 A1 1/2007 Childre et al.
2007/0027368 A1 2/2007 Collins et al.
2007/0032733 A1 2/2007 Burton et al.
2007/0038050 A1 2/2007 Sarussi
2007/0055116 A1 3/2007 Clark et al.
2007/0055544 A1 3/2007 Jung et al.
2007/0060798 A1 3/2007 Krupnik et al.
2007/0073116 A1 3/2007 Kiani et al.
2007/0088406 A1 4/2007 Bennett et al.
2007/0096897 A1 5/2007 Weiner
2007/0100222 A1 5/2007 Mastrototaro et al.
2007/0118028 A1 5/2007 Kitajima
2007/0118399 A1 5/2007 Avinash et al.
2007/0140475 A1 6/2007 Kurtock et al.
2007/0142715 A1 6/2007 Banet et al.
2007/0156033 A1 7/2007 Causey et al.
2007/0157285 A1 7/2007 Frank et al.
2007/0159332 A1 7/2007 Koblasz
2007/0163589 A1 7/2007 DeVries et al.
2007/0180140 A1 8/2007 Welch et al.
2007/0185390 A1 8/2007 Perkins et al.
2007/0185393 A1 8/2007 Zhou et al.
2007/0232941 A1 10/2007 Rabinovich
2007/0244377 A1 10/2007 Cozad et al.
2007/0244724 A1 10/2007 Pendergast et al.
2007/0250286 A1 10/2007 Duncan et al.
2007/0255114 A1 11/2007 Ackermann et al.
2007/0255116 A1 11/2007 Mehta et al.
2007/0255250 A1 11/2007 Moberg
2007/0276261 A1 11/2007 Banet et al.
2007/0276262 A1 11/2007 Banet et al.
2007/0276632 A1 11/2007 Banet et al.
2007/0282478 A1 12/2007 Al-Ali et al.
2007/0287898 A1 12/2007 Lee et al.
2008/0000479 A1 1/2008 Elaz et al.
2008/0003200 A1 1/2008 Arap et al.
2008/0021854 A1 1/2008 Jung et al.
2008/0033661 A1 2/2008 Syroid et al.
2008/0051670 A1 2/2008 Banet et al.
2008/0053438 A1 3/2008 DeVries et al.
2008/0058614 A1 3/2008 Banet et al.
2008/0058657 A1 3/2008 Schwartz et al.
2008/0064965 A1 3/2008 Jay et al.
2008/0077024 A1 3/2008 Schnall
2008/0077026 A1 3/2008 Banet et al.
2008/0082004 A1 4/2008 Banet et al.
2008/0090626 A1 4/2008 Griffin et al.
2008/0091089 A1 4/2008 Guillory et al.
2008/0091090 A1 4/2008 Guillory et al.
2008/0091471 A1 4/2008 Michon et al.
2008/0094228 A1 4/2008 Welch et al.
2008/0097167 A1 4/2008 Yudkovitch et al.
2008/0099366 A1 5/2008 Niemiec et al.
2008/0103375 A1 5/2008 Kiani
2008/0114220 A1 5/2008 Banet et al.
2008/0119412 A1 5/2008 Tymianski et al.
2008/0138278 A1 6/2008 Scherz et al.
2008/0139354 A1 6/2008 Bell et al.
2008/0169922 A1 7/2008 Issokson
2008/0171919 A1 7/2008 Stivoric et al.
2008/0188795 A1 8/2008 Katz et al.
2008/0194918 A1 8/2008 Kulik et al.
2008/0208912 A1 8/2008 Garibaldi
2008/0221396 A1 9/2008 Garces et al.
2008/0221399 A1 9/2008 Zhou et al.
2008/0221418 A1 9/2008 Al-Ali et al.
2008/0221461 A1 9/2008 Zhou et al.
2008/0228077 A1 9/2008 Wilk et al.
2008/0275309 A1 11/2008 Stivoric et al.
2008/0281167 A1 11/2008 Soderberg et al.
2008/0281168 A1 11/2008 Gibson et al.
2008/0281181 A1 11/2008 Manzione et al.
2008/0287751 A1 11/2008 Stivoric et al.
2008/0292172 A1 11/2008 Assmann et al.
2008/0300020 A1 12/2008 Nishizawa et al.
2008/0312518 A1 12/2008 Jina et al.
2008/0312542 A1 12/2008 Banet et al.
2008/0319275 A1 12/2008 Chiu et al.
2008/0319327 A1 12/2008 Banet et al.
2008/0319354 A1 12/2008 Bell et al.
2009/0005651 A1 1/2009 Ward et al.
2009/0018409 A1 1/2009 Banet et al.
2009/0018422 A1 1/2009 Banet et al.
2009/0018453 A1 1/2009 Banet et al.
2009/0018808 A1 1/2009 Bronstein et al.
2009/0024008 A1 1/2009 Brunner et al.
2009/0036759 A1 2/2009 Ault et al.
2009/0043172 A1 2/2009 Zagorchev et al.
2009/0052623 A1 2/2009 Tome et al.
2009/0054735 A1 2/2009 Higgins et al.
2009/0054743 A1 2/2009 Stewart
2009/0062682 A1 3/2009 Bland et al.
2009/0069642 A1 3/2009 Gao et al.
2009/0069868 A1 3/2009 Bengtsson et al.
2009/0093687 A1 4/2009 Telfort et al.
2009/0095926 A1 4/2009 MacNeish, III
2009/0099480 A1 4/2009 Salgo et al.
2009/0112072 A1 4/2009 Banet et al.
2009/0118628 A1 5/2009 Zhou et al.
2009/0119843 A1 5/2009 Rodgers et al.
2009/0124867 A1 5/2009 Hirsch et al.
2009/0131759 A1 5/2009 Sims et al.
2009/0143832 A1 6/2009 Saba
2009/0157058 A1 6/2009 Ferren et al.
2009/0171170 A1 7/2009 Li et al.
2009/0171225 A1 7/2009 Gadodia et al.
2009/0177090 A1 7/2009 Grunwald et al.
2009/0182287 A1 7/2009 Kassab
2009/0226372 A1 9/2009 Ruoslahti et al.
2009/0247924 A1 10/2009 Lamego et al.
2009/0247984 A1 10/2009 Lamego et al.
2009/0264778 A1 10/2009 Markowitz et al.
2009/0275813 A1 11/2009 Davis
2009/0275844 A1 11/2009 Al-Ali
2009/0281462 A1 11/2009 Heliot et al.
2009/0309755 A1 12/2009 Williamson
2009/0322540 A1 12/2009 Richardson et al.
2010/0004518 A1 1/2010 Vo et al.
2010/0030040 A1 2/2010 Poeze et al.
2010/0030094 A1 2/2010 Lundback
2010/0036209 A1 2/2010 Ferren et al.
2010/0056886 A1 3/2010 Hurtubise et al.
2010/0099964 A1 4/2010 O'Reilly et al.
2010/0125217 A1 5/2010 Kuo et al.
2010/0130875 A1 5/2010 Banet et al.
2010/0144627 A1 6/2010 Vitek et al.
2010/0160794 A1 6/2010 Banet et al.
2010/0160795 A1 6/2010 Banet et al.
2010/0160796 A1 6/2010 Banet et al.
2010/0160797 A1 6/2010 Banet et al.
2010/0160798 A1 6/2010 Banet et al.
2010/0168536 A1 7/2010 Banet et al.
2010/0168589 A1 7/2010 Banet et al.
2010/0185101 A1 7/2010 Sakai et al.
2010/0198622 A1 8/2010 Gajic et al.
2010/0210958 A1 8/2010 Manwaring et al.
2010/0234718 A1 9/2010 Sampath et al.
2010/0261982 A1 10/2010 Noury et al.
2010/0270257 A1 10/2010 Wachman et al.
2010/0298650 A1 11/2010 Moon et al.
2010/0298651 A1 11/2010 Moon et al.
2010/0298652 A1 11/2010 McCombie et al.
2010/0298653 A1 11/2010 McCombie et al.
2010/0298654 A1 11/2010 McCombie et al.
2010/0298655 A1 11/2010 McCombie et al.
2010/0298656 A1 11/2010 McCombie et al.
2010/0298657 A1 11/2010 McCombie et al.
2010/0298658 A1 11/2010 McCombie et al.
2010/0298659 A1 11/2010 Mccombie et al.
2010/0298660 A1 11/2010 McCombie et al.
2010/0298661 A1 11/2010 Mccombie et al.
2010/0298742 A1 11/2010 Perlman et al.
2010/0305412 A1 12/2010 Darrah et al.

(56) References Cited

U.S. PATENT DOCUMENTS

2010/0312103 A1 12/2010 Gorek et al.
2010/0317951 A1 12/2010 Rutkowski et al.
2010/0324384 A1 12/2010 Moon et al.
2010/0324385 A1 12/2010 Moon et al.
2010/0324386 A1 12/2010 Moon et al.
2010/0324387 A1 12/2010 Moon et al.
2010/0324388 A1 12/2010 Moon et al.
2010/0324389 A1 12/2010 Moon et al.
2011/0004079 A1 1/2011 Al-Ali et al.
2011/0021930 A1 1/2011 Mazzeo et al.
2011/0023130 A1 1/2011 Gudgel et al.
2011/0028806 A1 2/2011 Merritt et al.
2011/0028809 A1 2/2011 Goodman
2011/0040197 A1 2/2011 Welch et al.
2011/0046495 A1 2/2011 Osypka
2011/0066051 A1 3/2011 Moon et al.
2011/0077473 A1 3/2011 Lisogurski
2011/0077488 A1 3/2011 Buxton et al.
2011/0078596 A1 3/2011 Rawlins et al.
2011/0080294 A1 4/2011 Tanishima et al.
2011/0082711 A1 4/2011 Poeze et al.
2011/0087081 A1 4/2011 Kiani et al.
2011/0087084 A1 4/2011 Jeong et al.
2011/0087117 A1 4/2011 Tremper et al.
2011/0087756 A1 4/2011 Biondi
2011/0092831 A1 4/2011 Herscovivi-Cohen et al.
2011/0092857 A1 4/2011 Herscovivi-Cohen et al.
2011/0098583 A1 4/2011 Pandia et al.
2011/0105956 A1 5/2011 Hirth
2011/0118561 A1 5/2011 Tari et al.
2011/0118573 A1 5/2011 Mckenna
2011/0125060 A1 5/2011 Telfort et al.
2011/0137297 A1 6/2011 Kiani et al.
2011/0152629 A1 6/2011 Eaton et al.
2011/0172498 A1 7/2011 Olsen et al.
2011/0172967 A1 7/2011 Al-Ali et al.
2011/0184252 A1 7/2011 Archer et al.
2011/0184253 A1 7/2011 Archer et al.
2011/0208015 A1 8/2011 Welch et al.
2011/0208073 A1 8/2011 Matsukawa et al.
2011/0212090 A1 9/2011 Pedersen et al.
2011/0224498 A1 9/2011 Banet et al.
2011/0224499 A1 9/2011 Banet et al.
2011/0224500 A1 9/2011 Banet et al.
2011/0224506 A1 9/2011 Moon et al.
2011/0224507 A1 9/2011 Banet et al.
2011/0224508 A1 9/2011 Moon et al.
2011/0224556 A1 9/2011 Moon et al.
2011/0224557 A1 9/2011 Banet et al.
2011/0224564 A1 9/2011 Moon et al.
2011/0230733 A1 9/2011 Al-Ali
2011/0257489 A1 10/2011 Banet et al.
2011/0257544 A1 10/2011 Kaasinen et al.
2011/0257551 A1 10/2011 Banet et al.
2011/0257552 A1 10/2011 Banet et al.
2011/0257553 A1 10/2011 Banet et al.
2011/0257554 A1 10/2011 Banet et al.
2011/0257555 A1 10/2011 Banet et al.
2011/0263950 A1 10/2011 Larson et al.
2011/0288421 A1 11/2011 Banet et al.
2011/0295094 A1 12/2011 Doyle et al.
2012/0004579 A1 1/2012 Luo et al.
2012/0029300 A1 2/2012 Paquet
2012/0029304 A1 2/2012 Medina et al.
2012/0029879 A1 2/2012 Sing et al.
2012/0059230 A1 3/2012 Teller et al.
2012/0071771 A1 3/2012 Behar
2012/0075464 A1 3/2012 Derenne et al.
2012/0095778 A1 4/2012 Gross et al.
2012/0101353 A1 4/2012 Reggiardo et al.
2012/0108983 A1 5/2012 Banet et al.
2012/0123231 A1 5/2012 O'Reilly
2012/0123799 A1 5/2012 Nolen et al.
2012/0132717 A1 5/2012 Maizlin et al.
2012/0136221 A1 5/2012 Killen et al.
2012/0157806 A1 6/2012 Stelger
2012/0165629 A1 6/2012 Merritt et al.
2012/0165630 A1 6/2012 Knight et al.
2012/0165688 A1 6/2012 Liu
2012/0179011 A1 7/2012 Moon et al.
2012/0184120 A1 7/2012 Basta et al.
2012/0190949 A1 7/2012 McCombie et al.
2012/0197619 A1 8/2012 Namer Yelin et al.
2012/0203078 A1 8/2012 Sze et al.
2012/0209082 A1 8/2012 Al-Ali
2012/0209084 A1 8/2012 Olsen et al.
2012/0226117 A1 9/2012 Lamego et al.
2012/0226160 A1 9/2012 Kudoh
2012/0239434 A1 9/2012 Breslow et al.
2012/0242501 A1 9/2012 Tran et al.
2012/0282583 A1 11/2012 Thaler et al.
2012/0283524 A1 11/2012 Kiani et al.
2012/0284053 A1 11/2012 Rosenfeld
2012/0294801 A1 11/2012 Scherz et al.
2012/0296174 A1 11/2012 McCombie
2012/0303476 A1 11/2012 Krzyzanowski et al.
2013/0006131 A1 1/2013 Narayan et al.
2013/0006151 A1 1/2013 Main et al.
2013/0023775 A1 1/2013 Lamego et al.
2013/0035603 A1 2/2013 Jarausch et al.
2013/0041591 A1 2/2013 Lamego
2013/0046197 A1 2/2013 Dlugos et al.
2013/0060147 A1 3/2013 Welch et al.
2013/0092805 A1 4/2013 Funk et al.
2013/0096405 A1 4/2013 Garfio
2013/0096936 A1 4/2013 Sampath et al.
2013/0109929 A1 5/2013 Menzel
2013/0109937 A1 5/2013 Banet et al.
2013/0116515 A1 5/2013 Banet et al.
2013/0123616 A1 5/2013 Merritt et al.
2013/0197364 A1 8/2013 Han
2013/0243021 A1 9/2013 Siskavich
2013/0253334 A1 9/2013 Al-Ali et al.
2013/0261494 A1 10/2013 Bloom et al.
2013/0279109 A1 10/2013 Lindblad et al.
2013/0296672 A1 11/2013 O'Neil et al.
2013/0296713 A1 11/2013 Al-Ali et al.
2013/0297330 A1 11/2013 Kamen et al.
2013/0317393 A1 11/2013 Weiss et al.
2013/0324804 A1 12/2013 McKeown et al.
2013/0324808 A1 12/2013 Al-Ali et al.
2013/0331036 A1* 12/2013 Baker .................... G16H 40/63
455/41.3
2013/0331660 A1 12/2013 Al-Ali et al.
2013/0340176 A1 12/2013 Stevens et al.
2013/0345921 A1 12/2013 Al-Ali et al.
2014/0005502 A1 1/2014 Klap et al.
2014/0012100 A1 1/2014 Al-Ali et al.
2014/0022081 A1 1/2014 Ribble et al.
2014/0025010 A1 1/2014 Stroup et al.
2014/0046674 A1 2/2014 Rosenfeld
2014/0051953 A1 2/2014 Lamego et al.
2014/0081099 A1 3/2014 Banet et al.
2014/0088385 A1 3/2014 Moon et al.
2014/0120564 A1 5/2014 Workman et al.
2014/0121482 A1 5/2014 Merritt et al.
2014/0127137 A1 5/2014 Bellott et al.
2014/0142445 A1 5/2014 Banet et al.
2014/0152673 A1 6/2014 Lynn et al.
2014/0163344 A1 6/2014 Al-Ali
2014/0163393 A1 6/2014 McCombie et al.
2014/0166076 A1 6/2014 Kiani et al.
2014/0171763 A1 6/2014 Diab
2014/0180038 A1 6/2014 Kiani
2014/0180154 A1 6/2014 Sierra et al.
2014/0180160 A1 6/2014 Brown et al.
2014/0187973 A1 7/2014 Brown et al.
2014/0188516 A1 7/2014 Kamen
2014/0200415 A1 7/2014 McCombie et al.
2014/0200420 A1 7/2014 Al-Ali
2014/0213864 A1 7/2014 Abdul-Hafiz et al.
2014/0221797 A1 8/2014 Bailey
2014/0235964 A1 8/2014 Banet et al.
2014/0249431 A1 9/2014 Banet et al.

(56) References Cited

U.S. PATENT DOCUMENTS

| | | | |
|---|---|---|---|
| 2014/0249432 A1 | 9/2014 | Banet et al. | |
| 2014/0249433 A1 | 9/2014 | Banet et al. | |
| 2014/0249434 A1 | 9/2014 | Banet et al. | |
| 2014/0249435 A1 | 9/2014 | Banet et al. | |
| 2014/0249440 A1 | 9/2014 | Banet et al. | |
| 2014/0249441 A1 | 9/2014 | Banet et al. | |
| 2014/0249442 A1 | 9/2014 | Banet et al. | |
| 2014/0257056 A1 | 9/2014 | Moon et al. | |
| 2014/0257057 A1 | 9/2014 | Reis Cunha et al. | |
| 2014/0266787 A1 | 9/2014 | Tran | |
| 2014/0275816 A1 | 9/2014 | Sandmore | |
| 2014/0275835 A1 | 9/2014 | Lamego et al. | |
| 2014/0275871 A1 | 9/2014 | Lamego et al. | |
| 2014/0275872 A1 | 9/2014 | Merritt et al. | |
| 2014/0276145 A1 | 9/2014 | Banet et al. | |
| 2014/0276175 A1 | 9/2014 | Banet et al. | |
| 2014/0288400 A1 | 9/2014 | Diab et al. | |
| 2014/0301893 A1 | 10/2014 | Stroup et al. | |
| 2014/0316217 A1 | 10/2014 | Purdon et al. | |
| 2014/0316218 A1 | 10/2014 | Purdon et al. | |
| 2014/0316228 A1 | 10/2014 | Blank et al. | |
| 2014/0323825 A1 | 10/2014 | Al-Ali et al. | |
| 2014/0323897 A1 | 10/2014 | Brown et al. | |
| 2014/0323898 A1 | 10/2014 | Purdon et al. | |
| 2014/0330092 A1 | 11/2014 | Al-Ali et al. | |
| 2014/0330098 A1 | 11/2014 | Merritt et al. | |
| 2014/0336517 A1 | 11/2014 | Schnall | |
| 2014/0343889 A1 | 11/2014 | Ben Shalom et al. | |
| 2014/0357966 A1 | 12/2014 | Al-Ali et al. | |
| 2015/0005600 A1 | 1/2015 | Blank et al. | |
| 2015/0011907 A1 | 1/2015 | Purdon et al. | |
| 2015/0032029 A1 | 1/2015 | Al-Ali et al. | |
| 2015/0038859 A1 | 2/2015 | Dalvi et al. | |
| 2015/0073241 A1 | 3/2015 | Lamego | |
| 2015/0080754 A1 | 3/2015 | Purdon et al. | |
| 2015/0087936 A1 | 3/2015 | Al-Ali et al. | |
| 2015/0094546 A1 | 4/2015 | Al-Ali | |
| 2015/0094618 A1 | 4/2015 | Russell et al. | |
| 2015/0099950 A1 | 4/2015 | Al-Ali et al. | |
| 2015/0101844 A1 | 4/2015 | Al-Ali et al. | |
| 2015/0106121 A1 | 4/2015 | Muhsin et al. | |
| 2015/0112151 A1 | 4/2015 | Muhsin et al. | |
| 2015/0164437 A1 | 6/2015 | McCombie et al. | |
| 2015/0165312 A1 | 6/2015 | Kiani | |
| 2015/0196249 A1 | 7/2015 | Brown et al. | |
| 2015/0216459 A1 | 8/2015 | Al-Ali et al. | |
| 2015/0238722 A1 | 8/2015 | Al-Ali | |
| 2015/0245773 A1 | 9/2015 | Lamego et al. | |
| 2015/0245794 A1 | 9/2015 | Al-Ali | |
| 2015/0257689 A1 | 9/2015 | Al-Ali et al. | |
| 2015/0272514 A1 | 10/2015 | Kiani et al. | |
| 2015/0282708 A1 | 10/2015 | Schlottau et al. | |
| 2015/0282717 A1 | 10/2015 | McCombie et al. | |
| 2015/0351697 A1 | 12/2015 | Weber et al. | |
| 2015/0359429 A1 | 12/2015 | Al-Ali et al. | |
| 2015/0366507 A1 | 12/2015 | Blank et al. | |
| 2016/0022224 A1 | 1/2016 | Banet et al. | |
| 2016/0029932 A1 | 2/2016 | Al-Ali | |
| 2016/0045163 A1 | 2/2016 | Weisner et al. | |
| 2016/0058347 A1 | 3/2016 | Reichgott et al. | |
| 2016/0066824 A1 | 3/2016 | Al-Ali et al. | |
| 2016/0081552 A1 | 3/2016 | Wojtczuk et al. | |
| 2016/0095543 A1 | 4/2016 | Telfort et al. | |
| 2016/0095548 A1 | 4/2016 | Al-Ali et al. | |
| 2016/0103598 A1 | 4/2016 | Al-Ali et al. | |
| 2016/0106366 A1 | 4/2016 | Banet et al. | |
| 2016/0143546 A1 | 5/2016 | McCombie et al. | |
| 2016/0166182 A1 | 6/2016 | Al-Ali et al. | |
| 2016/0166183 A1 | 6/2016 | Poeze et al. | |
| 2016/0183836 A1* | 6/2016 | Muuranto ............. | A61B 5/369 600/300 |
| 2016/0196388 A1 | 7/2016 | Lamego | |
| 2016/0197436 A1 | 7/2016 | Barker et al. | |
| 2016/0213281 A1 | 7/2016 | Eckerbom et al. | |
| 2016/0228043 A1 | 8/2016 | O'Neil et al. | |
| 2016/0233632 A1 | 8/2016 | Scruggs et al. | |
| 2016/0234944 A1 | 8/2016 | Schmidt et al. | |
| 2016/0270735 A1 | 9/2016 | Diab et al. | |
| 2016/0283665 A1 | 9/2016 | Sampath et al. | |
| 2016/0287090 A1 | 10/2016 | Al-Ali et al. | |
| 2016/0287786 A1 | 10/2016 | Kiani | |
| 2016/0296169 A1 | 10/2016 | McHale et al. | |
| 2016/0310052 A1 | 10/2016 | Al-Ali et al. | |
| 2016/0314260 A1 | 10/2016 | Kiani | |
| 2016/0321420 A1 | 11/2016 | Klee et al. | |
| 2016/0324488 A1 | 11/2016 | Olsen | |
| 2016/0327984 A1 | 11/2016 | Al-Ali et al. | |
| 2016/0331332 A1 | 11/2016 | Al-Ali | |
| 2016/0367173 A1 | 12/2016 | Dalvi et al. | |
| 2017/0000394 A1 | 1/2017 | Al-Ali et al. | |
| 2017/0007134 A1 | 1/2017 | Al-Ali et al. | |
| 2017/0007198 A1 | 1/2017 | Al-Ali et al. | |
| 2017/0014083 A1 | 1/2017 | Diab et al. | |
| 2017/0014084 A1 | 1/2017 | Al-Ali et al. | |
| 2017/0024748 A1 | 1/2017 | Haider | |
| 2017/0042488 A1 | 2/2017 | Muhsin | |
| 2017/0055851 A1 | 3/2017 | Al-Ali | |
| 2017/0055882 A1 | 3/2017 | Al-Ali et al. | |
| 2017/0055887 A1 | 3/2017 | Al-Ali | |
| 2017/0055896 A1 | 3/2017 | Al-Ali | |
| 2017/0055905 A1 | 3/2017 | Cohrs et al. | |
| 2017/0079594 A1 | 3/2017 | Telfort et al. | |
| 2017/0086723 A1 | 3/2017 | Al-Ali et al. | |
| 2017/0119252 A1 | 5/2017 | Kim et al. | |
| 2017/0143281 A1 | 5/2017 | Olsen | |
| 2017/0147774 A1 | 5/2017 | Kiani | |
| 2017/0156620 A1 | 6/2017 | Al-Ali et al. | |
| 2017/0173632 A1 | 6/2017 | Al-Ali | |
| 2017/0187146 A1 | 6/2017 | Kiani et al. | |
| 2017/0188919 A1 | 7/2017 | Al-Ali et al. | |
| 2017/0196464 A1 | 7/2017 | Jansen et al. | |
| 2017/0196470 A1 | 7/2017 | Lamego et al. | |
| 2017/0224262 A1 | 8/2017 | Al-Ali | |
| 2017/0228516 A1 | 8/2017 | Sampath et al. | |
| 2017/0245790 A1 | 8/2017 | Al-Ali et al. | |
| 2017/0251974 A1 | 9/2017 | Shreim et al. | |
| 2017/0251975 A1 | 9/2017 | Shreim et al. | |
| 2017/0258403 A1 | 9/2017 | Abdul-Hafiz et al. | |
| 2017/0311851 A1 | 11/2017 | Schurman et al. | |
| 2017/0311891 A1 | 11/2017 | Kiani et al. | |
| 2017/0325728 A1 | 11/2017 | Al-Ali et al. | |
| 2017/0332976 A1 | 11/2017 | Al-Ali | |
| 2017/0332980 A1 | 11/2017 | Fifield et al. | |
| 2017/0340293 A1 | 11/2017 | Al-Ali et al. | |
| 2017/0360310 A1 | 12/2017 | Kiani | |
| 2017/0367632 A1 | 12/2017 | Al-Ali et al. | |
| 2018/0008146 A1 | 1/2018 | Al-Ali et al. | |
| 2018/0013562 A1 | 1/2018 | Haider et al. | |
| 2018/0014752 A1 | 1/2018 | Al-Ali et al. | |
| 2018/0028124 A1 | 2/2018 | Al-Ali et al. | |
| 2018/0055385 A1 | 3/2018 | Al-Ali | |
| 2018/0055390 A1 | 3/2018 | Kiani et al. | |
| 2018/0055430 A1 | 3/2018 | Diab et al. | |
| 2018/0064381 A1 | 3/2018 | Shakespeare et al. | |
| 2018/0069776 A1 | 3/2018 | Lamego et al. | |
| 2018/0070867 A1 | 3/2018 | Smith et al. | |
| 2018/0082767 A1 | 3/2018 | Al-Ali et al. | |
| 2018/0085068 A1 | 3/2018 | Telfort | |
| 2018/0087937 A1 | 3/2018 | Al-Ali et al. | |
| 2018/0097373 A1 | 4/2018 | McSweyn et al. | |
| 2018/0103874 A1 | 4/2018 | Lee et al. | |
| 2018/0103905 A1 | 4/2018 | Kiani | |
| 2018/0110478 A1 | 4/2018 | Al-Ali | |
| 2018/0116575 A1 | 5/2018 | Perea et al. | |
| 2018/0125368 A1 | 5/2018 | Lamego et al. | |
| 2018/0125430 A1 | 5/2018 | Al-Ali et al. | |
| 2018/0125445 A1 | 5/2018 | Telfort et al. | |
| 2018/0130325 A1 | 5/2018 | Kiani et al. | |
| 2018/0132769 A1 | 5/2018 | Weber et al. | |
| 2018/0132770 A1 | 5/2018 | Lamego | |
| 2018/0146901 A1 | 5/2018 | Al-Ali et al. | |
| 2018/0146902 A1 | 5/2018 | Kiani et al. | |
| 2018/0153442 A1 | 6/2018 | Eckerbom et al. | |
| 2018/0153446 A1 | 6/2018 | Kiani | |

(56) References Cited

U.S. PATENT DOCUMENTS

2018/0153447 A1 6/2018 Al-Ali et al.
2018/0153448 A1 6/2018 Weber et al.
2018/0161499 A1 6/2018 Al-Ali et al.
2018/0168491 A1 6/2018 Al-Ali et al.
2018/0174679 A1 6/2018 Sampath et al.
2018/0174680 A1 6/2018 Sampath et al.
2018/0182484 A1 6/2018 Sampath et al.
2018/0184917 A1 7/2018 Kiani
2018/0192924 A1 7/2018 Al-Ali
2018/0192953 A1 7/2018 Shreim et al.
2018/0192955 A1 7/2018 Al-Ali et al.
2018/0199871 A1 7/2018 Pauley et al.
2018/0206795 A1 7/2018 Al-Ali
2018/0206815 A1 7/2018 Telfort
2018/0213583 A1 7/2018 Al-Ali
2018/0214031 A1 8/2018 Kiani et al.
2018/0214090 A1 8/2018 Al-Ali et al.
2018/0218792 A1 8/2018 Muhsin et al.
2018/0225960 A1 8/2018 Al-Ali et al.
2018/0238718 A1 8/2018 Dalvi
2018/0242853 A1 8/2018 Al-Ali
2018/0242921 A1 8/2018 Muhsin et al.
2018/0242923 A1 8/2018 Al-Ali et al.
2018/0242924 A1 8/2018 Barker et al.
2018/0242926 A1 8/2018 Muhsin et al.
2018/0247353 A1 8/2018 Al-Ali et al.
2018/0247712 A1 8/2018 Muhsin et al.
2018/0249933 A1 9/2018 Schurman et al.
2018/0253947 A1 9/2018 Muhsin et al.
2018/0256087 A1 9/2018 Al-Ali et al.
2018/0256113 A1 9/2018 Weber et al.
2018/0285094 A1 10/2018 Housel et al.
2018/0289325 A1 10/2018 Poeze et al.
2018/0289337 A1 10/2018 Al-Ali et al.
2018/0296161 A1 10/2018 Shreim et al.
2018/0300919 A1 10/2018 Muhsin et al.
2018/0310822 A1 11/2018 Indorf et al.
2018/0310823 A1 11/2018 Al-Ali et al.
2018/0317826 A1 11/2018 Muhsin et al.
2018/0317841 A1 11/2018 Novak, Jr.
2018/0333055 A1 11/2018 Lamego et al.
2018/0333087 A1 11/2018 Al-Ali
2019/0000317 A1 1/2019 Muhsin et al.
2019/0000362 A1 1/2019 Kiani et al.
2019/0015023 A1 1/2019 Monfre
2019/0021638 A1 1/2019 Al-Ali et al.
2019/0029574 A1 1/2019 Schurman et al.
2019/0029578 A1 1/2019 Al-Ali et al.
2019/0038143 A1 2/2019 Al-Ali
2019/0058280 A1 2/2019 Al-Ali et al.
2019/0058281 A1 2/2019 Al-Ali et al.
2019/0069813 A1 3/2019 Al-Ali
2019/0069814 A1 3/2019 Al-Ali
2019/0076028 A1 3/2019 Al-Ali et al.
2019/0082979 A1 3/2019 Al-Ali et al.
2019/0090748 A1 3/2019 Al-Ali
2019/0090760 A1 3/2019 Kinast et al.
2019/0090764 A1 3/2019 Al-Ali
2019/0104973 A1 4/2019 Poeze et al.
2019/0110719 A1 4/2019 Poeze et al.
2019/0117070 A1 4/2019 Muhsin et al.
2019/0117139 A1 4/2019 Al-Ali et al.
2019/0117140 A1 4/2019 Al-Ali et al.
2019/0117141 A1 4/2019 Al-Ali
2019/0117930 A1 4/2019 Ai-Ali
2019/0122763 A1 4/2019 Sampath et al.
2019/0133525 A1 5/2019 Al-Ali et al.
2019/0142283 A1 5/2019 Lamego et al.
2019/0142344 A1 5/2019 Telfort et al.
2019/0150800 A1 5/2019 Poeze et al.
2019/0150856 A1 5/2019 Kiani et al.
2019/0167161 A1 6/2019 Al-Ali et al.
2019/0175019 A1 6/2019 Al-Ali et al.
2019/0192076 A1 6/2019 McHale et al.
2019/0200941 A1 7/2019 Chandran et al.
2019/0201623 A1 7/2019 Kiani
2019/0209025 A1 7/2019 Al-Ali
2019/0214778 A1 7/2019 Scruggs et al.
2019/0216319 A1 7/2019 Poeze et al.
2019/0216370 A1 7/2019 Schurman et al.
2019/0216379 A1 7/2019 Al-Ali et al.
2019/0221966 A1 7/2019 Kiani et al.
2019/0223804 A1 7/2019 Blank et al.
2019/0231199 A1 8/2019 Al-Ali et al.
2019/0231241 A1 8/2019 Al-Ali et al.
2019/0231270 A1 8/2019 Abdul-Hafiz et al.
2019/0239787 A1 8/2019 Pauley et al.
2019/0239824 A1 8/2019 Muhsin et al.
2019/0254578 A1 8/2019 Lamego
2019/0261857 A1 8/2019 Al-Ali
2019/0269370 A1 9/2019 Al-Ali et al.
2019/0274606 A1 9/2019 Kiani et al.
2019/0274627 A1 9/2019 Al-Ali et al.
2019/0274635 A1 9/2019 Al-Ali et al.
2019/0290136 A1 9/2019 Dalvi et al.
2019/0298270 A1 10/2019 Al-Ali et al.
2019/0304601 A1 10/2019 Sampath et al.
2019/0304605 A1 10/2019 Al-Ali
2019/0320906 A1 10/2019 Olsen
2019/0320988 A1 10/2019 Ahmed et al.
2019/0374139 A1 12/2019 Kiani et al.
2019/0374173 A1 12/2019 Kiani et al.
2019/0374713 A1 12/2019 Kiani et al.
2020/0021930 A1 1/2020 Iswanto et al.
2020/0060869 A1 2/2020 Telfort et al.
2020/0085321 A1 3/2020 Hatch
2020/0111552 A1 4/2020 Ahmed
2020/0113435 A1 4/2020 Muhsin
2020/0113488 A1 4/2020 Al-Ali et al.
2020/0113496 A1 4/2020 Scruggs et al.
2020/0113497 A1 4/2020 Triman et al.
2020/0113520 A1 4/2020 Abdul-Hafiz et al.
2020/0138288 A1 5/2020 Al-Ali et al.
2020/0138368 A1 5/2020 Kiani et al.
2020/0163597 A1 5/2020 Dalvi et al.
2020/0196877 A1 6/2020 Vo et al.
2020/0253474 A1 8/2020 Muhsin et al.
2020/0253544 A1 8/2020 Belur Nagaraj et al.
2020/0275841 A1 9/2020 Telfort et al.
2020/0288983 A1 9/2020 Telfort et al.
2020/0321793 A1 10/2020 Al-Ali et al.
2020/0329983 A1 10/2020 Al-Ali et al.
2020/0329984 A1 10/2020 Al-Ali et al.
2020/0329993 A1 10/2020 Al-Ali et al.
2020/0330037 A1 10/2020 Al-Ali et al.
2021/0022628 A1 1/2021 Telfort et al.
2021/0104173 A1 4/2021 Pauley et al.
2021/0113121 A1 4/2021 Diab et al.
2021/0117525 A1 4/2021 Kiani et al.
2021/0118581 A1 4/2021 Kiani et al.
2021/0121582 A1 4/2021 Krishnamani et al.
2021/0161465 A1 6/2021 Barker et al.
2021/0236729 A1 8/2021 Kiani et al.
2021/0251501 A1 8/2021 Moon et al.
2021/0256267 A1 8/2021 Ranasinghe et al.
2021/0256835 A1 8/2021 Ranasinghe et al.
2021/0275101 A1 9/2021 Vo et al.
2021/0290060 A1 9/2021 Ahmed
2021/0290072 A1 9/2021 Forrest
2021/0290080 A1 9/2021 Ahmed
2021/0290120 A1 9/2021 Al-Ali
2021/0290177 A1 9/2021 Novak, Jr.
2021/0290184 A1 9/2021 Ahmed
2021/0296008 A1 9/2021 Novak, Jr.
2021/0330228 A1 10/2021 Olsen et al.
2021/0386382 A1 12/2021 Olsen et al.
2021/0402110 A1 12/2021 Pauley et al.
2022/0026355 A1 1/2022 Normand et al.
2022/0039707 A1 2/2022 Sharma et al.
2022/0053892 A1 2/2022 Al-Ali et al.
2022/0071562 A1 3/2022 Kiani
2022/0096603 A1 3/2022 Kiani et al.
2022/0125377 A1 4/2022 Mendes-Roter et al.
2022/0148724 A1 5/2022 Pasternak et al.

(56) References Cited

U.S. PATENT DOCUMENTS

| | | | |
|---|---|---|---|
| 2022/0151521 | A1 | 5/2022 | Krishnamani et al. |
| 2022/0181018 | A1 | 6/2022 | Dyell et al. |
| 2022/0211323 | A1 | 7/2022 | Schnall |
| 2022/0218244 | A1 | 7/2022 | Kiani et al. |
| 2022/0225878 | A1 | 7/2022 | Al-Ali et al. |
| 2022/0287574 | A1 | 9/2022 | Telfort et al. |
| 2022/0296161 | A1 | 9/2022 | Al-Ali et al. |
| 2022/0331065 | A1 | 10/2022 | Shah et al. |
| 2022/0346724 | A1 | 11/2022 | Ferber et al. |
| 2022/0361819 | A1 | 11/2022 | Al-Ali et al. |
| 2022/0378344 | A1 | 12/2022 | Telfort et al. |
| 2022/0379059 | A1 | 12/2022 | Yu et al. |
| 2022/0386909 | A1 | 12/2022 | Triman et al. |
| 2022/0386951 | A1 | 12/2022 | Novak, Jr. |
| 2022/0392610 | A1 | 12/2022 | Kiani et al. |
| 2022/0400962 | A1 | 12/2022 | Al-Ali et al. |
| 2023/0009812 | A1 | 1/2023 | Al-Ali |
| 2023/0014737 | A1 | 1/2023 | Scruggs et al. |
| 2023/0017784 | A1 | 1/2023 | Scruggs et al. |
| 2023/0018925 | A1 | 1/2023 | Al-Ali |
| 2023/0019452 | A1 | 1/2023 | Lamego et al. |
| 2023/0019476 | A1 | 1/2023 | Al-Ali et al. |
| 2023/0019901 | A1 | 1/2023 | Muhsin et al. |
| 2023/0028745 | A1 | 1/2023 | Al-Ali |
| 2023/0036658 | A1 | 2/2023 | Lamego |
| 2023/0037434 | A1 | 2/2023 | Al-Ali et al. |
| 2023/0038381 | A1 | 2/2023 | Al-Ali et al. |
| 2023/0038389 | A1 | 2/2023 | Vo |
| 2023/0039850 | A1 | 2/2023 | Poeze et al. |
| 2023/0045000 | A1 | 2/2023 | Al-Ali et al. |
| 2023/0045647 | A1 | 2/2023 | Vo |
| 2023/0047155 | A1 | 2/2023 | Poeze et al. |
| 2023/0047651 | A1 | 2/2023 | Poeze et al. |
| 2023/0052722 | A1 | 2/2023 | Poeze et al. |
| 2023/0054992 | A1 | 2/2023 | Muhsin et al. |
| 2023/0058052 | A1 | 2/2023 | Al-Ali |
| 2023/0058342 | A1 | 2/2023 | Kiani |
| 2023/0069789 | A1 | 3/2023 | Koo et al. |
| 2023/0084326 | A1 | 3/2023 | Kiani |
| 2023/0087671 | A1 | 3/2023 | Telfort et al. |
| 2023/0110152 | A1 | 4/2023 | Forrest et al. |
| 2023/0111198 | A1 | 4/2023 | Yu et al. |
| 2023/0115397 | A1 | 4/2023 | Vo et al. |
| 2023/0116371 | A1 | 4/2023 | Mills et al. |
| 2023/0135297 | A1 | 5/2023 | Kiani et al. |
| 2023/0138098 | A1 | 5/2023 | Telfort et al. |
| 2023/0145155 | A1 | 5/2023 | Krishnamani et al. |
| 2023/0147605 | A1 | 5/2023 | Nazari |
| 2023/0147750 | A1 | 5/2023 | Barker et al. |
| 2023/0210417 | A1 | 7/2023 | Al-Ali et al. |
| 2023/0222805 | A1 | 7/2023 | Muhsin et al. |
| 2023/0222887 | A1 | 7/2023 | Muhsin et al. |
| 2023/0226331 | A1 | 7/2023 | Kiani et al. |
| 2023/0284916 | A1 | 9/2023 | Telfort |
| 2023/0284943 | A1 | 9/2023 | Scruggs et al. |
| 2023/0301562 | A1 | 9/2023 | Scruggs et al. |
| 2023/0346993 | A1 | 11/2023 | Kiani et al. |
| 2023/0368221 | A1 | 11/2023 | Haider |
| 2023/0371893 | A1 | 11/2023 | Al-Ali et al. |
| 2023/0389837 | A1 | 12/2023 | Krishnamani et al. |
| 2024/0016418 | A1 | 1/2024 | Devadoss et al. |
| 2024/0016419 | A1 | 1/2024 | Devadoss et al. |
| 2024/0047061 | A1 | 2/2024 | Al-Ali et al. |
| 2024/0049310 | A1 | 2/2024 | Al-Ali et al. |
| 2024/0049986 | A1 | 2/2024 | Al-Ali et al. |
| 2024/0081656 | A1 | 3/2024 | DeJong et al. |
| 2024/0122486 | A1 | 4/2024 | Kiani |
| 2024/0180456 | A1 | 6/2024 | Al-Ali |
| 2024/0188872 | A1 | 6/2024 | Al-Ali et al. |
| 2024/0245855 | A1 | 7/2024 | Vo et al. |
| 2024/0252046 | A1 | 8/2024 | Jansen et al. |
| 2024/0260894 | A1 | 8/2024 | Olsen |
| 2024/0267698 | A1 | 8/2024 | Telfort et al. |
| 2024/0277233 | A1 | 8/2024 | Ai-Ali |
| 2024/0277280 | A1 | 8/2024 | Al-Ali |
| 2024/0298920 | A1 | 9/2024 | Fernkbist et al. |
| 2024/0306985 | A1 | 9/2024 | Vo et al. |
| 2024/0324953 | A1 | 10/2024 | Telfort |
| 2024/0380246 | A1 | 11/2024 | Moran |
| 2024/0380247 | A1 | 11/2024 | Moran |
| 2024/0398234 | A1 | 12/2024 | Al-Ali |
| 2024/0404549 | A1 | 12/2024 | Campbell et al. |
| 2025/0000458 | A1 | 1/2025 | Abdul-Hafiz et al. |
| 2025/0037836 | A1 | 1/2025 | Kiani |
| 2025/0100482 | A1 | 3/2025 | Al-Ali et al. |
| 2025/0118415 | A1 | 4/2025 | Olsen |

FOREIGN PATENT DOCUMENTS

| | | |
|---|---|---|
| CN | 108370502 | 8/2018 |
| EM | 01198584-0059 | 6/2010 |
| EP | 0 735 499 | 10/1996 |
| EP | 0 880 936 | 12/1998 |
| EP | 2 335 569 | 6/2011 |
| EP | 2 766 834 | 8/2014 |
| EP | 2 811 894 | 12/2014 |
| EP | 2 901 921 | 8/2015 |
| JP | H08-080288 | 3/1996 |
| JP | H10-336064 | 12/1998 |
| JP | 2002-513602 | 5/2002 |
| JP | 2002-165764 | 6/2002 |
| JP | 2002-172096 | 6/2002 |
| JP | 2002-542493 | 12/2002 |
| JP | 2004-337605 | 12/2004 |
| JP | 2005-218036 | 8/2005 |
| JP | 2005-295375 | 10/2005 |
| JP | 2005-532863 | 11/2005 |
| JP | 2007-021213 | 2/2007 |
| JP | 2007-095365 | 4/2007 |
| JP | 2007-174051 | 7/2007 |
| JP | 2008-061663 | 3/2008 |
| JP | 2008-126017 | 6/2008 |
| JP | 2008-519635 | 6/2008 |
| JP | 2008-541045 | 11/2008 |
| JP | 2009-017959 | 1/2009 |
| JP | 2009-207836 | 9/2009 |
| JP | 2010-503134 | 1/2010 |
| JP | 2010-506625 | 3/2010 |
| JP | 2010-524510 | 7/2010 |
| JP | 2011-519607 | 7/2011 |
| JP | 2011-152261 | 8/2011 |
| JP | 2014-533997 | 12/2014 |
| JP | 2015-511840 | 4/2015 |
| JP | 2016-505297 | 2/2016 |
| JP | 2016-538015 | 12/2016 |
| JP | 2017-506121 | 3/2017 |
| JP | 2018-005338 | 1/2018 |
| JP | D1605226 | 5/2018 |
| JP | 2018-527996 | 9/2018 |
| JP | D1614787 | 10/2018 |
| JP | D1665851 | 4/2019 |
| TW | D169966 | 8/2015 |
| TW | D182804 | 5/2017 |
| TW | D126452 | 12/2018 |
| TW | D207721 | 10/2020 |
| WO | WO 98/004182 | 2/1998 |
| WO | WO 98/029790 | 7/1998 |
| WO | WO 99/013766 | 3/1999 |
| WO | WO 99/056613 | 11/1999 |
| WO | WO 00/063713 | 10/2000 |
| WO | WO 00/074551 | 12/2000 |
| WO | WO 01/064101 | 9/2001 |
| WO | WO 2004/056266 | 7/2004 |
| WO | WO 2004/059551 | 7/2004 |
| WO | WO 2006/051461 | 5/2006 |
| WO | WO 2011/001302 | 1/2011 |
| WO | WO 2011/002904 | 1/2011 |
| WO | WO 2011/025549 | 3/2011 |
| WO | WO 2012/112891 | 8/2012 |
| WO | WO 2013/056160 | 4/2013 |
| WO | WO 2013/119982 | 8/2013 |
| WO | WO 2013/184283 | 12/2013 |
| WO | WO 2015/054665 | 4/2015 |
| WO | WO 2017/040700 | 3/2017 |

(56) References Cited

FOREIGN PATENT DOCUMENTS

| | | |
|---|---|---|
| WO | WO 2018/102142 | 6/2018 |
| WO | WO 2019/0241753 | 12/2019 |
| WO | WO 2020/077149 | 4/2020 |
| WO | WO 2023/132952 | 7/2023 |

OTHER PUBLICATIONS

US 2024/0016391 A1, 01/2024, Lapotko et al. (withdrawn)
International Search Report and Written Opinion received in PCT Application No. PCT/US2019/055722, dated Mar. 23, 2020.
PCT Invitation to Pay Additional Search Fees issued in application No. PCT/US2019/055722 on Jan. 30, 2020.
International Preliminary Report on Patentability and Written Opinion received in PCT Application No. PCT/US2021/031625, dated Nov. 24, 2022.
International Preliminary Report on Patentability and Written Opinion received in PCT Application No. PCT/US2019/055722, dated Apr. 22, 2021.
International Search Report and Written Opinion received in PCT Application No. PCT/US2021/031625, dated Aug. 25, 2021.
U.S. Appl. No. 12/973,392, filed Dec. 20, 2010, Kiani et al.
U.S. Appl. No. 29/537,221 filed Aug. 24, 2015, Al-Ali et al.
ADInstruments: "Human NIBP Controller Owner's Guide Human NIBP Owner's Guide", Jan. 1, 2014, XP055673095, Retrieved from the Internet: http://cdn.adinstruments.com/adi-web/manuals/human-nibp-OG.pdf [retrieved on Mar. 3, 2020), p. 16; figures 2-4, pp. 90.
Aminian et al., "Spatio-Temporal Parameters of Gait Measured by an Ambulatory System Using Miniature Gyroscopes", Journal of Biomechanics, 2002, vol. 35, pp. 689-699.
Anliker et al., "AMON: A Wearable Multiparameter Medical Monitoring and Alert System", IEEE Transactions on Information Technology in Biomedicine, vol. 8, No. 4, Dec. 2004, pp. 415-427.
Asada et al., "Mobile Monitoring with Wearable Photoplethysmographic Biosensors", IEEE Engineering in Medicine and Biology Magazine, May/Jun. 2003, pp. 28-40.
Ayello et al., "How and Why to Do Pressure Ulcer Risk Assessment", Advances in Skin & Wound Care, May/Jun. 2002, vol. 15, No. 3., pp. 125-133.
Bergstrom et al., "A Prospective Study of Pressure Sore Risk Among Institutionalized Elderly", Journal of the American Geriatrics Society, Aug. 1992, vol. 40, No. 8, pp. 747-758.
Bourke et al., "Evaluation of a Threshold-Based Tri-Axial Accelerometer Fall Detection Algorithm", Gait & Posture, vol. 26, 2007, pp. 194-199.
Campo et al., "Wireless Fall Sensor with GPS Location for Monitoring the Elderly", 30th Annual International IEEE EMBS Conference Vancouver, British Columbia, Canada, Aug. 20-24, 2008, pp. 498-501.
Caporusso et al., "A Pervasive Solution for Risk Awareness in the Context of Fall Prevention", Pervasive Health, 2009, pp. 8.
Capuano et at. "Remote Telemetry—New Twists for Old Technology." Nursing Management. vol. 26, No. 7. Jul. 1995.
Chen et al., "In-Bed Fibre Optic Breathing and Movement Sensor for Non-Intrusive Monitoring", Proceedings of SPIE vol. 7173, 2009, pp. 6.
Chen et al., "Wearable Sensors for Reliable Fall Detection", Proceedings of the 2005 IEEE Engineering in Medicine and Biology 27th Annual Conference, Shanghai, China, Sep. 1-4, 2005, pp. 3551-3554.
Degen et al., "Speedy: A Fall Detector in a Wrist Watch", Proceedings of the Seventh IEEE International Symposium on Wearable Computers (ISWC'03), 2003, pp. 184-187.
Dhillon et al., "Towards the Prevention of Pressure Ulcers with a Wearable Patient Posture Monitor Based on Adaptive Accelerometer Alignment", 34th Annual International Conference of the IEEE EMBS, San Diego, CA, Aug. 28-Sep. 1, 2012, pp. 4513-4516.
Di Rienzo et al., "MagIC System: a New Textile-BasedWearable Device for Biological Signal Monitoring. Applicability in Daily Life and Clinical Setting", Proceedings of the 2005 IEEE Engineering in Medicine and Biology 27th Annual Conference Shanghai, China, Sep. 1-4, 2005, pp. 7167-7169.
Dinh et al., "A Fall and Near-Fall Assessment and Evaluation System", The Open Biomedical Engineering Journal, 2009, vol. 3, pp. 1-7.
Elmer-Dewitt, Philip, Apple's iWatch: The killer apps may be in hospitals, not health clubs, Fortune.com, Feb. 3, 2014, http://fortune.com/2014/02/03/apples-iwatch-the-killer-apps-may-be-in-hospitals-not-health-clubs/, in 4 pages.
Giansanti et al., "Assessment of Fall-Risk by Means of a Neural Network Based on Parameters Assessed by a Wearable Device During Posturography", Medical Engineering & Physics, vol. 30, 2008, pp. 367-372.
Giansanti, Daniele, "Investigation of Fall-Risk Using a Wearable Device with Accelerometers and Rate Gyroscopes", Institute of Physics Publishing, Physiological Measurement, vol. 27, 2006, pp. 1081-1090.
Grundy et al. "Telemedicine in Critical Care: An Experiment in Health Care Delivery." Oct. 1977.
Grundy et al. "Telemedicine in Critical Care: Problems in design, implementation and assessment." vol. 10, No. 7. Jul. 1982.
Gunningberg et al., "Improved Quality and Comprehensiveness in Nursing Documentation of Pressure Ulcers after Implementing an Electronic Health Record in Hospital Care", Journal of Clinical Nursing, 2009, vol. 18, pp. 1557-1564.
Harada et al., "Portable Orientation Estimation Device Based on Accelerometers, Magnetometers and Gyroscope Sensors for Sensor Network", IEEE Conference on Multisensor Fusion and Integration for Intelligent Systems 2003, 2003, pp. 191-196.
Hwang et al., "Development of Novel Algorithm and Real-time Monitoring Ambulatory System Using Bluetooth Module for Fall Detection in the Elderly", Proceedings of the 26th Annual International Conference of the IEEE EMBS, Sep. 1-5, 2004, pp. 2204-2207.
International Search Report and Written Opinion received in PCT Application No. PCT/US2022/053988 on Jun. 26, 2023.
Kärki et al., "Pressure Mapping System for Physiological Measurements", XVIII IMEKO World Congress, Metrology for a Sustainable Development, Sep. 17-22, 2006, Rio de Janeiro, Brazil, pp. 5.
Li et al., "Accurate, Fast Fall Detection Using Gyroscopes and Accelerometer-Derived Posture Information", Conference Paper, Sixth International Workshop on Wearable and Implantable Body Sensor Networks, BSN 2009, Berkeley, CA, USA, Jun. 3-5, 2009, pp. 6.
Lindemann et al., "Evaluation of a Fall Detector Based on Accelerometers: A Pilot Study", Medical & Biological Engineering & Computing, vol. 43, 2005, pp. 548-551.
Linder-Ganz et al., "Real-Time Continuous Monitoring of Sub-Dermal Tissue Stresses Under the Ischial Tuberosities in Individuals with Spinal Cord Injury", Proceedings of the ASME 2008 Summer Bioengineering Conference (SBC2008), Jun. 25-29, 2008, Marriott Resort, Marco Island, Florida, p. 2.
Luo et al., "A Dynamic Motion Pattern Analysis Approach to Fall Detection", 2004 IEEE International Workshop on Biomedical Circuits & Systems, Dec. 1-3, 2004, pp. S2.1-5 - S2.1-8.
Masimo Sleep™, posted at masimopersonalhealth.com, no posting date, retrieved Nov. 17, 2021, online, https://www.masimopersonalhealth.com/pages/masimo-sleep (Year: 2021).
Masimo, "Radius-7—The Power of Masimo's Breakthrough Measurements in a Patient-worn Monitor," 2015, in 2 pages.
Mathie et al., "A System for Monitoring Posture and Physical Activity Using Accelerometers", Engineering in Medicine and Biology Society, 2001. Proceedings of the 23rd Annual International Conference of the IEEE, Oct. 25-28, 2001, pp. 3654-3657.
McInerney, Joan A., "Reducing Hospital-Acquired Pressure Ulcer Prevalence Through a Focused Prevention Program", Advances in Skin & Wound Care, vol. 21, No. 2, Feb. 2008, pp. 75-78.
Merbitz et al., "Wheelchair Push-ups: Measuring Pressure Relief Frequency", Archives of Physical Medicine and Rehabilitation, vol. 66, No. 7, Juy 1985, pp. 433-438.
Narayanan et al., "Falls Management: Detection and Prevention, Using a Waist-Mounted Triaxial Accelerometer", Proceedings of the

(56) References Cited

OTHER PUBLICATIONS

29th Annual International Conference of the IEEE EMBS Cité Internationale, Lyon, France, Aug. 23-26, 2007, pp. 4037-4040.
Notice of Allowance received in Taiwan Patent Office Application No. 108302030, dated Aug. 14, 2020 in 6 pages.
Notice of Allowance received in Taiwan Patent Office Application No. 108302035, dated Mar. 13, 2020 in 6 pages.
Notice of Allowance received in Taiwan Patent Office Application No. 108302046, dated Mar. 18, 2020 in 6 pages.
Notice of Allowance received in Taiwan Patent Office Application No. 109301079, dated Jul. 8, 2020 in 6 pages.
Notice of Allowance received in Taiwan Patent Office Application No. 109301080, dated Jul. 7, 2020 in 6 pages.
Notice of Allowance received in Taiwan Patent Office Application No. 109301129, dated Jul. 8, 2020 in 6 pages.
Notice of Allowance received in Taiwan Patent Office Application No. 109301130, dated Jul. 8, 2020 in 6 pages.
Notice of Allowance received in Taiwan Patent Office Application No. 109303055, dated Jan. 21, 2021 in 6 pages.
Notice of Allowance received in Taiwan Patent Office Application No. 109303056, dated Jan. 21, 2021 in 6 pages.
Notice of Allowance received in Taiwan Patent Office Application No. 109303057, dated Jan. 21, 2021 in 6 pages.
Noury, Norbert, "A Smart Sensor for the Remote Follow Up of Activity and Fall Detection of the Elderly", 2nd Annual International IEEE-EMBS Special Topic Conference on Microtechnologies in Medicine & Biology, May 2-4, 2002, pp. 314-317.
Nyan et al., "A Wearable System for Pre-Impact Fall Detection", Journal of Biomechanics, vol. 41, 2008, pp. 3475-3481.
Nyan et al., "Garment-Based Detection of Falls and Activities of Daily Living Using 3-Axis MEMS Accelerometer", Institute of Physics Publishing, International MEMS Conference 2006, Journal of Physics: Conference Series 34, 2006, pp. 1059-1067.
O'Donovan et al., "A Context Aware Wireless Body Area Network", Pervasive Health, 2009, pp. 8.
Patil et al., "Telemonitoring Physiological Parameters of a Patient from a Distance by Near Field Communication Mobile", 2014 Fourth International Conference on Advanced Computing & Communication Technologies, pp. 345-348.
Pérolle et al., "Automatic Fall Detection and Activity Monitoring for Elderly", Jan. 2007, pp. 6.
Philips, "Small, lightweight, and cableless—Philips Mobile CL cuffs, sensors, and accessories" brochure, 2013, in 2 pages.
Po et al., "Overview of MEMSWear II—Incorporating MEMS Technology Into Smart Shirt for GeriatricCare", Institute of Physics Publishing, International MEMS Conference 2006, Journal of Physics: Conference Series 34, 2006, pp. 1079-1085.
Prado et al., "Distributed Intelligent Architecture for Falling Detection and Physical Activity Analysis in the Elderly", Proceedings of the Second Joint EMBS/BMES Conference, Oct. 23-26, 2002, pp. 1910-1911.
"Radius PPG™ Tetherless Pulse Oximetry", masimo.com, site visited Mar. 18, 2022: https://www.masimo.com/products/sensors/radius-ppg/, pp. 2.
Rithalia et al., "Quantification of Pressure Relief Using Interface Pressure and Tissue Perfusion in Alternating Pressure Air Mattresses", Archives of Physical Medicine and Rehabilitation, vol. 81, Oct. 2000, pp. 1364-1369.
Rysavy, "Making the Call with Two-Way Paging", Network Computing, Published Jan. 15, 1997, www.rysavy.com/Articles/twoway.htm.
Sakai et al., "Continuous Monitoring of Interface Pressure Distribution in Intensive Care Patients for Pressure Ulcer Prevention", Journal of Advanced Nursing, vol. 65, No. 4, 2009, pp. 809-817.
Spillman Jr., et al., "A 'Smart' Bed for Non-Intrusive Monitoring of Patient Physiological Factors", Measurement Science and Technology, Aug. 2004, vol. 15, No. 8, pp. 1614-1620.
Wachter, S. Blake; Journal of the American Medical Informatics Association; The Employment of an Iterative Design Process to Develop a Pulmonary Graphical Display; vol. 10, No. 4, Jul/Aug. 2003; pp. 363-372.
Wayback Machine search for "Masimo Sleep™", first found Sep. 24, 2020, retrieved Nov. 17, 2021, online, https://web.archive.org/web/20200924015943/https://www.masimopersonalhealth.com/pages/masimo-sleep (Year: 2020), pp. 8.
Webster, John G., "A Pressure Mat for Preventing Pressure Sores", IEEE Engineering in Medicine & Bioloogy Society 11th Annual International Conference, 1989, pp. 2.
Williams et al., "A Remote Electronic Monitoring System for the Prevention of Pressure Sores",Proceedings of the 19th International Conference, IEEE/EMBS Oct. 30-Nov. 2, 1997, Chicago, IL, pp. 1076-1079.
Wu et al., "Portable Preimpact Fall Detector With Inertial Sensors", IEEE Transactions on Neural Systems and Rehabilitation Engineering, vol. 16, No. 2, Apr. 2008, pp. 178-183.
Yongwu, Shi, "Research progress of wearable medical devices", Medical Equipment, Mar. 2018, vol. 31, No. 5, pp. 3.

* cited by examiner

SYSTEM FOR TRANSMISSION OF SENSOR DATA USING DUAL COMMUNICATION PROTOCOL

RELATED APPLICATIONS

This application is a continuation-in-part of U.S. patent application Ser. No. 16/599,017, filed Oct. 10, 2019, entitled SYSTEM FOR TRANSMISSION OF SENSOR DATA USING DUAL COMMUNICATION PROTOCOL, which claims the benefit of U.S. Provisional Application No. 62/744,988, filed Oct. 12, 2018, entitled SYSTEM FOR TRANSMISSION OF SENSOR DATA USING DUAL COMMUNICATION PROTOCOL. This application claims the benefit of U.S. Provisional Application No. 63/023,711, filed May 12, 2020, entitled SYSTEM FOR TRANSMISSION OF SENSOR DATA USING DUAL COMMUNICATION PROTOCOL and U.S. Provisional Application No. 63/062,939, filed Aug. 7, 2020, entitled SYSTEM FOR TRANSMISSION OF SENSOR DATA USING DUAL COMMUNICATION PROTOCOL. The entire disclosure of each of the above-identified applications is incorporated by reference and made part of this specification.

FIELD OF THE DISCLOSURE

The present disclosure relates to physiological sensors and wireless pairing devices. More specifically, the present disclosure relates to collection of physiological data using physiological sensors and transmitting the data to nearby computing systems using a wireless pairing device.

BACKGROUND

Conventional physiological measurement systems are limited by the patient cable connection between sensor and monitor. A patient must be located in the immediate vicinity of the monitor. Also, patient relocation requires either disconnection of monitoring equipment and a corresponding loss of measurements or an awkward simultaneous movement of patient equipment and cables. Various devices have been proposed or implemented to provide wireless communication links between sensors and monitors, freeing patients from the patient cable tether.

SUMMARY

This disclosure describes, among other things, embodiments of systems, devices, and methods for collecting patient physiological data and transmitting the data to nearby computing systems via wireless transmission.

According to one aspect of the present disclosure, a system for collecting physiological data from a patient is disclosed. The system can include a disposable module and a reusable module. The disposable module can include a sensor element that can collect physiological data from a patient, a memory, and a battery. The reusable module can include a processor, a memory, and a wireless communication module that can establish a wireless communication with a patient monitoring system. The memory of the reusable module can store the physiological data prior to the wireless communication module establishing the wireless communication. The processor of the reusable module can receive the physiological data from the sensor element of the disposable module when the reusable module is coupled with the disposable module.

The system can include one or more of following features: the disposable module can include a dock coupled to the attachment mechanism and a housing. The housing can house the memory and the battery. The sensor element can be housed within the housing. The sensor element can be coupled to the housing via a cable assembly. The processor of the reusable module can transmit sensor signal to the sensor element of the disposable module. The sensor signal can cause the sensor element to collect the physiological data from the patient. The wireless communication module can establish the wireless communication with the patient monitoring system when the wireless communication module is within a predetermined distance from the patient monitoring system. The wireless communication module can transmit an identification information to the patient monitoring system when the wireless communication module is within the predetermined distance from the patient monitoring system. The patient monitoring system, upon receiving the identification information from the wireless communication module, can create association with the wireless communication module. The identification information can include an identifier that uniquely identifies the disposable module. The patient monitoring system can use the identifier to establish the wireless communication with the reusable module. The disposable module can include an attachment mechanism, wherein the attachment mechanism can couple the disposable module to the patient. The attachment mechanism can be a hospital band. The attachment mechanism can include a radio frequency identifier. The battery of the disposable module can provide power for the reusable module when the disposable module is coupled with the reusable module. The memory of the reusable module can store the physiological data between about 6 hours and about 30 days. The memory of the reusable module may store the physiological data for a length of time prior to establishing or detecting wireless communication. The length of time may be provided by a user and may be user configurable. In some cases, the user may not provide the length of time for storing the physiological data within the memory of the reusable module. The memory of the reusable module can store the physiological data for a default length of time, for example, prior to the wireless communication module of the reusable module establishing wireless communication. The default length of time may be stored within the memory of the reusable module. The physiological data can be collected and stored in the memory of the disposable module when irregularities are sensed. The irregularities can include at least one of: low blood pressure readings, high blood pressure readings, low respiratory rate readings, high respiratory rate readings, blood oxygen desaturations, irregular heartbeats, consistently low or declining blood oxygen saturation readings, low heart rates, or high heart rates. The processor of the reusable module can transmit the physiological data to a local or a remote storage when a wireless communication between the wireless communication module and an online server is established. The transmission of the stored physiological data can occur automatically or manually. The physiological data collected by the sensor element can have high fidelity. The physiological data collected by the sensor element can have low fidelity. The fidelity of the physiological data stored in the memory can vary. The fidelity of the stored physiological data can vary based at least in part on a length of time specified for storing the physiological data within the memory of the reusable module. The fidelity of the stored physiological data can vary based at least in part a type of physiological data or a type of health-related events. The fidelity of the physiological data collected by the sensor element can vary. The fidelity of the physiological data collected by the sensor element can vary based at least in part on a length of time specified for storing the physiological data within the memory of the reusable module. The fidelity of the stored physiological data collected by the sensor element can vary based at least in part a type of physiological data or a type of health-related events. The physiological data stored in the memory of the reusable module may be downloaded when the battery of the disposable module is depleted. The memory can store the physiological data collected by the sensor element from time reusable module is attached to the disposable module until time the reusable portion is detached from the disposable module or the battery of the disposable module fails.

According to another aspect of the present disclosure, a method for collecting physiological data from a patient using a reusable module that can couple with a disposable module including a non-invasive sensor element is disclosed. The method can include detecting a coupling between a reusable module and a disposable module. The method can further include collecting physiological data from the disposable module, wherein the physiological data is collected via a sensor element of the disposable module, and wherein the physiological data is stored within the memory of the reusable module. The method can further include establishing a wireless communication with a remote computing device. The method can further include transmitting the physiological data to the remote computing device via the wireless communication.

The method can include one or more of following features: the physiological data can be stored within the memory of the reusable module for a length of time prior to establishing the wireless communication, wherein the length of time can range between about 6 hours to about 30 days. The length of time can be configurable via a configuration provided by a care provider. The memory can store a default length of time and, when the length of time is not provided, the physiological data can be stored within the memory of the disposable module for the default length of time prior to the wireless communication established between the reusable module and the remote computing device. The physiological data can include health-related events related to the patient. The physiological data can be collected and stored when irregularities are sensed. The irregularities can include at least one of: low blood pressure readings, high blood pressure readings, low respiration rate readings, high respiration rate readings, blood oxygen desaturations, irregular heartbeats, consistently low or declining blood oxygen saturation readings, low heart rates, or high heart rates. The physiological data can be transmitted to the remote computing device when the wireless communication is established. Fidelity of the physiological data can vary at least in part on a length of time specified for storing the physiological data within the memory of the reusable module. The fidelity of the physiological data can vary based at least in part a type of physiological data or a type of health-related events. The physiological data stored in the memory of the reusable module may be downloaded when the battery of the disposable module is depleted.

According to another aspect of the present disclosure, a system for collecting physiological data from a patient is disclosed. The system can include a reusable module and a disposable module. The reusable module can include a processor, a first memory, and a wireless communication module configured to establish a wireless communication with a patient monitoring system. The disposable module can include a sensor element that can collect physiological data from a patient, a memory, and a battery. The memory can store operation data associated with the sensor element. The disposable module can be validated based at least in part on the operation data. The first memory can store the physiological data collected by the sensor element of the disposable module.

The system can include one or more of following features: The operation data can include sensor type information associated with the disposable module. The sensor type information can indicate one or more types of sensors associated with the disposable module. The reusable module assembly can be associated with a sensor type, and wherein the disposable module can be validated based at least in part on a comparison between the sensor type associated with the reusable module assembly and the sensor type information associated with the disposable module. Sensor life expectancy can be determined based at least in part on the operation data and sensor life data, and wherein the sensor life expectancy can represent the expected operation time of the disposable module. The sensor life data can include sensor use information and one or more functions, and wherein sensor life data can be stored in the memory of the disposable module. The sensor life expectancy can be automatically updated when there is a change in patient condition or a change in operation condition for the disposable module. The physiological data can be stored in the first memory for a length of time. The length of time can range between about 6 hours to about 30 days. The length of time can be configurable via a configuration provided by a care provider. The first memory can store a default length of time, and wherein the first memory can store the physiological data for the default length of time prior to the wireless communication module establishing the wireless communication when the length of time is not provided. The physiological data can include health-related events related to the patient. The physiological data can be stored when irregularities are sensed. The irregularities may include at least one of: low blood pressure readings, high blood pressure readings, low respiratory rate readings, high respiratory rate readings, blood oxygen desaturations, irregular heartbeats, consistently low or declining blood oxygen saturation readings, low heart rates, or high heart rates. The processor of the reusable module can transmit the stored physiological data to a local or a remote storage via the wireless communication module when a wireless communication between the wireless communication module and an online server is established. The transmission of the stored physiological data can occur automatically or manually. The physiological data collected by the sensor element can have high fidelity. The physiological data collected by the sensor element can have low fidelity. Fidelity of the physiological data stored in the memory can vary. The fidelity of the stored physiological data can vary based at least in part on the predetermined length of time. The fidelity of the stored physiological data can vary based at least in part a type of physiological data or a type of health-related events. Fidelity of the physiological data collected by the sensor element can vary. The fidelity of the physiological data collected by the sensor element can vary based at least in part on the predetermined length of time. The fidelity of the stored physiological data collected by the sensor element can vary based at least in part a type of physiological data or a type of health-related events. The memory can store the physiological data collected by the sensor element from time reusable module is attached to the disposable module until time the reusable portion is detached from the disposable module or the battery of the disposable module fails.

According to another aspect of the present disclosure, a method of validating a disposable module is disclosed. The method can include detecting a coupling between a disposable module and a reusable module. The method can further include accessing operation data associated with the disposable module. The method can further include analyzing the operation data. The method can further include, based at least in part on the analysis of the operation data, validating the disposable module.

The method can include one or more of following features: detecting the coupling between the disposable module and the reusable module can include determining that the reusable module is receiving power from the disposable sensor module. The disposable module can include a memory that can store the operation data. Analyzing the operation data can include identifying sensor type information form the operation data. comparing the sensor type information with a sensor type associated with the reusable module, and based at least in part on the comparison between the sensor type information with a sensor type associated with the reusable module, determining that the disposable module is compatible with the reusable transmitter module.

For purposes of summarizing the disclosure, certain aspects, advantages, and novel features have been described herein. Of course, it is to be understood that not necessarily all such aspects, advantages, or features will be embodied in any particular embodiment.

DETAILED DESCRIPTION

Introduction

Figure 1:
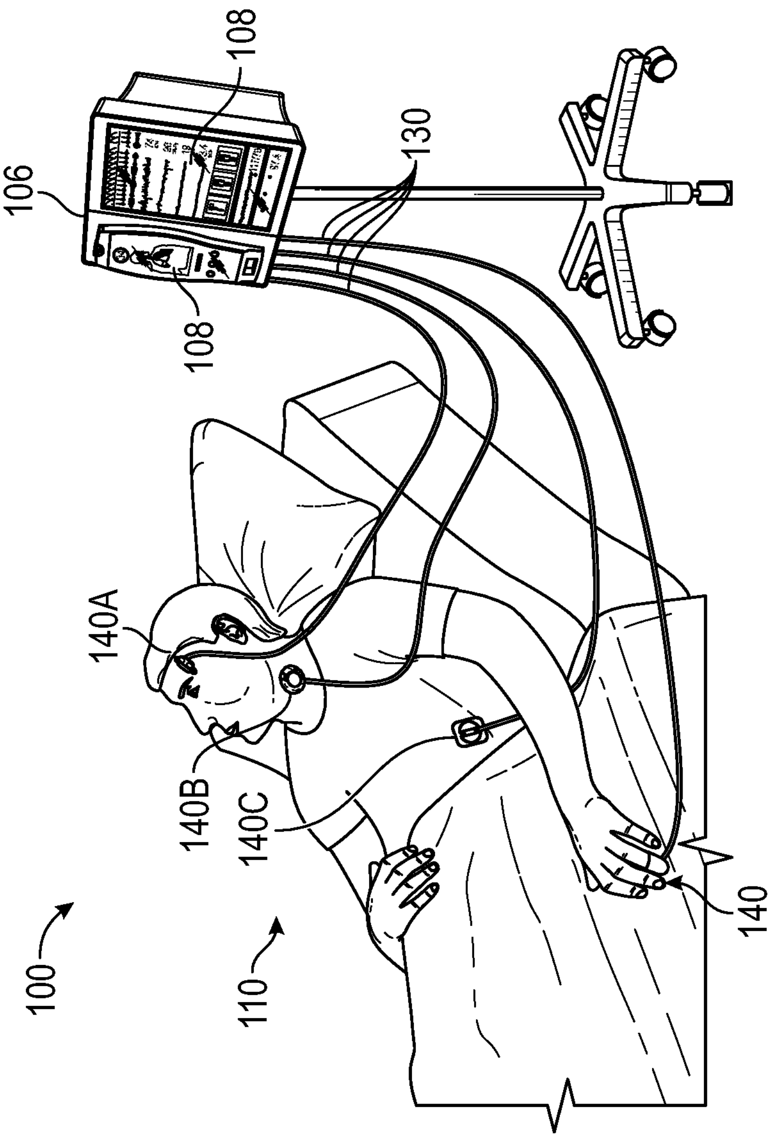
FIG. 1 (Prior Art)
FIG. 1 illustrates an embodiment of a sensor system including sensors attached to a patient and transmitting patient physiological data to a computing device via cable.

Wired solution for sensors may be cumbersome and difficult to manage when there are multiple sensors attached to a patient as shown in FIG. 1. For example, the cable for the sensors can be tangled and damaged after repeated use. Moreover, since the sensors are tethered to a patient health monitor, patients have to be located proximate to the health monitor and movement of the patients can be limited. If a longer cable is required, the sensor and the cable have to be replaced together. Similarly, the sensors being tethered to the monitor can make transportation of the patient very difficult as it would require the patient to remain close to the monitor during transportation or disconnecting the sensors which would result in loss of measurements.

Overview

FIG. 1 illustrates an example of a sensor system 100 including a computing device 106 coupled sensors 140A, 140B, 140C, 140D via a cable 130, where the sensors are attached to a patient 110. The computing system 106 can include a display 108 that can display various physiological parameters. The sensors 140A, 140B, 140C, 140D can collect various types of physiological data from the patient 110 and transmit the data to the computing system 106 via the cable 130. Some example of the sensors 140A, 140B, 140C, 140D include, but not limited to, a rainbow acoustic monitoring sensor (RAM), O3 Regional Oximetry sensor, SpO2 sensor, a blood pressure sensor, an ECG sensor, and the like.

However, the cables 130 can be cumbersome to the patient and prone to tangling. The cables 130 can develop kinks and be damaged over time. In addition, because the sensors 140A, 140B, 140C, 140D are connected to the computing system 106 via the cables 130, location of the computing system 106 can be restricted to the lengths of the cables 130 attached to the sensors 140A, 140B, 140C, 140D. The cables 130 can also restrict patient movements. Therefore, a wireless solution including wireless communication capacity between the sensors and the computing device may resolve some of the concerns of the wired configuration. The wireless configuration can eliminate the need of the cables 130 between the sensors and the computing device and thus provide greater patient mobility.

However, the wireless solutions may have their own limitations. For example, wireless patient monitoring sensors require internal power source (for example, battery), which can have limited capacity due to size of the sensors. In addition, since continuous data collection and wireless transmission can require significant power usage, operation of the sensors can be very limited. Moreover, it may be expensive to replace the entire device when the internal battery is depleted. Furthermore, having a rechargeable battery may not be suitable in a hospital environment where nurses might not have enough time to wait for the battery to recharge. Also, it may not be ideal for a patient to wait for the battery to recharge in time of need. Accordingly, it can be advantageous to provide a sensor system that is compatible with existing sensors and monitors and is capable of wireless communication as discussed herein.

Figure 2A:
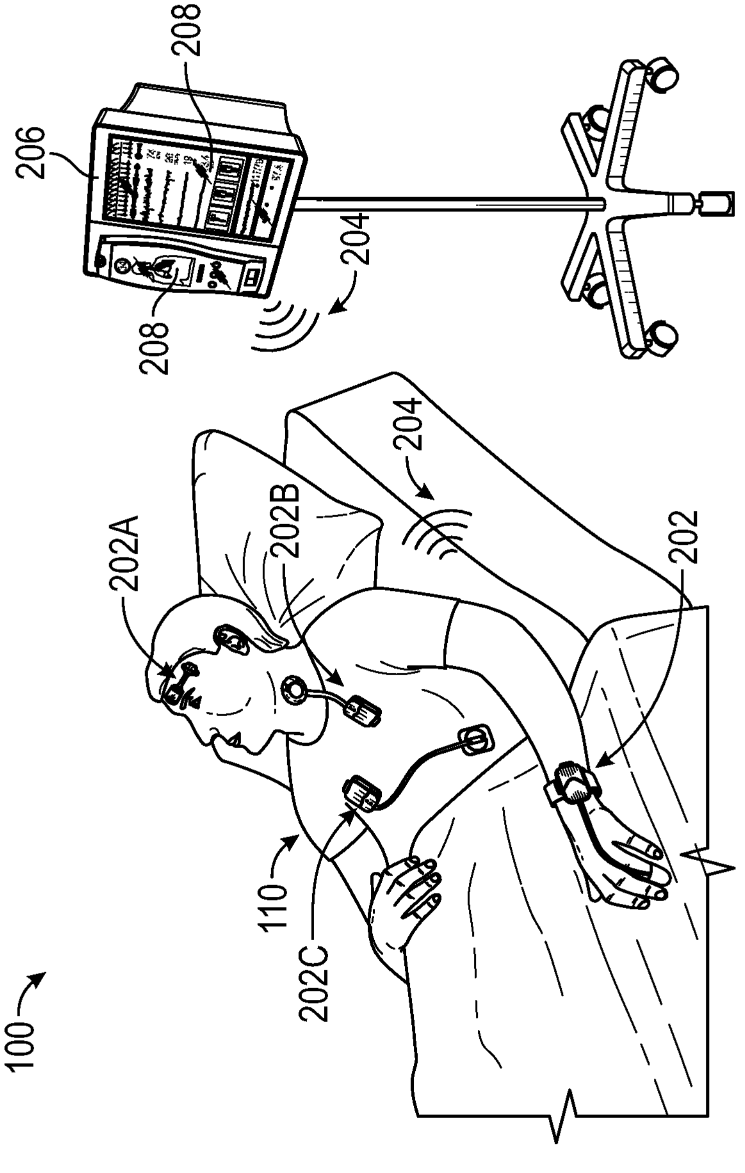
FIG. 2A illustrates another embodiment of a sensor system including sensor assemblies collecting and wirelessly transmitting patient physiological data to a computing device.

FIG. 2A illustrates the sensor system 100 including a computing device 206 wirelessly receiving patient physiological data of the patient 110 from sensor assemblies 202A, 202B, 202C, 202D. The sensor assemblies 202A, 202B, 202C, 202D can establish communication with the computing device 206 such that data can be wirelessly transmitted between the sensor assemblies 202A, 202B, 202C, 202D and the computing device 206. The computing device 206 can include a display 208 that can display patient parameters determined from the patient physiological data received from the sensor assemblies 202A, 202B, 202C, and 202D.

Figure 2B:
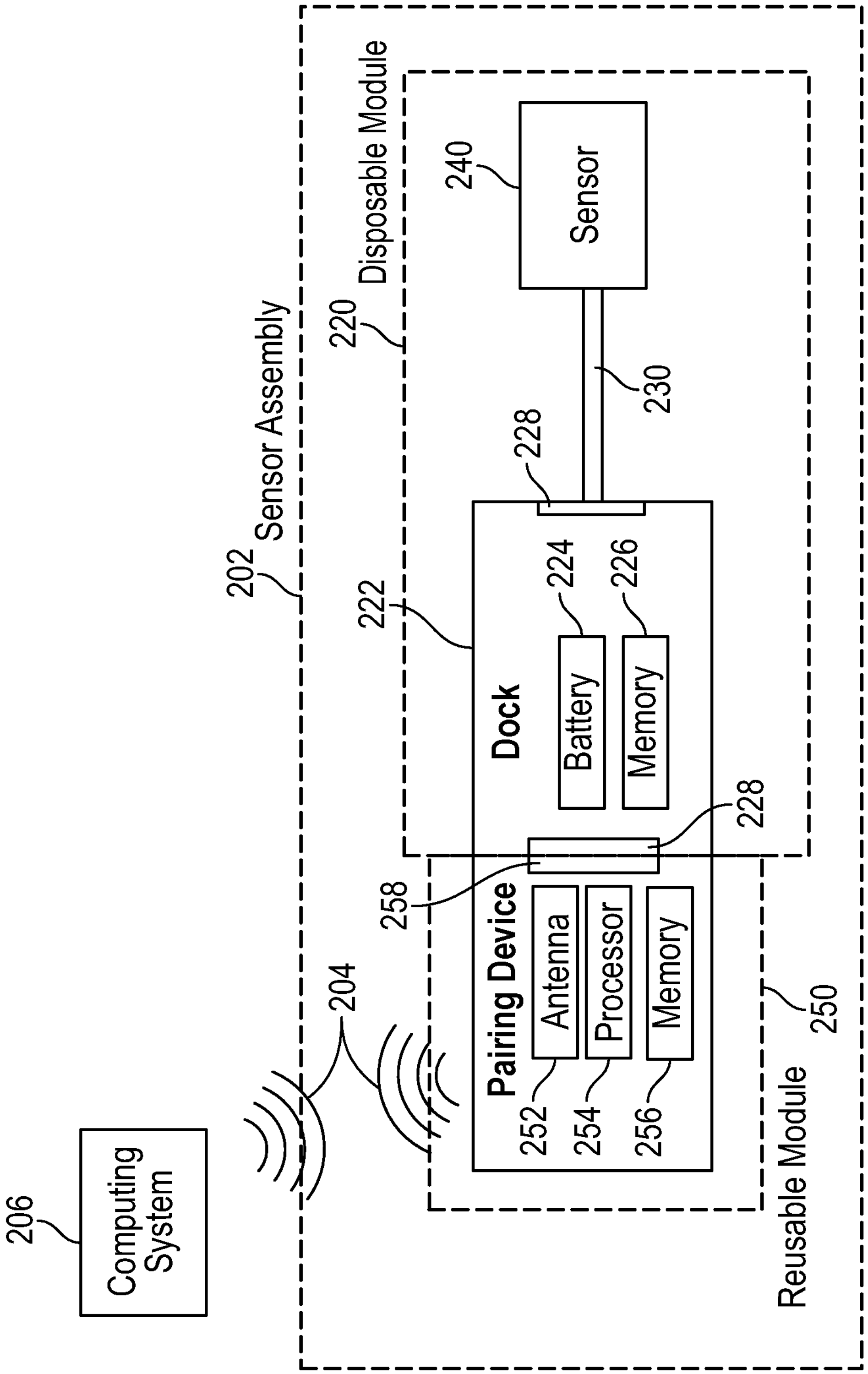
FIG. 2B illustrates a schematic diagram of an embodiment of a sensor assembly and a computing device, showing additional details of the sensor assembly.

FIG. 2B illustrates a schematic diagram the sensor assembly 202 wirelessly connected to a computing device 206. The sensor assembly 202 can include a disposable module 220 and a reusable module 250. The reusable module 250 can be a pairing device capable of establishing wireless connection with the computing device 206. In some implementations, reusable module 250 is a transmitter device that can transmit to and receive data from nearby computing devices, for example, the computing device 206.

The disposable module 220 can include a dock 222 coupled to a sensor 240 via a cable 230. The dock 222 can be removably connected to the reusable module 250. The reusable module 250 and the computing device 206 can together establish a wireless communication 204 and perform wireless transmission of data between. The reusable module 250 can transmit patient physiological parameters to the computing device 206, where the parameters are calculated from raw physiological data collected by the sensor 240. The transmitted patient data can be raw data collected by the sensor 240.

The reusable module 250 alone or in combination with the dock 222 can perform signal processing on the raw physiological data and transmit the processed physiological data to the computing device 206. The reusable module 250 can establish wireless communication 204 with the computing device 206 to allow data be transmitted between the reusable module 250 and the computing device 206. The reusable module 250 can establish wireless communication 204 with one or more computing devices 206. As shown in FIG. 2A, the computing device 206 can establish wireless communication 204 with the sensor assemblies 202A, 202B, 202C, and 202D. The computing device 206 can establish wireless communication 204 with less than four or more than four sensor assemblies 202.

The reusable module 250 can establish wireless communication 204 with portable mobile devices such as mobile phone, smartphone, tablets, and the like. The computing device 206 can be a hospital patient monitoring system, which includes various types of monitors capable of displaying patient health data. The computing device 206 can be a mobile monitoring system or a personal mobile device. The computing device 206 can be Root® Platform, a patient monitoring and connectivity platform available at Masimo Corporation, Irvine, Calif. A mobile physiological parameter monitoring system usable with the cable is described in U.S. Pat. No. 9,436,645, issued on Sep. 6, 2016, titled "MEDICAL MONITORING HUB," the disclosure of which is hereby incorporated by reference in its entirety.

The cable 230 can be flexible or non-flexible. The cable 230 can be a thin film including electrical circuitries. The cable 230 can be surrounded by different types of electrical insulating material. The cable 230 can be substantially flat or round.

The sensor 240 can be an acoustic sensor, ECG sensor, EEG sensor, SpO2 sensor, or any other types of patient monitoring sensors. The sensor 240 can include one or more emitters and detectors. The emitters can be low-power, high-brightness LEDs (light-emitting diodes) to increase the life of the batteries 224. The sensor 240 can measure raw physiological data responsive to various types of patient physiological parameters including, but not limited to, temperature, blood pressure, blood oxygen saturation, hemoglobin level, electrocardiogram, and the like. The sensor measurements can be used by physicians to determine patient conditions and treatment for the patient. The sensor 240 can transmit the raw physiological data to the dock 222 via the cable 230. The sensor 240 and the dock 222 may form a unitary body such that the dock 222 receives the physiological data directly from the sensor 240 without the cable 230. The dock 222 can be integrated with one or more of the sensors 340.

The sensor 240 can output a raw sensor signal or a conditioned sensor signal. The sensor 240 can include a signal processor that can process the raw or conditioned sensor signal to derive and calculate physiological parameters associated with the raw or conditioned sensor signal.

The sensor 240 can perform mixed analog and digital pre-processing of an analog sensor signal to generate a digital output signal. As discussed above, the sensor 240 can include a signal processor that can perform digital post-processing of the front-end processor output. The input sensor signal and the output conditioned signal may be either analog or digital. The front-end processing may be purely analog or purely digital. The back-end processing may be purely analog or mixed analog or digital.

The sensor 240 can include an encoder, which translates a digital word or serial bit stream, for example, into a baseband signal. The baseband signal can include the symbol stream that drives the transmit signal modulation, and may be a single signal or multiple related signal components. The encoder can include data compression and redundancy.

The sensor 240 can include a signal processor, an encoder, and a controller. The sensor 240 can utilize emitters 242 and the detectors 244 to generate sensor signals, such as a plethysmograph signal. The signal processor then can use the sensor signal to derive a parameter signal that can include a real time measurement of oxygen saturation and pulse rate. The parameter signal may include other parameters, such as measurements of perfusion index and signal quality. The signal processor can be an MS-5 or MS-7 board available from Masimo Corporation, Irvine, CA. The signal processing step can be performed by the processor 254 of the reusable module 250, as described above.

The dock 222 can be placed on various locations of a patient's body. For example, the dock 222 is placed on the patient's chest. The dock 222 can be placed on other locations on the patient including, but not limited to, torso, back, shoulder, arms, legs, neck, or head. Various means can be used to affix the dock 222 to the patient. For example, the dock 222 is affixed to the patient with an adhesive. In another example, the dock 222 is affixed to the patient with a fastener, such as tape, laid over at least a portion of the dock 222. The dock 222 can be mechanically attachable to at least one strap, which can wrap around the patient.

The reusable module 250 can receive physiological data from the sensor 240 via the dock 222. The reusable module 250 can wirelessly transmit the physiological data to the computing device 206. The reusable module 240 can couple with the dock 222 to establish an electronic communication between the reusable module 250 and the dock 222. The electrical communication between the dock 222 and the reusable module 250 can allow physiological data to be transmitted from the dock 222 to the pairing device 250. The coupling between the reusable module 250 and the dock 222 can be waterproof or shockproof. The disposable module 220 and the reusable module 250 may be shockproof or waterproof. The disposable module 220 and the reusable module 250 can be durable under various types of environments. For example, the reusable module 250 can be fully enclosed, allowing it to be washed, sanitized, and reused.

As shown in FIG. 2B, the dock 222 can include a memory 226 and battery 224. The reusable module 250 can include an antenna 252, a processor 254, and a memory 256. The antenna 252, the processor 254, and the memory 256 can be operatively connected with one another to allow electronic communication or transmission between them.

The antenna 252 can be an RFID (radio-frequency identification) antenna. The antenna 252 can be a Bluetooth® antenna. The reusable module 250 can include one or more antennae 252. In some aspects, the reusable module 250 includes a first antenna and a second antenna, where first antenna is a receiving antenna and the second antenna is a transmitting antenna. The first antenna can be a transmitting antenna and the second antenna can be a receiving antenna. Both the first antenna and the second antenna can both receive data from or transmit data to the computing device 206. The first antenna can be a passive antenna while the second antenna can be an active antenna. The first antenna can be an active antenna while the second antenna can be a passive antenna. An active antenna can include a built-in amplifier that can amplify certain spectrum or frequency of signals. The first antenna can establish an RFID or NFC (near field communication) connection with the computing device 206 while the second antenna can establish a Bluetooth® connection with the computing device 206. In another aspect, both the first and the second antenna are capable of establishing RFID and/or Bluetooth® wireless connection. The process of establishing wireless communication 204 with the computing device 206 and wirelessly transmitting the patient physiological data to the computing device 206 will be further described below in detail.

The memory 256 can be computer hardware integrated circuits that store information for immediate use for a computer (for example, the processor 254). The memory 256 can store the patient physiological data received from the sensor 240. The memory 256 can be volatile memory. For example, the memory 256 is a dynamic random access memory (DRAM) or a static random access memory (SRAM). The memory 256 can be a non-volatile memory. For example, the memory 256 is a flash memory, ROM (read-only memory), PROM (programmable read-only memory), EPROM (erasable programmable read-only memory), and/or EEPROM (electrically erasable programmable read-only memory).

The memory 256 of the reusable module 250 can store patient physiological data received from the sensor 240. The memory 256 can store electronic instructions that, when accessed, prompts the processor 254 to receive patient physiological data from the memory 226 of the dock 222, store the data in the memory 256, retrieve the data from the memory 256, transmit the data to the antenna 252, and use the antenna 252 to wirelessly transmit the data to the computing device 206. One or more of the actions discussed above can be performed simultaneously. For example, the processor 254 of the reusable module 250 can receive patient physiological data from the memory 226 of the dock 222 and simultaneously store the data in the memory 256. In some implementations, the reusable module 250 receives the patient physiological data directly from the sensor 240 without the memory 226 storing the patient physiological data. The memory 226, as described herein, can store other types of data such as operation data and sensor life data.

The memory 256 can store patient physiological data and/or health-related events related to a patient when the sensor assembly 202 is no longer in range with or is otherwise unable to communicate with the computing system 206. The memory 256, as noted above, can have sufficient capacity to store patient health data and/or health-related events. Optionally, the memory 256 can store patient physiological data regardless of whether the reusable module 250 is paired with the computing device 206. Some examples of the health-related events include arrhythmia, low blood pressure, blood oxygen level (SpO2), and the like.

Such data and/or health-related events may be accessed via a mobile application on a mobile device (for example, a smartphone, tablet, and the like). The data collected and stored in the memory 256 may be downloaded and/or transferred to local or remote storage. For example, data can be transferred to a cloud server or doctor's office computer system. The transfer of data can automatically or manually occur when wireless communication between the sensor assembly 202 and, for example, an online server or the computing system 206 is established.

Patient data and/or health-related events can be relayed to a device without a display. In such circumstances, the device can have a light source (for example, an LED) that can, for example, blink in different colors or patterns to tell the patients or medical personnel data has been transferred, an error occurred, the data needs to be reviewed, or something else has happened. Different rules can be used to determine when or in what situations can patient physiological information be transmitted from the sensor assembly 202 to other external devices (for example, monitoring devices, mobile devices, and the like).

In some implementations, the memory 256 may only store patient data and/or health-related events related to a patient when the sensor assembly 202 is no longer in range with or is otherwise unable to communicate with the computing system 206. In some implementations, the patient data and/or health-related events may be stored when irregularities are sensed. The irregularities may include, but not limited to, low blood pressure readings, high blood pressure readings, low respiratory rate readings, high respiratory rate readings, blood oxygen desaturations, irregular heartbeats, consistently low or declining blood oxygen saturation readings, low heart rates, high heart rates, and the like. In some implementations, a combination of irregularities or irregular combination of patient status and/or health parameters may cause the sensor assembly 202 to store patient data and/or health-related events. For example, the sensor assembly 202 can store patient data and/or health-related events when high blood pressure readings and low heartbeat rates. In another example, the sensor assembly 202 can store patient data and/or health-related events when patient movement is low and high heart rate or high blood pressure is detected. In yet another example, the sensor assembly 202 can store patient data and/or health-related events when patient movement is low and blood oxygen level is also low. Any suitable combinations of irregularities or abnormal conditions may be used to trigger the sensor assembly 202 to store patient data and/or health-related events.

In some implementations, the memory 256 may only store select health-related event data. Such a configuration may advantageously maximize or increase the life of the battery 224 and/or the memory 256. For example, this data can be as simple as a time stamp when an event or trigger occurred or it can be a snapshot of data taken just before and just after an event or trigger. Events can include physiologically important events such as a heartbeat abnormality or drop in oxygen saturation. The trigger, indicating the start of an event, can cause a window of data to be stored in the memory. For example, the system can continuously hold a window of data for a certain period of time, for example, 5 minutes. When a trigger is detected, data in the window starting several minutes before the event and leading for several minutes the event can be stored in the memory and held until the data is downloaded to another device. Of course, different amounts of time can be stored before and after a trigger, for example, it could be in the range of 1 second to 24 hours.

In some implementations, the memory 256 can store large amount of data, for example days or weeks of data, prior to establishing wireless communication with, for example, the computing system 206. In some implementations, the memory 256 can store up to 96 hours or more of data prior to establishing wireless communication with, for example, the computing system 206. In some implementations, the memory 256 can store up to 30 days of data. The length of time the sensor assembly 202 can collect and store patient data and/or health-related events prior to establishing wireless communication with, for example, the computing system 206, can vary between about 1 hour and about 30 days, between about 3 hours and about 28 days, between about 6 hours and about 21 days, between about 12 hours and about 14 days, between about 24 hours and 7 days, or about 1 hour, about 3 hours, about 6 hours, about 12 hours, about 24 hours, about 72 hours, about 7 days, about 14 days, about 21 days, about 28 days, about 30 days, or ranges between any two of aforementioned values. In this configuration, the device can be worn by a patient at home for a period of monitoring and then downloaded by a doctor at a doctor's office via a wired or wireless connection. The data can also be stored during a period of time when no network connection is detected and then downloaded as soon as a wired or wireless network connection is detected.

In some implementations, users may provide a length of time for which the memory 256 stores patient physiological data prior to establishing or detecting wireless communication. This can be advantageous in non-critical situations in which real-time patient monitoring and management may not be necessary. For example, a care provider may request a patient to revisit a doctor's office in a week and provide a sensor assembly 202 configured to store patient physiological data in the memory 256 for the next seven days. As such, when the patient visits the doctor's office a week later, the care provider can access the data collected and stored in the memory 256 via the reusable module 250. In some implementations, the sensor assembly 202 may be dropped off at the doctor's office, shipped (e.g., via a mail) to the doctor's office. Additionally or alternatively, the data stored in the memory 256 may be automatically or manually uploaded to and stored in a server (e.g., cloud server) to which the care provider (e.g., a doctor) has an access to. In some implementations, the data stored in the memory 256 may be uploaded via, for example, a web interface or a mobile application interface accessible via a user computing device (e.g., a mobile phone, a laptop computer, a desktop computer, a smart phone, a smart device, and the like) as described herein. The sensor assembly 202 may establish wireless communication (e.g., via Bluetooth®) with user computing devices and upload the data stored in the memory 256 to a server accessible to care providers via network communication (e.g., Wi-Fi, 4G, 4G LTE, 5G, 5G LTE, ZigBee, and the like) available to the user computing devices.

In some implementations, users may provide a frequency at which data is collected and stored in the memory 256. For example, a care provider may provide a sensor assembly 202 configured to collect and store patient physiological data in the memory 256 every other second, every 10 seconds, every minute, every 5 minutes, every 10 minutes, every hour, every day, and the like. This can be advantageous in preventing the sensor assembly 202 from collecting and storing superfluous amount of data, especially in situations in which periodic measurement of, for example, blood oxygen level, blood pressure, heart rate, and the like, is sufficient. Additionally, by adjusting the frequency at which data is collected and stored in the memory 256, the life of the battery 224 and the memory 256 can be extended.

In some implementations, users may configure the sensor assembly 202 to specify a specific time period for collecting patient physiological data. For example, a care provider may wish to collect or measure blood glucose level between 7 a.m. and 10 a.m. every day. In another example, a care provider may wish to collect or measure blood oxygen level once during the morning between 8 a.m. and 10 a.m. and once during the evening between 6 p.m. and 8 p.m. Additionally, users may configure the sensor assembly 202 to specify data collection and storage frequency for a specific time period. The specific time period can be a specific day of a week, a day of a month, and the like. For example, a care provider can configure the sensor assembly 202 to measure heart rate every hour between 6 a.m. and 10 a.m., every 2 hours between 10 a.m. and 6 p.m., and every 3 hours between 6 p.m. and 6 a.m. As such, a sensor assembly 202 may be customized to collect patient physiological data depending on a patient's conditions and physiological data monitored. This can allow care providers to, for example, more easily identify general trends without having to search for data during specific time periods at specific intervals.

In some implementations, the memory 256 may store a default length of time for collecting and storing patient data and/or health-related events prior to establishing wireless communication with, for example, the computing system 206. As described herein, care providers may provide a configuration identifying a certain length of time for the sensor assembly 202 to collect and store patient data and/or health-related events. However, when no such configuration is provided, the sensor assembly 202 may access the default length of time from the memory 256 and proceed to collect and store patient data and/or health-related events. The default length of time may be configurable. The default length of time may vary between about 1 hour and about 30 days. In some implementations, the default length of time may be greater than 30 days.

Figure 15A:
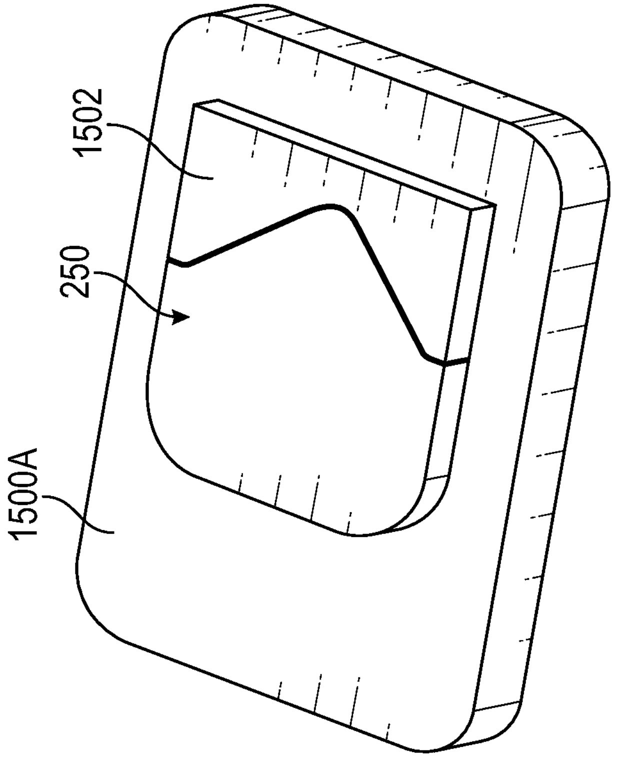
FIGS. 15A and 15B illustrates various embodiments of a backup power device for a sensor assembly.

Since the battery 224 has a limited charge capacity, it may be depleted over time. Since the battery 224 provides power for the reusable module 250, depleted battery 224 may prevent the reusable module 250 from storing patient physiological data in the memory 256 and/or wirelessly transmitting data, for example, to the computing device 206 and/or a remote server. In some implementations, a backup power device 1500A may be used to provide power for the reusable module 250. An example of a backup power device 1500A is shown in FIG. 15A.

The backup power device 1500A may be coupled to the reusable module 250. When coupled to the reusable module 250, the backup power device 1500, as described herein, can provide power for the reusable module 250. The reusable module 250 then can use the power from the backup power device 1500A to access patient physiological data stored in the memory 256 and wirelessly transmit the data to, for example, the computing device 206. The backup power device 1500 can be useful when a replacement disposable device is not readily available. The backup power device 1500A may include one or more electrical contacts that can come into contact with the electrical contacts 258 of the reusable module 250 and allow power to be transmitted from the backup power source 1500A to the reusable module 250. In some implementations, the backup power device 1500A can include a holder 1502 that can hold the reusable module 250 in place. Optionally, the holder 1502 can magnetically hold the reusable module 250 in place. Optionally, the backup power device 1500A may be mounted to a wall.

In some implementations, the backup power device 1500A has an internal power supply device and power from the internal power supply device can be used to provide power for the reusable module 250. Alternatively, as described herein, the backup power device 1500A may be mounted to a wall and can receive power from an external power source, for example, power grid of a building. The power from the external power source can be used to provide power for the reusable module 250.

Figure 15B:
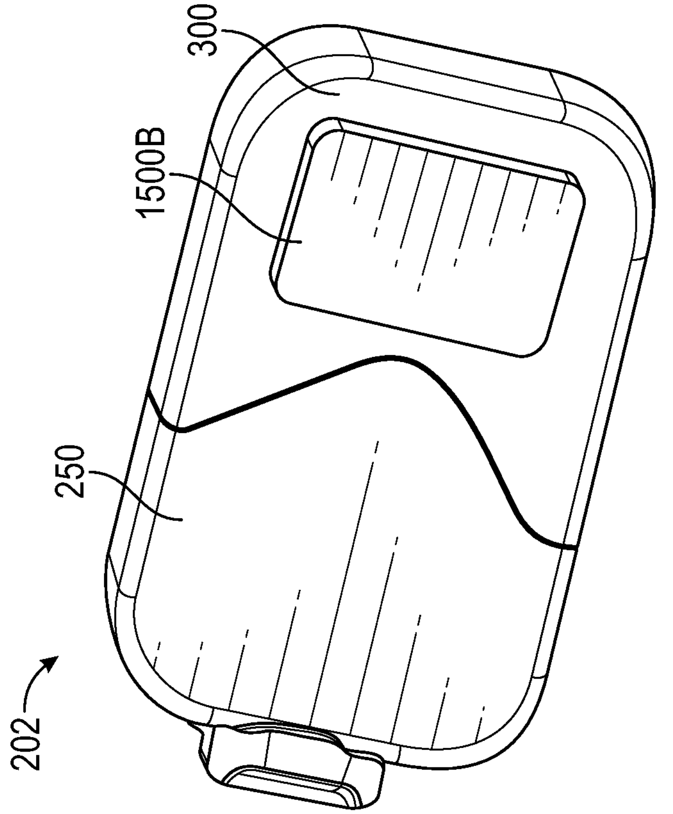

Additionally or alternatively, the backup power device 1500A may wirelessly provide power for the reusable module 250. As such, the backup power device 1500A may be a device with wireless charging capacity. In some implementations, as shown in FIG. 15B, the backup power device 1500B may be magnetically coupled to the sensor assembly 202. In some implementations, the backup power device 1500B may be magnetically coupled to the reusable module 250 or to the disposable module 220 as shown in FIG. 15B. The backup power device 1500 may be able to magnetically attach to the reusable module 250 while the reusable module 250 is coupled to the disposable module 220. As described herein, the backup power device 1500 may wirelessly provide power to the reusable module 250, which can in turn provide the power provided by the backup power device 1500 to the disposable module 220. As such, the backup power device 1500 may be used to power the sensor assembly 202 and allow the sensor assembly 202 to collect and wirelessly transmit patient physiological data. Alternatively, as described herein, the backup power device 1500 can attach to the disposable module 220, for example, the housing 300, to provide power for the batteries 224. As such, the backup power device 1500 may directly provide power for the disposable module 220, which can transmit power to the reusable module 250 for, for example, processing patient physiological data and/or wirelessly transmitting the data to, for example, the computing device 206.

The patient data and/or health-related events stored in the memory 256 may vary in fidelity (that is, the degree to which the patient data collected by the sensor assembly 202 accurately reflects the actual patient data). In some implementations, the fidelity of the patient data (for example, heart rate) may vary based at least in part on the length of time the sensor assembly 202 is configured to collect and store patient data and/or health-related events. For example, the longer the length of time the sensor assembly 202 is configured to collect and store patient data and/or health-related events, the lower the fidelity of the patient data and/or health-related events may be, and vice versa. Such variance in fidelity may be caused by the limited storage capacity of the memory 256.

In some implementations, the fidelity may vary between different patient data or health-related events. In certain situations, certain patient data (for example, blood oxygen level) may be more important than other patient data (for example, body temperature). For example, for patients suffering from Malaria, it may be more important to monitor blood oxygen level more closely than other patient data such as heart rate or core body temperature. Accordingly, care providers may provide fidelity settings for the sensor assembly 202 that provides different level of fidelity for collecting patient data and/or health-related events. In some aspects, the data stored in the memory 256 can be transmitted to an outside server. The memory 256 can transfer the entire patient physiological information to the outside server or transmit only certain portions of the information. For example, the memory 256 can transmit timestamp information and associated event information to the external server.

In another example, the memory 256 can transmit a snapshot of patient physiological information.

The processor 254 can be a chip, an expansion card/board, or a stand-alone device that interfaces with peripheral devices. For example, the processor 254 is a single integrated circuit on a circuit board for the reusable module 250. The processor 254 can be a hardware device or a software program that manages or directs the flow of data.

The processor 254 can communicate with the antenna 252 and the memory 256 of the reusable module 250. For example, the processor 254 communicates with the antenna 252 and the memory 256 of the reusable module 250 to retrieve or receive patient physiological data and to transmit the data to external devices via the antenna 252. The processor 254 can be a Bluetooth® chipset. For example, the processor 254 is a SimpleLink™ Bluetooth® low energy wireless MCU (microcontroller unit) by Texas Instruments Incorporated.

The processor 254 of the reusable module 250 can be connected to the sensor 240 such that it receives patient physiological data from the sensor 240 when the reusable module 250 is mated with the dock 222. The processor 254 can retrieve the patient physiological data from the memory 226 of the dock 222 and transmit the data to the antenna 252. The processor 254 can be operatively connected to the antenna 252 such that the processor 254 can use the antenna 252 to wirelessly transmit the patient physiological parameters to the computing device 206. The patient physiological data transmitted from the reusable module 250 to the computing device 206 can be raw patient physiological data in analog format (for example, 1131001310113100) or patient physiological parameters in a digital format (for example, 60% SpO2).

The sensor 240 can transmit raw or analog patient physiological data to the processor 254 of the reusable module 250. The processor 254 can then perform signal processing on the raw data to calculate patient physiological parameters. It can be advantageous to have the processor 254 to perform signal processing on the raw patient physiological data instead of having the computing device 206 perform signal processing on the raw data. Raw data can comprise strings of binary bits, whereas processed data can comprise digital (not binary) data (for example, 36 degrees Celsius, 72 beats per minute, or 96% blood oxygen level). Therefore transmitting digital data can require less power consumption than transmitting raw data. Thus, by performing signal processing on the raw data using the processor 254 and transmitting the processed data (as opposed to raw data) to the computing device 206, life of the battery 224 can be extended.

The battery 224 of the dock 222 can provide power for the sensor 240. Additionally, the battery 224 can provide power for the reusable module 250. In some aspects, the reusable module 250 may not have an internal power source to transmit patient data to the computing device 206. When the reusable module 250 is mated with the dock 222, the processor 254 of the reusable module 250 can draw power from the battery 224. The processor 254 can use the power from the battery 224 to process patient physiological data from the sensor 240 and to wirelessly transmit the data to the computing device 206. The battery 224 may or may not be rechargeable. The battery 224 can have wireless charging capacity.

Figure 2C:
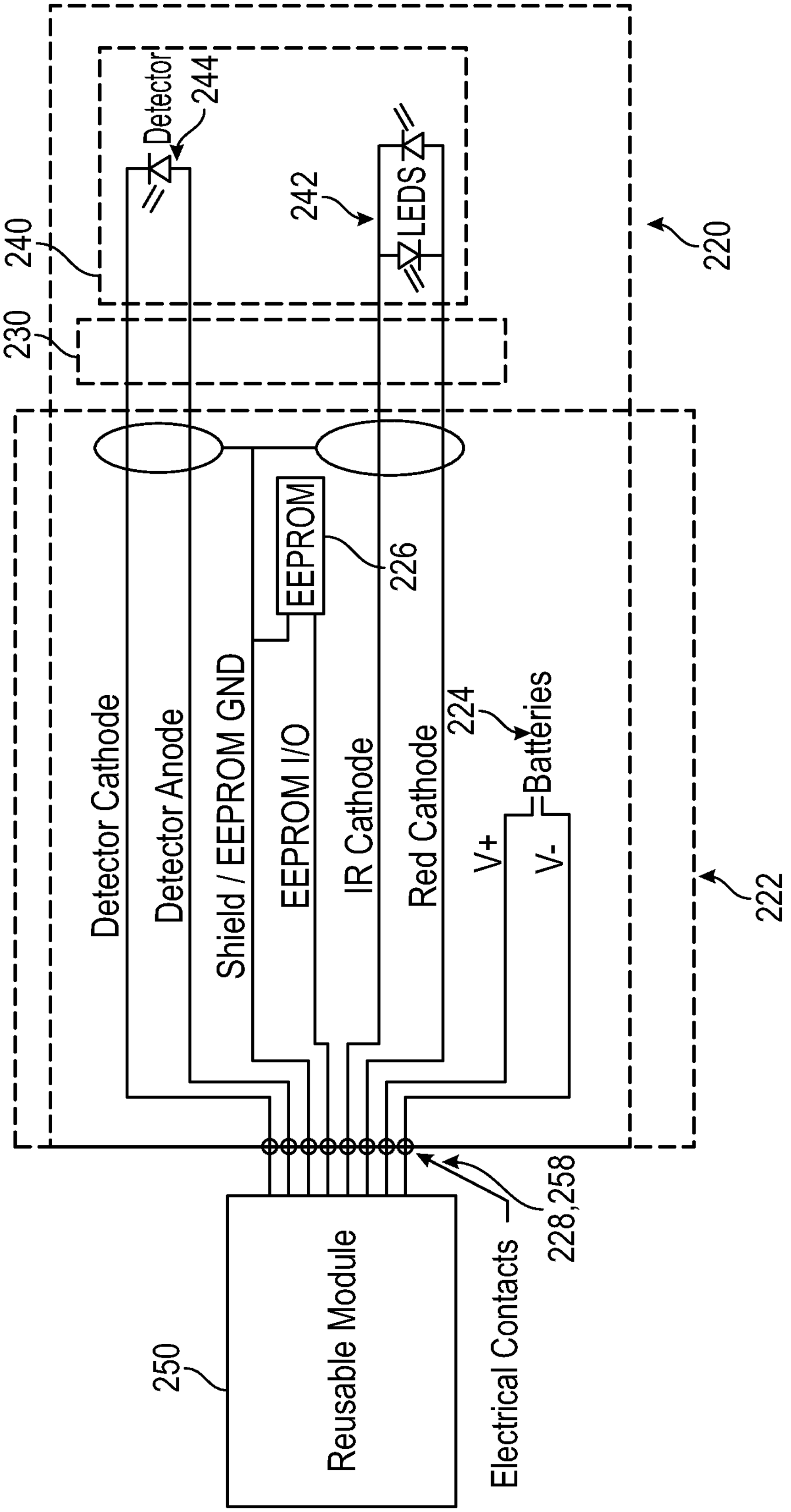
FIG. 2C illustrates a wiring diagram of an embodiment of a sensor assembly.

FIG. 2C illustrates a wiring diagram for the sensor system 202. The sensor 240 can include one or more detectors 244 and one or more emitters 242. The detectors 244 and the emitters 242 can be optical. The emitters 242 can be LEDs. The detectors 244 can detect light generated by the emitters 242. The emitters 242 and the detectors 244 are used to collect different types of patient physiological data, such as blood oxygen level, heart rate, and respiratory rate. As discussed below, the sensor 240 can include one of the following sensor elements including, but not limited to, piezoelectric elements for acoustic sensors, electrodes for EEG sensors, electrodes for ECG sensors, and the like.

The dock 222 and the reusable module 250 can include one or more electrical contacts 228 and electrical contacts 258, respectively. The electrical contacts 228 and 258 can establish electronic communication between the dock 222 and the reusable module 250 when the reusable module 250 is mated with the dock 222. The electrical communication between the electrical contacts 228 and 258 can allow the reusable module 250 to receive power from the battery 224 of the disposable module 220. Additionally and/or alternatively, the electrical connection between the electrical contacts 228 and 258 can allow the reusable module 250 to receive patient physiological data from the memory 226 of the dock 222. In some implementations, the reusable module 250 receives the patient physiological data from the sensor 240 such that the memory 226 does not store the patient physiological data. The coupling of the reusable module 250 and the dock 222 will be further described below.

Sensor Assembly

Figure 3A:
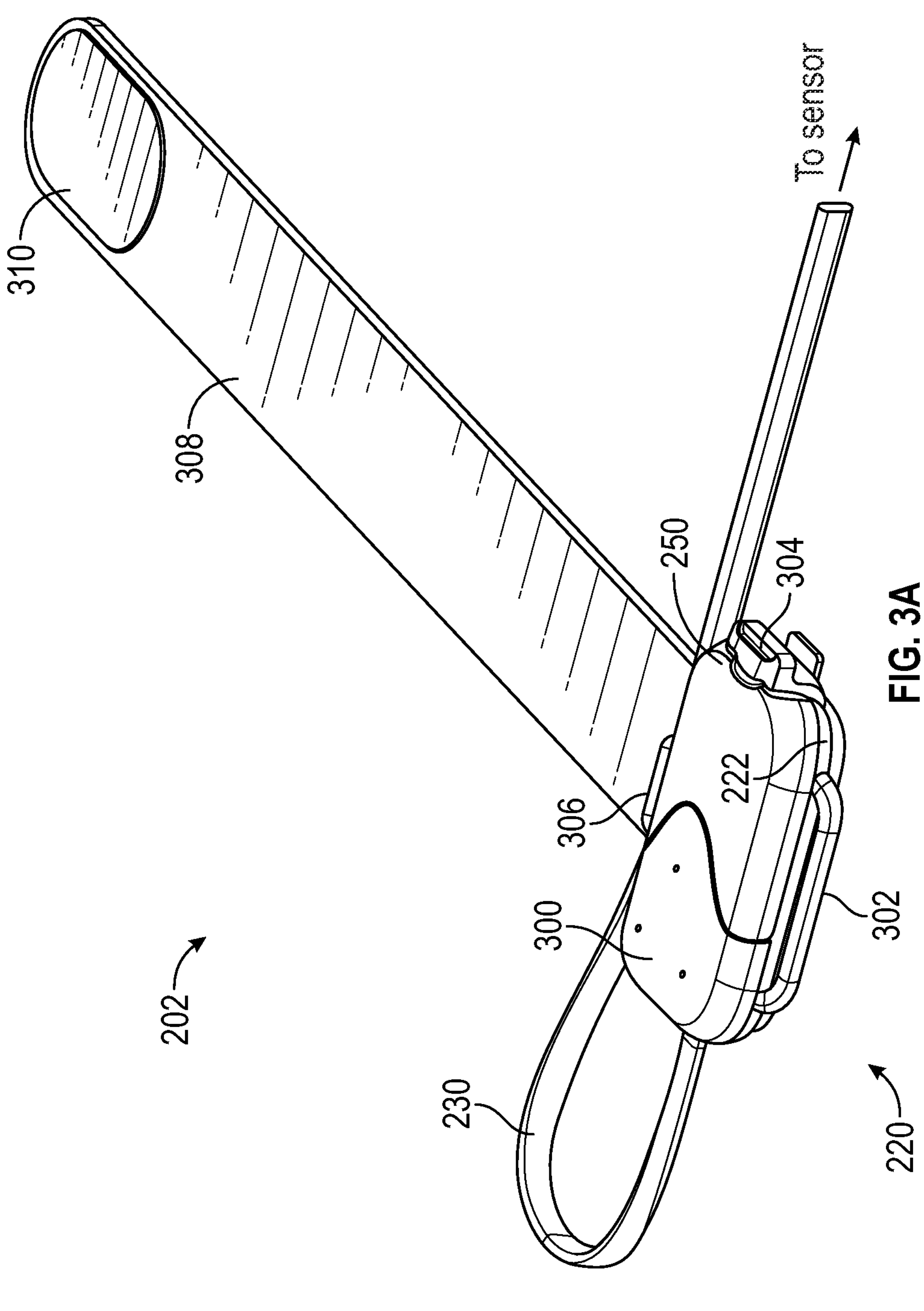
FIG. 3A illustrates a perspective view of an embodiment of a sensor assembly for collecting and wirelessly transmitting patient physiological data to a computing device.

FIG. 3A shows a front perspective view of an example of the sensor assembly 202 including the reusable module 250 and the disposable module 220. As discussed above, the reusable module 250 can be a pairing device that can establish wireless connection with the computing device 206. The disposable device 220 can include the dock 222 and the cable 230 coupling the dock 222 to the sensor 240 (not shown).

The dock 222 can include a strap 308 that is coupled to a bottom portion of the dock 222. The strap 308 can loop around a patient (e.g., a wrist or an arm) to removably attach the dock 222 to the patient (see FIG. 7H). The dock 222 can also include a strap loop 302 having a slot for the strap 308 to extend through. The strap 308 can extend through the strap loop 302 and loop around to removably attach the dock 222 to the patient. The strap 308 can include a fastener 310 disposed near a distal end of the strap 308 that can interact with the strap 308 to fix the distal end of the strap 308. The fastener 310 can be located at a distal end of the strap 308, as shown in FIG. 3A. The fastener 310 can be located at other locations of the strap 308. The dock can also include a retainer 304 that holds the reusable module 250 within the dock 222 to maintain electrical connection between the reusable module 250 and the dock 222. Moreover, the dock 222 can include a housing 300 that can house the battery 224 and the memory 226.

The dock 222 can include a cable retainer 306 disposed on a side of the dock 222. The cable retainer 306 can be dimensioned and sized to retain the cable 230. The cable retainer 306 can be removably connected to the dock 222. At least a portion of the cable retainer 306 may be flexible to facilitate insertion of the cable 230 into the cable retainer 306. The cable retainer 306 can advantageously limit movement of the cable 230 to prevent possible tangling of cables of different sensor assemblies. The cable retainer 306 can include a channel to through which the cable 230 can extend. The channel of the cable retainer 306 can be dimensioned such that the cable 230 is snug within the channel, thereby limiting movement of the cable 230.

Figure 3B:
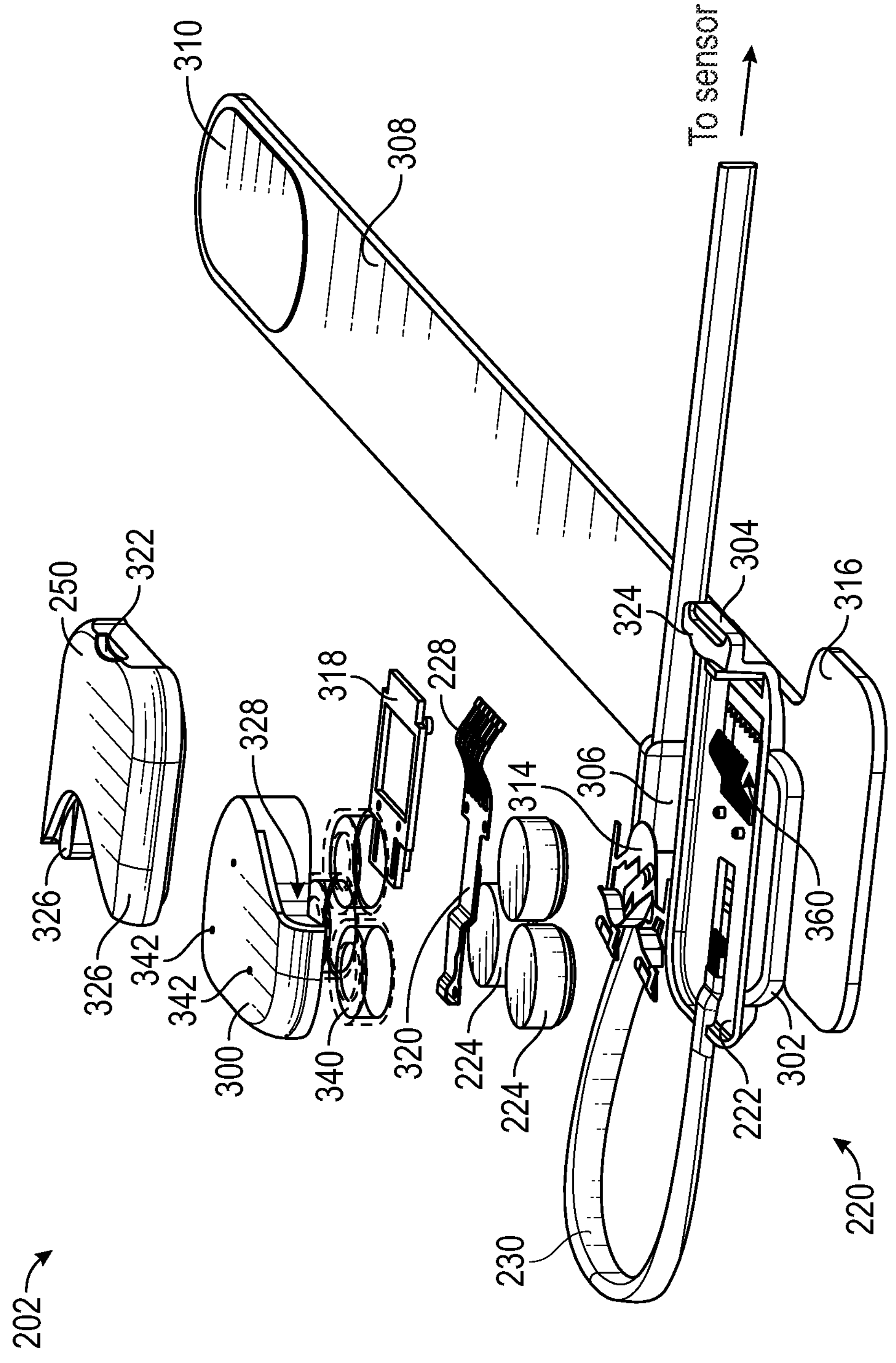
FIG. 3B illustrates an exploded, top perspective view of the sensor assembly of FIG. 3A.
Figure 3C:
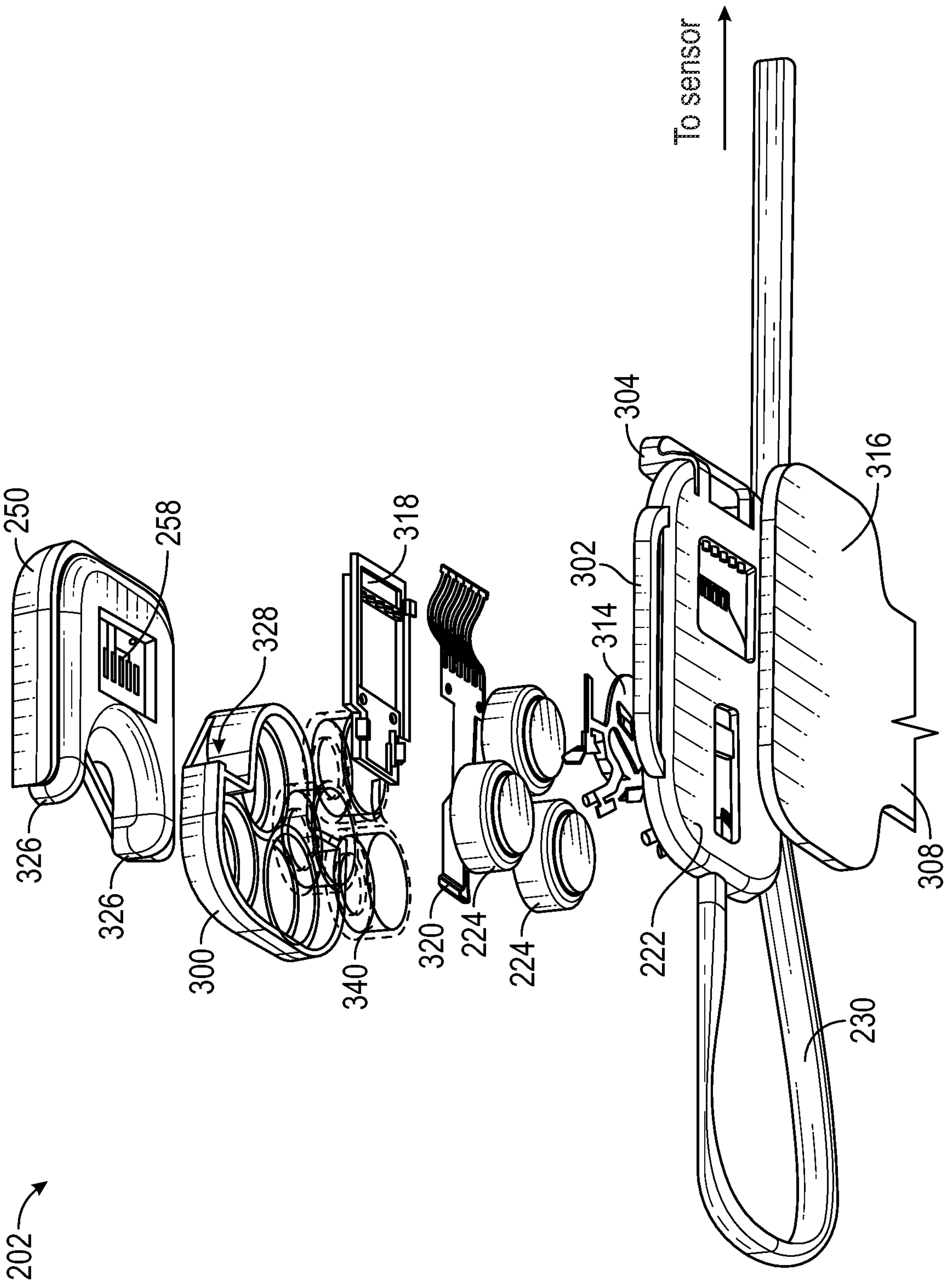
FIG. 3C illustrates an exploded, bottom perspective view of the sensor assembly of FIG. 3A.

FIG. 3B illustrates an exploded, top perspective view of the sensor assembly 202 of FIG. 3A. FIG. 3C illustrates an exploded, bottom perspective view of the sensor assembly 202 of FIG. 3A. The dock 222 of the disposable module 220 can include a support plate 316 disposed under the dock 222. The support plate 316 can be integrated with the strap 308. The strap 308 can be modular with respect to the support plate 316 and/or the dock 222. The dock 222 may not include the support plate 316 such that the strap 308 is coupled directly to the dock 222.

The retainer 304 of the dock 222 can include a protrusion 324 that can interact with a groove 322 of the reusable module 250. The interaction between the groove 322 and the protrusion 324 can maintaining coupling between the reusable module 250 and the dock 222. For example, when the reusable module 250 is inserted into the dock 222, the retainer 304 is pushed in a direction away from the housing 300 of the dock 222 in order to allow the reusable module 250 to mate with the dock 222. When the reusable module 250 is fully inserted into the dock 222, the retainer 304 can snap back to its original position to engage the groove 322 of the reusable module 250. The retainer 304 and the groove 322 can together prevent vertical displacement of the reusable module 250.

The retainer 304 can have a first position and a second position. When in the first position, the retainer 304 is substantially vertical with respect to the dock 222. When in the second position, the retainer 304 is pushed in a direction away from the housing 300 so that the retainer 304 forms an angle greater than 90 degrees with respect to the dock 222. Before the reusable module 250 is inserted into the dock 222, the retainer 304 can be in the first position. While the reusable module 250 is being pushed into the dock 220, the reusable module 250 interacts with the retainer 304 and causes the retainer 304 to be in the second position. When the reusable module 250 is fully engaged with the dock 222, the retainer 304 reverts to the first position so that the protrusion 324 engages the groove 322.

The dock 222 can also include a flex circuit 320 and a cover 318 to retain the flex circuit 320. The flex circuit 320 can include the electrical contacts 228 of the dock 222, where the flex circuit 320 serves as a connection between the cable 230 and the electrical contact 228. Therefore any information or data transmitted from the sensor 240 via the cable 230 to the dock 222 can be transmitted to the electrical contacts 228 via the flex circuit 320. Additional details of the flex circuit 320 will be provided below.

The housing 300 of the dock 222 can include one or more slots 328 that can interact with one or more legs 326 of the reusable module 250. The slots 328 can be dimensioned and shaped to allow the legs 326 of the reusable module 250 to slide into the slots 328. The legs 326 can slide into the slots 328 to assist in maintaining connection between the reusable module 250 and the dock 222. Once the legs 326 are inserted into the slots 328, the legs 326 can prevent vertical displacement of the reusable module 250.

It can be advantageous to have the battery 224 in a disposable portion such as the dock 222 or the sensor 240. Establishing wireless communication 204 and performing wireless transmission requires a significant amount of power. If the reusable module 250 has an internal power source, its functionalities (for example, establishing wireless communication 204 and performing wireless transmission) can be limited by the capacity of the internal power source. In such configuration, the reusable module 250 needs to be replaced once its internal power source is depleted. In a wireless patient monitoring context, it is desirable to keep the same pairing device for each patient because having to use multiple pairing devices for the same patient often can lead to confusion and can create a need to reestablish connections between pairing devices and display devices. When the reusable module 250 has an external power source such as battery 224 of the dock 222, it does not need to be replaced when the battery 224 is depleted.

The batteries 224 can be zinc-air batteries powered by oxidizing zinc with oxygen in the air. It can be advantageous to use zinc-air batteries because they have higher energy density and thus have greater capacity than other types of batteries for a given weight or volume. In addition, zinc-air batteries have a long shelf life if properly sealed to keep the air out. The housing 300 can include one or more openings 332 that allow air to enter and react with the batteries 224. The one or more openings 332 can be sealed prior to use to prevent the air from entering and reacting with the batteries 224, thereby reducing capacity of the batteries 224. Once ready to use, the seal placed on the one or more openings 332 may be removed to allow the batteries 224 to provide power for the reusable module 250. The housing 300 may include a gasket 330 to seal the batteries 224 from the air. The gasket 330 can further increase the capacity of the batteries 224.

Having a disposable element (for example, the disposable module 220) as a power source for the reusable module 250 can address the above issues by eliminating the need to replace the reusable module 250. In this configuration, only the dock 222 or the sensor 240 needs to be replaced when the battery 224 is depleted. Since the cost of replacing the dock 222 or the sensor 240 can be much less than the cost of replacing the reusable module 250, this configuration can be advantageous in reducing operation costs. The sensor 240 may include the battery 224 that provides power to the reusable module 250. Both the sensor 240 and the dock 222 can include the battery 224. The reusable module 250 can include a battery consumption priority setting such that the reusable module 250 receives power first from the sensor 240 then from the dock 222.

The dock 222 can include a battery circuit 314 in contact with the batteries 224. The battery circuit 314 can be in contact with the flexible circuit 320. When the reusable module 250 is mated with the dock 222, the electronic contacts 258 can be in contact with the electronic contacts 228 of the flexible circuit 320 to allow the reusable module 250 to receive power from the batteries 224 via the flexible circuit 320.

The dock 222 can include an opening 362 and one or more supports 360. The one or more supports 360 can be formed on a side of the opening 362 and extend over a substantial portion of the opening 362. The supports 360 can be arcuate. The supports 360 can extend over the length of the opening 362. The cover 318 for the flexible circuit 320 can be placed over the opening 362 to hold the flexible circuit 320 over the opening 362.

The dock 222 can include a slot dimensioned to retain the reusable module 250 during the use of the sensor assembly 202. The reusable module 250 can be disposed between the housing 300 and the retainer 304. The slot of the dock 222 can include one or more arcuate surfaces or one or more angular corners. The slot of the dock 222 may be substantially rectangular or circular in shape. The slot can have substantially the same size, shape, and/or dimensions as that of the reusable module 250.

The reusable module 250 can include one or more electrical contacts 258. The electrical contacts 258 can be located on a bottom surface of the reusable module 250. The electrical contacts 258 can be substantially rectangular or circular in shape. The electrical contacts 258 can establish contact with electrical contacts 228 of the dock 222 when the reusable module 250 is mated with the dock 222. The contact between the electrical contacts 228 and electrical contacts 258 can allow information or data be transmitted between the reusable module 250 and the dock 222 of the disposable module 220.

As disclosed herein, the batteries 224 can be zinc-air batteries powered by oxidizing zinc with oxygen in the air. The openings 332 formed on the housing 300 can allow the air to enter through and react with the battery 224. The battery 224 then provides power for the disposable module 220 and the reusable module 250. However, the openings 332 may sometimes be covered by blankets, clothes, and the like, which can prevent the air from entering through the openings 332 and react with the battery 224. Consequently, power supply for the disposable module 220 and the reusable module 250 can be interrupted if the openings 332 are covered.

Figure 3D:
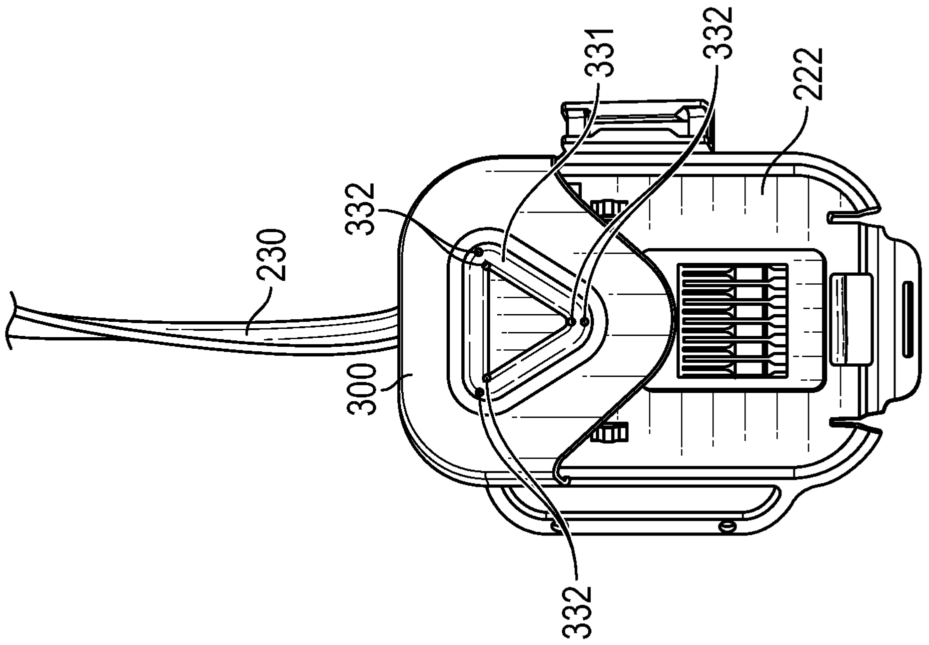
FIG. 3D illustrates a top view of an embodiment of a sensor assembly.

As shown in FIG. 3D, the housing 300 can include one or more recesses 331, such as, for example, channels, that can facilitate the air to enter through the openings 332. The recesses 331 can be formed on a top surface of the housing 300 such that the recesses 331 form openings that allow air flow. The openings 332 may be formed on an inner surface of the recesses 331. The inner surfaces of the recesses 331 are at least a predetermined distance away from the top surface of the housing 300 so that even when the housing 300 is covered, the openings 332 may remain uncovered and exposed to the air. The housing can have a single channel or multiple recesses, such as dimples or cutouts of any shape or size.

The number, dimensions, orientation, or positions of the channels 331 may be varied depending on the size of the housing 300 of the reusable module 250. The channels 331 can be oriented such that they together form a shape on the housing 300. The channels 331 may be oriented in a triangular shape (as shown in FIG. 3D), rectangular shape, pentagonal shape, hexagonal shape, and the like. The cross-sectional shape of the channels 331 can be circular, triangular, rectangular, or the like. In some examples, the channels 331 can extend to one or more edges of the housing 300 so that even when the top surface of the housing 300 is covered, the channels 331 extending to the edges of the housing 300 can ensure that the openings 332 remain exposed to the air.

Figure 4:
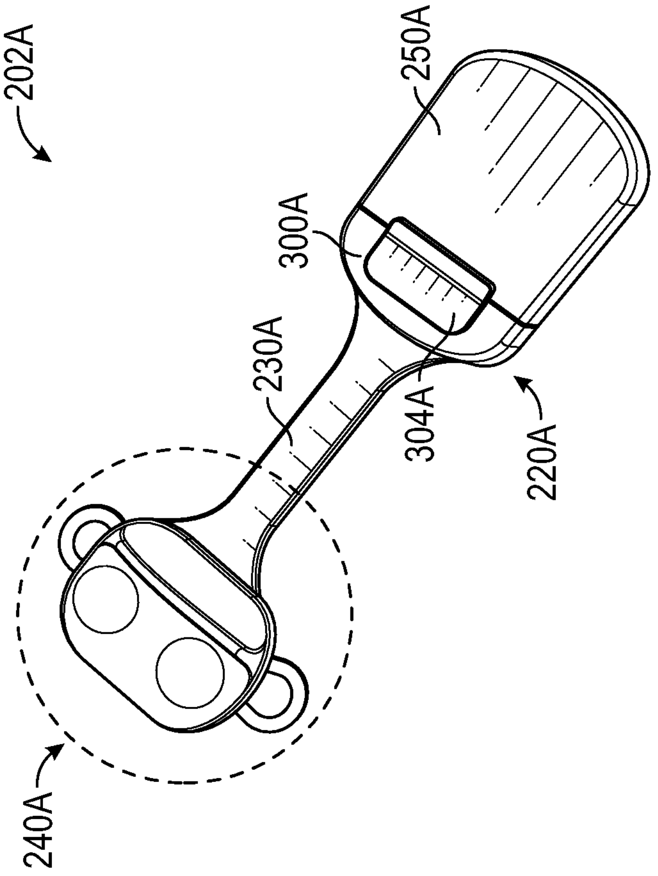
FIG. 4 illustrates a perspective view of another embodiment of a sensor assembly for collecting and wirelessly transmitting patient physiological data to a computing device.

FIG. 4 illustrates an example the sensor assembly 202, identified generally by the reference numeral 202A. Parts, components, and features of the sensor assembly 202A are identified using the same reference numerals as the corresponding parts, components, and features of the sensor assembly 202, except that a letter "A" has been added thereto. The illustrated example includes a disposable module 220A and a reusable module 250A coupled to each other.

The sensor assembly 202A can include a sensor 240A. The sensor 240A can be an O3 sensor that can be adhered to a forehead of a patient. The sensor assembly 202A can include a cable 230A that couples the sensor 240A and a dock 222A of the disposable module 220A. The cable 230A can be flat or round. As discussed above, the sensor 240A can include one or more batteries that can provide power for a reusable module 250A. The mating of the dock 222A and the reusable module 250A can facilitate electronic communication therebetween. The dock 222A can include a housing 300A that includes a retainer member 304A. Pressing down the retainer member 304A can allow the reusable module 250A to be coupled with or removed from the dock 222A.

Figure 5:
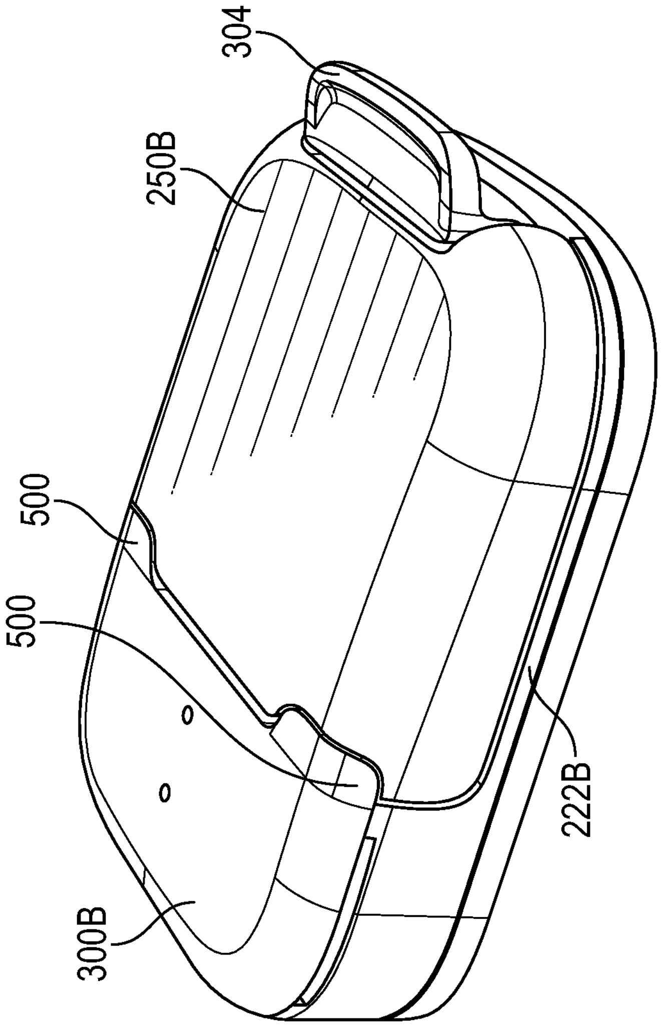
FIG. 5 illustrates a perspective view of another embodiment of a sensor assembly for collecting and wirelessly transmitting patient physiological data to a computing device.

FIG. 5 illustrates an example of the sensor assembly 202, identified generally by the reference numeral 202B. Parts, components, and features of the sensor assembly 202B are identified using the same reference numerals as the corresponding parts, components, and features of the sensor assembly 202, except that a letter "B" has been added thereto. The illustrated example includes a disposable module 220B and a reusable module 250B coupled to each other.

The sensor assembly 202B can include a sensor 240B. The sensor 240B can be a RAM sensor adhered to a neck of a patient. The sensor 240B can be an ECG sensor that can be adhered to a chest or abdominal area of a patient. The dock 222B can include a housing 300B and a retainer member 304B. The housing 300B can include one or more extensions 500 that can extend from the body of the housing 300B towards the retainer member 304B. The reusable module 250B can include cutouts that correspond to the one or more extensions 500. When the reusable module 250B is coupled with the dock 222B, the extensions 500 can extend over the cutouts of the reusable module 250B, preventing the reusable module 250B from being dislodged from the dock 222B.

Flexible Circuit

Figure 6A:
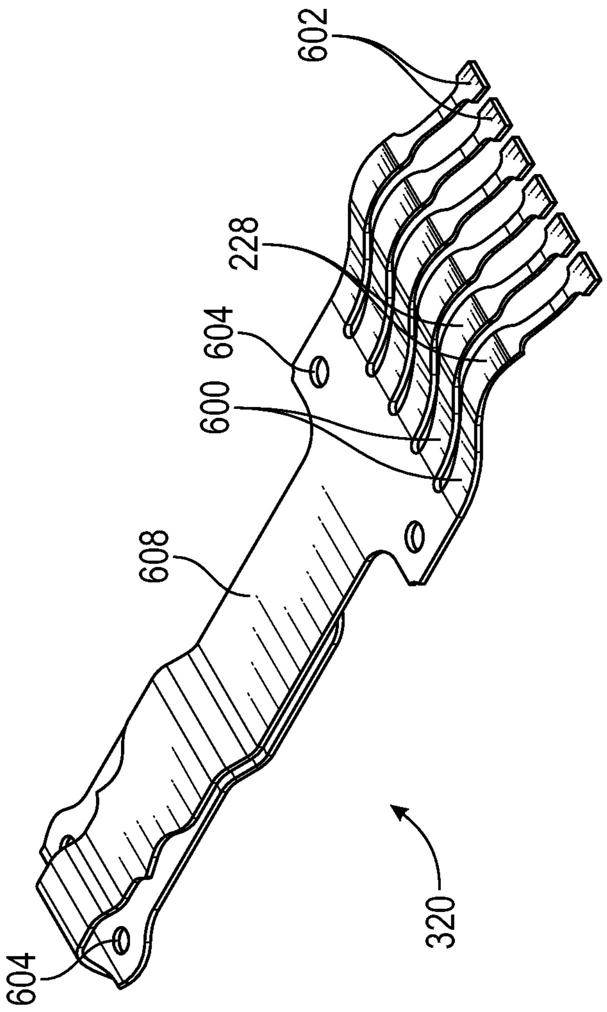
FIGS. 6A and 6B illustrate various views of a flex circuit of a disposable module of a sensor assembly.

FIG. 6A illustrates a perspective view of the flex circuit 320. The flex circuit 320 can include one or more elongate members 600 that can each include a tip 602, and a body 608. The electrical contracts 228 can be disposed on the one or more elongate members 600. The elongate members 600 can extend distally from the body 608. The tips 602 can be located at distal ends of the elongate members 600 of the flex circuit 320. The elongate members 600 can be flat or arcuate as shown in FIG. 6A. The elongate members 600 can become arcuate due to their interaction with the supports 360 and the cover 318. The elongate members 600 can include one or more substantially flat portions and/or one or more arcuate portions. Each of the one or more tips 602 can correspond to each of the one or more elongate members 600 of the flex circuit 320. Some of the elongate members 600 may not have electrical contacts 228. The flex circuit 320 can include the same or different number of the elongate members 600 and the tips 602. The flex circuit 320 can include one or more openings 604 that couple the flex circuit 320 to the dock 222.

Figure 6B:
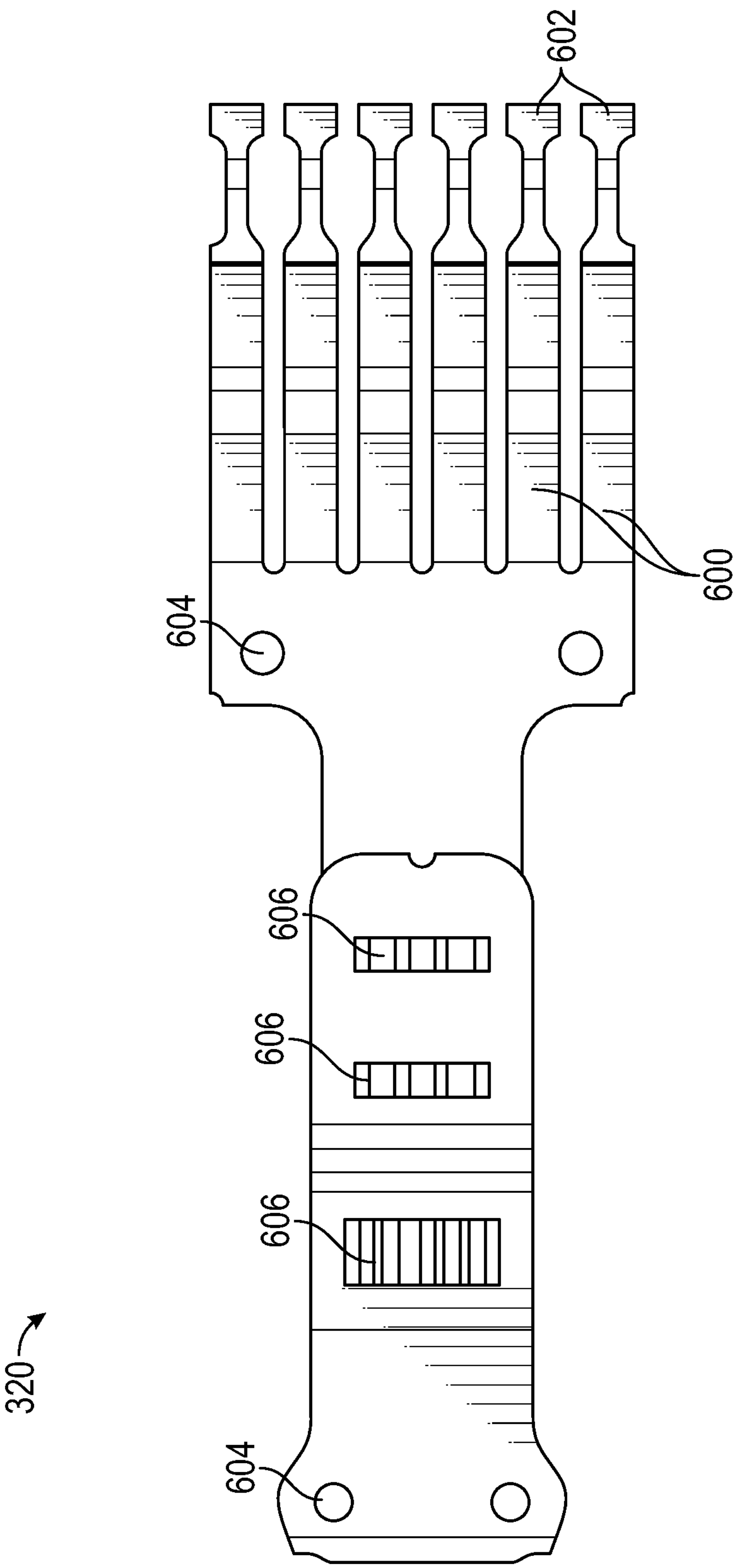
Figure 6C:
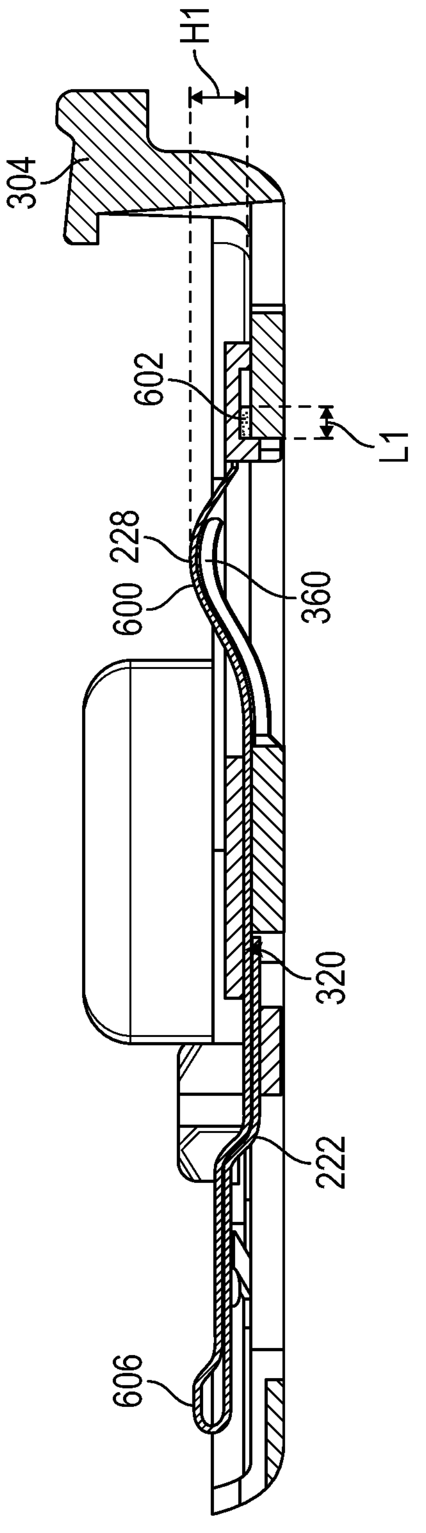
FIGS. 6C and 6D illustrate sides views of the flex circuit of FIG. 6A, showing a change of a configuration of the flex circuit.
Figure 6D:
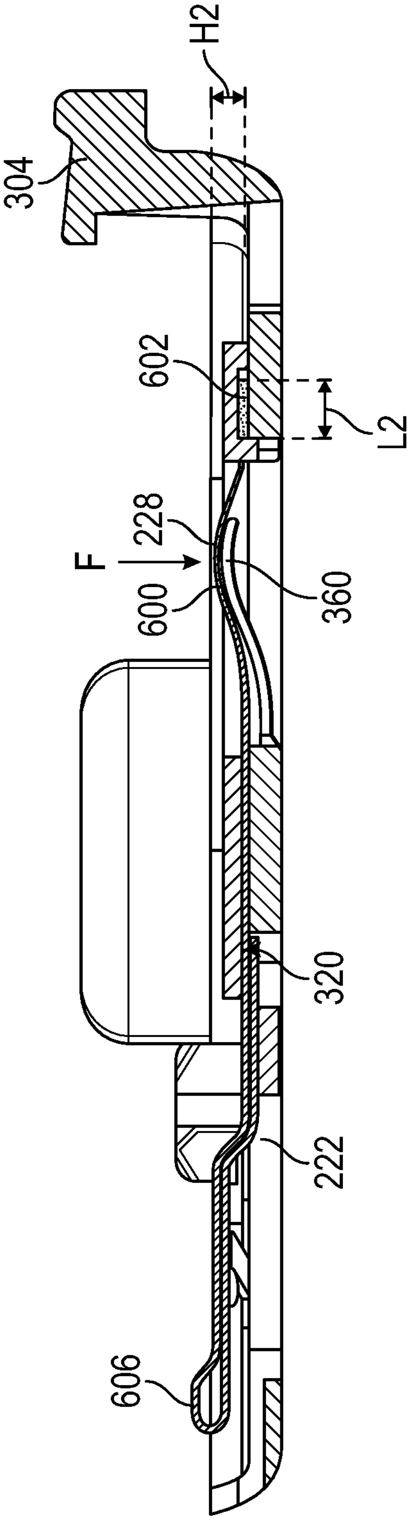

As shown in FIGS. 6C and 6D, the tips 602 of the elongate members 600 can be positioned under the cover 318 while the elongate members 600 are supported by supports 360. Because the tips 602 can be wedged under the cover 318, the elongate members 600 can retain its arcuate shape over the supports 360.

FIG. 6B illustrates a bottom view of the flex circuit 320. The flex circuit 320 can include one or more electrical contacts 606 that can be connected to the cable 230 and the battery circuit 314 (see FIGS. 3A and 3C). Therefore, power from the battery 224 can be transmitted to the electrical contacts 228 of the dock 222 via the electrical contacts 606 of the flex circuit 320. Moreover, the electrical contacts 606 can establish connection between the electrical contacts 228 and the sensor 240 via the cable 230.

The number of the elongate members 600 can correspond to the number of electrical contacts 258 of the reusable module 250 (see FIG. 3C). For example, the reusable module 250 has six electrical contacts 258 and the flex circuit 320 has six fingers, where each of the six fingers includes an electrical contact 228. The number of electrical contacts 258 of the reusable module 250 can be different from the number of elongate members 600 of the flex circuit 320. For example, the flex circuit 320 can include six elongate members 600 each having a corresponding electrical contact 310*a*, while the reusable module 250 has only four electrical contacts 258. The number of electrical contacts 258 of the reusable module 250 may be different from or the same with the number of electrical contacts 228 disposed on the elongate members 600 of the flex circuit 320.

Each the elongate members 600 of the flex circuit 320 can include an arcuate portion with a first curvature. The arcuate portions of the elongate members 600 can be laid over the opening 362 of the dock 222. The one or more electrical contacts 228 of the flex circuit 320 can be disposed over a portion of the elongate members 600 of the flex circuit 320. For example, the one or more electrical contacts 228 are located at an apex of each of the elongate members 600 of the flex circuit 320. In another example, the entire upper surface of each of the elongate members 600 defines the electrical contacts 228. The elongate members 600 of the flex circuit 320 can be configured such that the apex of the arcuate portions of the elongate members 600 of the flex circuit 320 are located at a predetermined distance away from the opening 362 of the dock 222. The apex of the elongate members 600 of the flex circuit 320 can point away from the opening 362 of the dock 222 such that the arcuate portions of the elongate members 600 define a concave surface facing the opening of the dock 222. The apex of the elongate members 600 can be arcuate in shape or substantially flat.

It can be advantageous to have the elongate members 600 of the flex circuit 320 include a curved portion upward and away (for example, concave downward) from the opening 362 of the dock 222. Such configuration can allow the elongate members 600 to act as springs providing reactive upward forces when pressed downward by the reusable module 250. Such upward forces provided by the elongate members 600 can allow the electrical contacts 228, 258 of the dock 222 and the reusable module 250, respectively, to maintain adequate contact between them.

The elongate members 600 of the flex circuit 320 can have different curvatures. For example, a first elongate member of the flex circuit 320 has a first curvature while a second elongate member of the flex circuit 320 has a second curvature. The first curvature of the first elongate member and the second curvature of the second elongate member can be the same or different. The first curvature of the first elongate member is greater than, less than, or equal to the second curvature of the second elongate member.

The elongate members 600 of the flex circuit 320, in their resting positions, may not have any arcuate portions. The elongate members 600 of the flex circuit 320 can be substantially linear prior to being installed on the dock 222. The elongate members 600, can be linear or curved. The elongate members 600 of the flex circuit 320 can include more than one linear portions.

The elongate members 600 of the flex circuit 320 can be flexible or not flexible. The flex circuit 320 can be laid on the dock 222 such that the elongate members 600 are laid over one or more supports 360 of the dock 222. The elongate members 600 can extend distally away from the body 608 of the flex circuit 320. The flex circuit 320 can include more than one elongate members 600. The flex circuit 320 can include one or more elongate members 600 that are flexible. Some the elongate members 600 may be flexible while other elongate members 600 are not.

As discussed above, the dock 222 can include the opening 362 over which the elongate members 600 of the flex circuit 320 can extend over. The dock 222 can include one or more supports 360 dimensioned and shaped to support the elongate members 600 of the flex circuit 320. When the flex circuit 320 is installed on the dock 222, the supports 360 can provide a surface on which the elongate members 600 of the flex circuit 320 can be placed on.

The supports 360 of the dock 222 can be curved and define the curvature of the arcuate portions of the elongate members 600. The supports 360 can be arcuate. It can be advantageous to have the supports that correspond to each of the elongate members 600 of the flex circuit 320. For example, the dock 222 has six independent supports 360 associated with each of the six elongate members 600 of the flex circuit 320. Such configuration allows each of the corresponding elongate members 600 and the supports 360 of the dock 222 to move independently from other elongate members 600 and supports 360 as opposed to all of the elongate members 600 and the supports 360 moving that the same time. Such configuration can make inserting the reusable module 250 into the slot 940 of the dock 222 easier. Moreover, this can allow interoperability between the dock 222 and the reusable module 250 that have different height configurations for the electrical contacts 258.

It can be advantageous to have the supports 360 for the flex circuit 320 include a curved portion upward and away (e.g., concave downward) from a bottom portion of the dock 222. Such configuration can allow the supports to act as springs providing reactive upward force when pressed downward by the reusable module 250. Such upward forces can allow the electrical contacts 228, 258 of the dock 222 and the reusable module 250, respectively, to maintain adequate contact between them. The supports 360 can include a first upward portion that is concave upward, a second upward portion that is concave downward, and a third downward portion that is concave downward. The supports 360 may include a first upward portion that is concave upward and a second upward portion that is concave downward. The supports 360 can include one or more inflection point, defined as a point where the supports 360 changes from being concave to convex, or vice versa. The supports 360 can also include one or more linear portions.

The supports 360 may also provide sufficient force to push the reusable module 250 away the dock 222 when the retainer member 304 is pulled away from the reusable module 250. The support 360 may push the reusable module 250 away from the dock 222 when the retainer member 304 is in its second position, as discussed above. When the retainer 304 no longer engages the groove 322 of the reusable module 250, it may no longer provide force to counteract the force generated by the supports 360, allowing the supports 360 to push the reusable module 250 away from the dock 222.

The supports 360 can have a length that is greater than, less than, or equal to the length of the elongate members 600 of the flex circuit 320. The supports 360 have a width that is greater than, less than, or equal to the width of the elongate members 600. The supports 360 can have a thickness that is greater than, less than, or equal to the thickness of the elongate members 600 to allow the supports 360 to provide sufficient mechanical support and to withstand the downward force exerted on the elongate members 600 and the supports 360 by the reusable module 250. The interaction between the elongate members 600, supports 360, and the reusable module 250 will be further described below.

The supports 360 can be made out of the same or different material as the dock 222.

The body 608 of the flex circuit 320 can be laid under the housing 300 of the dock 222. The body 608 can be connected to the cable 230 connected to the dock 222 such that the flex circuit 320 allows the health monitoring data from sensor 240 to be transmitted to the electrical contacts 606 of the flex circuit 320.

FIGS. 6C and 6D illustrate a change in a configuration of the flex circuit 320. When the reusable module 250 is inserted into the slot 940 of the dock 222, the engagement between the reusable module 250 and the dock 222 can change the position of the tips 602 of the flex circuit 320. FIGS. 6C and 6D show relative positions of the tips 602 before and after the reusable module 250 is mated with the dock 222. The relative positions of the tips 602 before the reusable module 250 is inserted into the dock 222 are denoted by L1. When the reusable module 250 is inserted into the slot 940 of the dock 222, the reusable module 250 can apply a downward force (denoted as F) to the arcuate portions of the elongate members 600 and the supports 360. This downward force F can cause the arcuate portions and the supports 360 to move downward. This downward movement of the elongate members 600 and the supports 360 can cause the tips 602 to move distally along an axis defined by the elongate members 600 of the flex circuit 320. Specifically, such downward motion can cause the relative positions of the tips 602 to change from L1 to L2, where L2 is greater than L1.

FIGS. 6C and 6D illustrate another change in configuration of the flex circuit 320. When the reusable module 250 is inserted into the dock 222, the engagement between the reusable module 250 and the dock 222 can change the position of the tips 602 of the flex circuit 320. The relative difference between the heights of the apex of the arcuate portions of the elongate members 600 and the body 608 before for reusable module 250 is inserted is denoted by H1. When the reusable module 250 is inserted into the dock 222, the reusable module 250 can apply a downward force (denoted as F) to the arcuate portions of the elongate members 600 and the supports 360. This downward force F can cause the arcuate portions and the supports 360 to move downward. Such downward motion can cause the relative difference between the heights of the apex of the arcuate portions of the elongate members 600 and the body 608 to change from H1 to H2, where H2 is less than H1. It is possible that the relative different between the heights of the apex of the arcuate portions of the elongate members 600 and the body 608 can change while the relative positions of the tips 602 do not change from L1 to L2, or vice versa.

The downward force F in a first direction can cause the supports 360 of the dock 222 to provide a reactive force in a second direction. The second direction of the reactive force can be an opposite direction then the first direction of the downward force F. Specifically, the reactive force by the supports 360 can be upward away from the dock 222. The supports 360 can act as a spring such that as the supports 360 moves further downward from its natural position (for example, as H1 changes to H2), the magnitude of the reactive force increases. The directions of F and the reactive force may be opposite from each other. The magnitude of the reactive force is less than the downward force F in order to allow the supports 360 to move downward and allow the reusable module 250 to be inserted into the slot 940 of the dock 222. The magnitude of the downward force F caused by the reusable module 250 may correlate to the following: the change in the relative height difference between the apex of the elongate members 600 and the body 608 (for example, from H1 to H2) and the change in the positions of the tips 602 (for example, from L1 to L2).

The elongate members 600 of the flex circuit 320 can have a first degree of curvature before the reusable module 250 is inserted into the dock 222. The elongate members 600 can have a second degree of curvature after the reusable module is inserted into the dock 222. The first degree of curvature of the elongate members 600 can be greater than, less than, or equal to the second degree of curvature. The first degree of curvature can correspond to a first position of the tips 602 (for example, L1). The second degree of curvature can correspond to a second position of the tips 602 (for example, L2). Moreover, the first degree of curvature can correspond to a first position of the apex (for example, H1) of the elongate members 600. The second degree of curvature can correspond to a second position of the apex (for example, H2) of the elongate members 600.

The reactive force provided by the supports 360 can maintain sufficient contact between the electrical contacts 310*a* of the dock 222 and the electrical contacts 310*b* of the reusable module 250 to allow electrical signals be transmitted between the contacts.

Attachment Mechanisms

FIGS. 7A-7I illustrate various examples of an attachment mechanism for the disposable module 220 of the sensor assembly 202.

Figure 7A:
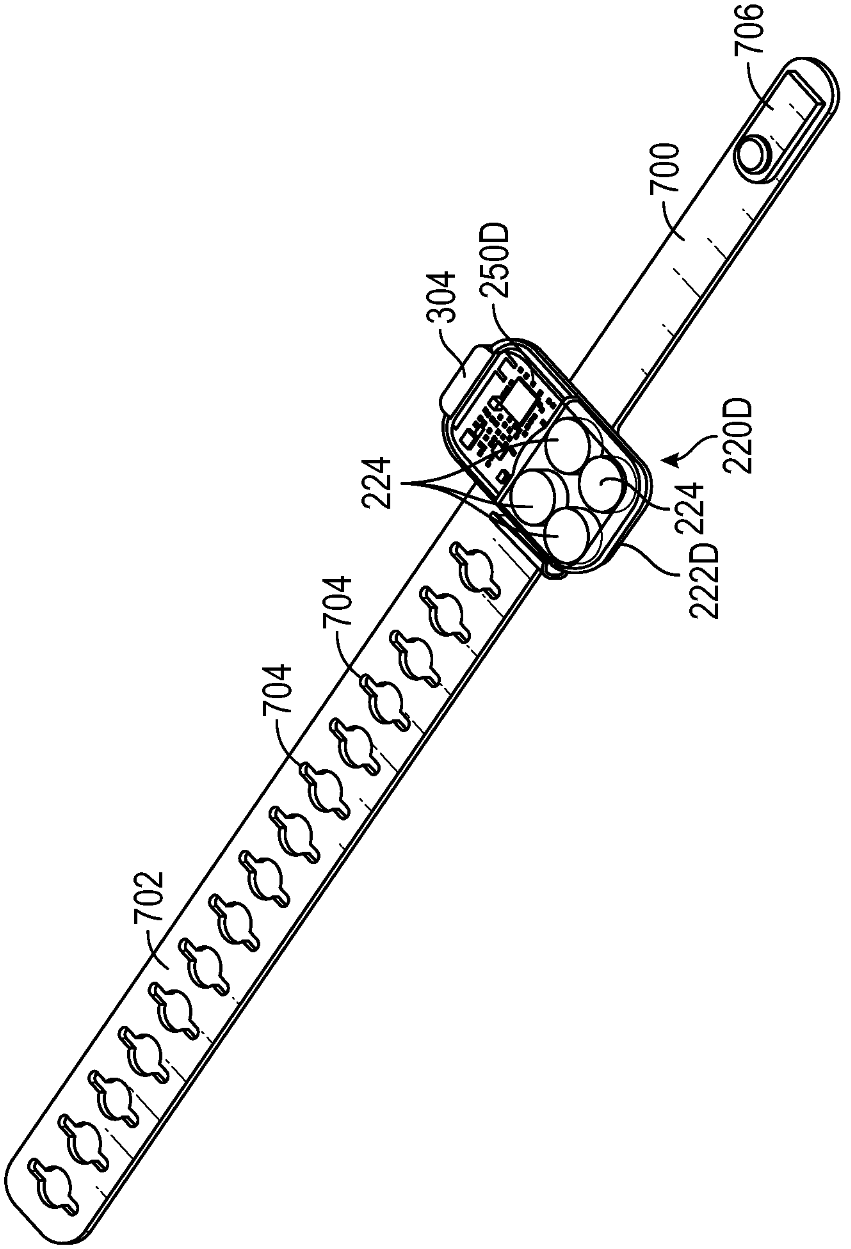
FIGS. 7A-7K illustrate various perspective view of different embodiments of sensor assembly coupled with various embodiments of attachment mechanisms.
Figure 7B:
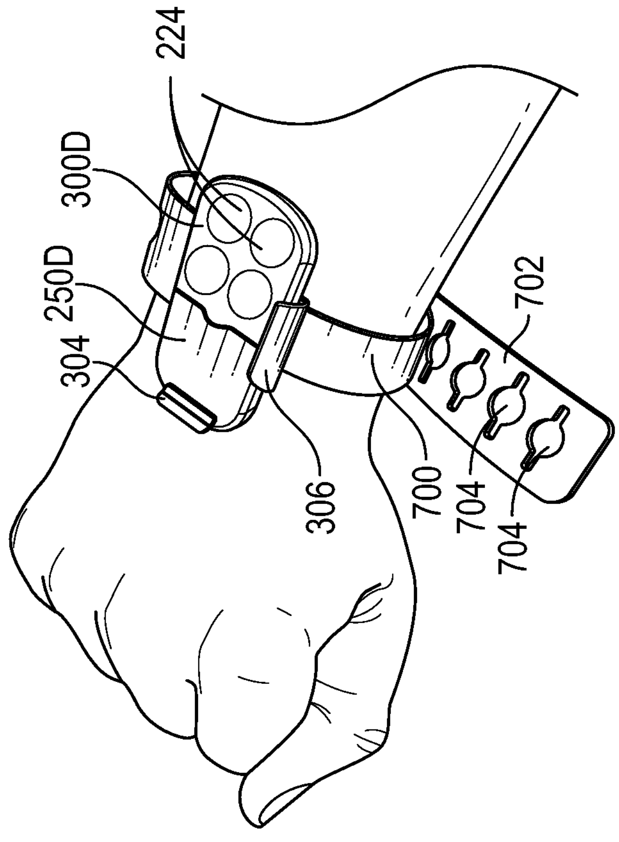
Figure 7C:
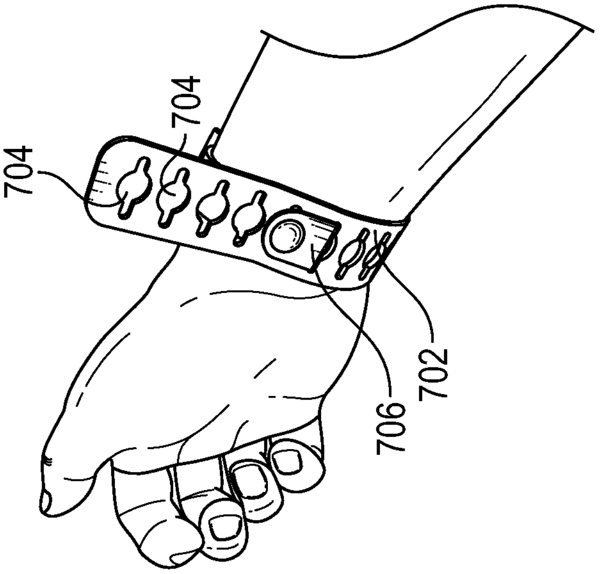

With reference to FIGS. 7A-7C, the dock 222 can be coupled to a first strap 700 and a second strap 702. The first strap 700 and the second strap 702 can be mechanically coupled to the dock 222. The straps 700, 702 may be removably coupled to the dock 222. Alternatively, the straps 700, 702 can be integrated to the dock 222. The second strap 702 can include one or more openings 704. The first strap 700 can include a fastener 706 configured to affix the second strap 702 to the first strap 700. The openings 704 can be dimensioned receive the fastener 706. The first strap 700 can be inserted through one of the openings 704 to removably attach the dock 222 to a patient. The straps 700, 702 can have varying thicknesses, lengths, and flexibility. The straps 700, 702 may be stretchable. The first strap 700 can include one or more openings 704 while the second strap 702 includes the fastener 706.

A distal end of the first strap 700 can be inserted into one of the openings 704 of the second strap 702. The fastener 706 of the first strap 700 may be inserted into one of the openings 704 of the second strap 702. The interaction between the fastener 706 and openings 704 can removably affix the dock 222 as shown in FIGS. 7B and 7C.

Figure 7E:
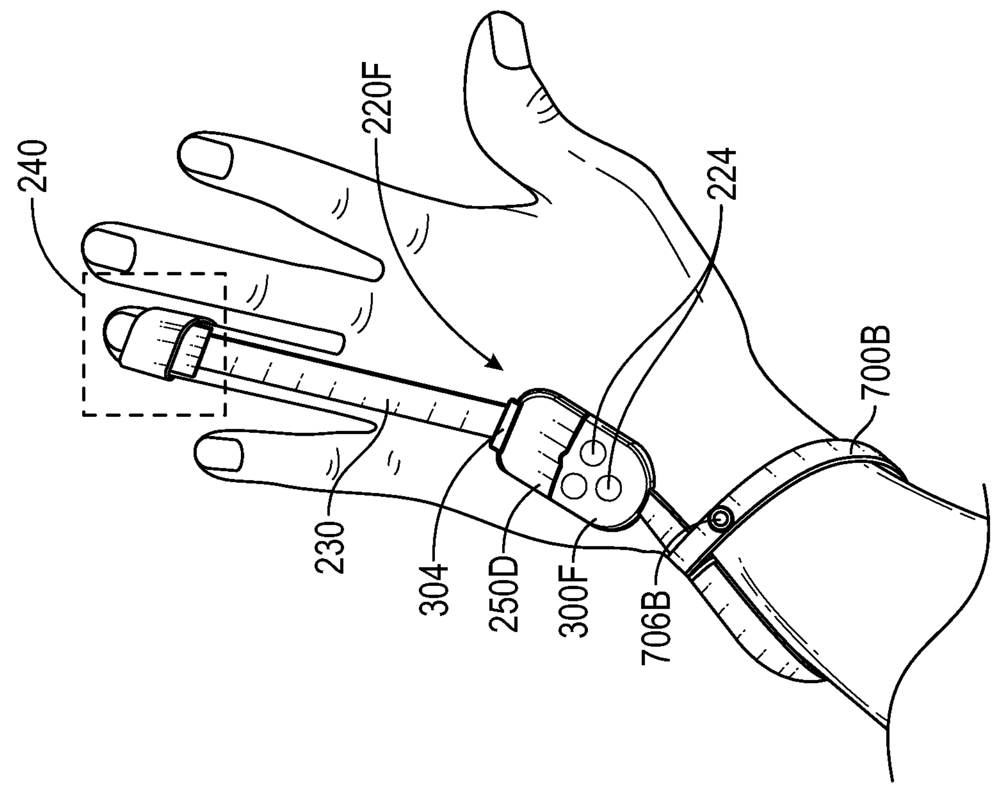
Figure 7D:
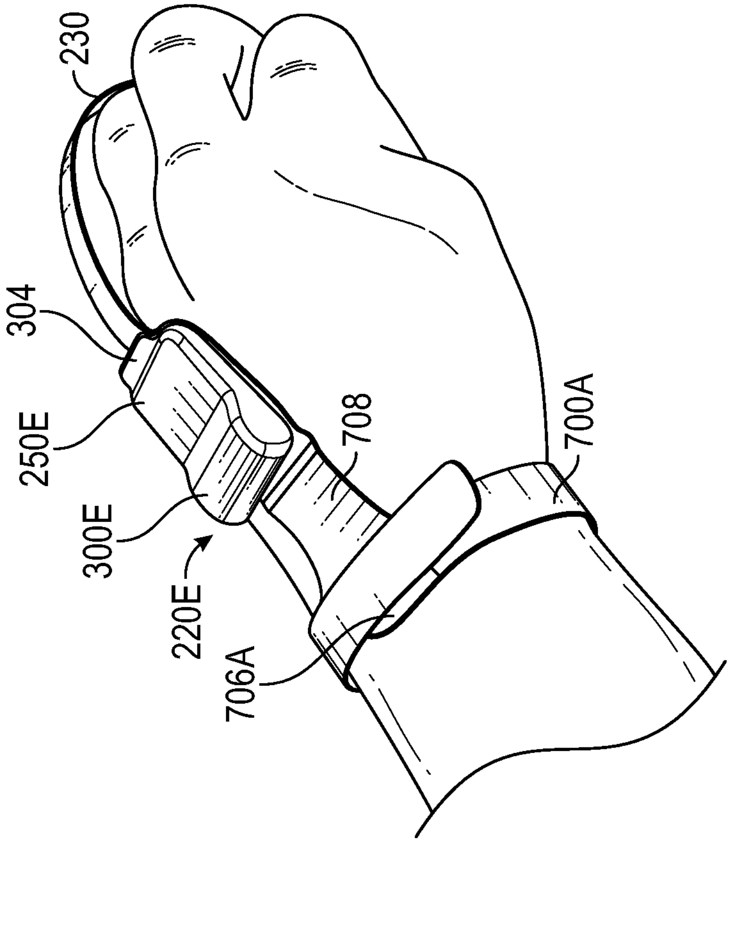
Figure 7F:
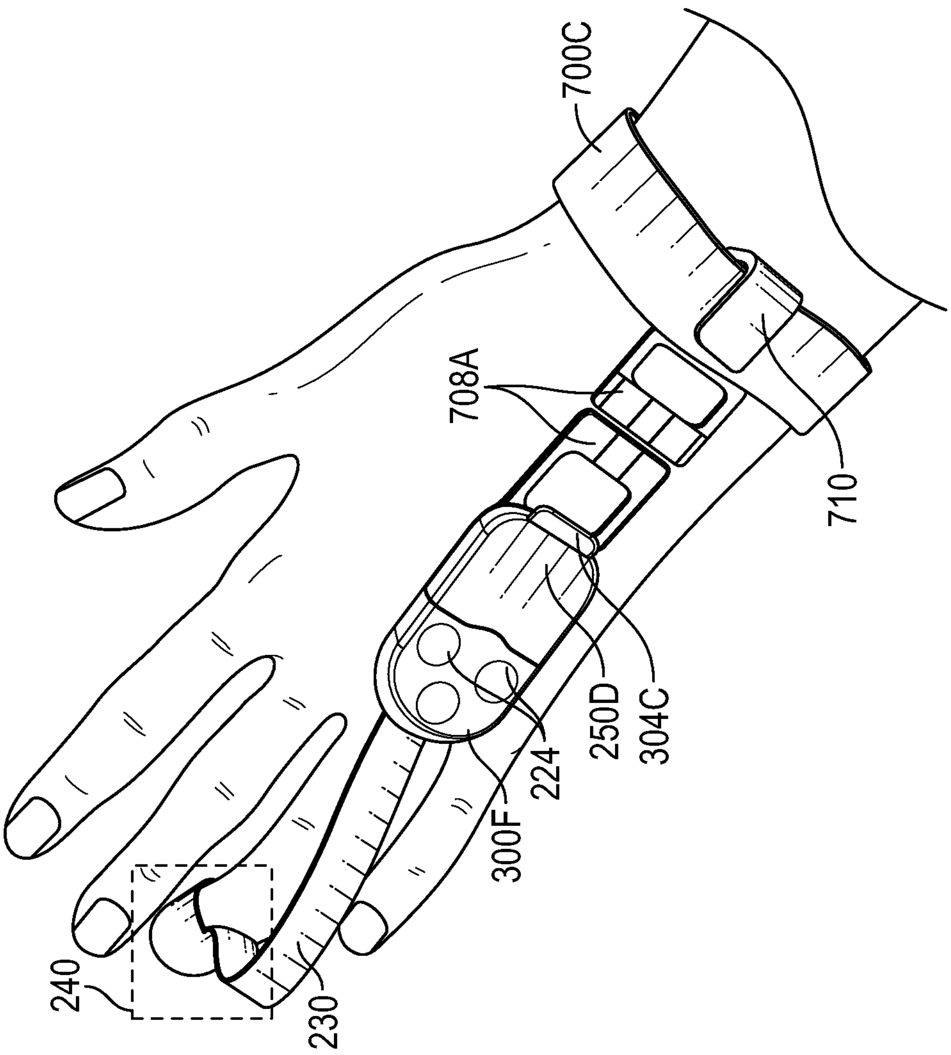
Figure 7G:
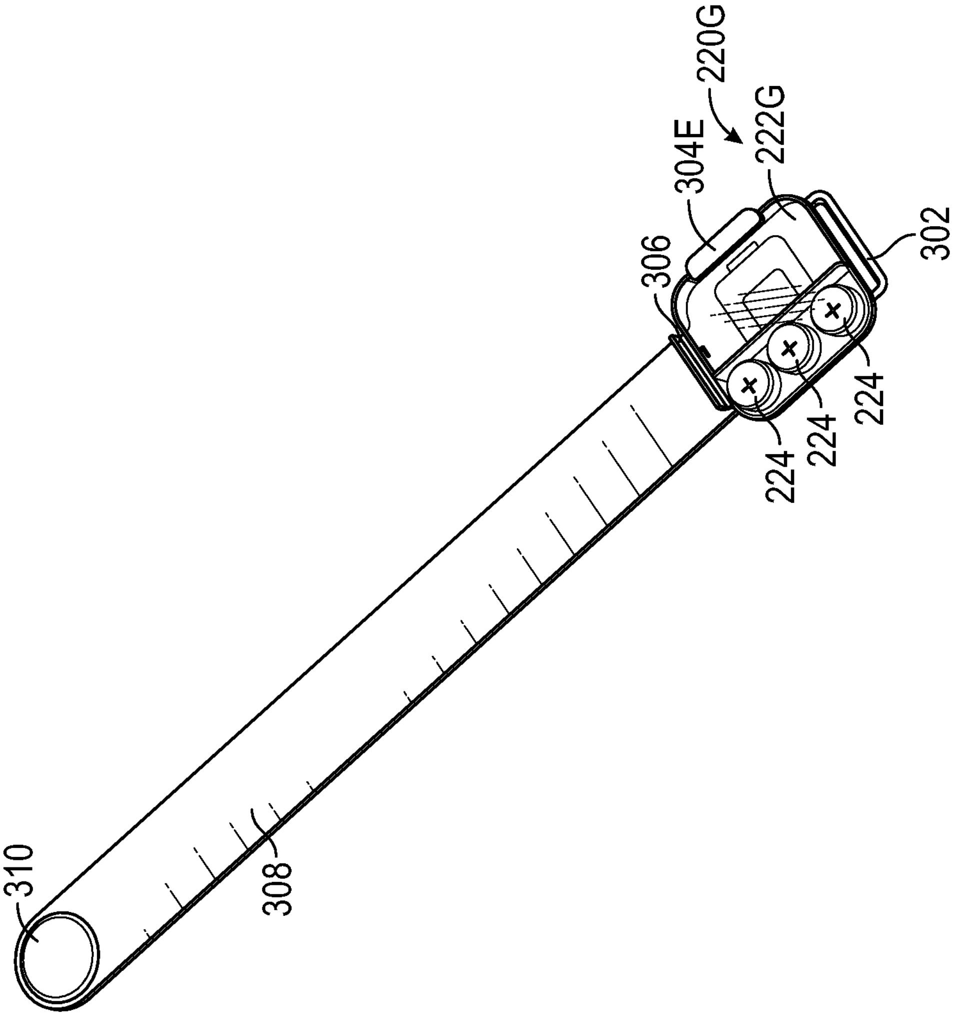
Figure 7I:
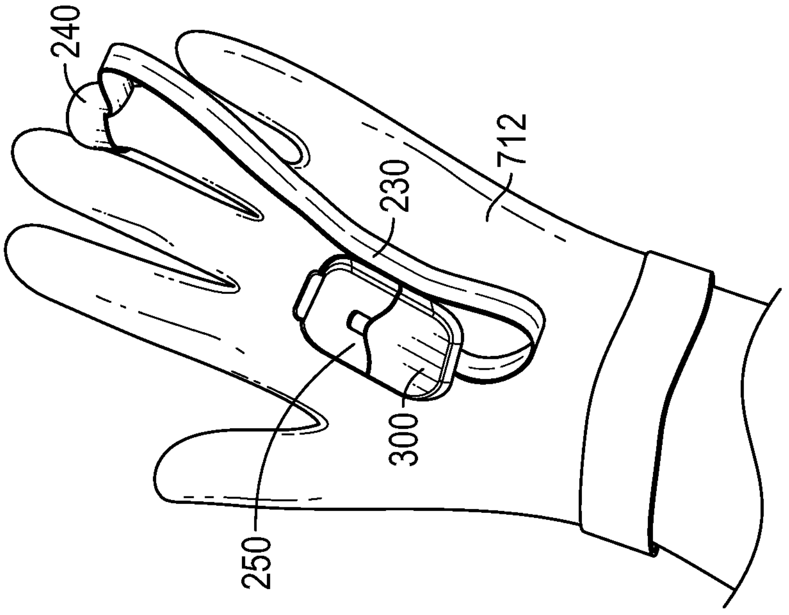
Figure 7H:
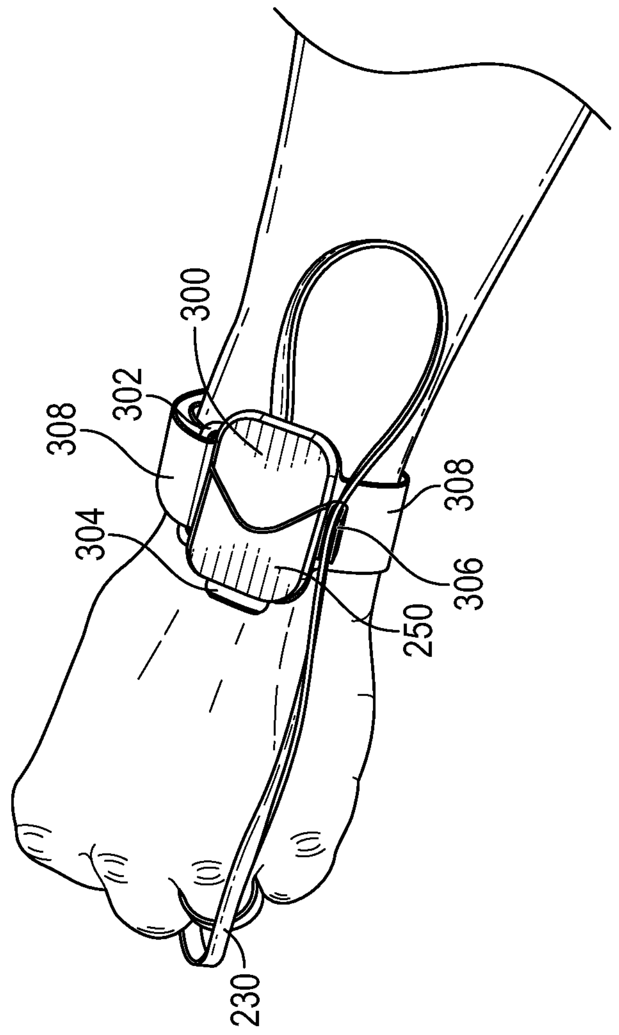
Figure 7K:
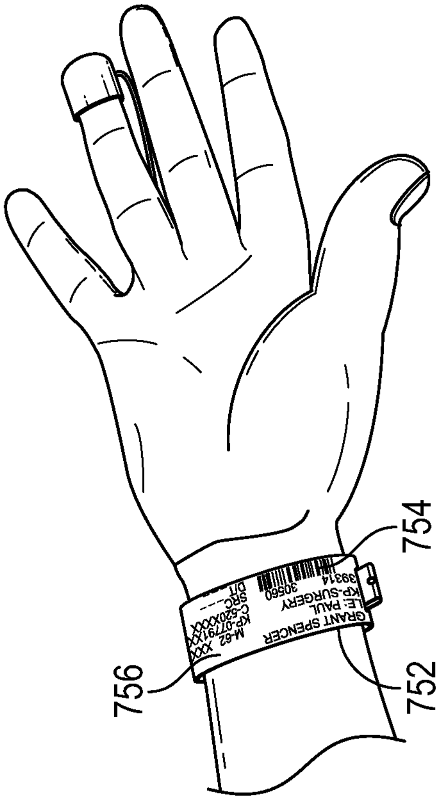
Figure 7J:
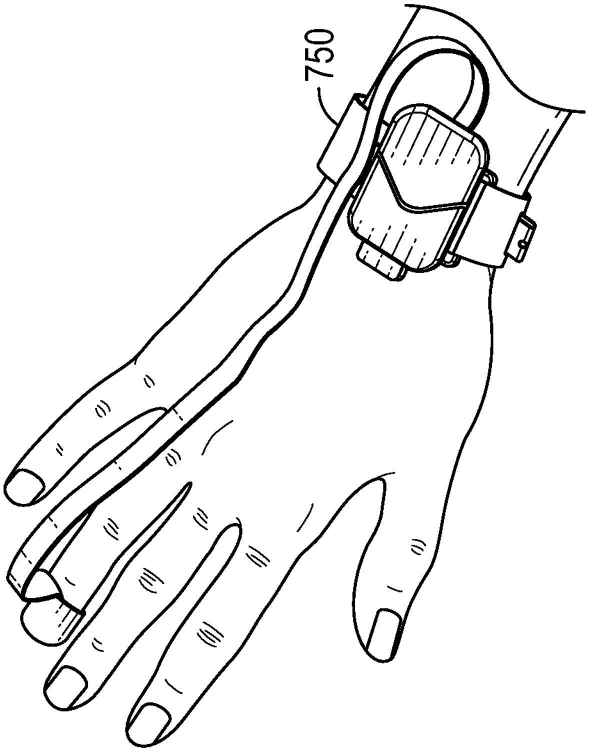

In some implementations, the sensor assembly 202 can be coupled to a hospital band 750 as shown in FIGS. 7J and 7K. The band 750 may include any of straps disclosed herein or any suitable strap or band to attach the sensor assembly 202 to a patient. The sensor assembly 202 may not include the strap (e.g., the strap 308 shown in FIG. 3B) and the dock 222 of the disposable module 220 may be coupled to the band 750. In some implementations, the dock 222 may include two strap loops (e.g., the strap loop 302) and the band 750 may be fed through the strap loops to couple the sensor assembly 202 to the band 750. The band securement mechanism can be non-removable once attached to the patient, requiring the band to be cut in order to be removed. The band can also include tamper detections and alarms which indicate the band has been removed improperly or tampered with. The band may include patient identifying information 752, a bar code 754, and medication information 756. The patient identifying information 752 can include the name of a patient, a contact information, doctor information, and the like. The bar code 754 can represent the patient identifying information 752 and may serve as an identifier that can be used to associate a patient with one or more devices (for example, patient monitoring devices). The bar code 754, in some example, may be a QR code. The medication information 756 may identify, for example, allergy information of a patient, medications provided to the patient, dosage information, and the like. In some implementations, the band 750 can include an RFID (radio frequency identification) tag that can, for example, allow patients and/or family members to get through security checkpoints. Optionally, the sensor assembly 202 may be wrist-mounted and include a one or more physiological sensors measuring parameters at the wrist. Optionally, the band 750 can include a location determination device that can determine exact or approximate locations of a patient.

By coupling the sensor assembly 202 to, for example, a hospital band 750, a number of items worn by a patient can be reduced. For example, if a patient is already wearing a medical wearable device (e.g., wearable fitness trackers, smart health watches, wearable ECG monitors, wearable blood pressure monitors, and the like), the sensor assembly 202 may be coupled to (e.g., adhered via adhesives or coupled via strap loops) the medical wearable device. Additionally or alternatively, the sensor assembly 202 may be coupled to non-medical devices such as a traditional watch or jewelry that may be worn on the wrist or other parts (e.g., ankle, neck, arm, leg, and the like) of a patient's body.

In some implementations, at least one of the patient identifying information 752, the bar code 754, or the medication information 756 may be printed separately and attached to, for example, the strap 308 shown in FIG. 3B of the sensor assembly 202. This configuration can obviate the need to, for example, detach the strap 308 from the dock 222 of the sensor assembly 202 and attaching the band 750 to the dock 222 (e.g., looping the band 750 to the strap loops 302 of the dock 222).

In some implementations, the appearance of the band 750 can include one or more light sources (e.g., light emitting diodes) that may be actuated (e.g., switched on/off) to reflect, for example, changes in patient condition. Optionally, various colors can be used to denote different patient conditions. For example, the color green may represent good and/or excellent patient condition, whereas the color yellow and the color red may represent suboptimal and critical patient conditions, respectively. The band 750 can include a processor and a wireless communication module that can receive physiological data of the patient wearing the band 750 from the sensor assembly 202 and cause the light sources to change the appearance of the band 750 based at least in part on the physiological data. In some implementations, the processor of the band 750 may receive patient status data (e.g., great, good, suboptimal, bad, critical, and the like) from the sensor assembly 202 (as opposed to receiving raw or processed patient physiological data) and change the display of the light sources based on the patient status data. This can be advantageous when a patient and/or care providers (or family members) do not have access to the patient's physiological data. By monitoring the appearance (for example, the color) of the band 750, patients, care providers, and family members can easily recognize and monitor patient conditions.

Optionally, the identifier can be used as a security tag that can cause an alarm system to generate an alarm if the identifier passes a geo-fence location. For example, a hospital or a care provider facility may have, for example, RF scanners located at various locations. Such RF scanners may be installed at a main entrance of a care provider facility or at certain checkpoints for, for example, emergency rooms, intensive care units, maternity wards, neonatal units and the like. RF scanner may detect the identifier of the hospital band attached to the sensor assembly 202 and generate an alarm. Such use of the identifier as security tags can prevent unauthorized and/or accidental movement of patients, removal or movement of the hospital bands with the sensor assembly 202, leaving the hospital without returning the sensor device and the like.

FIG. 7D shows the dock 222 of the disposable module 220 coupled to yet another example of an attachment mechanism. The dock 222 can be coupled to an extension 708 extending away from the disposable module 220. For example, as shown in FIG. 7D, the disposable module 220 can be placed on top of a hand and the extension 708 can extend towards a wrist of a patient. The extender 708 can include a strap 700A that can loop around the wrist to secure the disposable module 220 and the extension 708 to the wrist. The strap 700A can include a fastener 706A that can adhere the strap 700A to a top surface of the extension 708. The fastener 706A can be disposed at a distal end or a proximal end of the strap 700A. The fastener 706A may adhere to a top surface or a bottom surface of the 700A. The fastener 706A can incorporate one of the following mechanisms including a hook and loop system, Velcro, buttons, snaps, magnets, and the like.

FIG. 7E illustrates another example of an attachment mechanism for the disposable module 220. As shown here, the dock 222 can be coupled to a strap 700B. A first, proximal end of the strap 700B can be attached to the dock 222, while a second, distal end of the strap 700B can extend away from the dock 222. The distal end of the strap 700B can include a fastener 706B. The strap 700B can affix the dock 222 to a wrist of a patient by having the second, distal end looped around the wrist. The distal end of the strap 700B can be affixed by looping over or under the proximal end of the strap 700B. Once the distal end of the strap 700B looped around the first, proximal end of the strap 2310, the fastener 706B can be used to secure the distal end of the strap 700B. The fastener 706B can incorporate one of the following mechanisms including, but not limited to, a hook and loop system, Velcro, buttons, snaps, and/or magnets.

FIG. 7F shows yet another example of an attachment mechanism for the sensor assembly 202. The sensor assembly 202 can be coupled to an extender 708A which includes a hook 710. The extender 708A can extend away from the dock 222 of the sensor assembly 202, where the hook 710 is coupled to a distal end of the extender 708A. The hook 710 can wrap around the strap 700C such that the extender 708A and the dock 222 are substantially held in place with respect to a wrist of a patient. The strap 700C can be modular. The strap 700C may be removably connected or affixed to the hook 710 of the extender 708A. The strap 700C can be a flexible band that can tightly wrap around a patient's wrist, as shown in FIG. 7F.

FIG. 7G shows yet another example of an attachment mechanism for the sensor assembly 202. The dock 222 can include the strap 308 extending from a first side of the dock 222, the strap 308 dimensioned to wrap around a patient's wrist in a first direction, and the strap loop 302 extending from a second side of the dock 222. The strap 308 can include the fastener 310 disposed near its distal end. The strap 3810 can be routed around the patient's wrist and through the strap loop 302 of the dock 222. Once routed through the strap loop 302 of the dock 222, the strap 308 can be routed around the strap loop 302 and wrap the wrist in a second direction. The first direction of wrapping the strap 308 around the wrist can be clockwise or counterclockwise. The second direction of wrapping the strap 308 around the wrist can be clockwise or counterclockwise. FIG. 7H shows the sensor assembly 202 of FIG. 3A affixed to a patient's wrist.

FIG. 7I illustrates yet another example of an attachment mechanism for the sensor assembly 202. The dock 222 and the sensor 240 can be coupled to a glove 712. When the glove 712 is placed on a patient's hand, the sensor 240 of the sensor assembly 202 can be placed one of the fingertips. The dock 222 can be attached to a top portion of the glove 712 as shown in FIG. 7I. The sensor 240 of the sensor assembly 202 can be built inside or outside the fingers of the glove 712. The sensor 240 can be integrated to the fingers of the glove 712. The cable 230 of the sensor assembly 202 can be integrated to the glove 712.

Dongle and Pairing

Given the time demands placed on clinicians in busy hospitals and the number of patients and patient monitoring devices, manual interaction to establish connection between the computing device 206 (for example, a mobile patient monitoring display device) and the reusable module 250 can be burdensome. In some cases, the time required to manually interact with a patient monitor device in order to establish connection with a pairing device can even jeopardize a patient's well-being in particularly urgent circumstances. For at least the foregoing reasons, it would be advantageous for the computing device 206, such as bedside patient monitors, central monitoring stations, and other devices, to have the capability to detect the presence of the reusable module 250 nearby and establish a wireless communication 204 with the reusable module 250.

Figure 8B:
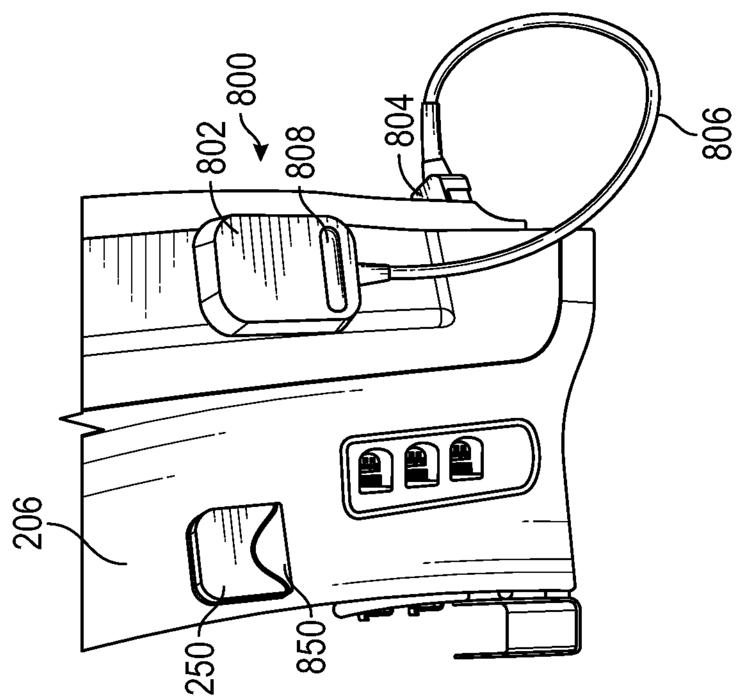
FIGS. 8A-8C illustrate various views of a dongle operatively connected to the computing device.
Figure 8A:
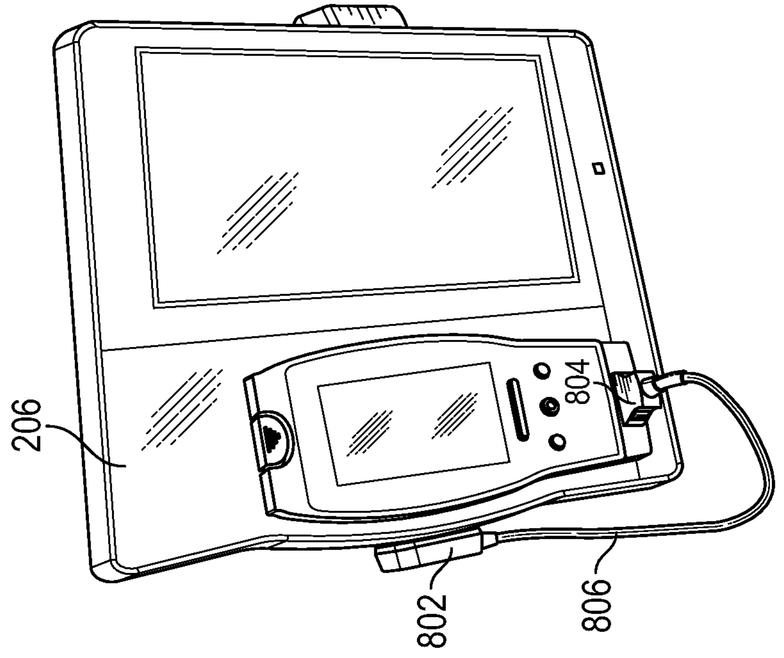
Figure 8C:
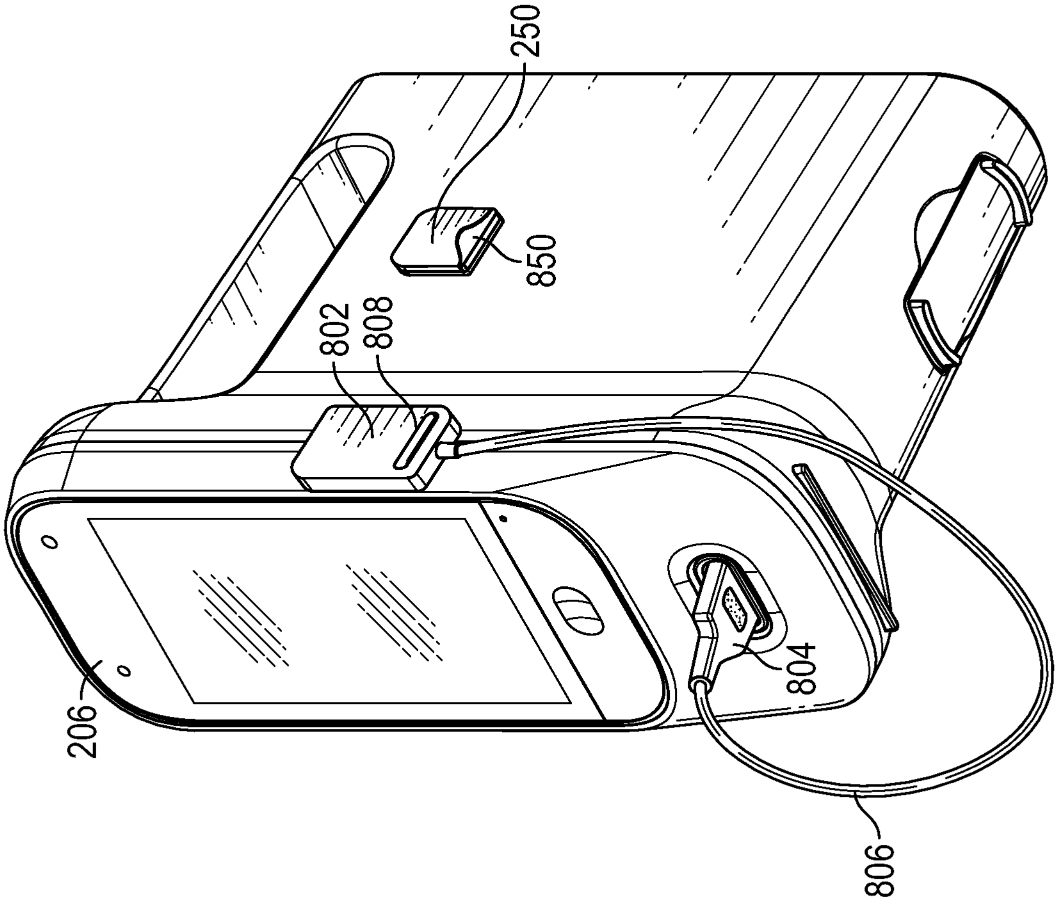

FIGS. 8A-8C illustrate various view of a dongle 800 connected to the computing device 206. The dongle 800 can include a body 802 and a connector 804 coupled to the body 802 via a cable 806. The connector 804 can connect to the computing device 206 to allow transmissions between the dongle 800 and the computing device 206. The cable 806 can include one or more conductive wires that can transmit data and/or power between the body 802 and the connector 804. The body 802 of the dongle 800 can be removably attached to the computing device 206. The body 802 can receive power from the computing device 206 via the connector 804 and the cable 806.

When the dongle 800 is connected to the computing device 206 via the connector 804, the computing device 206 can automatically detect the connector 804. The computing device 206 can determine a type of connector 804 and automatically change its settings. The settings may include, but not limited to, display settings for the display 208, display setting for the computing device 206 (for example, color of lights used to denote pair or communication status), communication protocol settings (for example, type of wireless communication utilized), communication signal settings (for example, varying communication signal type or strength based on different types of communications), and the like. Additionally, the settings for the dongle 800 can change to accommodate different types of computing devices 206 and their displays 208. Such setting can include display settings (for example, colors or messages denoting communication/pairing status), communication signal settings (for example, frequency of wireless signal used), communication protocol settings (for example, types of wireless communication used), and the like.

The computing device 206 can receive processed physiological parameter data and display on a display screen. This feature can be advantageous because it can reduce the amount of processing power required by the computing device 206. As discussed above, the reusable module 250 can perform signal processing on raw patient physiological data collected by the sensor 240 and calculate patient physiological parameters. Therefore, the data transmitted from the reusable module 250 to the computing device 206 via the body 802 includes patient physiological parameters that do not require further signal processing.

The reusable module 250 can transmit patient physiological parameters with low resolution and the dongle 800 can fill in the data using various methods. For example, the dongle 800 may use different types of averages to fill in the data transmitted from the reusable module 250. The reusable module 250 can send waveform data, for example, at a low resolution and the dongle 800 can increase the resolution of the waveform. This feature can further increase the life of the battery 224 of the disposable module 220.

The body 802 of the dongle 800 can include a transceiver or receiver, and a communication module for communicatively coupling the computing device 206 to other patient monitoring devices such as the reusable module 250. When the reusable module 250 is sufficiently proximate, the body 802 can communicate with the reusable module 250 so as to identify the reusable module 250. The body 802 can include a radio-frequency identification (RFID) reader and while the reusable module 250 can include an embedded RFID chip containing an identifying information unique to the reusable module 250. The RFID reader of the body 802 can identify the embedded RFID chip inside the reusable module 250 and establish a wireless communication 204 between the reusable module 250 and the body 802. The body 802 can include a transceiver that complies with one or more short-range wireless communications standards, such as Bluetooth®. Other types of wireless communication protocols may be utilized to establish communication and transfer data between the dongle 800 and the reusable module 250.

The body 802 can include a groove 808 dimensioned to receive a portion of the reusable module 250. The groove 808 can indicate a medical personnel where to place the reusable module 250 in order to associate (for example, pair) the reusable module 250 with the computing device 206.

The dongle 800 can include a holder 850 that can retain the reusable module 250 when not in use. The holder 850 can be separate from the dongle 800 as shown in FIG. 8B. The holder 850 can include a surface dimensioned and shaped to engage with a surface of the reusable module 250 to assist in retaining the reusable module 250. The holder 850 can use a magnet to retain the reusable module 250. The holder 850 can be attached on the computing device 206 via various mechanisms including, but not limited to, adhesives, Velcro, magnet, and the like.

Figure 9B:
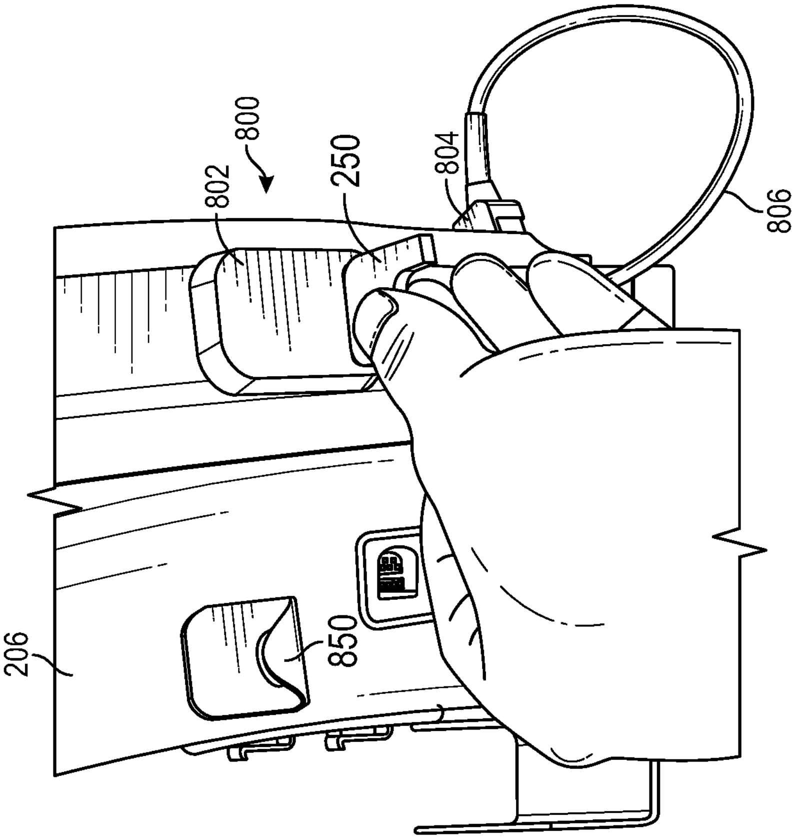
FIGS. 9A-9C illustrate a reusable module and a computing device coupled to a dongle, providing additional details for a method of pairing the reusable module with the computing device.
Figure 9A:
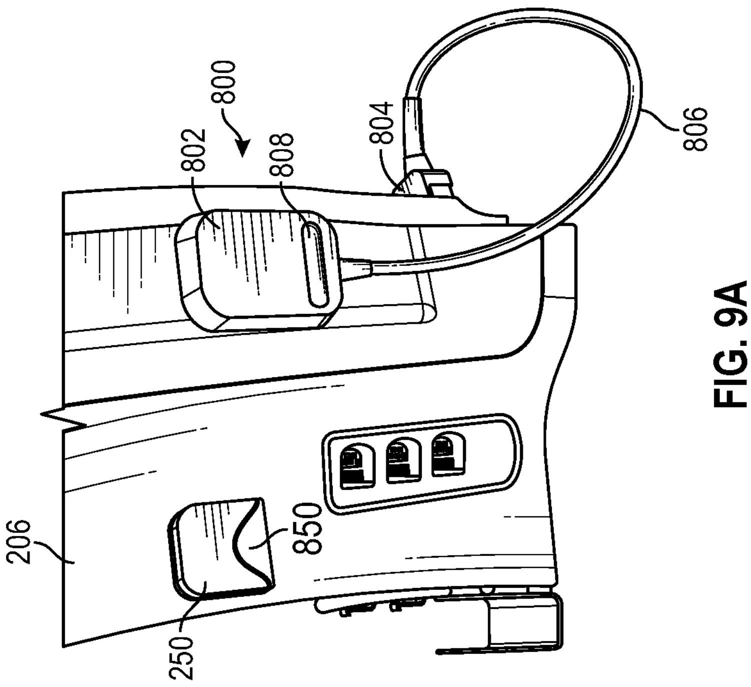
Figure 9C:
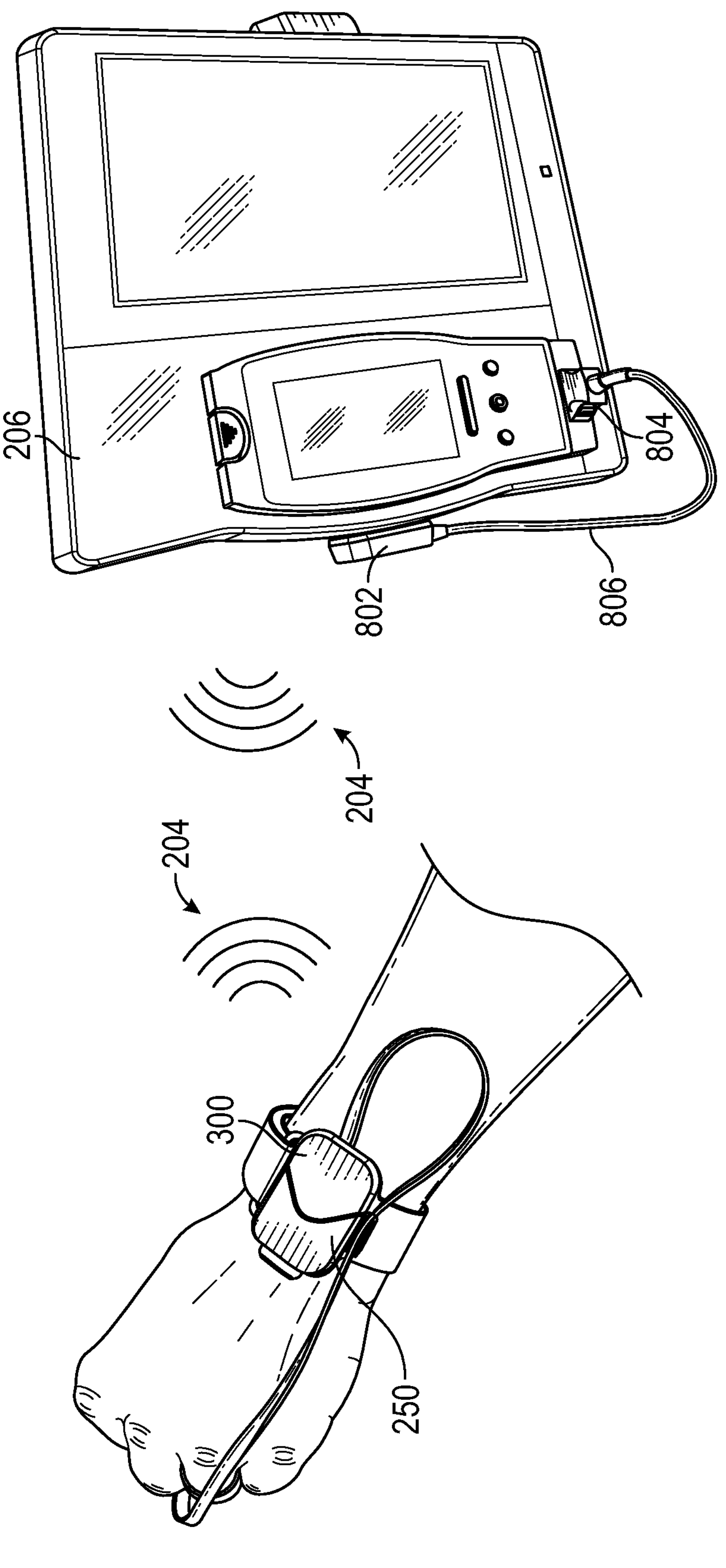

FIGS. 9A-9C illustrate a process of pairing the reusable module 250 with the computing device 206 using the dongle 800. Wireless communication 204 between the reusable module 250 and the computing device 206 can be initiated by coupling the connector 804 of the dongle 800 with the computing device 206 and placing the reusable module 250 within a certain distance away from the body 802 of the dongle 800. The reusable module 250 may or may not require a physical contact with the body 802 to transfer its identifying information to the dongle 800.

When the reusable module 250 is brought sufficiently close to the body 802 of the dongle 800, the body 802 can, for example, use RFID technology to receive from the reusable module 250 information that can identify the reusable module 250 to the computing device 206. The identifying information can be an ID tag of a token specific or unique to the reusable module 250. The identifying information can include Bluetooth® parameters of the reusable module 250. Other types of identification mechanisms can be used to allow the computing device 206 to identify and associate with the reusable module 250.

The identifying information of the reusable module 250 can be stored in the memory 256. The identifying information may be hardwired into the memory 256 or programmable. The identifying information can include pairing parameters (for example, a pairing device ID) that is unique to the reusable module 250. The identifying information may be unique to the patient to whom the reusable module is assigned. The identifying information of the reusable module 250 may also include other information such as, for example, the pairing device's information, information regarding the sensor 240 the reusable module 250 is operatively connected to, or a code or other indicator for initiating a predetermined action to be performed by the computing device 206. Additionally and/or alternatively, the identifying information of the reusable module 250 can be generated using physiological data collected by the sensors 240 of the sensor assembly 202.

The body 802 of the dongle 800 can include a RFID reader. The RFID reader can communicatively couple the computing device 206 to other patient monitoring devices such as the reusable module 250. When the reusable module 250 is proximate to the body 802, as shown in FIG. 9B, the RFID reader of the body 802 can receive the identifying information from the reusable module 250. Once the body 802 receives the identifying information, the identifying information can be transmitted to the computing device 206 via the cable 806 and the connector 804.

The computing device 206 can use the identifying information to associate the reusable module 250 with the computing device 206. For example, the Bluetooth® parameters of the reusable module 250 can be used to associate the reusable module with the computing device 206. Once associated, the reusable module 250 can connect with the computing device 206 using the pairing parameters (for example, Bluetooth® parameters) included in the identifying information. The computing device 206 can identify the reusable module 250 and allow wireless communication 204 with the reusable module 250 using the Bluetooth® parameters it received from the reusable module 250. After establishing connection with the computing device 206, the reusable module 250 can communicate with the dongle 800 and the computing device 206 via Bluetooth® transmission. Other types or standards of wireless communication can be used, including, for example, ultrasound, Near Field Communication (NFC), and the like. If multiple reusable modules 250 are proximate to the computing device 206, a priority scheme or a user acknowledgment may be used to determine which reusable modules 250 are accommodated.

The reusable module 250 can use the NFC to provide instructions to program the dongle 800 to take certain actions in certain situations. The NFC communication circuitry of the reusable module 250 can have an associated memory that can have read/write capabilities. For example, the reusable module 250 can use NFC to indicate how long the dongle 206 must wait before deleting the pairing parameters ("giving up"). In another example, the reusable module 250 can use the NFC to indicate when the dongle 800 is disallowed from deleting the pairing parameters ("not giving up"). The NFC can be used to allow the dongle 800 to associate with one or more reusable modules 250 at the same time.

The dongle 800 can use the NFC to receive various types of information from the reusable module 250. The dongle 800 can receive information associated with NFC components of the reusable module 250 and determine sensor types, patient types, patient information, physician information, hospital information, authorized uses, authorized supplies, authorized manufacturers, emitter wavelengths, or indications of the usage or life of the reusable module 250, parameters the reusable module 250 is capable of measuring, and the like. For example, the dongle 800 can receive information via the NFC to determine that a particular reusable module 250 is designed to work with sensor assembly 202. The dongle 800 can also write back using NFC. For example, the dongle 800 can provide programming information through NFC to the reusable module 250. The dongle 800 can also write sensor usage information to the reusable module 250. For example, the reusable module 250 may only be allowed to be used a certain number of times before it must be discarded in order to maintain quality. This information can be written to the reusable module 250 through NFC communication.

Throughout the present disclosure, it is to be understood that the dongle 800 may be incorporated directly into the computing device 206. For example, the dongle 800 can be built into the circuitry of the computing device 206 such that the dongle 800 and the computing device 206 are in the same housing. In another example, the dongle 800 and the computing device 206 are in the same housing but the dongle 800 is not built into the circuitry of the computing device 206. The dongle 800 can be incorporated into the computing device 206 such that the dongle 800 is located near an outer housing or body of the computing device 206. Such a configuration can allow the reusable module 250 to readily establish wireless communication 204 with the dongle 800. The dongle 800 incorporated directly into the computing device 206 can prevent possible connection issues between the dongle 800 and the computing device 206.

Once the computing device 206 is associated with the reusable module 250, it can transmit a signal to the reusable module 250 indicating that the reusable module 250 is associated with the computing device 206. Different types of notifications can be generated when the reusable module 250 has successfully established wireless communication 204 with the computing device 206. The notifications can be generated by the computing device 206, the reusable module 250, or both.

The computing device 206 can provide an auditory notification or a visual notification on the display 208. For example, the computing device 206 can play a pattern of beeps or a predetermined melody for successful pairing. In another example, the computing device can play an auditory message such as "$SpO_2$ sensor number 1234 has been successfully paired with patient monitoring device A123." Visual notifications can include a blinking LED on the display 208. Another example of a visual notification can be in a form of text such as "Pairing successful" displayed on the display 208. The reusable module 250 has one or more LEDs to indicate status of wireless communication 204 with the computing device 206. For example, the reusable module 250 can include a red LED to indicate that no wireless communication 204 has been established between the reusable module 250 and the computing device 206. In another example, the reusable module 250 can include a blue LED to indicate that the reusable module 250 has established the wireless communication 204 with the computing device 206. A blinking green LED may be used to indicate that the computing device 206 is waiting for the reusable module 250 to establish the wireless communication 204 with the computing device 206. Different color LEDs and different schemes can be used to indicate different status of wireless communication 204 between the reusable module 250 and the computing device 206.

After receiving the pairing parameters from the reusable module 250, the computing device 206 can wait for a predetermined time period for the reusable module 250 to establish the wireless communication 204 (for example, Bluetooth® connection). If the wireless communication 204 is not established within the predetermined time period, the pairing parameters can expire, requiring the reusable module 250 to retransmit the pairing parameters to the computing device 206 again. The predetermined time period can be modified.

Once the computing device 206 receives the pairing parameters from the reusable module 250, the reusable module 250 can be mated with the dock 222, as shown in FIG. 9C. Once the reusable module 250 is mated with the dock 222, it can draw power from the battery 224 to establish wireless communication 204 with the computing device 206. The reusable module 250 can use the power drawn from the battery 224 to perform signal processing on the raw data to calculate physiological parameters. Once the physiological parameters are determined, the reusable module 250 can use the power from the battery to transmit the physiological parameters to the computing device 206 via the wireless communication 204.

The computing device 206 can receive the patient data including patient physiological parameters from the reusable module 250 and display the parameters on the display 208. The computing device 206 can receive the patient data via the body 802 of the dongle 800. In other words, the body 802 of the dongle 800 can receive patient physiological parameters from the reusable module 250 and in turn transmit the parameters to the computing device 206. As discussed above, Bluetooth® can be used to transmit the patient data between the reusable module 250 and the computing device 206 (or the body 802). For example, the reusable module 250 operatively connected to a $SpO_2$ sensor can establish Bluetooth® communication with the computing device 206. The computing device 206 can receive the patient data including SpO2 parameters from the reusable module 250 and display the parameters on the display 208. In another example, the reusable module 250 operatively connected to a temperature sensor can establish Bluetooth® communication with the computing device 206. The computing device 206 can receive the patient data including temperature parameters from the reusable module 250 and display the parameters on the display 208. The computing device 206 can receive one or more parameters from the reusable modules 250 and display the one or more parameters on the display 208.

The reusable module 250 can include an ID tag that is active or passive RFID tag. An active RFID tag may be WiFi-enabled, for example. The ID tag can be a barcode (e.g., two-dimensional or three-dimensional) or a WiFi-enabled RFID tag. By communicating with the WiFi access points, the computing device 206 can triangulate its position relative to that WiFi access points. Likewise, the position of the reusable module 250 (and the sensor 240 if the reusable module 250 is operatively connected to the sensor 240) can be triangulated. Thus, the distributed WiFi access points can be used by, for example, the computing device 206 to determine the approximate position of the reusable module 250 (and/or the sensor 240) with respect to the computing device 206. The computing device 206 may also communicate directly with the reusable module 250 in order to, for example, enhance the position approximation determined using the distributed WiFi access points.

Positions of one or more reusable modules 250 can be used to determine relative or absolute positions of the one or more reusable modules 250. For example, consider reusable modules 250A, 250B, 250C, and 250D. When locations of the reusable modules 250A, 250B, and 250C are known, their positional information can be used to determine a position of the reusable module 250D.

The presence or proximity of the reusable module 250 to the computing device 206 may be determined by the reusable module 250 including an RFID tag. An "RFID tag" or simply "tag" can include any wireless communication device and/or communication standard (e.g., RFID, NFC, Bluetooth, ultrasound, infrared, and the like) that can remotely identify a proximate user to a monitor. Tags include, but are not limited to, devices in the form of badges, tags, clip-ons, bracelets or pens that house an RFID chip or other wireless communication components. Tags also encompass smart phones, PDAs, pocket PCs and other mobile computing devices having wireless communications capability. The RFID tag can include identifying information or pairing parameters for the reusable module 250.

The computing device 206 may respond to the departure of all proximate reusable modules 250 by automatically removing displays associated with the reusable modules 250. This feature can provide display patient physiological data only for sensors 240 associated with reusable modules 250 proximate to the computing device 206. The computing device 206 may respond in a similar manner by automatically silencing pulse "beeps" or other non-critical sounds when there are no proximate reusable modules 250 and associated sensors 240.

The computing device 206 can generate alarms when its wireless communication 204 with the reusable module 250 is disrupted or no longer exists. For example, the computing device 206 can create at least one of auditory and visual alarm when the reusable module 250 is no longer mated with the disposable sensor 220.

The computing device 206 can monitor signal strength of the wireless communication 204 between the computing device 206 and the reusable module 250. Under some circumstances, the reusable module 250 may move out of the range of the computing device 206 which may cause the wireless communication 204 to be disrupted. For example, a patient equipped with the reusable module 250 may visit an x-ray room for a routine visit and disrupt the wireless communication 204 between the reusable module 250 and the computing device 206. If the same reusable module 250 becomes available within the range within a period of time, the computing device 206 can automatically reestablish the wireless communication 204. For example, if the patent returns from the x-ray room within 30 minutes, the computing device 206 may be able to reestablish the wireless communication between the reusable module 250 and the computing device 206. Upon reestablishing communications, any information stored on the reusable module 250 for the time period where communication was disrupted can be downloaded to the computing device 206.

The computing device 206 can be configured to not lose (or delete) the pairing parameters received from the reusable dongle 250. This feature can prevent other reusable modules 250 from pairing with the computing device 206 even when the reusable module 250 is no longer wirelessly communicating with the computing device 206. For example, a first computing device 206 and a first reusable module 250 are in a first wireless communication 204. The first computing device 206 can be configured to not "give up" or "give up" the first reusable module 250 even after the first wireless communication 204 is terminated. When configured to "give up," a second reusable module 250 can be paired with the first computing device 206. When configured to "not give up," a second reusable module 250 cannot be paired with the first computing device 206.

This feature can also apply in situations in which the battery 224 of the disposable module 220 is about to be depleted or when the reusable module 250 is removed from the disposable module 220. Without power from the battery 224, the reusable module 250 cannot maintain the wireless communication 204 with the computing device 206. The computing device 206 can be configured to prevent or not prevent other computing device 206 from establishing wireless communication 204 with the reusable module 250. The reusable module 250 can also send a "dying" signal to the computing device 206 providing instructions on pairing or other instructions as the device is removed from the disposable module 220 or when the batteries are depleted. This dying instruction allows the pairing to be maintained.

Computing devices 206 (or dongle 800) can communicate to other computing devices 206 (or other dongles 800) to ensure that each computing device 206 (or dongle 800) is paired to a single reusable module 250 at any time. For example, when a first reusable module 250 is paired (or associated) with a first computing device 206, a second reusable module 250 may not be paired (or associated) with the first computing device 206. However, the first reusable module 250 may be able to pair with a second computing device 206. Pairing the first reusable module 250 with the second computing device 206 can cause the second computing device 206 to inform the first computing device 206 to release its pairing with the first reusable module 250.

The computing device 206 can identify the sensors 240 and the reusable modules 250 associated with the computing device 206. When one or more sensors 240 and reusable modules 250 are wirelessly associated to the computing device 206, it may be advantageous for the computing device 206 to distinguish and indicate different physiological parameters from different sensors 240 or reusable devices 250. For example, the computing device 206 can be associated with two different sensors 240 (and their respective reusable modules 250) for detecting peripheral capillary oxygen saturation ($SpO_2$) and acoustic respiration rate (RRa). The computing device 206 can display information pertaining to the sensors 240 or the reusable modules 250 (for example, sensor name, sensor type, sensor location, sensor ID, reusable module ID, reusable module name) to distinguish patient parameters from different sensors and/or reusable modules.

The reusable module 250 of the sensor assembly 202 can establish wireless communication 204 with mobile devices such as smartphones, tablets, smartwatches, laptops, and the like. The mobile devices can include a mobile application that allows the mobile devices to establish wireless communication 204 with the reusable module 250 of the sensor assembly 202, receive patient physiological parameters from the reusable module 250, and display the patient physiological parameters. In addition to the patient physiological parameters, the mobile application can also display other patient information including, but not limited to, name, age, past medical history, current medications, address, gender, and the like.

The wireless communication 204 between the mobile devices and the reusable module 250 can be in a form of Bluetooth®. The wireless communication 204 between the mobile devices and the reusable module 250 can be established via the Internet. For example, the computing device 206 can be connected to the Internet or a secured network server. Once wireless communication 204 between the reusable module 250 and the computing device 206 is established, the mobile devices can access the Internet or the secure network server to receive and display the patient physiological parameters via the mobile application described above.

The mobile application can include various security measures to prevent third-parties from accessing patient information. The mobile application can be associated with certain mobile devices that has been identified by a healthcare provider. Identification and a passcode may be required for using the application to connect to the reusable module 250 (or the computing device 206), receive patient data (for example, patient data and/or patient physiological parameters), and display patient data. Each of the mobile applications can be associated with a unique access code or an identification code that may be required for receiving patient data from the Internet or the secured network server. The unique access code or the identification code can be associated with the mobile device or the mobile application. The unique access code can be a media access control (MAC) address associated with each of the mobile devices.

Mating of the Dock and Reusable Module

Figure 10A:
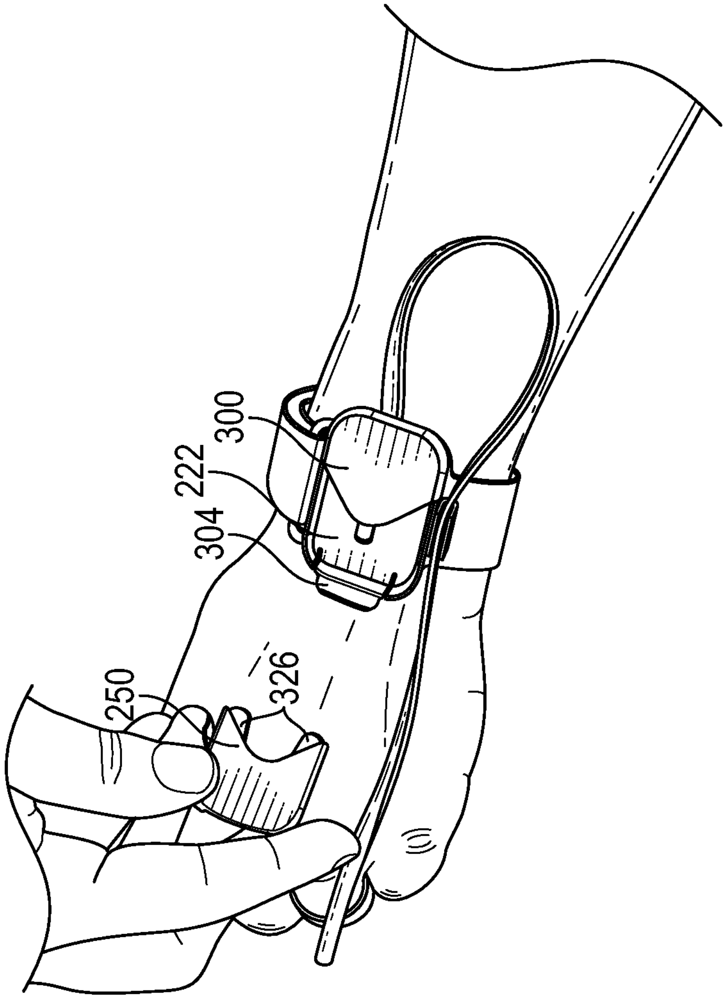
FIGS. 10A-10D illustrate various perspective views of the reusable module and the disposable module of FIG. 3A attached to a wrist of a patient, showing additional details for a method of mating the reusable module with the disposable module.

FIGS. 10A-10D illustrates the process of mating the reusable module 250 with the dock 222 of the disposable module 220. The dock 222 of the disposable module 220 can be attached to a wrist of a patient as shown in FIG. 10A. The dock 222 can include a housing 300 that includes slots 328 (see FIG. 3B) that correspond to the legs 326 of the reusable module 250.

Figure 10B:
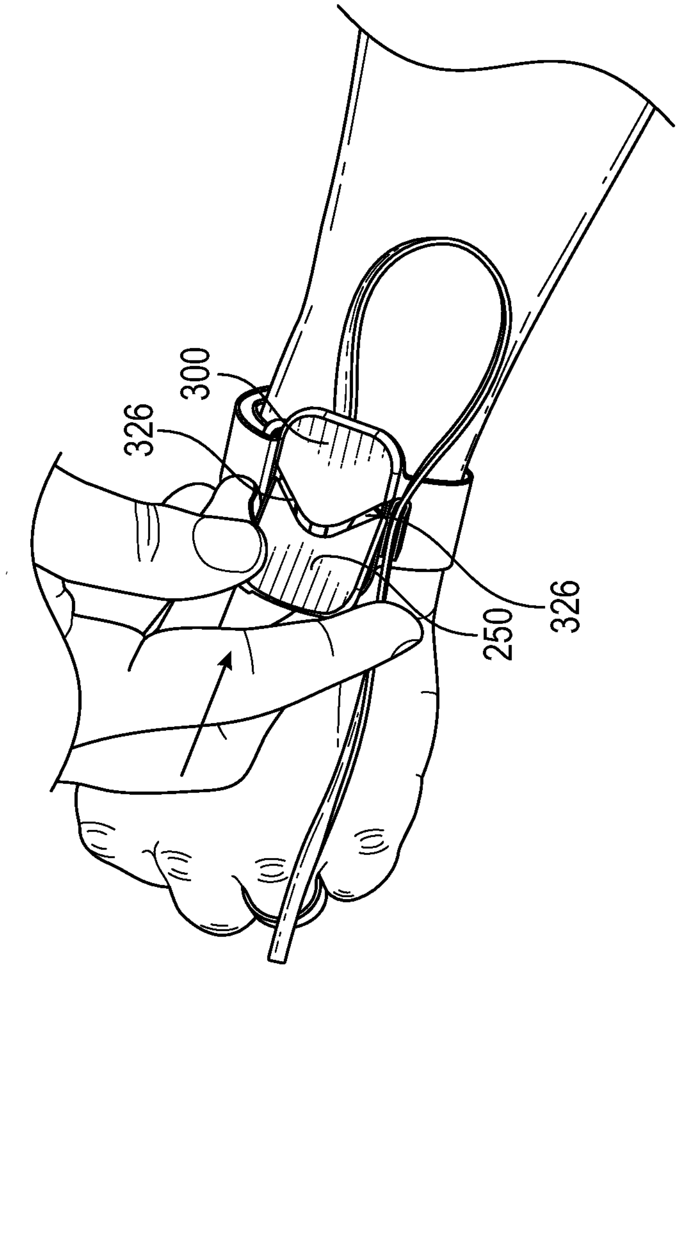

FIG. 10B illustrates the reusable module 250 being inserted into the dock 222. The legs 326 can face the slots 328 of the dock 222 as the reusable module 250 is inserted. When the legs 326 are substantially positioned within the slots 328 of the dock 222, body of the reusable module 250 can be positioned at an angle with respect to the dock 222. One end of the reusable module 250 may be positioned on top of the retainer 304 while at least a portion of the legs 326 are positioned in the slots 328 of the dock 222.

Figure 10C:
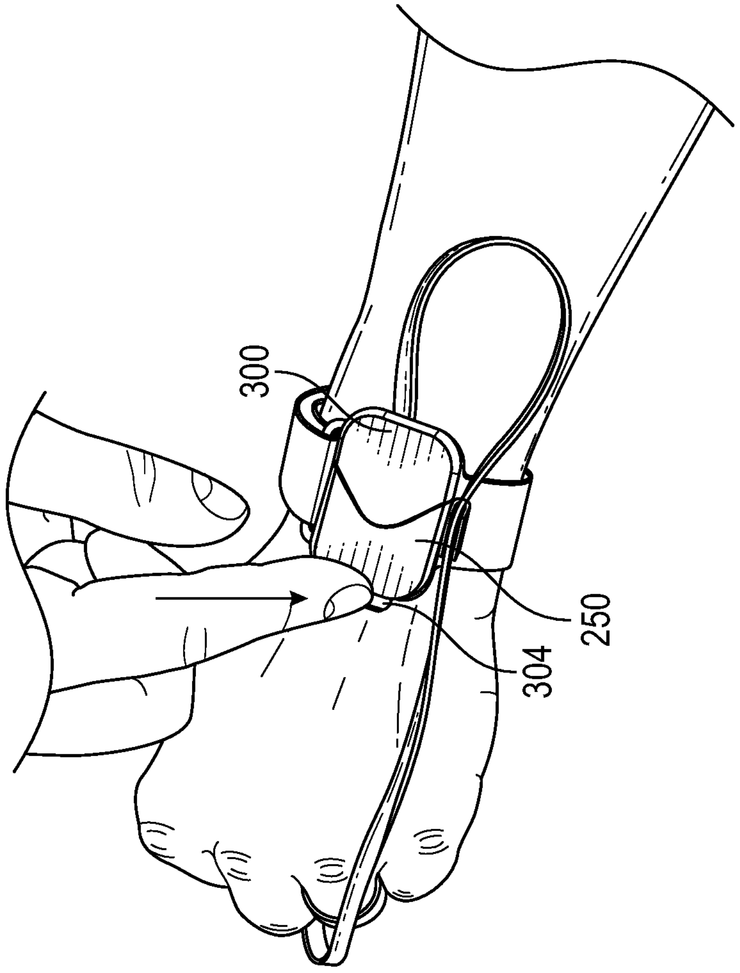
Figure 10D:
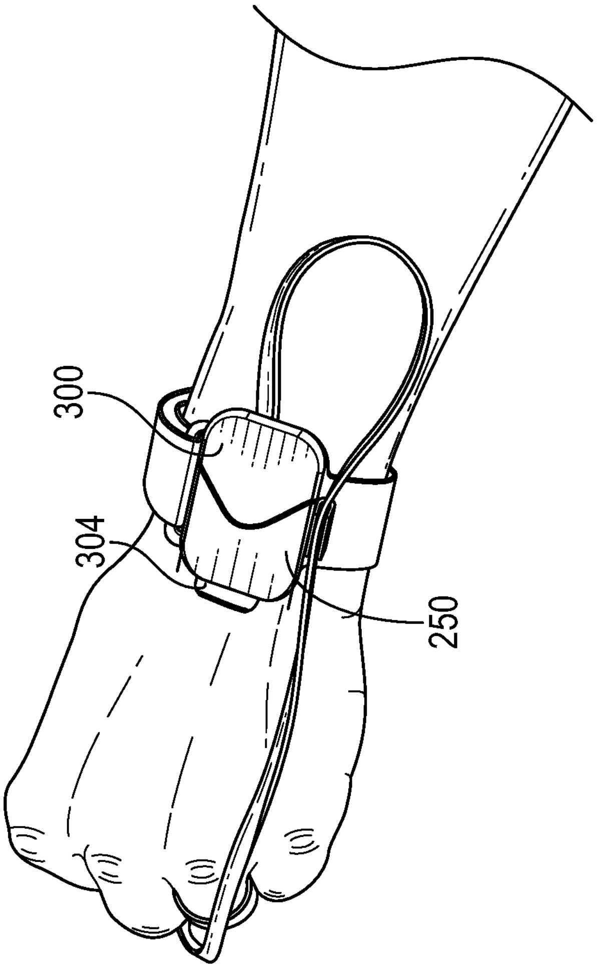

FIG. 10C illustrates the reusable module 250 being pushed down towards the dock 222. As shown in the FIG. 10C, the legs 326 can be partially inserted in the slots 328. The reusable module 250 can be pushed down, which causes the retainer 304 to move away from the housing 300, thus allowing the reusable module 250 to be fully inserted in the dock 222 and mated with the dock 222 as shown in FIG. 10D. When the reusable module 250 is fully inserted, the retainer 304 can snap back in a direction towards the housing 300 and engage with the groove 322 of the reusable module 250 (FIG. 3B). Mating between the reusable module 250 and the dock 222 can cause the legs 326 engage the slots 328 of the housing 300. The engagement between the groove 322 and the protrusion 324 (FIG. 3B) of the retainer 304 can hold the reusable module 250 in place while mated with the dock 222. The engagement between the slots 328 and the legs 326 can hold the reusable module 250 in place.

Figure 11A:
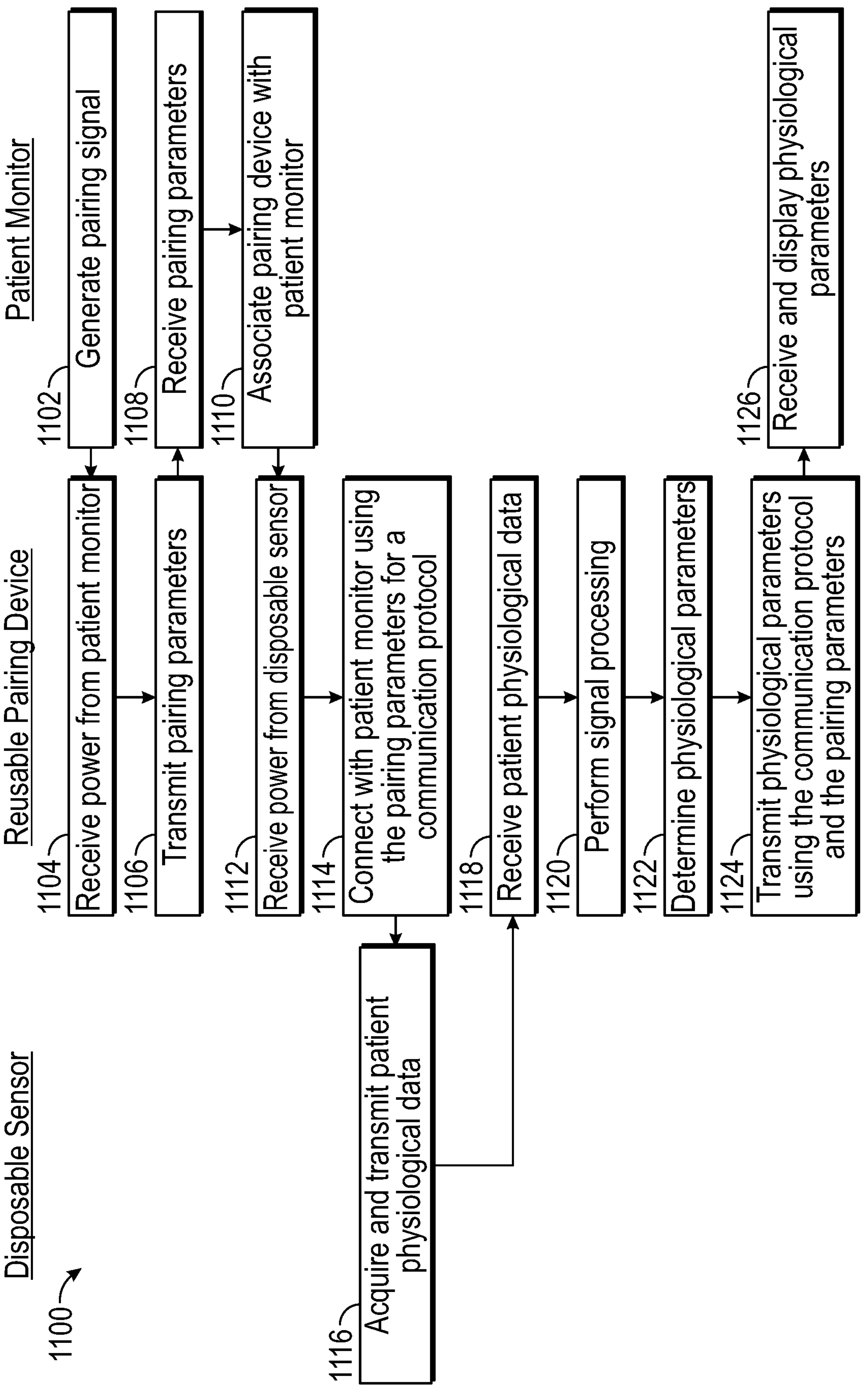
FIG. 11A illustrates a method of establishing a wireless communication using a reusable module, a disposable module, and a computing device for acquiring and displaying patient physiological parameters.

Methods of Pairing, Collecting Data, and Transmitting Data to Computing Device FIG. 11A illustrates a method 1100 of establishing wireless communication between the reusable module 250 and the computing device 206, determining patient physiological parameters using the sensor assembly 202, and displaying the physiological parameters using the computing device 206.

At block 1102, a patient monitor (for example, the computing device 206) can generate and transmit a pairing signal. Generating the transmitting the pairing signal can be done automatically or manually. The pairing signal may be a radio signal. The pairing signal can be configured such that a nearby device, upon receiving the signal, is triggered to transmit an identification information in response. The nearby device may be the reusable module 250. The pairing signal can also contain sufficient power to enable nearby devices to transmit pairing parameters in response to the pairing signal.

Generating and transmitting the pairing signal can be done by different devices. The computing device 206 can generate the pairing signal while the dongle 800 attached to the computing device 206 via the connector 804 can transmit the pairing signal. The dongle 800 can generate and transmit the pairing signal for the computing device 206.

The reusable module 250 located within a predetermined distance from the computing device 206 can receive the pairing signal. This can be advantageous in hospital environments where many patients can be placed within a short distance from an electronic device such as the computing device 206. Such configuration can allow the electronic device (for example, the computing device 206) to receive patient health data only from a patient who is nearby and prevent the electronic device from receiving patient health data from other patients who may not be a patient-in-interest. Strength of the pairing signal can be varied to allow the signal to travel further or closer.

At block 1104, the reusable module 250 can receive power from the pairing signal generated by the computing device 206. The pairing signal can be a high-frequency alternating current which can be used to create a voltage potential. The pairing signal of the computing device 206 may be received when the reusable module 250 is within a predetermined distance. As discussed above, physical contact between the computing device 206 (or the dongle 800) and the reusable module 250 may be required for the reusable module 250 to receive the power from the pairing signal. The reusable module 250 can automatically receive power from the pairing signal. By receiving power from the pairing signal, the antenna 252 of the reusable module may not need to draw power from the battery 224 of the disposable device 220.

At block 1106, the reusable module 250 can use the power received from the pairing signal to transmit identification information to the computing device 206. The identification information can include pairing parameters of the reusable module 250. The identification information may be a tag serial number unique to the reusable module 250. The identification information can include, but not limited to, stock number, lot number, batch number, production date, or other specific information. The computing device 206 can use the identification information to uniquely identify the reusable module 206. The transmission of the identification information can occur automatically.

The reusable module 250 can include a feature that prevents automatic transmission of the identification information to the computing device 206. This feature can be advantageous to prevent inadvertent pairing of the reusable module 205 with the computing device 206. Medical personnel can deal with patients in need of many different types of sensors. In such circumstances, reusable modules 250 may inadvertently be brought proximal to the computing device 206 (or dongle 800). Thus it can be advantageous for the reusable module 250 to have the feature to prevent the reusable modules 250 from automatically pairing with the computing device 206 (or dongle 800) to prevent inadvertent pairing.

At block 1108, the computing device 206 can receive the identification information from the reusable module 250. The dongle 800 connected to the computing device 206 can receive the identification information and relay it to the computing device 206. At block 1110, the computing device 206 can associate with the reusable module 250, which allows the wireless communication 204 to be established between the reusable module 250 and the computing device 206.

The association between the computing device 206 and the reusable module 250 can occur automatically. On the other hand, the association can require a user input via the computing device 206. For example, upon receiving the pairing parameters from the reusable module 250, the computing device 206 can generate a notification prompting a user to allow or disallow the computing device 206 to associate with the reusable module 250. If allowed, the computing device 206 can associate with the reusable module 250 and the reusable module 250 can establish a wireless communication 204 with the computing device 206. If not allowed, the computing device 206 may not associate with the reusable module 250 and the reusable module 250 may not establish a wireless communication 204 with the computing device 206.

Establishing wireless communication 204 can require the reusable module 250 to have an external power source. The battery 224 provides sufficient power for the reusable module 250 to receive raw patient physiological data from the sensor 240 and perform signal processing on the raw data to calculate patient physiological parameters. Moreover, the reusable module 250 can use the power from the battery 224 to use the antenna 252 to wirelessly transmit the calculated parameters to the computing device 206. Without the battery 224 connected to the dock 222, the reusable module 250 cannot receive power via the electrical contacts 228, 258.

At block 1112, the reusable module 250 can mate with the dock 222 and receives power from the battery 224 via the battery circuit 314 and the electrical contacts 228, 258. At block 1114, the reusable module 250 can establish wireless communication 204 with the computing device 206. The wireless communication 204 can be established using the pairing parameters. The wireless communication 204 can be via Bluetooth®, as discussed above. The wireless communication 204 can be one-way or two-way communication between the reusable module 250 and the computing device 206. For example, the reusable module 250 can transmit calculated physiological parameters to the computing device 206. The computing device 206, in return, can transmit a confirmation signal back to the reusable module 250 to let the reusable module 250 know that the calculated parameters were received. The reusable module 250 can include one or more light sources (for example, LEDs) that can generate light when the reusable module 250 receives the confirmation signal from the computing device 206.

At block 1116, the sensor 240 can acquire raw patient physiological data and transmits the data to the dock 222 via the cable 230 and the flex circuit 320. The raw physiological data can be transferred to the reusable module 250 via the electrical contacts 228, 258. The sensor 240 can include, but not limited to, an acoustic sensor, ECG sensor, EEG sensor, respiratory acoustic sensor (RAS), $SpO_2$ sensor, and the like. The sensor 240 can include one or more different types of sensors.

The sensor 240 can be placed on various areas of a patient. The location of the sensor 240 can depend on the type of sensor used for the sensor 240. For example, the sensor 240 can be an O3 sensor typically adhered to a patient's forehead to monitor cerebral oxygenation. In another example, the sensor 240 can be a respiratory acoustic sensor typically attached to a patient's neck near the trachea to detect vibrations associated with respiration.

At block 1118, the processor 254 of the reusable module 250 can receive the raw patient physiological data from the sensor 240 of the disposable module 220. The raw patient physiological data can be stored in the memory 256.

At block 1120, the processor 254 of the reusable module 250 can perform signal processing on the raw physiological data. Various types of signal processing used on the physiological data raw can include, but not limited to, analog signal processing, continuous-time signal processing, discrete-time signal processing, digital signal processing, or nonlinear signal processing. For example, continuous-time signal processing such as time domain, frequency domain, and complex frequency domain can be used. Some of the signal processing methods that can be used on the raw physiological data include, but not limited to, passive filters, active filters, additive mixers, integrators, delay lines, compandors, multiplicators, voltage-controlled filters, voltage-controlled oscillators, phase-locked loops, time domain, frequency domain, fast Fourier transform (FFT), finite impulse response (FIR) filter, infinite impulse response (IIR) filter, and adaptive filters. Such processing techniques can be used to improve signal transmission, storage efficiency, and subjective quality. In addition, such processing techniques can be used to emphasize or detect components of interest in the raw physiological data. Noise filtering can be used to filter out raw physiological data corrupted by noise due to patient movement, electromagnetic interference, or ambient light.

Signal processing can determine the absorbance's of the light due to pulsating arterial blood. For example, pulse oximeter generates a blood-volume plethysmograph waveform from which oxygen saturation of arterial blood, pulse rate, and perfusion index, among other physiological parameters, can be determined. In the context of pulse oximetry, the sensor 240 can use adaptive filter technology to separate an arterial signal, detected by a pulse oximeter sensor, from the non-arterial noise for example, venous blood movement during motion). During routine patient motions (shivering, waving, tapping, etc.), the resulting noise can be quite substantial and can easily overwhelm a conventional ratio based oximetry system. This can provide accurate blood oxygenation measurements even during patient motion, low perfusion, intense ambient light, and electrocautery interference.

At block 1122, the processor 254 of the reusable module 250 can determine patient physiological parameters by processing the raw physiological data. The processor 254 can then store the processed data and the calculated parameters in the memory 256 before transmitting them to the computing device 206.

The processed data can be indicative of an amount of attenuation of predetermined wavelengths (ranges of wavelengths) of light by body tissues, such as, for example, a digit, portions of the nose or year, a foot, or the like. For example, the predetermined wavelengths correspond to specific physiological parameter data desired including, but not limited, blood oxygen information such as oxygen content (SpOC®), oxygen saturation ($SpO_2$), blood glucose, total hemoglobin (SbHb), methemoglobin (SpMet®), carboxyhemoglobin (SpCO), bulk tissue property measurements, water content, pH, blood pressure, respiration related information, cardiac information, perfusion index (PI), pleth variability indices (PVI®), or the like, which can be used by the mobile computing device to determine the condition of the user. The processed data can provide information regarding physiological parameters such as EEG, ECG, heart beats per minute, acoustic respiration rate (RRa), breaths per minute, end-tidal carbon dioxide ($EtCO_2$), respiratory effort index, return of spontaneous circulation (ROSC), or the like, which can be used to determine the physiological condition of the user.

At block 1124, the processor 254 of the reusable module 250 can transmit the patient physiological parameters to the computing device 206 via the antenna 252 using the communication protocol and the pairing parameters. It can be advantageous to transmit the calculated physiological parameters (for example, 60% $SpO_2$) as opposed to transmit the raw physiological data to the computing device 206. Compared to calculated physiological parameters, the raw physiological data can be larger in size and thus require larger bandwidth during transmission to the computing device 206. Calculated physiological parameters, on the other hand, can be much smaller in size and can require smaller bandwidth to transmit. Therefore, transmitting patient physiological parameters instead of raw physiological data can lead to decreased battery consumption and longer battery life for the disposable module 220.

The transmission of the physiological parameters can occur wirelessly via NFC. For example, the transmission of the physiological parameters occur wirelessly via Bluetooth. The transmission of the physiological parameters may occur via a cable.

At block 1126, the computing device 206 can receive the patient physiological parameters and displays them using the display 208. As discussed above, the computing device can include the display 208 that can display various patient physiological parameters including, but not limited to, body temperature, heart rate, blood oxygen level, blood pressure, and the like.

Figure 11B:
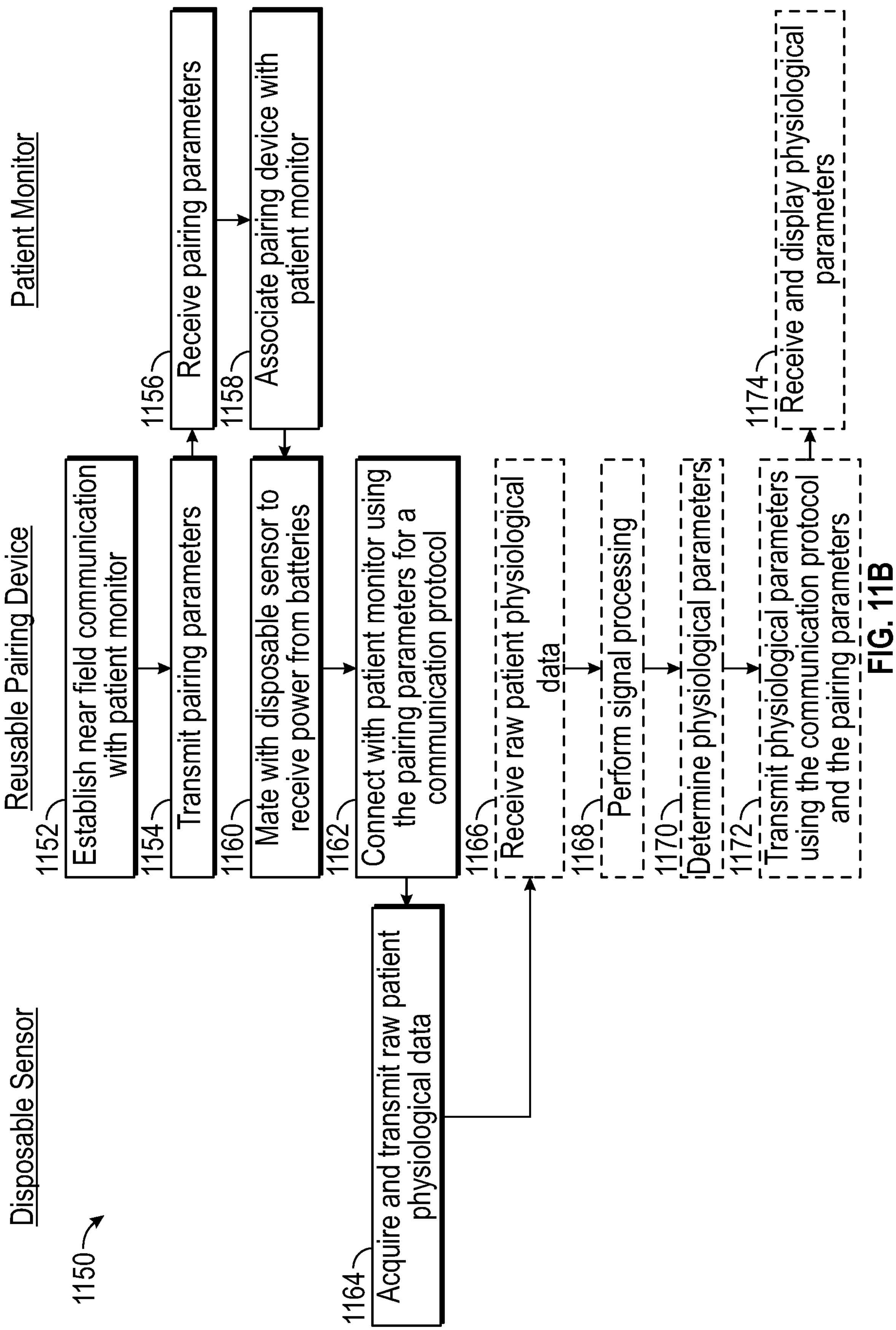
FIG. 11B illustrates another method of establishing wireless communication using a reusable module, a disposable module, and a computing device for acquiring and displaying patient physiological parameters.

FIG. 11B illustrates another method 1150 of establishing wireless communication between the reusable module 250 and the computing device 206, determining patient physiological parameters using the sensor assembly 202, and displaying the physiological parameters using the computing device 206.

At block 1152, the reusable module 250 can establish a NFC (near field communication) with the computing device 206. As discussed above, establishing a NFC can require the reusable module 250 to be within a predetermined distance of the computing device 206. As noted above, the NFC can be established between the body 802 of the dongle 800 and the reusable module 250.

At block 1154, the reusable module 250 can transmit pairing parameters to the computing device 206. The transmission of the pairing parameters to the computing device 206 can occur when the reusable module 250 establishes the NFC with the computing device 206. At block 1156, the computing device 206 can receive the pairing parameters from the reusable module 250. The computing device 206 can use the dongle 800 to receive the pairing parameters. For example, the body 802 of the dongle 800 can wirelessly receive the pairing parameters and transmit the pairing parameters to the computing device 206 via the cable 806 and the connector 804.

At block 1158, the computing device 206 or the body 802 can associate with the reusable module 250 using the pairing parameters. Once associated, the computing device 206 or the body 802 may wait for the wireless communication 204 from the reusable module 250. As noted above, the wireless communication 204 can be made via Bluetooth®. At block 1164, the sensor 240 of the disposable module 220 can acquire physiological data and transmit the data to the reusable module 250. The physiological data acquired by the sensor 240 and transmitted to the reusable module 250 can be raw physiological data.

Blocks 1166 through 1174 may be optional. At block 1166, the reusable module can receive the patient physiological data from the disposable module 220. At block 1168, the reusable module 250 can perform signal processing on the patient physiological data. At block 1170, the reusable module 250 can determine patient physiological parameters using the processed physiological data. At block 1172, the reusable module 250 can transmit patient physiological parameters using the wireless communication 204 established between the reusable module 250 and the computing device 206. The body 802 of the dongle 800 may wirelessly receive the patient physiological parameters from the reusable module 250 and transmit the parameters to the computing device via the cable 806 and the connector 804. At block 1174, the computing device 206 receives the patient physiological parameters and displays the parameters on the display 208.

Figure 12:
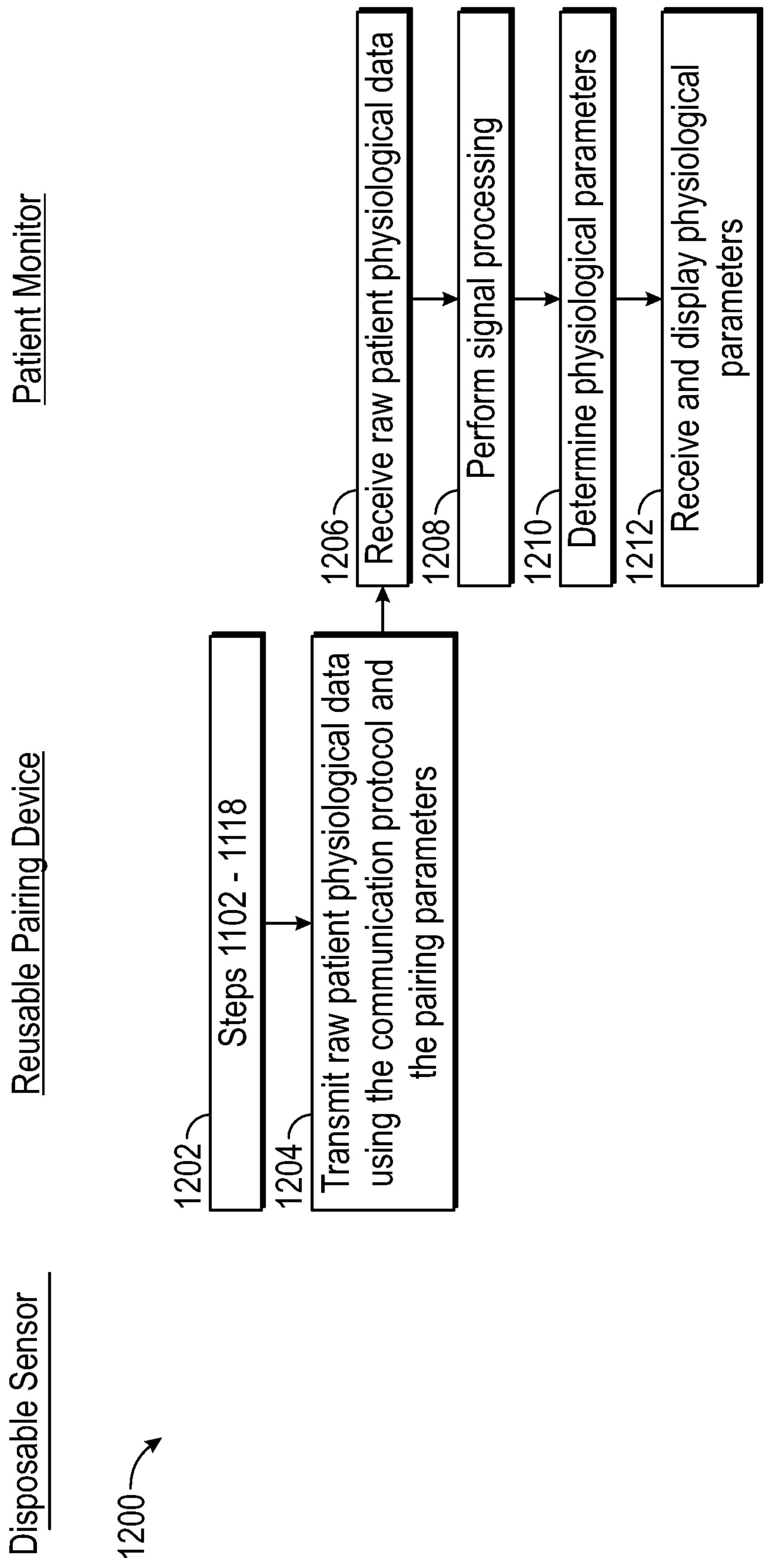
FIG. 12 illustrates another embodiment of a method of acquiring and displaying patient physiological parameters using a reusable module, a disposable module, and a computing device.

FIG. 12 illustrates another method 1200 of determining patient physiological parameters using the sensor assembly 202 and displaying the physiological parameters using the computing device 206.

At block 1202, the processor 254 of the reusable module 250 receives raw patient physiological data from the sensor 240 of the disposable module 220 according to the blocks 1102-1120 of FIG. 11.

At block 1204, the processor 254 of the reusable module 250 transmits the raw patient physiological data to the computing device 206. The process 254 can use the antenna 252 to transmit the raw data via the wireless communication 204 established between the reusable module 250 and the computing device 206. As mentioned above, the wireless communication 204 can be one-way or two-way between the reusable module 250 and the computing device 206.

At block 1206, the computing device 206 receives the raw patient physiological data. At block 1208, the computing device 206 performs signal processing on the raw patient physiological data. At block 1210, the computing device 206 determines patient physiological parameters using processed raw patient physiological data. At block 1212, the computing device 206 displays the determined physiological parameters on the display 208.

Mobile Application

As discussed above, the computing device 206 can be a mobile device 1300 such as a phone, tablet, watch and the like. The mobile device 1300 can include a mobile application that can establish wireless communication with the reusable module 250 via a wireless communication protocol, such as Bluetooth or the like.

Figure 13B:
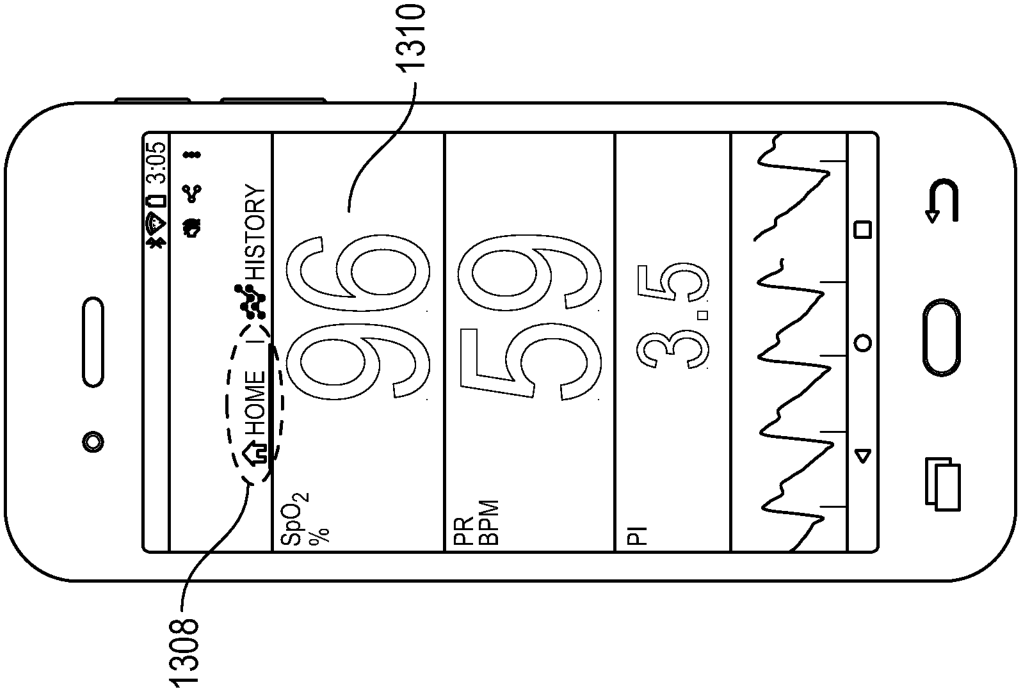
FIGS. 13B-13E illustrate various views of the mobile application of FIG. 13A displaying patient parameters in various display formats.
Figure 13A:
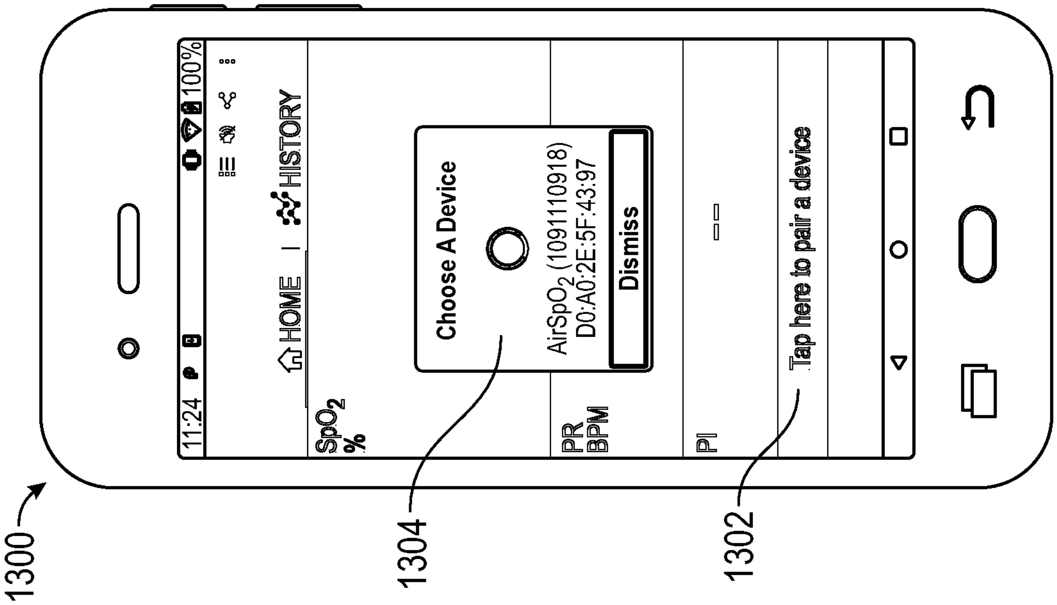
FIG. 13A illustrates a mobile application for establishing a wireless communication with a reusable module.

FIG. 13A illustrates a mobile application being executed on the mobile device 1300 (for example, a mobile phone) to establish a wireless communication with the reusable module 250. The mobile application can pair with nearby reusable modules 250. In an example, a user can press a pair button 1302 to cause the mobile application to search for nearby reusable modules 250. The mobile application can create a screen 1304 to display nearby reusable modules 250. The screen 1304 can provide MAC address or any other pairing information unique to the reusable modules 250. The mobile application may automatically search for nearby reusable modules 250 without any user intervention or input.

FIGS. 13B-13E illustrate various examples the mobile application displaying patient parameters. Triggering a home button 1308 can cause the mobile application to show real-time, numerical and graphical illustration of patient parameters, as shown in FIG. 13A. The mobile application can show numerical parameters 1310 (for example, patient's $SpO_2$, PR BPM, and PI readings) in real time or with a predetermined delay. The mobile application may show graphical illustration 1314 of patient parameters that show real-time trend of the parameters. For example, a user can trigger an $SpO_2$ portion of the display to cause the mobile application to show real-tine trend of the $SpO_2$ parameters.

Figure 13C:
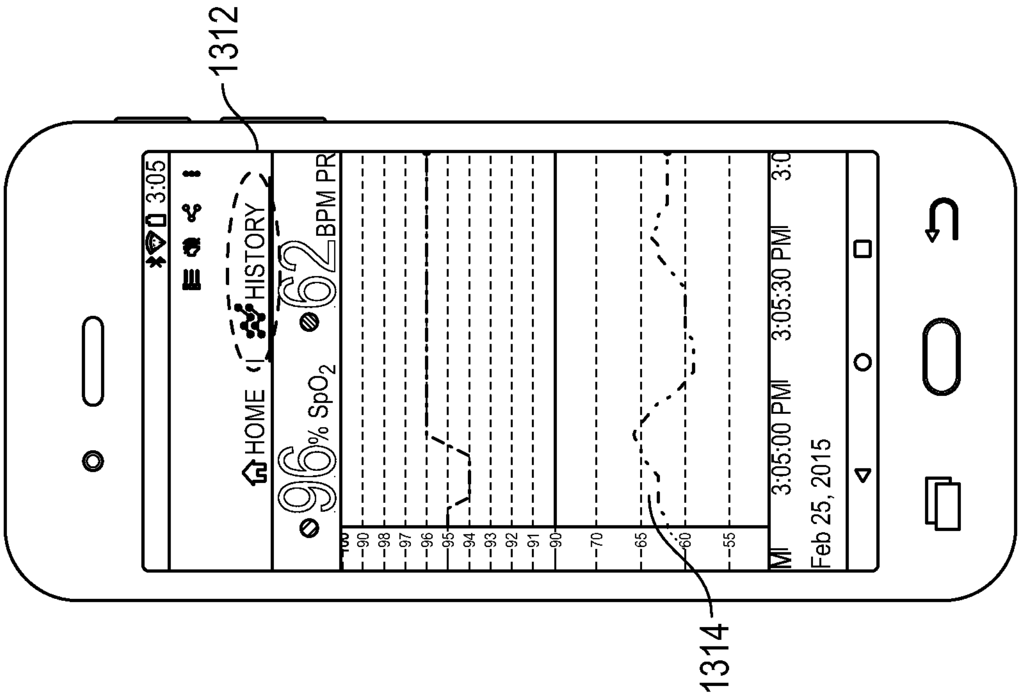

As shown in FIG. 13C, triggering a history button 1312 can cause the mobile application to show the graphical illustration 1314 showing historical trends of patient health parameters. The graphical illustration 1314 can have an x-axis showing timestamp and a y-axis showing parameter values. The mobile application may show real-time numerical values of patient health parameter above or below the graphical illustration 1314. The real-time numerical values can be embedded within the graphical illustration 1314.

Figure 13D:
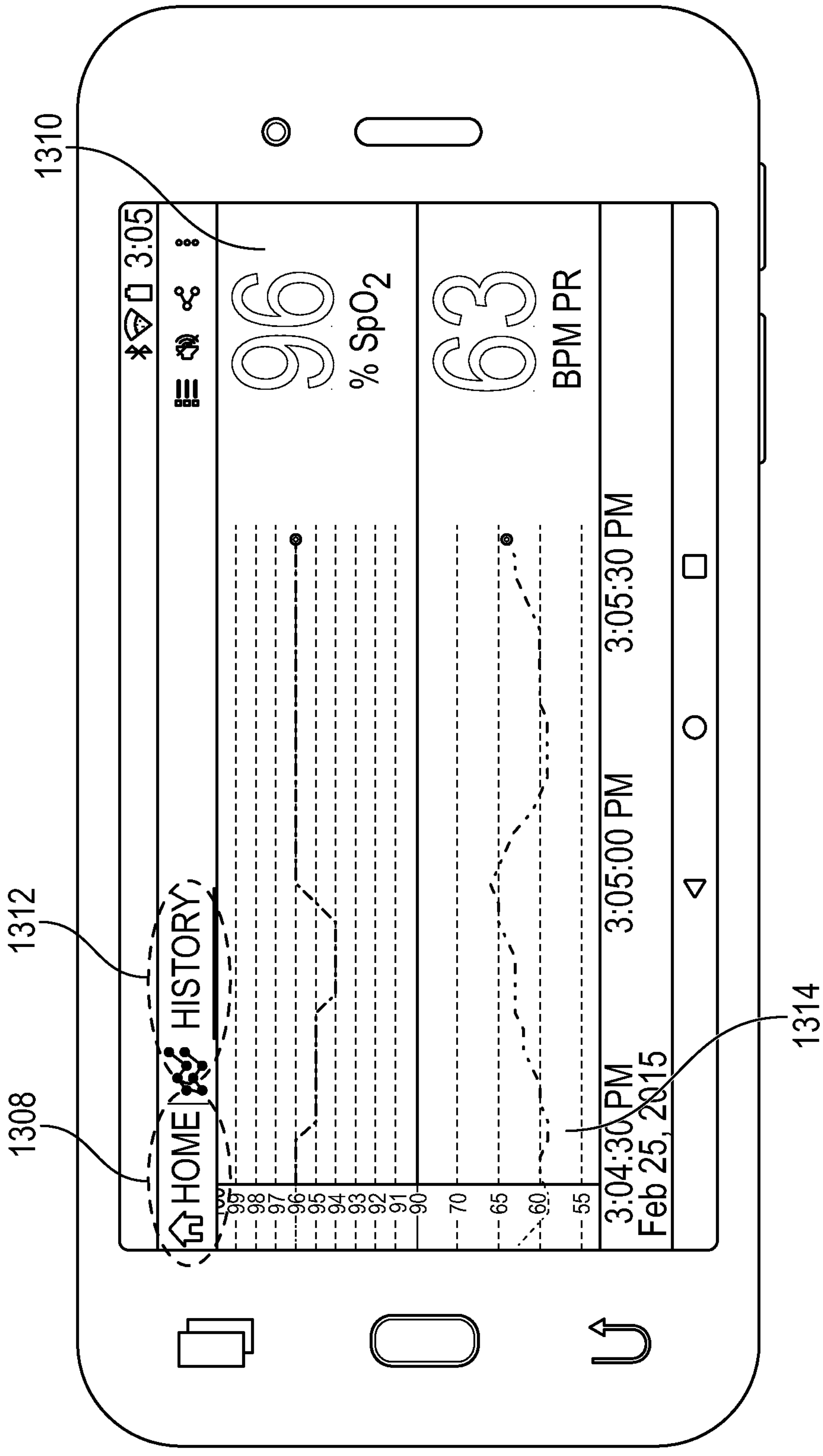
Figure 13E:
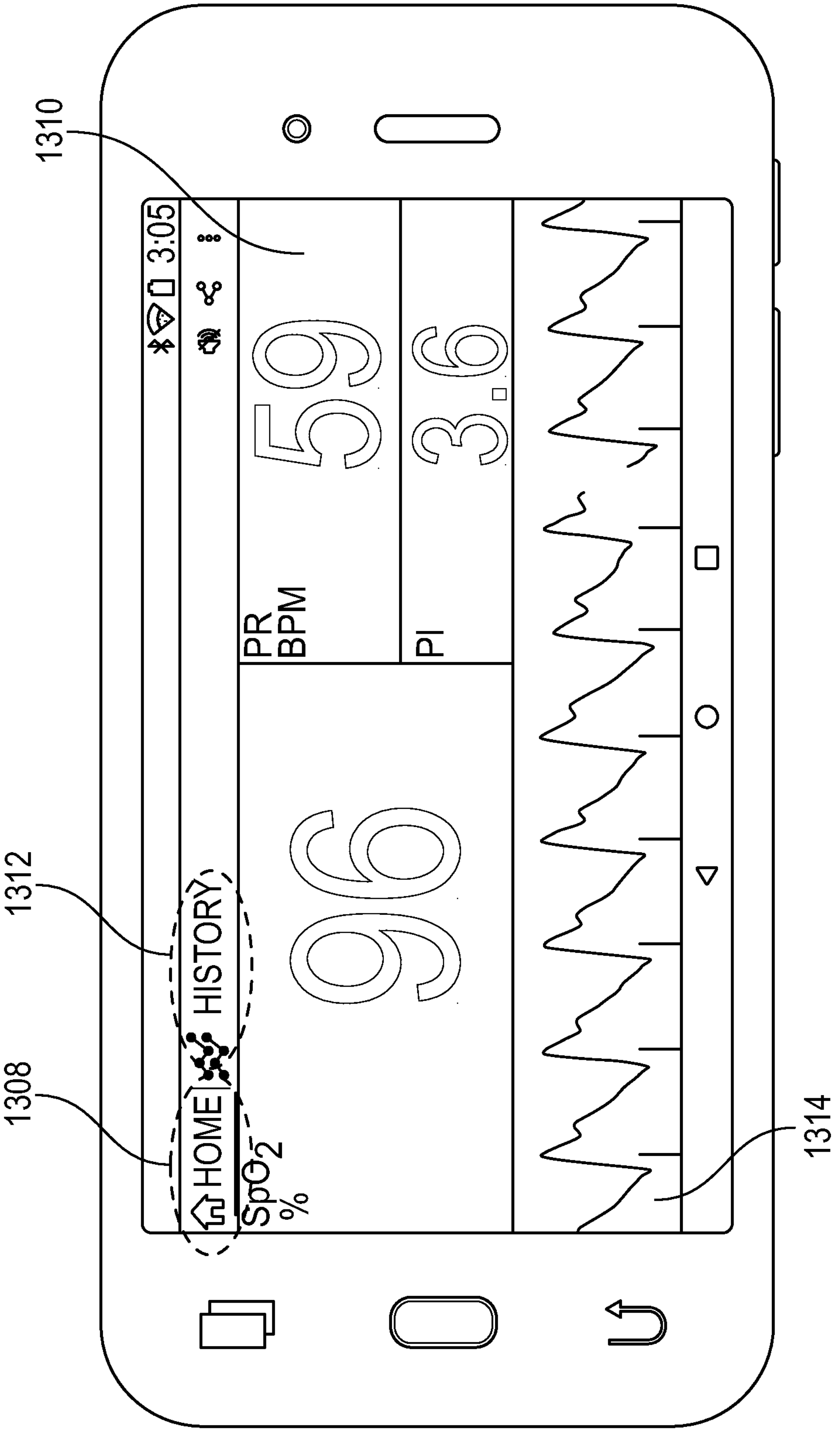

As shown in FIGS. 13D and 13E, the mobile application can display at least one of the numerical parameters 1310 and the graphical illustration 1314 in a landscape view.

Methods of Identifying and/or Validating Disposable Module

As discussed herein, the disposable module 220 can include a sensor assembly 240 that can include various types of sensors. Accordingly, it may be advantageous for the reusable module 250 to be able to identify the disposable module 220. This can be advantageous, for example, to check or ensure that the sensor assembly 240 of the disposable module 220 has a desired or correct type of sensor suitable for certain situations, circumstance, and the like. In addition, the reusable module 250 can also obtain identification and/or operating parameters to ensure that the reusable module 250 uses a correct algorithm or calibration curve for the attached disposable sensor.

Figure 14A:
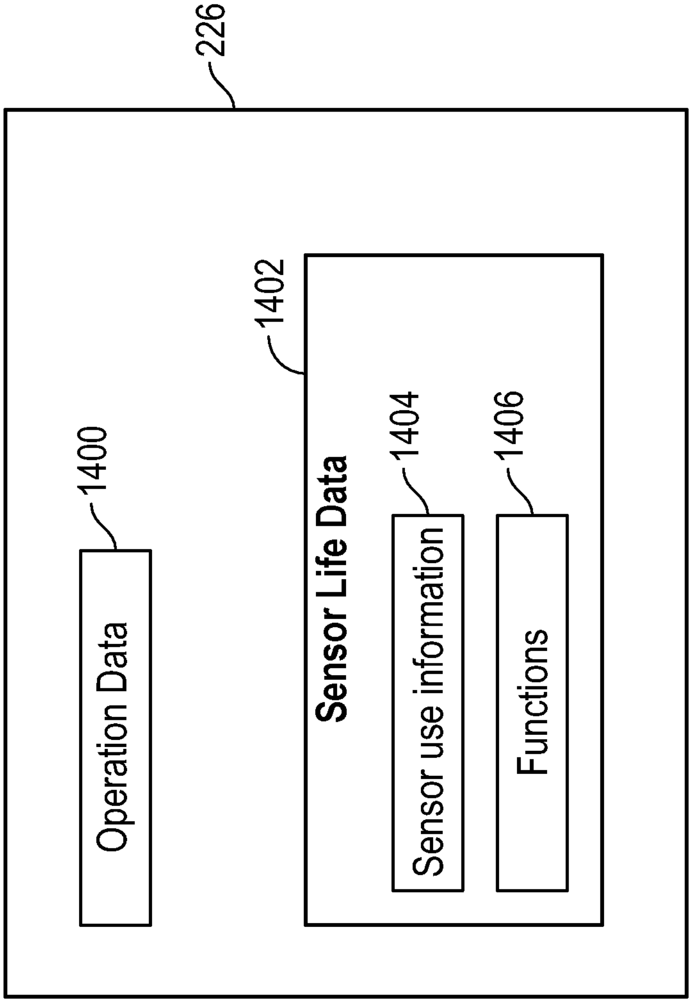
FIG. 14A illustrates a block diagram of an embodiment of a memory of a disposable module.

A memory of the disposable module 220, for example, the memory 226 shown in FIG. 2B, can be configured to store operation data 1400 as shown in FIG. 14A. The operation data 1400 may or may not be unique to the disposable module 220. The operation data may indicate a type of sensor, or types of sensors, associated with a given disposable module 220 at any given time. For example, the operation data 1400 may automatically be updated when a new sensor 240 is provided for the disposable module 220. Accordingly, the operation data 1400 can accurately reflect what sensors 240 are associated with a given disposable module 220 and provide such information to care providers. This can be useful in situations in which different types of sensors may look similar or when care providers do not have sufficient amount of time to check and ensure all sensors are properly identified.

Optionally, a reusable module, for example, the reusable module 250 shown in FIG. 2B, may be programmed to be associated with specific types of sensors or specific types of patient health data. For example, the reusable module may be programmed to be associated with patient health data such as, for example, pulse oximetry related data, including, but not limited to, blood oxygen saturation level ($SpO_2$). As such, the reusable module may, when connected with a disposable module, access and analyze operation data of the disposable module to ensure that sensor assembly associated with or of the disposable module is, for example, compatible with the reusable module, or, for example, capable of collecting patient health data associated with blood oxygen saturation level.

The memory of the disposable module 220 may include sensor life data 1402. The sensor life data 1402 that may be used to monitor, for example, life expectancy of the disposable module 220. The sensor life data 1402 can include one or more sensor use information 1404 and one or more functions 1408 that can be used to determine sensor life expectancy. The sensor life expectancy can represent expected operation time of the disposable module 220. Some examples of sensor use information 1404 may include, but are not limited to, an age of the sensor, a user time of the sensor, a current supplied to the sensor, a temperature of the sensor, a number of times a sensor is depressed, a number of times the sensor is calibrated, a number of times the sensor is powered up, and the like. Various examples of systems and methods of determining sensor life expectancy using the sensor life data, for example, sensor use information and functions, is disclosed in U.S. application Ser. No. 11/580,214, filed Oct. 12, 2006, entitled "SYSTEM AND METHOD FOR MONITORING THE LIFE OF A PHYSIOLOGICAL SENSOR," now U.S. Pat. No. 7,880,626, issued Feb. 1, 2011, entirety of which is incorporated by reference herein. In some configurations, the life of the sensor is the life of the battery included on the sensor. When the battery is exhausted, the sensor records an end of life event on the sensor memory.

In some implementations, the sensor life expectancy may be automatically updated when there is a change in patient condition or a change in operation condition for the disposable module 220. For example, based at least in part on physiological data collected by the disposable module 220, a change in patient condition, for example, a sudden increase in blood pressure and decrease in blood oxygen level, may be identified. As described herein, detecting such change in patient condition may trigger the disposable module 220 to collect physiological data, for example, more frequently or at a higher fidelity, which may cause increased power consumption by the disposable module 220. In another example, the temperature of the disposable module 220 (and its sensor element) may increase and the sensor life expectancy may be automatically updated when the increase in the temperature of the disposable module 220 is detected. By automatically calculating and updating the sensor life expectancy under such example conditions described herein, care providers may have access to more accurate forecast of sensor life expectancy. This can be advantageous in situations in which, for example, a patient may be experiencing an emergency situation and the disposable sensor is having to, for example, collect more data points at higher fidelity. By automatically updating sensor life expectancy, the care providers may accurately monitor predicted operation time of the disposable module 220 and determine whether additional disposable module(s) 220 may be needed.

In some implementations, the sensor life expectancy may be automatically updated at a predetermine time interval. The predetermined time interval for updating the sensor life expectancy may range between about 1 minute and about 1 hour, between about 2 minutes and about 30 minutes, between about 5 minutes and about 20 minutes, between about 10 minutes and about 15 minutes, or about 1 minute, about 2 minutes, about 5 minutes, about 10 minutes, about 15 minutes, about 20 minutes, about 30 minutes, about 1 hours, or range between any two of aforementioned values.

Figure 14B:
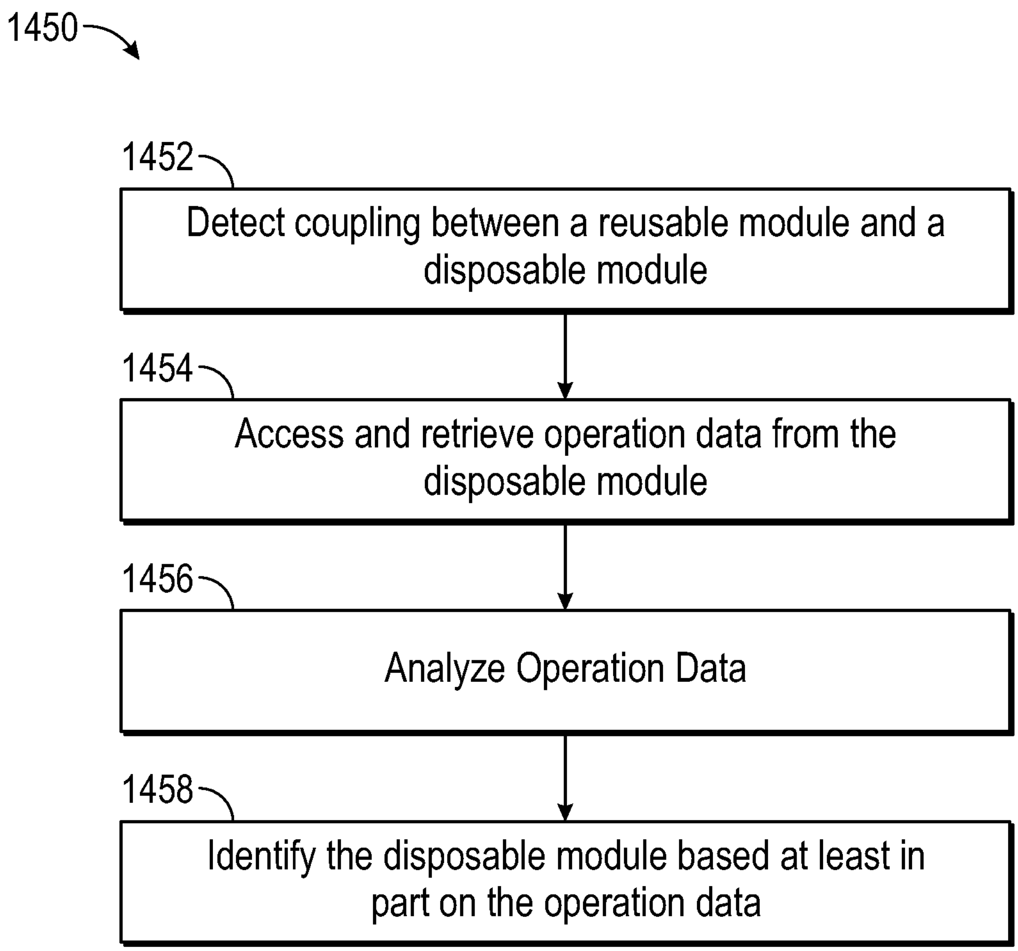
FIG. 14B illustrates a method of identifying a disposable module based at least in part on operation data stored in a memory of the disposable module.

FIG. 14B illustrates an example method of 1450 of identifying or validating a disposable module. At block 1452, coupling between a disposable module and a reusable module is detected. A processor, for example the processor 254 of the reusable module 250, of a reusable module may detect coupling between the reusable module and a disposable module by detecting an electronic input or signal transmitted between the reusable module and the disposable module. The electronic input or signal can be patient health data and/or current flowing from a battery, for example, the battery 224 of the disposable module 220, to the reusable module, and the like. Optionally, the computing system 206 can detect coupling between a reusable module and a disposable module by, for example, detecting patient health data and/or parameters transmitted from the reusable module 250.

At block 1454, operation data is accessed from the disposable module 220. As discussed herein, the operation data can be stored within a memory, for example, the memory 226, of the disposable module 220. In some examples, the processor, for example, the processor 254, of the reusable module may access the operation data from the disposable module 220. As discussed herein, the operation data may include operation data and sensor life data.

At block 1456, the operation data is analyzed. The processor 254 of the reusable module 250 may perform the analysis. Optionally, the reusable module 250 may relay the operation data to the computing system 206, and the computing system 206 may perform the analysis of the operation data.

At block 1458, the disposable module 220 is identified based at least in part on the operation data and the analysis of the operation data. The identification of the disposable module 220 can include determination of a sensor type associated with the disposable module 220, determination of whether the sensor type associated with the disposable module corresponds to a configuration of the reusable module, determination of sensor life expectancy of a sensor associated with the disposable module, and the like.

Communication With Other Sensor Devices

Figure 16A:
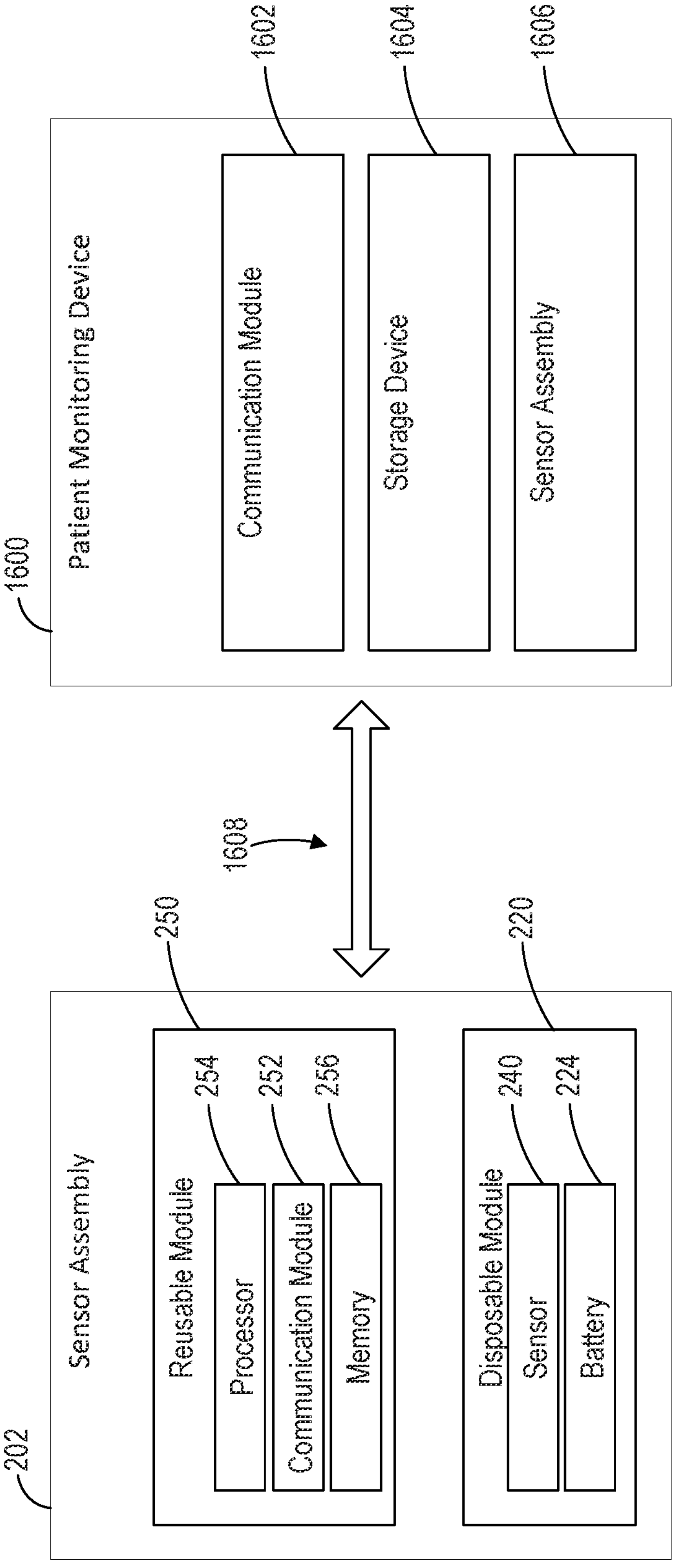
FIG. 16A illustrates a block diagram of an example sensor assembly and an example patient monitoring device in wireless communication.

In some implementations, the sensor assembly 202 can communicate with other monitoring devices, such as a patient monitoring device 1600. FIG. 16A illustrates a block diagram of the sensor assembly 202 in wireless communication with the patient monitoring device 1600. The patient monitoring device 1600 can include a communication module 1602, a storage device 1604, and a sensor assembly 1606. The patient monitoring device 1600 can be an activity tracker, a bedside monitor, a handheld monitor, and a wearable device. For example, the patient monitoring devices 1600 can be an electrocardiogram (ECG), thermometer, Radical (a patient monitoring device available at Masimo Corporation, Irvine, CA), Rad (a patient monitoring device available at Masimo Corporation, Irvine, CA), Root (a patient monitoring and connectivity platform available at Masimo Corporation, Irvine, CA), and the like. The patient monitoring device 1600 may collect, analyze, or display data related to various types of physiological parameters including, electrocardiogram, pulse rate, respiratory rate, body temperature, blood oxygen saturation ($SpO_2$), perfusion index (PI), Pleth Variability Index (PVi®), total hemoglobin (SpHb®), oxygen content (SpOC™) methemoglobin (SpMet®), Carboxyhemoglobin (SpCO®), acoustic respiratory rate (RRa®), electroencephalogram (EEG), enhanced Patient State Index (PSi), density spectral array (DSA), and the like.

The communication module 1602 can establish wired or wireless communication with various devices, networks, and the like. The sensor assembly 1606 can collect data, for example, associated with or related to a physiological condition of a patient. The sensor assembly 1606 may be directly in contact with the patient. The storage device 1604 may store data collected by the sensor assembly 1606.

The sensor assembly 1606 may include one or more sensors that can collect one or more types of physiological data described herein. For example, the patient monitoring device 1600 may be a holter monitor and the sensor assembly 1606 may include one or more leads that can be attached to, for example, a torso area of a patient. In one example, the sensor assembly 1606 includes three (3) leads. In another example, the sensor assembly 1606 includes twelve (12) leads.

In some implementations, the sensor assembly 202 can communicate with the patient monitoring device 1600. The sensor assembly 202 may directly communicate with the patient monitoring device 1600 by establishing a direct communication with the patient monitoring device 1600. Alternatively and/or optionally, the sensor assembly 202 may indirectly communicate with the patient monitoring device 1600, for example, via a network 1620 (see FIG. 16B) or a server.

As described herein, the sensor assembly 202 may store collected patient physiological data in the memory 256 of the reusable module 250 when the sensor assembly 202 is unable to transmit the data to, for example, the computing system 206 via, for example, a wireless communication. The sensor assembly 202, upon determining that it is unable to transmit collected data to, for example, the computing system 206 (for example, because of interrupted wireless communication between the sensor assembly 202 and the computing device 206), the sensor assembly 202 may alternatively, transmit the collected patient physiological data to the patient monitoring device 1600 via wireless communication 1608. The patient monitoring device 1600 may receive the patient physiological data via the communication module 1602 and store the data. The data may be stored in the storage device 1604.

The patient monitoring device 1600 may transmit the patient physiological data back to the sensor assembly 202 when the communication between the sensor assembly 202 and the computing system 206 is restored. In some implementations, the sensor assembly 202 generates and transmits a notification to the patient monitoring device 1600 indicating that the communication between the sensor assembly 202 and the computing system 206 is restored. Upon receiving the notification from the sensor assembly 202, the patient monitoring device 1600 can transmit the stored patient physiological data (that is, the patient physiological data that the sensor assembly 202 transmitted to the patient monitoring device 1600 upon determining that it is unable to transmit collected data to, for example, the computing system 206) to the sensor assembly 202 via the wireless communication 1608. The sensor assembly 202, upon receiving the patient physiological data from the patient monitoring device 1600, can transmit the data to the computing device 206. As such, the sensor assembly 202 can use the patient monitoring device 1600 as a backup data storage device.

Figure 16B:
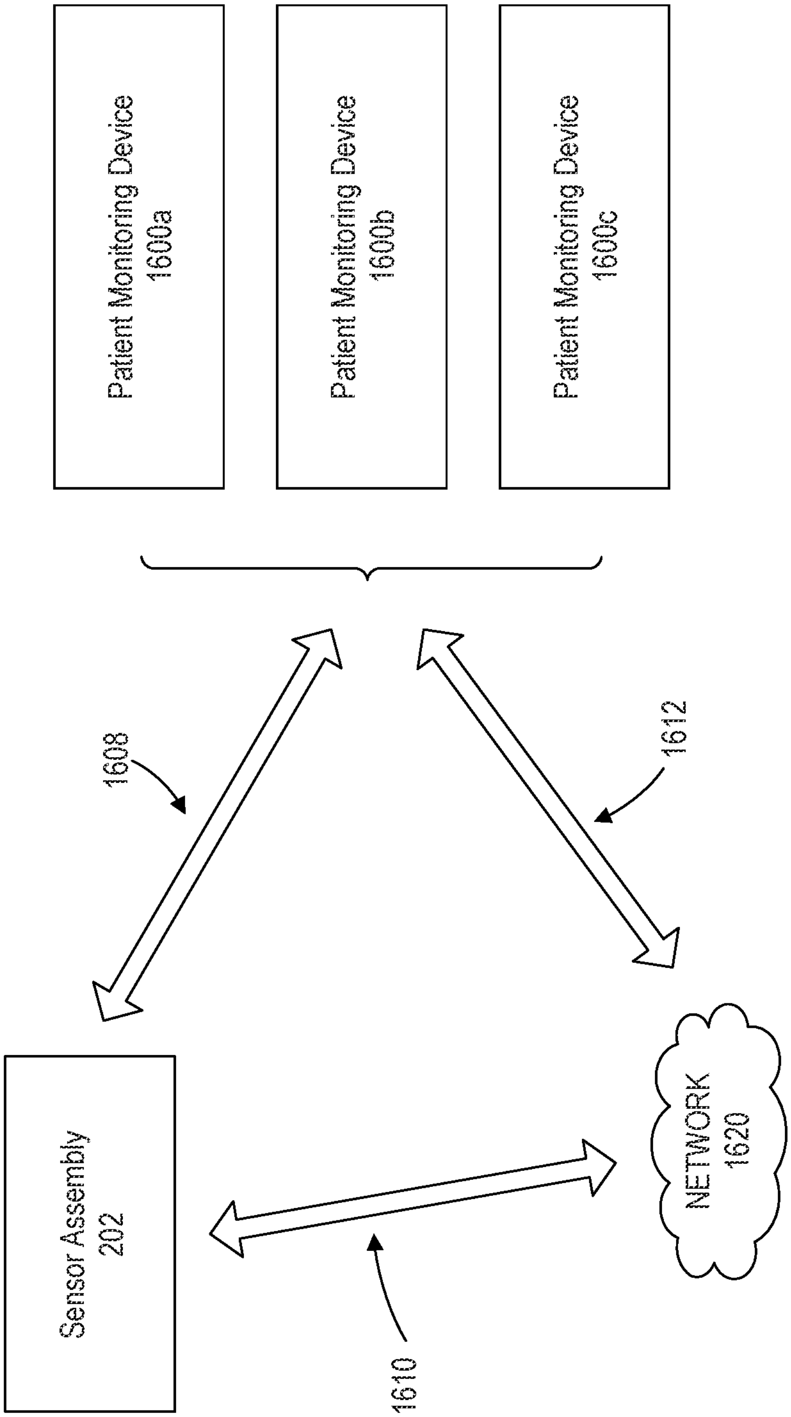
FIG. 16B illustrates a schematic diagram showing wireless communications between a sensor assembly, patient monitoring devices, and a network.

In some implementations, the sensor assembly 202 can communicate with one or more patient monitoring devices 1600. FIG. 16B illustrates a block diagram showing the sensor assembly 202 in wireless communication with the patient monitoring devices 1600*a*, 1600*b*, 1600*c*, and the network 1620. The sensor assembly 202 may establish with one or more of the patient monitoring devices 1600*a*, 1600*b*, 1600*c*, at any time. In some implementations, the sensor assembly 202, to preserve power stored in the battery 224 of the disposable module 220, may, by default, not establish wireless communication when it is able to communicate with, for example, the computing system 206. As such, the sensor assembly 202 may establish wireless communication with one or more of the patient monitoring devices 1600*a*, 1600*b*, 1600*c*, when it determines that a wireless communication with the sensor assembly 202 is no longer available and thus, for example, unable transmit patient physiological data to the computing device 206.

In some implementations, the sensor assembly 202 may be able to communicate with the network 1620 via wireless communication 1610. As noted herein, the network 1620 may be in communication with the computing system 206. Accordingly, even if the sensor assembly 202 is unable to establish communication with the computing system 206 directly, it nevertheless may be able to indirectly communicate with the computing system 206 via the network 1620.

In some implementations, the patient monitoring device 1600 may communicate with the network 1620 via wireless communication 1612. For example, the patient monitoring devices 1600*a*, 1600*b*, 1600*c*, upon receiving patient physiological data from the sensor assembly 202, may transmit the data to the network 1620 via wireless communication 1612. The network 1620 may be a server in communication with the computing device 206. Upon receiving the patient physiological data from the patient monitoring devices 1600*a*, 1600*b*, 1600*c*, the network 1620 can transmit the data to the computing device 206 for, for example, analysis of the data, determination of physiological parameters based on the data, and generate a display of the physiological parameters, for example, on a display. In some implementations, the transmission of the patient physiological data between the sensor assembly 202, the patient monitoring devices 1600*a*, 1600*b*, 1600*c*, and the network 1620 may occur with or without delay. For example, the patient monitoring devices 1600*a*, 1600*b*, 1600*c* may transmit the patient physiological data to the network 1620 immediately after it receives the patient physiological data from the sensor assembly 202. Alternatively, the patient monitoring devices 1600*a*, 1600*b*, 1600*c* may transmit the patient physiological data to the network 1620 after a predetermined time period is elapsed.

In some implementations, the sensor assembly 202 generates a packet that includes the patient physiological data and instructions for the patient monitoring devices 1600*a*, 1600*b*, 1600*c*. The instructions can cause the patient monitoring devices 1600*a*, 1600*b*, 1600*c* to transmit the patient physiological data to, for example, the computing device 206 or the network 1620 after receipt. In another example, the instructions can cause the patient monitoring devices 1600*a*, 1600*b*, 1600*c* to store the patient physiological data until the patient monitoring devices 1600*a*, 1600*b*, 1600*c* are connected to, for example, the computing system 206 or the network 1620. In yet another example, the instructions can cause the patient monitoring devices 1600*a*, 1600*b*, 1600*c* to store the patient physiological data.

In some implementations, the transmission of the patient physiological data between the sensor assembly 202, the patient monitoring devices 1600*a*, 1600*b*, 1600*c*, and the network 1620 may occur if a predetermined condition is met. For example, the sensor assembly 202 (or the reusable module 250 of the sensor assembly 202) may transmit collected patient physiological data to one or more of the patient monitoring devices 1600*a*, 1600*b*, 1600*c* when it is unable to establish wireless communication with, for example, the computing device 206 or the network 1620 for a predetermined amount of time. The predetermined amount of time (for example, a timer) may be ten (10) seconds, thirty (30) seconds, one (1) minute, two (2) minutes, five (5) minutes, ten (10) minutes, or any duration sufficient to prevent or reduce data loss or unnecessary power consumption from unsuccessful attempts to establish wireless communication.

In another example, the sensor assembly 202 (or the reusable module 250 of the sensor assembly 202) may transmit collected patient physiological data to one or more of the patient monitoring devices 1600*a*, 1600*b*, 1600*c* after a predetermined number of unsuccessful attempts to establish wireless communication with, for example, the computing device 206 or the network 1620. The predetermined number of unsuccessful attempts may be one (1), two (2), five (5), ten (10), twenty (20), or any number sufficient to prevent or reduce data loss or unnecessary power consumption from unsuccessful attempts to establish wireless communication.

The predetermined condition may be modifiable and may be modified by a user (for example, a patient) or a care provider (for example, a doctor). Alternatively, a user (for example, care provider such as a nurse or a doctor) input or request may cause or allow transmissions of patient physiological data between the sensor assembly 202, the patient monitoring devices 1600*a*, 1600*b*, 1600*c*, and the network 1620. For example, a nurse may determine that the sensor assembly 202 is no longer communicating with the computing system 206 and provide a user input to the sensor assembly 202 to allow the sensor assembly 202 to transmit patient physiological data to the patient monitoring devices 1600*a*, 1600*b*, 1600*c*.

In some implementations, a priority scheme may be used between the sensor assembly 202 and the patient monitoring devices 1600*a*, 1600*b*, 1600*c*. For example, the sensor assembly 202 may generate and transmit a request to the patient monitoring devices 1600*a*, 1600*b*, 1600*c* for connectivity information associated with the wireless communication 1612 between the patient monitoring devices 1600*a*, 1600*b*, 1600*c* and the network 1620. Upon receipt of the request for the connectivity information, the patient monitoring devices 1600*a*, 1600*b*, 1600*c* may, in response, transmit the connectivity information back to the sensor assembly 202. The connectivity information may be associated with, for example, connectivity strength between the patient monitoring devices 1600*a*, 1600*b*, 1600*c* and the network 1620.

Based on the received connectivity information, the sensor assembly 202 can identify a patient monitoring device (for example, patient monitoring device 1600*c*) for transmitting patient physiological data. The sensor assembly 202 can transmit patient physiological data to the identified patient monitoring device, and the identified patient monitoring device can relay the data to the network 1620 as discussed herein.

In another example, the priority scheme may be related to battery status and/or storage device status. For example, the sensor assembly 202 may generate and transmit a request to the patient monitoring devices 1600*a*, 1600*b*, 1600*c* for battery status and/or storage device status information associated with the patient monitoring devices 1600*a*, 1600*b*, 1600*c*. Upon receipt of the request for the battery status and/or storage device status information, the patient monitoring devices 1600*a*, 1600*b*, 1600*c* may, in response, transmit the battery status and/or storage device status information back to the sensor assembly 202. The battery status information may be related to (1) a charge level of battery, (2) power usage of the patient monitoring device 1600*a*, 1600*b*, 1600*c*, and (3) expected amount of power usage from data transmission between the sensor assembly 202 and the patient monitoring device 1600. The storage device status may be related to (1) an amount of data storage available, (2) expected amount of data from the sensor assembly 1606, and (3) expected amount of data from the sensor assembly 202.

Based on the received battery status and/or storage device status information, the sensor assembly 202 can identify a patient monitoring device (for example, patient monitoring device 1600*c*) for transmitting patient physiological data. The sensor assembly 202 can transmit patient physiological data to the identified patient monitoring device, and the identified patient monitoring device can store the patient physiological data.

The use of the patient monitoring devices 1600*a*, 1600*b*, 1600*c* may allow increased flexibility for handling, storage, and transmission of patient physiological data to the computing device 206. For example, the patient monitoring devices 1600*a*, 1600*b*, 1600*c* may have longer battery life and/or larger data storage capacity than the sensor assembly 202. By transmitting patient physiological data to the patient monitoring devices the patient monitoring devices 1600*a*, 1600*b*, 1600*c* for, for example, storage until wireless communication between the sensor assembly 202 and the computing system 206 is restored may allow recovery of greater amount of data. Moreover, the use of the patient monitoring devices 1600*a*, 1600*b*, 1600*c* may provide increased flexibility for data transmission as they provide additional avenues for transmission of data (for example, patient physiological data) between the sensor assembly 202 and the computing system 206—via the wireless communication 1608 between the sensor assembly 202 and the patient monitoring devices 1600*a*, 1600*b*, 1600*c*, and the wireless communication 1612 between the patient monitoring devices 1600*a*, 1600*b*, 1600*c* and the network 1620.

Figure 16C:
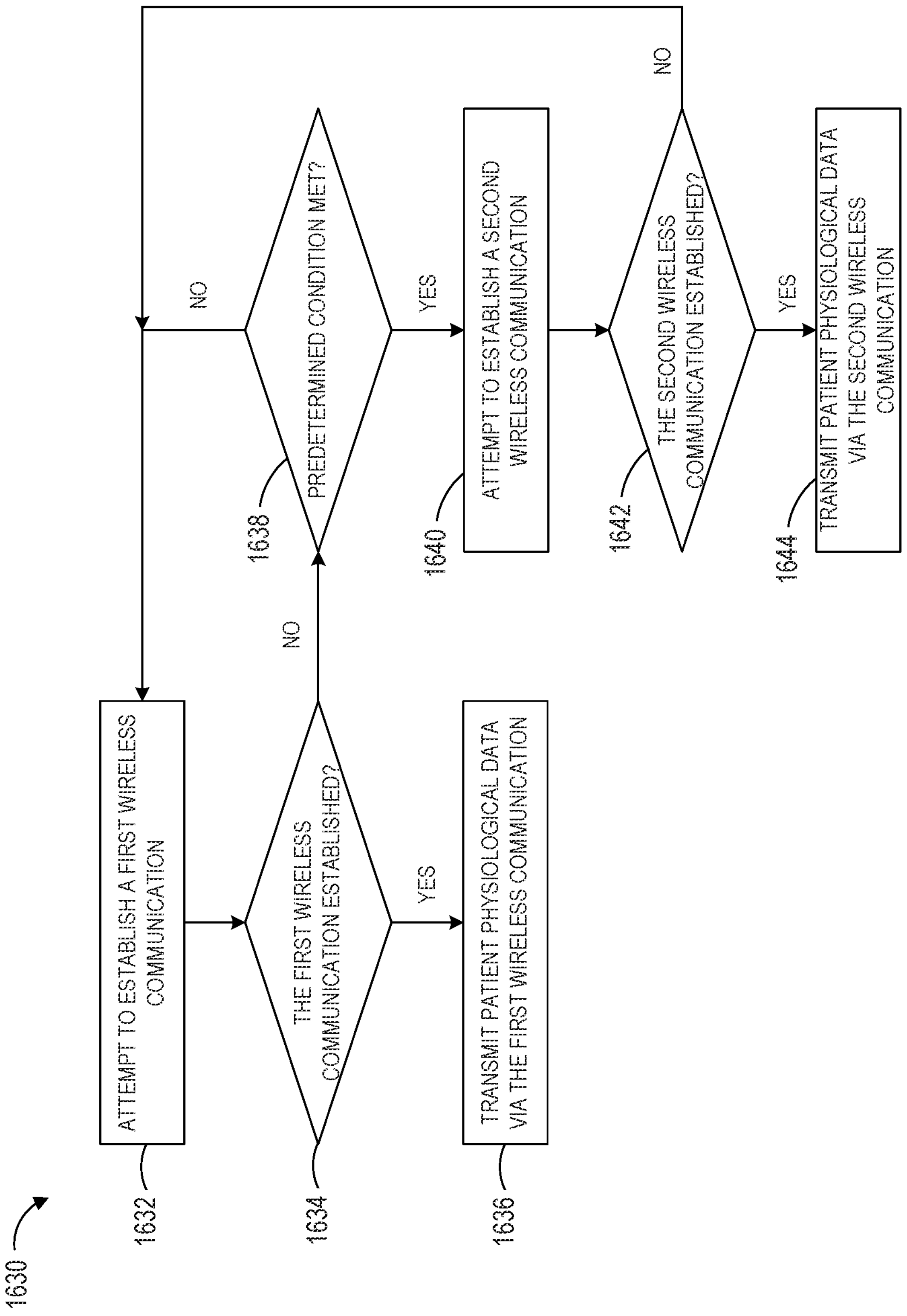
FIG. 16C illustrates an example method of transmitting physiological data using a sensor assembly.

FIG. 16C illustrates an example method 1630 for transmitting patient physiological data by the sensor assembly 202. The method 1630 may be performed by the sensor assembly 202 (or processor 254 of the reusable module 250) or any device in communication with the sensor assembly 202. At block 1632, the sensor assembly 202 attempts to establish a first wireless communication. The first wireless communication can be between the sensor assembly 202 and, for example, the computing system 206 or the network 1620.

At block 1634, the sensor assembly 202 determines whether the first wireless communication is established, for example, between the sensor assembly 202 and the computing system 206 or the network 1620. If the sensor assembly 202 determines that the first wireless communication is established, then the sensor assembly 202 transmits patient physiological data to, for example, the computing system 206 or the network 1620 via the first wireless communication at block 1636. If the sensor assembly 202 determines that the first wireless communication is not established, the sensor assembly 202 determines whether a predetermined condition is satisfied. As discussed herein, the predetermined condition can include, but not limited to, whether the sensor assembly 202 made a predetermined number of unsuccessful attempts of establishing the first wireless communication with, for example, the computing system 206 or the network 1620 or whether a predetermined amount of time has elapsed since the sensor assembly 202 failed to establish the first wireless communication with, for example, the computing system 206 or the network 1620.

If the sensor assembly 202 determines that the predetermined condition is not satisfied, the sensor assembly 202 attempts to establish the first wireless communication at block 1632. Alternatively, if the sensor assembly 202 determines that the predetermined condition is satisfied, then the sensor assembly 202 attempts to establish a second wireless communication with, for example, the patient monitoring devices 1600*a*, 1600*b*, 1600*c* at block 1640. At block 1642, the sensor assembly 202 determines whether the second wireless communication is established. If the second communication is established, then the sensor assembly 202 transmits patient physiological data to, for example, the patient monitoring devices 1600*a*, 1600*b*, 1600*c* via the second wireless communication. However, if the second wireless communication is not established, then the sensor assembly 202 attempts to establish the first wireless communication at block 1632. Optionally, upon determining that the second wireless communication is not established, then the sensor assembly 202, instead of attempting to establish the first wireless communication, may store the patient physiological data in the memory 256.

Figure 16D:
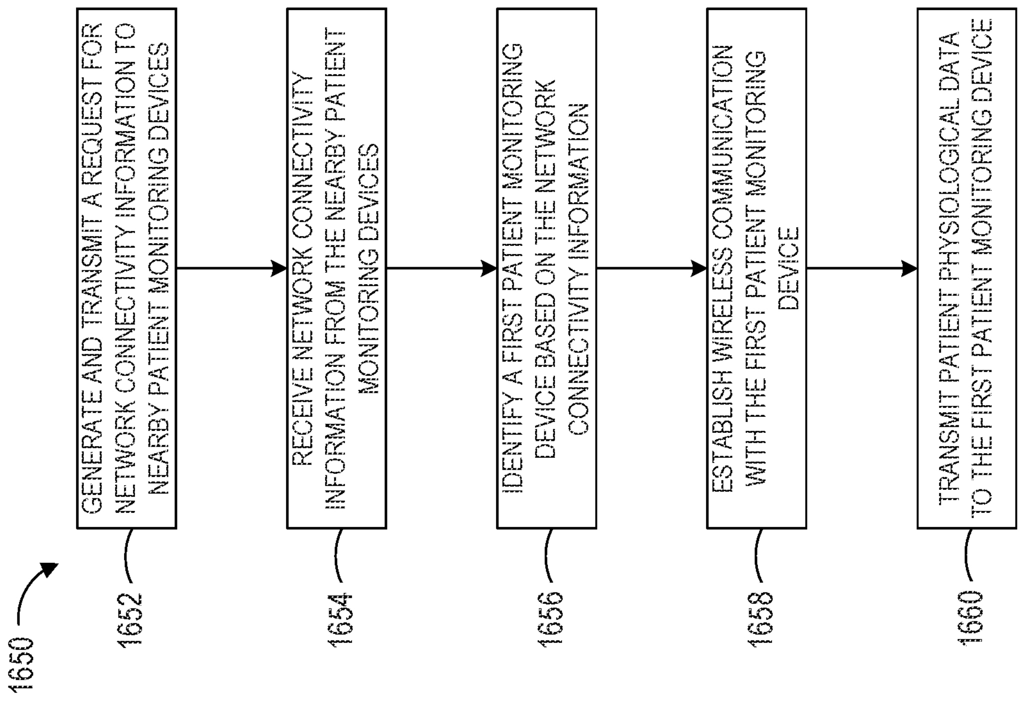
FIGS. 16D and 16E illustrate example methods of identifying a patient monitoring device and transmitting patient physiological data to the identified patient monitoring device.

FIG. 16D illustrates an example method 1650 for transmitting patient physiological data to a patient monitoring device. At block 1652, the sensor assembly 202 transmits a request for network connectivity information to one or more patient monitoring devices (for example, the patient monitoring devices 1600*a*, 1600*b*, 1600*c*). The one or more patient monitoring devices may be proximate to the sensor assembly 202. The one or more patient monitoring devices may or may not be coupled to a patient.

At block 1654, the sensor assembly 202 receives requested network connectivity information from the one or more patient monitoring devices. As discussed herein, the network connectivity information may be associated with, for example, network connectivity strength between the one or more patient monitoring devices and, for example, the network 1620. At block 1656, the sensor assembly 202 identifies a first patient monitoring device based on the network connectivity information. For example, in order to ensure uninterrupted, reliable, yet fast wireless transmission of patient physiological data, the sensor assembly 202 may identify a patient monitoring device that has the strongest, most reliable network connection with, for example, the network 1620 or the computing device 206.

At block 1658, the sensor assembly 202 (or the processor 254 of the reusable module 250) may establish a wireless communication with the first patient monitoring device (that is, one identified at block 1656). At block 1660, the sensor assembly 202 may transmit patient physiological data to the first patient monitoring device. As discussed herein, the first patient monitoring device may subsequently transmit the data to the network 1620.

Figure 16E:
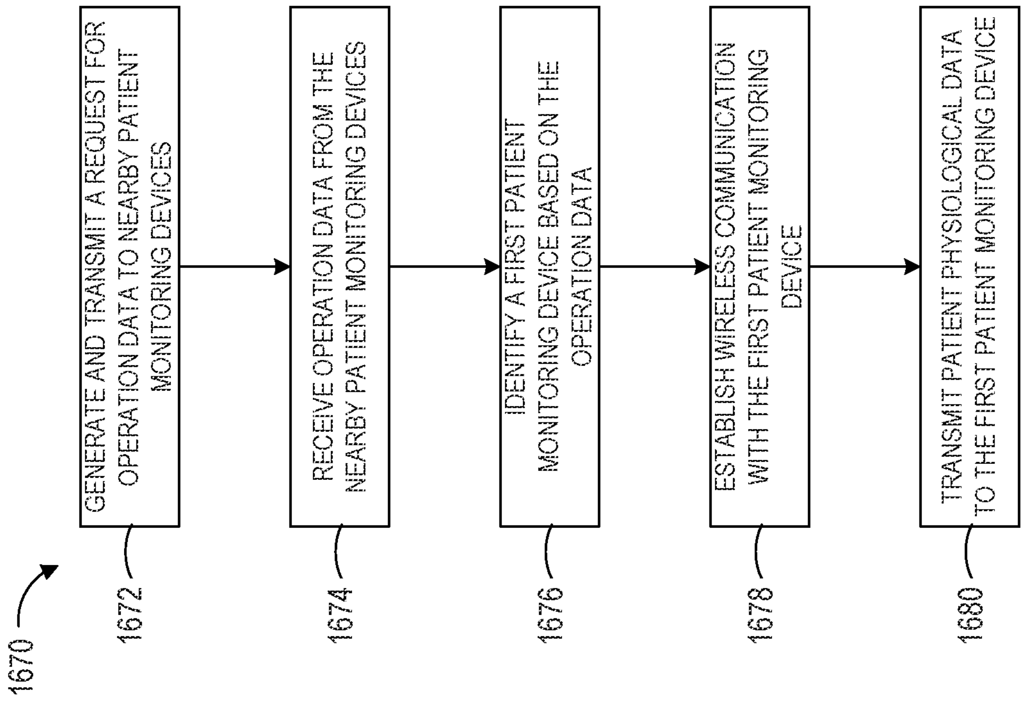

FIG. 16E illustrates an example method 1670 for transmitting patient physiological data to a patient monitoring device. At block 1672, the sensor assembly 202 transmits a request for operation data to one or more patient monitoring devices (for example, the patient monitoring devices 1600*a*, 1600*b*, 1600*c*). The one or more patient monitoring devices may or may not be proximate to the sensor assembly 202. The one or more patient monitoring devices may or may not be coupled to a patient.

At block 1674, the sensor assembly 202 receives requested operation data information form the one or more patient monitoring devices. As discussed herein, the operation data may be associated with, for example, (1) a battery charge level, (2) power consumption level, and (3) expected amount of power usage from data transmission. At block 1676, the sensor assembly 202 identifies a first patient monitoring device based on the battery status information. For example, in order to maximize the amount of patient physiological data stored, the sensor assembly 202 may identify a patient monitoring device that has the highest battery charge, lowest power usage, and/or least expected amount of power usage from data transmission.

At block 1678, the sensor assembly 202 (or the processor 254 of the reusable module 250) may establish a wireless communication with the first patient monitoring device (that is, one identified at block 1676). At block 1680, the sensor assembly 202 may transmit patient physiological data to the first patient monitoring device. As discussed herein, the first patient monitoring device may subsequently transmit the data to the network 1620.

Data Transmission to Care Providers

In some implementations, the communication module 252 of the reusable module 250 of the sensor assembly 202 is optional and the reusable module 250 may not include the communication module 252. As such, the reusable module 250 may not establish wireless communication with nearby devices, routers, access points, and the like, and may not transmit patient physiological data to, for example, the computing system 206 or the network 1620. Without the communication module 252, the reusable module 250 may receive physiological data from the sensor 240 of the disposable module 220 and store the data in, for example, the memory 256. Such a configuration can include a significantly larger memory to allow the communication module 252 to store high fidelity data for multiple days, for example three to seven days of continuous monitoring. This configuration can advantageously allow the reusable module 250 to operate for a longer period of time by reducing the amount of power consumption by storing patient physiological data in the memory 256 instead of wirelessly transmitting the data to, for example, the computing system 206, via the communication module 252.

In some implementations, the reusable module 250 includes the communication module 252 that can be disabled. For example, care providers or patients themselves may be able to disable functionality of the communication module 252 to prevent wireless transmission of patient physiological data from the sensor assembly 202 to, for example, the computing system 206 or the network 1620. As discussed herein, such wireless transmission of patient physiological data may be transmitted via wireless communication protocols including, but not limited to, Wi-Fi, ZigBee, Lo-Fi, Bluetooth®, Zwave, MiWI, near-field communication (NFC), and the like. In some implementations, the functionality of the communication module 252 can be enabled or disabled remotely.

Optionally, the reusable module 250 (or processor 254 of the reusable module 250) may generate and provide a notification upon determining that the storage capacity of the memory 256 satisfies a predetermined condition. For example, the predetermined condition may be a percentage of storage available in the memory 256 (e.g., less than or equal to 10% of available storage). In another example, the predetermined condition may be an estimated duration of time during which the sensor assembly 202 can collect and store data in the memory 256 (e.g., less than or equal to one (1) day's worth of patient physiological data).

The notification may be provided to, for example, a patient using the sensor assembly 202 (for example, at his or her home) or to a care provider having access to the sensor assembly 202. The sensor assembly 202 (for example, the reusable module 250 or the disposable module 220) can have an LED or a display that can display the notification about the storage capacity of the memory 256. Additionally and/or alternatively, the sensor assembly 202 (or the processor 254 of the reusable module 250) can, for example, transmit the notification to a care provider's computing device via, for example, the network 1620 or the computing system 206. The notification can include a message that will prompt the patient or the care provider that the memory 256, for example, is almost full. The notification can advantageously allow a patient using the sensor assembly 202 to, for example, send the reusable module 250 with stored patient physiological data to a care provider and/or request another reusable module 250, or allow a care provider to identify a patient with a reusable module 250 that needs to be replaced. Once a care provider identifies a patient with a reusable module 250 that needs to be replaced, the care provider can contact the patient to come into a care facility, for example, a hospital, to drop off the reusable module 250 and pick up a new reusable module 250, or send the reusable module 250 that needs to be replaced, for example, to a care facility via mail.

Figure 17:
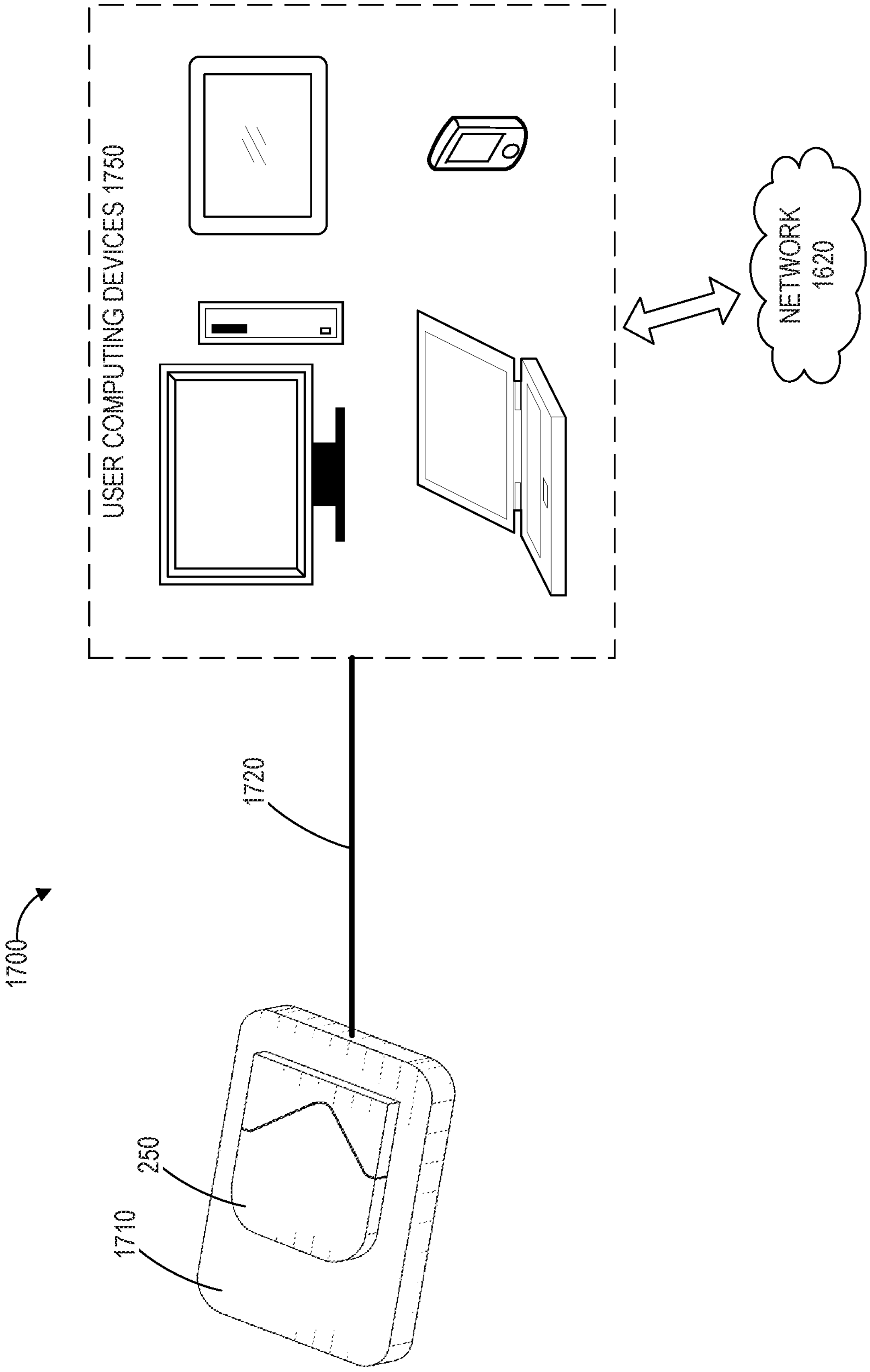
FIG. 17 illustrates a schematic diagram showing an example environment for transmitting patient physiological data from a reusable module to user computing devices.

FIG. 17 illustrates an example environment 1700 between the reusable module 250 and user computing devices 1750. In the example shown in FIG. 17, the reusable module 250 can be connected the user computing devices 1750 via a terminal 1710 and a cable 1720. The user computing devices 1750 can include a desktop computer, a tablet, a laptop computer, a mobile communication device, and the like.

The cable 1720 can allow transmission of data between the terminal 1710 and the user computing devices 1750. In some implementations, the cable 1720 is optional and the terminal 1710 can wirelessly communicate with the user computing devices 1750.

The terminal 1710 can receive and establish communication with the reusable module 250. In some implementations, the terminal 1710 can detect communication with the reusable module 250 and initiate transfer of patient physiological data (that is, patient physiological data stored in the memory 256 of the reusable module 250) from the reusable module 250 to the terminal 1710. Alternatively, the reusable module 250 (or the processor 254 of the reusable module 250) can detect communication with the terminal 1710 and initiate transfer of patient physiological data (that is, patient physiological data stored in the memory 256 of the reusable module 250) from the reusable module 250 to the terminal 1710.

In some implementations, a user input may cause or allow the data transfer between the reusable module 250 and the terminal 1710. For example, the terminal 1710 detects the connection with the reusable module 250 and sends a notification to the user computing devices 1750. The notification can include a request for data transfer between the reusable module 250 and the terminal 1710 (and/or the user computing devices 1750) and prompt a user input to allow or disallow the data transfer. If the user provides a user input allowing the data transfer, the data transfer between the reusable module 250 and the terminal 1710 can occur. If the user provides a user input disallowing the data transfer, the data transfer between the reusable module 250 and the terminal 1710 may not occur. Once the terminal 1710 receives patient physiological data from the reusable module 250, it can relay the data to the user computing devices 1750.

As shown in FIG. 17, the user computing devices 1750 can be connected to the network 1620. The user computing devices 1750 can transmit the data received from the reusable module 250 to the network 1620 for further analysis, processing, or storage of the data.

The user computing devices 1750 may be located remotely from a patient using the sensor assembly 202. As discussed herein, a patient may be located remotely from a care facility, for example, a hospital, for remote patient monitoring. Such remote monitoring of patients can be advantageous for reducing or preventing the likelihood of transmission of diseases such as COVID-19 between patients and care providers. In some implementations, the user computing devices can be a patient's desktop computer, a tablet, a laptop computer, or a mobile communication device, for example, a smartphone. Accordingly, the terminal 1710 can be located proximate to the patient's, for example, desktop computer. The terminal 1710 can facilitate transfer of patient physiological data between the sensor assembly 202 and the patient's desktop computer, as discussed herein, and the patient's desktop computer can subsequently transmit the data to the network 1620. Such setting can advantageously prevent delays caused by, for example, patients shipping their sensor systems 202 to their care providers or patients visiting his or her care provider to drop off their sensor systems 202. Moreover, it can further reduce the likelihood of transmission of diseases, for example COVID-19, by allowing the data transmission to occur at the patient's home and thereby preventing possibly-contaminated reusable modules 250 from being shipped to or entering care facilities (for example, hospitals).

Terminology

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the systems, devices or methods illustrated can be made without departing from the spirit of the disclosure. As will be recognized, certain embodiments described herein can be embodied within a form that does not provide all of the features and benefits set forth herein, as some features can be used or practiced separately from others.

The term "and/or" herein has its broadest, least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Although the foregoing disclosure has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not intended to be limited by the description of the preferred embodiments, but is to be defined by reference to claims.

What is claimed is:

1. A pulse oximeter configured to determine blood oxygen saturation of a tissue site on a finger of a user, said pulse oximeter comprising:

- a disposable module comprising:
  - a sensor comprising a plurality of emitters configured to transmit optical radiation towards the tissue site on the finger of the user and a plurality of detectors configured to detect attenuated light based on an interaction of transmitted optical radiation with the tissue site on the finger of the user;
  - a first housing secured on a strap, said strap configured to wrap around a wrist of the user, said first housing comprising a first outer surface, a power source, and a first electronic storage device; and
  - a wire configured to connect the sensor with the first housing; and
- a reusable module comprising:
  - a second housing configured to removably secure to the first housing, said second housing comprising:

a second outer surface, wherein the second outer surface is configured to be flush with the first outer surface when the second housing is secured to the first housing;

a second electronic storage device;

one or more hardware processors configured to:

receive a first set of signals from the plurality of detectors, said first set of signals collected at a first frequency, and process the first set of signals to determine a first blood oxygen saturation value of the user;

determine a first physiological condition of the user based at least in part on the first blood oxygen saturation value;

determine a second frequency based at least in part on the first physiological condition, wherein the second frequency is different from the first frequency;

receive a second set of signals from the plurality of detectors, said second set of signals collected at the second frequency, and process the second set of signals to determine a second blood oxygen saturation value of the user;

automatically determine a first disposable module life expectancy responsive to determining said first blood oxygen saturation value and based on said first frequency and transmit the first disposable module life expectancy to the first housing for storage in the first electronic storage device, wherein the first disposable module life expectancy is based on a life of the power source of the first housing;

automatically determine a second disposable module life expectancy responsive to determining said second blood oxygen saturation value and based on said second frequency and transmit the second disposable module life expectancy to the first housing for storage in the first electronic storage device, wherein the second disposable module life expectancy is based on the life of the power source of the first housing, and wherein the second disposable module life expectancy is different from the first disposable module life expectancy; and a wireless communication device configured to establish a first wireless communication with a first remote patient monitoring system when the pulse oximeter is within a predetermined distance from the first remote patient monitoring system.

2. The pulse oximeter of claim 1, wherein the one or more hardware processors are configured to store data associated with the first physiological condition of the user in the second electronic storage device for a length of time prior to establishing the first wireless communication with the first remote patient monitoring system.

3. The pulse oximeter of claim 2, wherein, in determination that the wireless communication device is unable to establish the first wireless communication with the first remote patient monitoring system, the one or more hardware processors are configured to cause the wireless communication device to establish a second wireless communication with a second remote patient monitoring system and transmit the data associated with the first physiological condition of the user to the second remote patient monitoring system.

4. The pulse oximeter of claim 3, wherein the one or more hardware processors are further configured to generate and transmit instructions configured to cause the second remote patient monitoring system to establish a third wireless communication with the first remote patient monitoring system and transmit the data associated with the first physiological condition of the user to the first remote patient monitoring system.

5. The pulse oximeter of claim 2, wherein the second electronic storage device stores a default length of time, and wherein the second electronic storage device is configured to store data associated with the first physiological condition of the user for the default length of time prior to establishing the first wireless communication with the first remote patient monitoring system.

6. The pulse oximeter of claim 1, wherein the first frequency is a default frequency for receiving signals from the plurality of detectors.

7. The pulse oximeter of claim 1, wherein the one or more hardware processors are further configured to store the first and/or second set of signals in the second electronic storage device when irregularities are sensed.

8. The pulse oximeter of claim 7, wherein the irregularities include at least one of: low blood pressure readings, high blood pressure readings, low respiratory rate readings, high respiratory rate readings, blood oxygen desaturations, irregular heartbeats, consistently low or declining blood oxygen saturation readings, low heart rates, or high heart rates.

9. The pulse oximeter of claim 1, wherein the one or more hardware processors are further configured to transmit the processed first and/or second set of signals to a local or a remote electronic storage system when a fourth wireless communication between the wireless communication device and an online server is established.

10. The pulse oximeter of claim 1, wherein a fidelity of the processed first and/or second set of signals varies based at least in part on a length of time specified for storing processed data in the second electronic storage device.

11. The pulse oximeter of claim 1, wherein a fidelity of the processed first and/or second set of signals varies based at least in part on types of health-related events detected from the processed first and/or second set of signals.

12. The pulse oximeter of claim 1, wherein a fidelity of the processed first set of signals varies based at least in part on the first physiological condition of the user.

13. The pulse oximeter of claim 1, wherein:

the one or more hardware processors are further configured to retrieve operation data from the sensor when the second housing is removably secured with the first housing; and wherein the one or more hardware processors are further configured to validate the sensor based at least in part on the operation data.

14. The pulse oximeter of claim 13, wherein the first electronic storage device stores the operation data.

15. The pulse oximeter of claim 13, wherein the validation of the sensor comprises determining whether a sensor type associated with the sensor is compatible with a configuration of the one or more hardware processors.

16. The pulse oximeter of claim 13, wherein the operation data comprises at least one of: a power source charge level, a power consumption level, or an expected amount of power usage from data transmission.

17. The pulse oximeter of claim 1, wherein the wireless communication device of the second housing is configured to wirelessly transmit said first and/or second blood oxygen saturation values of the user to the first remote patient monitoring system.

18. The pulse oximeter of claim 1, wherein the wireless communication device of the second housing is configured to wirelessly transmit said first and/or second disposable module life expectancy to the first remote patient monitoring system.

19. The pulse oximeter of claim 1, wherein the reusable module does not include a power source.

20. The pulse oximeter of claim 1, wherein the reusable module receives power from the power source of the first housing of the disposable module when the second housing is secured to the first housing.

* * * * *